US009388400B2

(12) United States Patent
Miller et al.

(10) Patent No.: US 9,388,400 B2
(45) Date of Patent: Jul. 12, 2016

(54) COMPOSITION FOR USE IN MYCOBACTERIA DIAGNOSIS

(71) Applicant: Lysando AG, Triesenberg (LI)

(72) Inventors: Stefan Miller, Regensburg (DE); Robert Andreas Fischer, Ingolstadt (DE)

(73) Assignee: LYSANDO AG, Triesenberg (LI)

( * ) Notice: Subject to any disclaimer, the term of this patent is extended or adjusted under 35 U.S.C. 154(b) by 0 days.

(21) Appl. No.: 14/411,758

(22) PCT Filed: Jul. 1, 2013

(86) PCT No.: PCT/EP2013/063845
§ 371 (c)(1),
(2) Date: Dec. 29, 2014

(87) PCT Pub. No.: WO2014/001571
PCT Pub. Date: Jan. 3, 2014

(65) Prior Publication Data
US 2015/0140572 A1 May 21, 2015

(30) Foreign Application Priority Data
Jun. 29, 2012 (EP) .................................. 12174469

(51) Int. Cl.
C07K 1/00 (2006.01)
C07H 21/04 (2006.01)
C12Q 1/00 (2006.01)
C12N 9/36 (2006.01)
C12Q 1/34 (2006.01)
G01N 33/569 (2006.01)
C12N 9/96 (2006.01)

(52) U.S. Cl.
CPC ............... *C12N 9/2462* (2013.01); *C12N 9/96* (2013.01); *C12Q 1/34* (2013.01); *G01N 33/5695* (2013.01); *C07K 2319/00* (2013.01); *C07K 2319/10* (2013.01); *C07K 2319/33* (2013.01)

(58) Field of Classification Search
CPC .................................................. C12N 9/2462
See application file for complete search history.

(56) References Cited

FOREIGN PATENT DOCUMENTS

| EP | 2468856 | 6/2012 |
|---|---|---|
| GB | 2015876 | 9/1979 |
| WO | WO 2008/128065 | 10/2008 |
| WO | WO 2010/149795 | 12/2010 |
| WO | WO 2011/134998 | 11/2011 |
| WO | WO 2014/001570 | 1/2014 |
| WO | WO 2014/001572 | 1/2014 |

OTHER PUBLICATIONS

Carroll et al., "Gene encoded antimicrobial peptides, a template for the design of novel anti-mycobacterial drugs", Bioeng Bugs., 1(6):408-12, 2010.
Cheng et al., "Removal of group B Streptococci colonizing the vagina and oropharynx of mice with a bacteriophage lytic enzyme", Antimicrob Agents Chemother., 49(1):111-7, 2005.
Gil et al., "Mycobacteriophage Ms6 LysB specifically targets the outer membrane of Mycobacterium smegmatis", Microbiology, 156(Pt 5): 1497-1504, 2010.
Hoffmann et al., "Disclosure of the mycobacterial outer membrane:cryo-electron tomography and vitreous sections reveal the lipid bilayer structure", Proc Nat Acd Sci U.S.A., 105(10):3963-7, 2008.
International Search Report and Written Opinion issued in International Application No. PCT/EP2013/063843, mailed Aug. 7, 2013.
International Search Report and Written Opinion issued in International Application No. PCT/EP2013/063845, mailed Aug. 19, 2013.
International Search Report and Written Opinion issued in International Application No. PCT/EP2013/063846, mailed Jul. 26, 2013.
Langemann et al., "The bacterial ghost platform system: production and applications", Bioeng Bugs., 1(5):326-36, 2010.
Loeffler et al., "Rapid killing of Streptococcus pneumoniae with a bacteriophage cell wall hydrolase", Science, 294(5549):2170-2, 2001.

(Continued)

Primary Examiner — Albert Navarro
(74) Attorney, Agent, or Firm — Parker Highlander PLLC

(57) ABSTRACT

The present invention relates to a composition having the activity of degrading the cell wall of a *Mycobacterium* species comprising: (a) a first fusion protein including (i) a domain with a first enzymatic activity, the enzymatic activity being at least one or more of the following: N-acetyl-b-D-muramidase (lysozyme, lytic transglycosylase), N-acetyl-b-D-glucosaminidase, N-acetylmuramoyl-L-alanine amidase, L-alanoyl-D-glutamate (LD) endopeptidase, c-D-glutamyl-meso-diaminopimelic acid (DL) peptidase, D-Ala-m-DAP (DD) endopeptidase, or m-DAP-m-DAP (LD) endopeptidase, (ii) at least one peptide stretch fused to the N- or C-terminus of the domain with the first enzymatic activity; and (iii) a protein transduction domain (PTD) being at the N- or C-terminus of the first fusion protein; and (b) a second fusion protein including (i) a domain with a second enzymatic activity, the enzymatic activity being at least one or more of the following: lipolytic activity, cutinase, mycolarabinogalactanesterase, or alpha/beta hydrolase; (ii) at least one peptide stretch fused to the N- or C-terminus of the domain of the second enzymatic activity; and (iii) a protein transduction domain (PTD) being at the N- or C-terminus of the second fusion protein for use as a diagnostic agent. Moreover, the present invention relates to nucleic acid molecules encoding said fusion protein. In addition, the present invention relates to methods for the detection of a *Mycobacterium* species in a sample and a kit comprising the fusion proteins for conduction the methods for the detection.

16 Claims, 6 Drawing Sheets

(56) References Cited

OTHER PUBLICATIONS

Figure 3A:
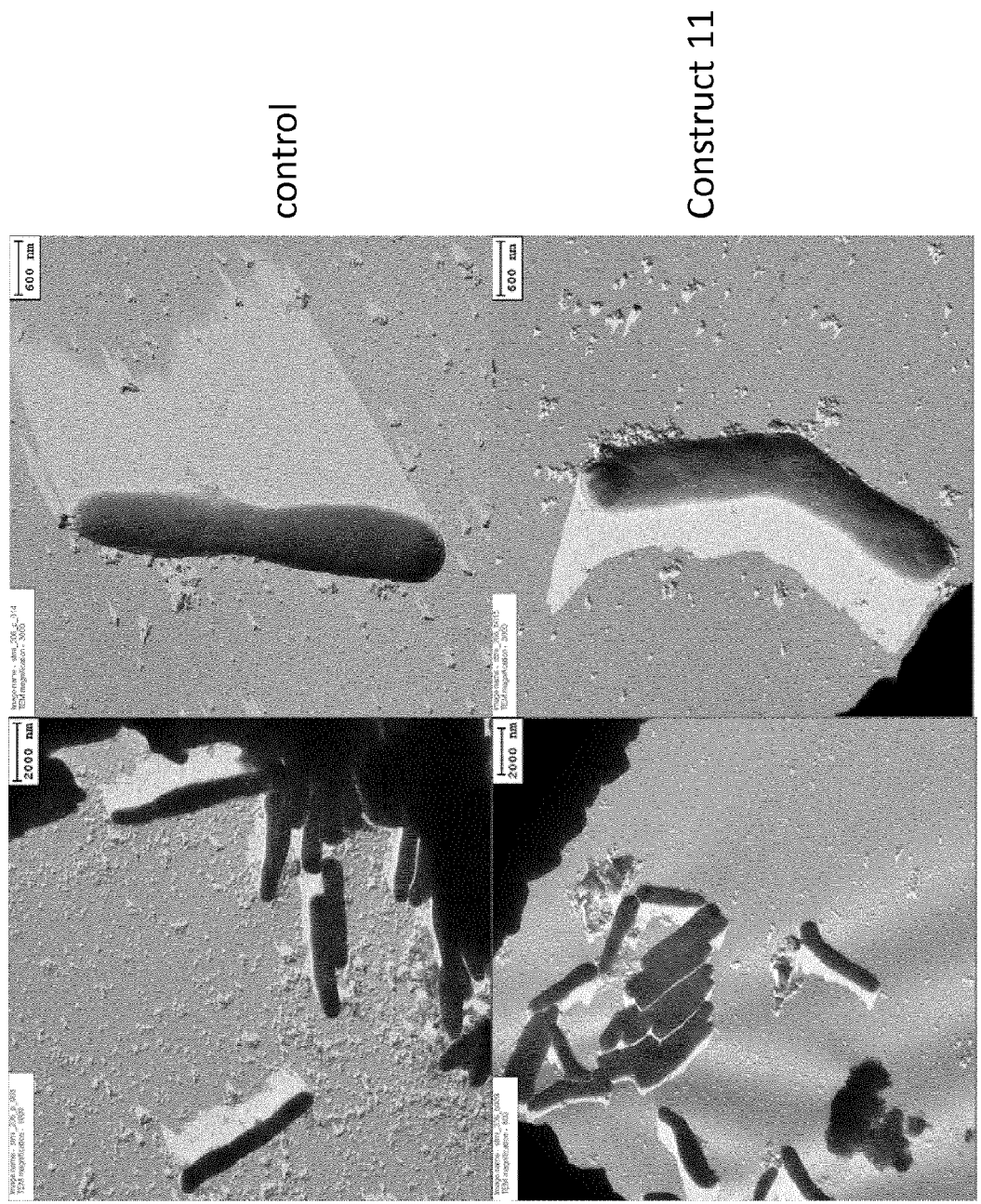

Nelson et al., "Prevention and elimination of upper respiratory colonization of mice by group A *streptococci* by using a bacteriophage lytic enzyme", Proc Natl Acad Sci U S A., 98(7):4107-12, 2001.
Payne et al., "Mycobacteriophage endolysins: diverse and modular enzymes with multiple catalytic activities", *PLOS One*, (7)3: e34052, 2012.
Payne et al., "Mycobacteriophage Lysin B is a novel mycolylarabinogalactan esterase", *Mol Microbiol*, 73(3): 369-381, 2009.
Rashel et al., "Efficient elimination of multidrug-resistant *Staphylococcus aureus* by cloned lysine derived from bacteriophage φMR11", *J Infect Dis.*, 196(8):1237-47, 2007.
Schuch et al., "A bacteriolytic agent that detects and kills *Bacillus anthracis*", Nature.;418(6900):884-9, 2002.
Shin and Jo, "Antimicrobial peptides in innate immunity against mycobacteria", *Immune Network*, 11(5):245-52, 2011.
Van den Berg and Dowdy, "Protein transduction domain delivery of therapeutic macromolecules", *Current Opinion in Biotechnology*, 22(6): 888-93, 2011.
Vollmer et al., "Bacterial peptidoglycan (murein) hydrolases", *FEMS Microbiol Rev.*, 32(2):259-86, 2008.
Walmagh et al., "Characterization of modular bacteriophage endolysins from Myoviridae phages OBP, 201ω2-1 and PVP-SE1", *PLOS One*, 7(5): e36991, 2012.
Zhou et al., "TrxA mediating fusion expression of antimicrobial peptide CM4 from multiple joined genes in *Escherichia coli*", *Protein Expr Purif.*, 64(2): 225-230, 2009.
Zuber et al., "Direct visualization of the outer membrane of mycobacteria and corynebaterica in their native state", J Bacteriol., 190(16):5672-80, 2008.

Fig. 1A

| construct | Fusion Protein | Peptide | | | | | | | | | | Nucleotide |
|---|---|---|---|---|---|---|---|---|---|---|---|---|
| | | Length | Weight | Isoelectric point | Extinction coefficient | | Hydrophobic residues | Hydrophilic residues | Charged residues | | Tags | Length |
| | | | | | Non-red. Cys | reduced Cys | | | negatively | positively | | |
| Pat 1 | TM4gp29/LL37/TAT47-57 | 605 | 65,807 | 7,43 | 91330/1,388 | 90610/1,377 | 305 | 138 | 71 | 70 | His | 1815 |
| Pat 2 | Bxz2gp11/alpha-defensin/PTD3 | 565 | 63,862 | 7,21 | 136480/2,137 | 135700/2,125 | 281 | 131 | 71 | 70 | His | 1695 |
| Pat 3 | PTD3/alpha-defensin/Bxz2gp11 | 566 | 64,091 | 7,6 | 136480/2,129 | 135700/2,117 | 282 | 130 | 71 | 71 | His | 1698 |
| Pat 4 | PTD3/alpha-defensin/Bxz2gp11/alpha-defensin | 598 | 67,709 | 8,13 | 146370/2,162 | 145230/2,145 | 296 | 142 | 73 | 75 | His | 1794 |
| Pat 5 | beta-defensin/L5gp10/TAT47-57 | 354 | 39,572 | 9,34 | 54450/1,376 | 53910/1,362 | 175 | 70 | 40 | 50 | His | 1062 |
| Pat 6 | alpha-defensin/hepcidin/L5gp10/TAT47-57 | 371 | 41,752 | 8,69 | 64460/1,544 | 63440/1,519 | 179 | 80 | 43 | 48 | His | 1113 |
| Pat 7 | D29gp12/alpha-defensin/TAT47-57 | 458 | 49,584 | 9,6 | 60430/1,219 | 60310/1,216 | 269 | 88 | 38 | 50 | His | 1374 |
| Pat 8 | D29gp12/alpha-defensin/PTD3 | 305 | 34,608 | 7,79 | 58110/1,679 | 57750/1,669 | 166 | 53 | 35 | 35 | His | 915 |
| Pat 9 | PTD3/alpha-defensin/D29gp12 | 306 | 34,837 | 8,25 | 58110/1,668 | 57750/1,658 | 167 | 52 | 35 | 36 | His | 918 |
| Pat 10 | PTD3/alpha-defensin/D29gp12/alpha-defensin | 338 | 38,455 | 8,52 | 68000/1,768 | 67280/1,75 | 181 | 64 | 37 | 40 | His | 1014 |
| Pat 11 | beta-defensin/D29gp12/TAT47-57 | 316 | 35,708 | 9,45 | 48580/1,36 | 48220/1,35 | 170 | 54 | 33 | 43 | His | 948 |
| Pat 12 | beta-defensin/L5gp12/TAT47-57 | 341 | 38,823 | 9,48 | 53470/1,377 | 52630/1,356 | 175 | 67 | 33 | 48 | His | 1023 |
| Bxz2gp11 | native Lysin | 522 | 58,831 | 6,06 | 125310/2,13 | 124890/2,123 | 264 | 117 | 69 | 60 | His | 1566 |
| Bxz2gp12 | native Lysin | 329 | 36,48 | 6,33 | 53400/1,464 | 53340/1,462 | 173 | 64 | 42 | 35 | His | 987 |
| D29gp10 | native Lysin | 501 | 55,887 | 6,23 | 99810/1,786 | 99570/1,782 | 256 | 105 | 66 | 56 | His | 1503 |
| D29gp12 | native Lysin | 262 | 29,576 | 6,27 | 46940/1,587 | 46940/1,587 | 149 | 39 | 33 | 25 | His | 786 |
| L5gp10 | native Lysin | 300 | 33,44 | 6,39 | 52810/1,579 | 52630/1,574 | 154 | 55 | 40 | 32 | His | 900 |
| L5gp12 | native Lysin | 262 | 29,912 | 6,58 | 51350/1,717 | 51350/1,717 | 146 | 41 | 32 | 27 | His | 786 |
| TM4gp29 | native Lysin | 555 | 59,646 | 6,01 | 90050/1,51 | 89330/1,498 | 287 | 130 | 66 | 51 | His | 1665 |
| TM4gp30 | native Lysin | 408 | 43,423 | 6,96 | 59150/1,362 | 59030/1,359 | 251 | 80 | 33 | 31 | His | 1224 |
| Pat 1 trx | TM4gp29/LL37/TAT47-57 | 732 | 79,078 | 6,52 | 105390/1,333 | 104550/1,322 | 375 | 163 | 90 | 82 | Trx/H | 2196 |
| Pat 2 trx | Bxz2gp11/alpha-defensin/PTD3 | 692 | 77,133 | 6,24 | 150540/1,952 | 149640/1,94 | 351 | 156 | 90 | 82 | Trx/H | 2076 |
| Pat 3 trx | PTD3/alpha-defensin/Bxz2gp11 | 693 | 77,362 | 6,33 | 150540/1,946 | 149640/1,934 | 352 | 155 | 90 | 83 | Trx/H | 2079 |
| Pat 4 trx | PTD3/alpha-defensin/Bxz2gp11/alpha-defensin | 725 | 80,98 | 6,53 | 160430/1,981 | 159170/1,966 | 366 | 167 | 92 | 87 | Trx/H | 2175 |
| Pat 5 trx | beta-defensin/L5gp10/TAT47-57 | 481 | 52,843 | 8,55 | 68510/1,296 | 67850/1,284 | 245 | 95 | 59 | 67 | Trx/H | 1443 |
| Pat 6 trx | alpha-defensin/hepcidin/L5gp10/TAT47-57 | 498 | 55,023 | 7,18 | 78520/1,427 | 77380/1,406 | 249 | 105 | 62 | 60 | Trx/H | 1494 |
| Pat 7 trx | TM4gp30/LL37/TAT47-57 | 585 | 62,855 | 8,91 | 74490/1,185 | 74250/1,181 | 339 | 113 | 57 | 62 | Trx/H | 1755 |

Fig. 1B

| construct | Fusion Protein | Peptide ||||||||| Nucleotide |
| | | Length | Weight | Isoelectric point | Extinction coefficient || Hydrophobic residues | Hydrophilic residues | Charged residues || Tags | Length |
| | | | | | Non-red. Cys | reduced Cys | | | negatively | positively | | |
|---|---|---|---|---|---|---|---|---|---|---|---|---|
| Pat 8 trx | D29gp12/alpha-defensin/PTD3 | 432 | 47,879 | 6,43 | 72170/1,507 | 71690/1,497 | 236 | 78 | 54 | 47 | Trx/H | 1296 |
| Pat 9 trx | PTD3/alpha-defensin/D29gp12 | 433 | 48,108 | 6,52 | 72170/1,5 | 71690/1,49 | 237 | 77 | 54 | 48 | Trx/H | 1299 |
| Pat 10 trx | PTD3/alpha-defensin/D29gp12/alpha-defensin | 465 | 51,726 | 6,75 | 82060/1,586 | 81220/1,57 | 251 | 89 | 56 | 52 | Trx/H | 1395 |
| Pat 11 trx | beta-defensin/D29gp12/TAT47-57 | 443 | 48,979 | 8,62 | 62640/1,279 | 62160/1,269 | 240 | 79 | 52 | 55 | Trx/H | 1329 |
| Pat 12 trx | beta-defensin/hepcidin/L5gp12/TAT47-57 | 468 | 52,094 | 8,94 | 67530/1,296 | 66570/1,278 | 245 | 92 | 52 | 60 | Trx/H | 1404 |
| Bxz2gp11 trx | native Lysin | 649 | 72,101 | 5,68 | 139370/1,933 | 138830/1,925 | 334 | 142 | 88 | 72 | Trx/H | 1947 |
| Bxz2gp12 trx | native Lysin | 456 | 49,751 | 5,84 | 67460/1,356 | 67280/1,352 | 243 | 89 | 61 | 47 | Trx/H | 1368 |
| D29gp10 trx | native Lysin | 628 | 69,158 | 5,85 | 113870/1,647 | 113510/1,641 | 326 | 130 | 85 | 68 | Trx/H | 1884 |
| D29gp12 trx | native Lysin | 389 | 42,847 | 5,79 | 61000/1,424 | 60880/1,421 | 219 | 64 | 52 | 37 | Trx/H | 1167 |
| L5gp10 trx | native Lysin | 427 | 46,711 | 5,95 | 66870/1,432 | 66570/1,425 | 224 | 80 | 59 | 44 | Trx/H | 1281 |
| L5gp12 trx | native Lysin | 389 | 43,183 | 6,01 | 65410/1,515 | 65290/1,512 | 216 | 66 | 51 | 39 | Trx/H | 1167 |
| TM4gp29 trx | native Lysin | 682 | 72,917 | 5,71 | 104110/1,428 | 103270/1,416 | 357 | 155 | 85 | 63 | Trx/H | 2046 |
| TM4gp30 trx | native Lysin | 535 | 56,694 | 6,12 | 73210/1,291 | 72970/1,287 | 321 | 105 | 52 | 43 | Trx/H | 1605 |

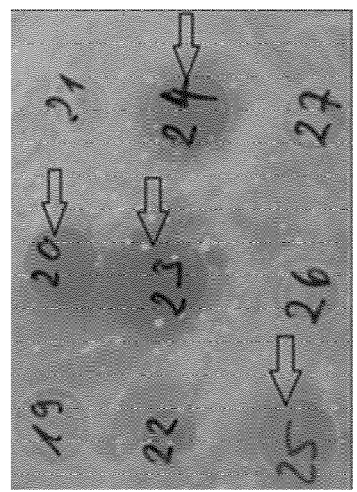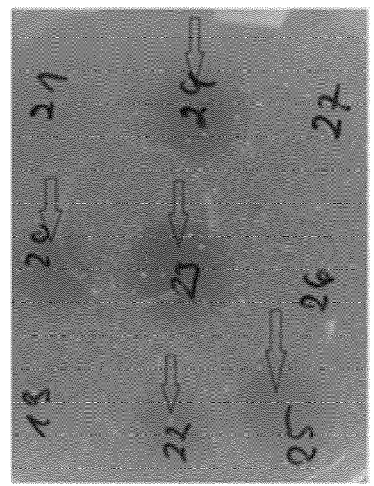
Fig. 2 A
Fig. 2 B

COMPOSITION FOR USE IN MYCOBACTERIA DIAGNOSIS

The present application is a national phase application under 35 U.S.C. §371 of International Application No. PCT/EP2013/063845, filed Jul. 1, 2013, which claims benefit of priority to European Application No. 12174469.2, filed Jun. 29, 2012, the entire contents of each of the applications being hereby incorporated by reference.

The present invention relates to a composition having the activity of degrading the cell wall of a *Mycobacterium species* comprising: (a) a first fusion protein including (i) a first endolysin or a first domain, both having a first enzymatic activity, the enzymatic activity being at least one or more of the following: N-acetyl-b-D-muramidase (lysozyme, lytic transglycosylase), N-acetyl-b-D-glucosaminidase, N-acetylmuramoyl-L-alanine amidase, L-alanoyl-D-glutamate (LD) endopeptidase, c-D-glutamyl-meso-diaminopimelic acid (DL) peptidase, L-alanyl-D-iso-glutaminyl-meso-diaminopimelic acid (D-Ala-m-DAP) (DD) endopeptidase, or m-DAP-m-DAP (LD) endopeptidase, (ii) at least one peptide stretch fused to the N- or C-terminus of the endolysin having the first enzymatic activity or the domain having the first enzymatic activity, wherein the peptide stretch is selected from the group consisting of synthetic amphipathic peptide, synthetic cationic peptide, synthetic polycationic peptide, synthetic hydrophobic peptide, synthetic antimicrobial peptide (AMP) or naturally occurring AMP; and (iii) a protein transduction domain (PTD) being at the N- or C-terminus of the first fusion protein, wherein the PTD is having the characteristic to deliver a cargo from the extracellular to the intracellular space of a cell; and (b) a second fusion protein including (i) a second endolysin or a second domain, both having a second enzymatic activity, the enzymatic activity being at least one or more of the following: lipolytic activity, cutinase, mycolarabinogalactanesterase, or alpha/beta hydrolase; (ii) at least one peptide stretch fused to the N- or C-terminus of the endolysin having a second enzymatic activity or the domain having the second enzymatic activity, wherein the peptide stretch is selected from the group consisting of synthetic amphipathic peptide, synthetic cationic peptide, synthetic polycationic peptide, synthetic hydrophobic peptide, synthetic antimicrobial peptide (AMP) or naturally occurring AMP; and (iii) a protein transduction domain (PTD) being at the N- or C-terminus of the second fusion protein, wherein the PTD is having the characteristic to deliver a cargo from the extracellular to the intracellular space of a cell, for use as diagnostic agent. In addition, the present invention relates to methods for the sample preparation and/or the detection of a *Mycobacterium species* in a sample and a kit comprising the fusion proteins for conduction the methods for sample preparation or the detection.

*Mycobacteria* are classified as Gram positive bacteria. In comparison to most of the Gram-positive bacteria however, the structure of the cell wall of mycobacteria is different in their composition. The complex structure of the cell wall of mycobacteria consists of a mycolic acid-rich outer membrane which is covalently linked to the arabinogalactan-peptidoglycan complex (Hoffmann et al., 2008; Zuber et al., 2008). The mycolic acids are alpha-alkyl, beta-hydroxy $C_{60-90}$ fatty acids. The distinct composition of the mycolic acids is dependent on the *Mycobacterium species* including short saturated alpha, $C_{20-25}$, and a longer meromycolate chain, the beta-hydroxy branch $C_{60}$, comprising doublebonds, cyclopropane rings and oxygenated groups. The outer membrane is linked with esterification to the terminal pentaarabinofuranosyl components of arabinogalactan (Payne et al., Molecular Microbiology, 73(3), 2009). The arabinogalactan is covalently linked to peptidoglycan. This covalently linked complex is known as mycolyl-arabinogalactan peptidoglycan (mAGP). This mAGP is known as the cell wall core and builds a stable scaffolding to anchor the outer non-covalently associated lipid and glycoplipids including trehalose 6,6'-dimycolate (TDM or cord factor) (Gil et al., Microbiology, 156, 2010). TDM is a secreted molecule which is important for the pathogenesis of mycobacteria (Brennan, 2003). The cell surface of mycobacteria has the characteristics of a highly hydrophobicity and fastness in view of acids due to the special structure of mAGP and TDM in combination with trehalose 6'-monomycolate. These special properties are leading to the fact that mycobacteria are resistant to dehydration and posses a natural impermeability to nutrients and antibacterial drugs (Gil et al., Microbiology, 156, 2010).

*Mycobacterium tuberculosis* is the cause for the tuberculosis, an infectious disease which typically affects the lungs. Tuberculosis is a health and life threatening disease. In 2009, 9.4 million new cases of tuberculosis and 1.7 million deaths are counted (Global Tuberculosis Control WHO Report 2010. World Health Organization; Geneva: 2010). *Mycobacterium tuberculosis* is spread as a primarily respiratory pathogen. Patients with an active infection can transmit the infection by coughing. A major part of infected human patients are not able to eliminate the bacteria completely. This results in the so called "latent" stage, defining a status, wherein the patient is still infected, but does not show any symptoms of the disease. This latent stage however can change in some patients due to a reactivation of the infection resulting in an active stage of tuberculosis. Typically, an infection with *mycobacterium tuberculosis* starts with the inhalation of the bacteria, followed by the presentation by antigen-presenting immune cells, such as macrophages or dendritic cells, in the airway. Infected macrophages include mycobacteria in intracellular vesicles. However, these vesicles are not accessible for a fusion with lysosomes, which would result in a killing of the mycobacteria.

After activation of the infected macrophages with a specific $T_H1$-cell, a lysosomal fusion occurs. Further to this first infection step, infected macrophages recruit uninfected macrophages. Thereby a so called granuloma is formed. The structure of such a granuloma, which is also called caseous granuloma because of the "cheese-like" look, comprises macrophages surrounding a necrotic area with adjacent of B and T cells.

*Mycobacteria* in general can be classified into several major groups for purpose of diagnosis and treatment: *M. tuberculosis* complex, which can cause tuberculosis: *M. tuberculosis, M. bovis, M. africanum*, and *M. microti; M. leprae*, which causes Hansen's disease or leprosy; Nontuberculous mycobacteria (NTM) define all the other mycobacteria, which can cause pulmonary disease resembling tuberculosis, lymphadenitis, skin disease, or disseminated disease. *Mycobacteria* not only cause human infections but also animal infections as well, e.g. *Mycobacterium avium, Mycobacterium avium* subsp. *paratuberculosis, Mycobacerium bovis*.

There are currently several possibilities for Mycobacterium diagnosis. For example, a skin test using tuberculin, which is a defined amount of filtrated antigens from mycobacteria, is used. This skin test is conducted with the injection of tuberculin in the epidermis. Subjects having been infected with mycobacteria before, develop an immune reaction at the site of injection. However, the skin test using tuberculin has the disadvantage that differentiating between different stages of the disease, such as latent infected or active infected stage of the disease—is not possible. Furthermore, false positive results occur in the case the subject had been in contact with atypical mycobacteria before. A further diagnostic possibility is imaging in form of e.g. a chest X ray of the lung. This imaging however has the disadvantage that it is not always possible to differentiate between tuberculosis and other diseases of the lung. Diagnosis of mycobacteria can be conducted on the detection of the mycobacteria per se. However, the detection of the mycobacteria is only possible in the case the subject provides a sufficient amount of the pathogen in the sputum, which is only the case during active disease stages, but during latent disease stages. The direct diagnosis of the pathogen provides the further disadvantage that mycobacteria have a slow growth on standard breeding matrices. Accordingly, culturing before the diagnostic procedure can be conducted is very time consuming. Finally, immunologic diagnostic methods are available. According to these methods interferon-gamma is detected as the distinct cytokine which is produced in disease specific immune cells. However, these immunologic methods suffer from sensitivity and specificity problems.

In addition molecular biology diagnostic methods like PCR or gen-probe or NASBA are available. However, the sensitivity, of those methods is hampered by the robust cell surface of the *Mycobacteria* which is difficult to break up. A lower sensitivity leads to longer times spans for the overall diagnostic process from sample preparation to result.

Mycobacteriophages are a subgroup of bacteriophages, which are bacterial viruses, which target mycobacterial hosts. In view of the special structure and composition of the cell wall of mycobacteria, it is necessary for the mycobacteriophages to degrade the peptidoglycan layer and further to lyse the mycolic acid-rich outer membrane attached to the mAGP complex.

Various types of agents having bactericidal or bacteriostatic activity are known, e.g. antibiotics, endolysins, antimicrobial peptides such as defensins. Further, phages are known to exert bactericidal activity as well. Increasingly microbial resistance to antibiotics, however, is creating difficulties in treating more and more infections caused by bacteria.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases, transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this concept of combating human pathogens with endolysins received interest. A compelling need to develop totally new classes of antibacterial agents emerged and endolysins used as 'enzybiotics'—a hybrid term of 'enzymes' and 'antibiotics'—seem to meet this need. In 2001, Fischetti and coworkers demonstrated for the first time the therapeutic potential of bacteriophage C1 endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al., 2007) have proven their efficacy as enzybiotics.

Distinct endolysins have been identified in mycobacteriophages (Payne and Hatfull, Plos ONE, 7(3), 2012; Payne et al., Mol Microbiol, 73(3), 2009). These particular endolysins are able to break down the mycobacterial cell wall characterized by the mycol-rich mycobacterial outer membrane attached to an arabinogalactan layer which is in turn linked to the peptidoglycan. These particular phage endolysins can be assigned to two groups, (i) enzymes that cleave the peptidoglycan, and (ii) enzymes that cleave the mycolic acid and arabinogalactan layer.

Antimicrobial peptides (AMPs) represent an important component of the innate immunity against infections against bacteria. Several antimicrobial peptides have been identified which possess an effect against mycobacteria. These antimicrobial peptides are involved not only in the killing of mycobacteria but also in the modulation of the immune defense in form of the secretion of cytokines and chemokines (Shin and Jo, Immune Network, 11(5), 2011).

Antimicrobial peptides (AMPs) represent a wide range of short, cationic or amphipathic, gene encoded peptide antibiotics that can be found in virtually every organism. Different AMPs display different properties, and many peptides in this class are being intensively researched not only as antibiotics, but also as templates for cell penetrating peptides. Despite sharing a few common features (e.g., cationicity, amphipathicity and short size), AMP sequences vary greatly, and at least four structural groups (α-helical, β-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs are typically in the low micromolar range, scepticism has understandably arisen regarding the relevance of these thresholds and their importance in vivo (Melo et al., Nature reviews, Microbiology, 2009, 245).

Cathelicidins are a family of AMPs which are derived from leukocytes and epithelial cells. Currently, the only identified human cathelicidin is hCAP-18/LL-37 Immunstimulatory effects have been reported for cathelicidins (Shin and Jo, Immune Network, 11(5), 2011).

Defensins are a large family of small, cationic or amphipathic, cysteine- and arginine-rich antimicrobial peptides, found in both vertebrates and invertebrates. Defensins are divided into five groups according to the spacing pattern of cysteines: plant, invertebrate, α-, β-, and θ-defensins. The latter three are mostly found in mammals. α-defensins are proteins found in neutrophils and intestinal epithelia. β-defensins are the most widely distributed and are secreted by leukocytes and epithelial cells of many kinds. θ-defensins have been rarely found so far e.g. in leukocytes of rhesus macaques. Defensins are active against bacteria, fungi and many enveloped and nonenveloped viruses. However, the concentrations needed for efficient killing of bacteria are mostly high, i.e. in the μ-molar range. Activity of many peptides may be limited in presence of physiological salt conditions, divalent cations and serum. Depending on the content of hydrophobic amino acid residues defensins also show haemolytic activity.

Hepcidin is a cationic amphipathic bactericidal peptide which is primarily produced in the liver. The expression of Hepcidin is induced during infectious and inflammatory conditions. Crucially, Hepcidin is expressed in macrophages after infection with intracellular pathogens *Mycobacterium avium* and *Mycobacterium tuberculosis*. Further, hepcidin causes damage to *Mycobacterium tuberculosis* and thus exerts immediate antimycobacterial activity (Shin and Jo, Immune Network, 11(5), 2011).

*Mycobacteria* with its special structure of the cell wall and the infection procedure which results in the intracellular survival of the mycobacteria within macrophages represent challenges for an effective diagnosis of mycobacterial infections, in particular of different stages of the mycobacterial infection. There are currently difficulties existing to target mycobacteria which are residing and replicating intracellularly, e.g. mycobacteria which are surviving within infected host cells, such as macrophages.

Thus, there is a need for new diagnostic agents and diagnostic methods.

This object is solved by the subject-matter defined in the claims.

The following figures describe the invention.

FIGS. 1 A and B provides an overview of distinct parameters of the first and second fusion proteins of the invention.

FIGS. 2 A and B is a picture of the spot test on agarose plates with mycobacterial lawn (FIG. 2 A) and an agarose-overlay spot test (FIG. 2 B).

Figure 3:
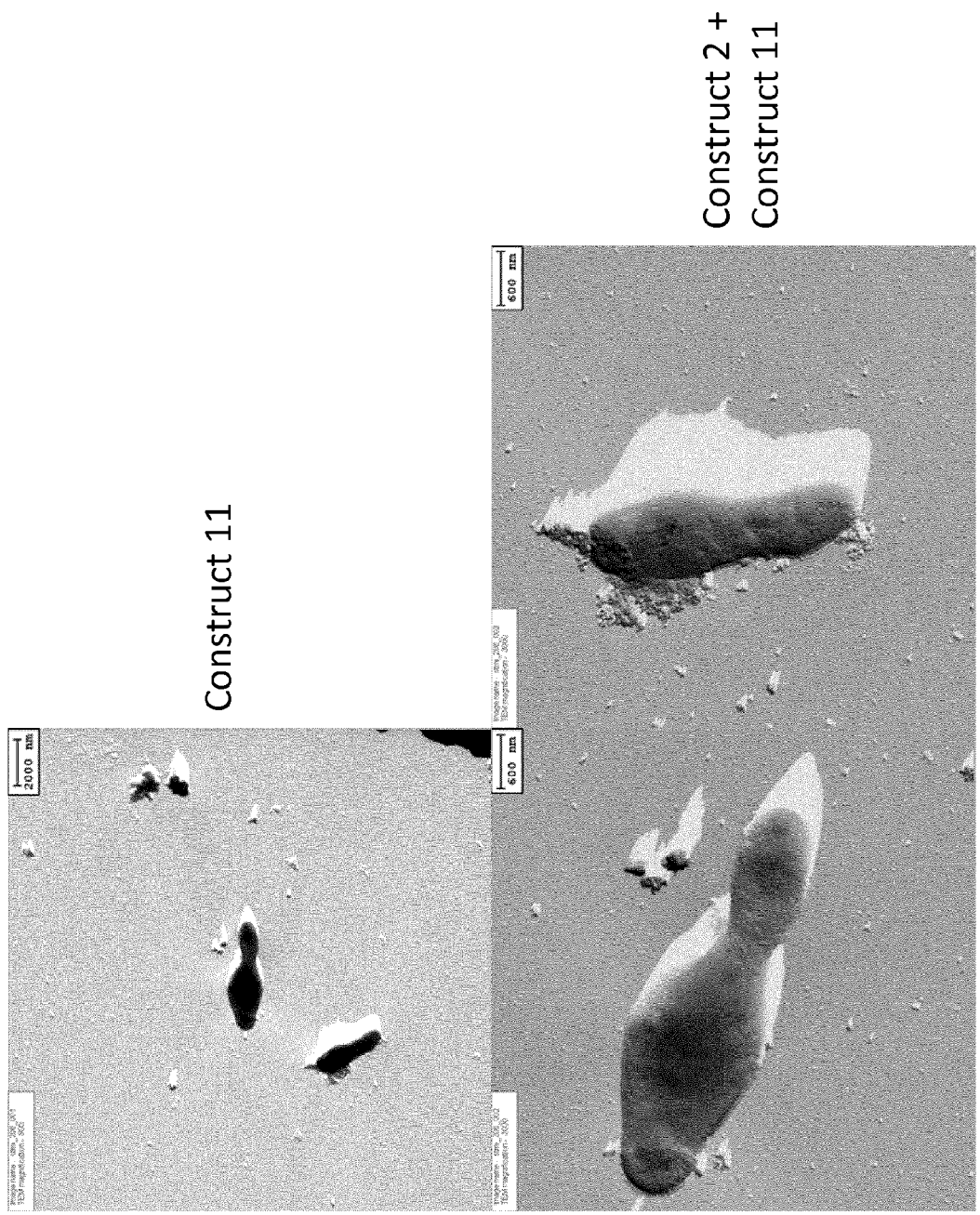

FIGS. 3 A and B is an electron microscopy picture of mycobacteria cells. Shown are pictures of untreated mycobacteria (FIG. 3 A upper row), treated only with construct 11 (FIG. 3 A lower row, and FIG. 3 B upper picture), and treated with first and second fusion protein of construct 2 and construct 11 according to the invention (FIG. 3 B lower row).

Figure 4:
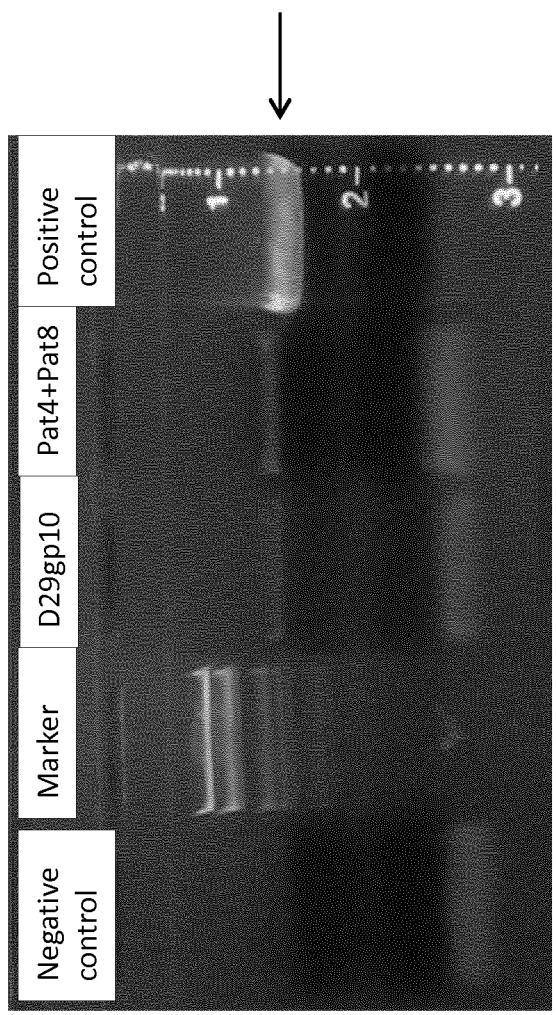

FIG. 4 shows a picture of an agarose gel electrophoresis.

The term "protein" as used herein refers to a linear polymer of amino acid residues linked by peptide bonds in a specific sequence. The amino-acid residues of a protein may be modified by e.g. covalent attachments of various groups such as carbohydrates and phosphate. Other substances may be more loosely associated with the protein, such as heme or lipid, giving rise to the conjugated proteins which are also comprised by the term "protein" as used herein. The protein may be folded in different ways. The various ways in which the protein fold have been elucidated, are in particular with regard to the presence of alpha helices and beta-pleated sheets. The term "protein" as used herein refers to all four classes of proteins being all-alpha, all-beta, alpha/beta and alpha plus beta. Moreover, the term "protein" refers to a complex, wherein the complex refers to a homomer.

The term "fusion protein" as used herein refers to an expression product resulting from the fusion of different nucleic acid sequences. Such a protein may be produced, e.g., in recombinant DNA expression systems. Moreover, the term "fusion protein" as used herein refers to a fusion of a first amino acid sequence having an enzymatic activity, e.g. an endolysin, with a second and a third amino acid sequence. The second amino acid sequence is preferably a peptide stretch, in particular selected from the group consisting of cationic, polycationic, hydrophobic, amphipathic peptides, and antimicrobial peptides. A third amino acid sequence is a protein transduction domain. Preferably, said second and third amino acid sequence is foreign to and not substantially homologous with any domain of the first amino acid sequence. Moreover, the fusion proteins of the present invention also refer to an expression product resulting from the fusion of at least three nucleic acid sequences.

The term "peptide stretch" as used herein refers to any kind of peptide linked to a protein such as an endolysin. In particular the term "peptide stretch" as used herein refers to a peptide stretch selected from the group consisting of cationic, polycationic, hydrophobic, amphipathic peptides, and antimicrobial peptides (AMP), in particular synthetic amphipathic peptide, synthetic cationic peptide, synthetic polycationic peptide, synthetic hydrophobic peptide, synthetic antimicrobial peptide (AMP) or naturally occurring AMP. In the context of the present invention, AMP are understood as peptides, which provide antimycobacterial activity.

However, a peptide stretch in the meaning of the present invention does not refer to His-tags, preferably $His_5$-tags, $His_6$-tags, $His_7$-tags, $His_8$-tags, $His_9$-tags, $His_{10}$-tags, $His_{11}$-tags, $His_{12}$-tags, $His_{16}$-tags and $His_{20}$-tags, Strep-tags, Avitags, Myc-tags, Gst-tags, JS-tags, cystein-tags, FLAG-tags or other tags known in the art, thioredoxin or maltose binding proteins (MBP). The term "tag" in contrast to the term "peptide stretch" as used herein refers to a peptide which can be useful to facilitate expression and/or affinity purification of a polypeptide, to immobilize a polypeptide to a surface or to serve as a marker or a label moiety for detection of a polypeptide e.g. by antibody binding in different ELISA assay formats as long as the function making the tag useful for one of the above listed facilitation is not caused by the positively charge of said peptide. However, the $His_6$-tag may, depending on the respective pH, also be positively charged, but is used as affinity purification tool as it binds to immobilized divalent cations and is not used as a peptide stretch according to the present invention.

The term "peptide" as used herein refers to short polypeptides consisting of from about 2 to about 100 amino acid residues, more preferably from about 4 to about 50 amino acid residues, more preferably from about 5 to about 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). Preferred naturally occurring peptides are e.g. antimicrobial peptides and defensins. Preferred synthetically produced peptides are e.g. polycationic, amphipathic or hydrophobic peptides. A peptide in the meaning of the present invention does not refer to His-tags, Strep-tags, thioredoxin or maltose binding proteins (MBP) or the like, which are used to purify or locate proteins.

The term "enzymatic activity" as used herein refers to the effect exerted by one or more enzyme(s) or enzyme like substance(s). An enzymatic activity refers in particular to the effects which are exerted by endolysins. The term "enzymatic activity" refers further in particular to the effect of distinct group of enzyme or enzymatic substances which are having the activity of degrading the cell wall of a *Mycobacterium species*. A group of these enzymes with this distinct characteristics are named as Lysin A (LysA), of the peptidoglycan-cleavage group, which are known or are proposed to cleave (Payne and Hatfull, Plos ONE, 7(3), 2012; Payne et al., Mol Microbiol, 73(3), 2009):

N-acetyl-b-D-muramidase (lysozyme, lytic transglycosylase);
N-acetyl-b-D-glucosaminidase;
N-acetylmuramoyl-L-alanine amidase;
L-alanoyl-D-glutamate (LD) endopeptidase;
c-D-glutamyl-meso-diaminopimelic acid (DL) peptidase;
D-Ala-m-DAP (DD) endopeptidase; and
m-DAP-m-DAP (LD) endopeptidase.

A further group of enzymes are named as Lysin B (LysB). These enzymes hydrolyze the linkage of the mycolic acids to the peptidoglycan-arabinogalactan complex and comprise at least the following or other lipolytic activities:
Esterase (mycolarabinogalactanesterase)
Cutinase
α/β hydrolase LysB like proteins are described e.g. in *Mycobacteriophage Lysin B is a novel mycolylarabinogalactan esterase* Kimberly Payne, Qingan Sun, James Sacchettini, Graham F. Hatfull *Mol Microbiol.* 2009 August; 73(3): 367-381; *Mycobacteriophage Ms6 LysB specifically targets the outer membrane of Mycobacterium smegmatis* Filipa Gil, Anna E. Grzegorzewicz, Maria João Catalão, João Vital, Michael R. McNeil, Madalena Pimentel *Microbiology.* 2010 May; 156 (Pt 5): 1497-1504.

A person skilled in the art is able to identify an enzymatic activity as mentioned above with applying a suitable test setting for the distinct enzyme or enzymatic activity.

The term "endolysin" as used herein refers to an enzyme which is a peptidoglycan hydrolase naturally encoded by bacteriophages or bacterial viruses and which is suitable to hydrolyse bacterial cell walls. According to the present invention "endolysins" may derive from mycobacteriophages. Thus, "endolysins" are in particular enzymes such as Lysin A, LysA, or Lysin A like enzymes or Lysin B, LysB, or Lys B like enzymes. "Endolysins" comprise at least one "enzymatically active domain" (EAD) having at least one or more of the following activities: N-acetyl-b-D-muramidase (lysozyme, lytic transglycosylase), N-acetyl-b-D-glucosaminidase, N-acetyl-muramoyl-L-alanine-amidase (amidase) peptidase, L-alanoyl-D-glutamate (LD) endopeptidase, L-alanyl-D-isoglutaminyl-meso-diaminopimelic acid (D-Ala-m-DAP) (DD) endopeptidase, or m-DAP-m-DAP (LD) endopeptidase. Furthermore, the EAD is having at least one or more of the following activities: lipolytic activity, cutinase, mycolarabinogalactanesterase, or alpha/beta hydrolase. In addition, the endolysins may contain also regions which are enzymatically inactive, and bind to the cell wall of the host bacteria, the so-called CBDs (cell wall binding domains). The endolysin may contain two or more CBDs. Generally, the cell wall binding domain is able to bind different components on the surface of bacteria. Preferably, the cell wall binding domain is a peptidoglycan binding domain and binds to the bacteria's peptidoglycan structure. The different domains of an endolysin can be connected by a domain linker.

The term "domain linker" as used herein refers to an amino acid sequence functioning to connect single protein domains with one another. As a rule domain linkers form no or only few regular secondary structure like α-helices or β-sheets and can occupy different conformations with the respective structural context. Methods to detect domain linker and properties of linker sequences are well known in the art as e.g. described in Bae et al., 2005, Bioinformatics, 21, 2264-2270 or George & Heringa, 2003, Protein Engineering, 15, 871-879.

The term "protein transduction domain" (PTD) or the term "cell penetrating peptides" (CPP) refers to an amino acid sequence functioning to deliver a cargo from the extracellular to the intracellular space of a cell. This transportation involves a three step process, including first, binding of the PTD to the cellular membrane; second, stimulation of cellular uptake by endocytosis; and third, escape of cargo into the cytoplasm (Van den Berg and Dowdy, Current Opinion in Biotechnology, 22, 2011). PTDs may be cationic. The term "cargo" in the context of the present invention refers to a substance which is transported from the outside to the inside of a cell. The term "cargo" in the context of the present invention refers in particular to peptides, such as AMPs, enzymes, such as endolysins, dyes, such as fluorescent dyes like fluorescein. A person skilled in the art is able to identify amino acid sequences which are PTDs e.g. in form of an experimental setting wherein it is foreseen to use an amino acid sequence which is supposed to be a PTD together with a dye, such as a fluorescent dye, as a cargo. Using e.g. fluorescent microscopy or Fluorescent-activated cell sorting (FACS) analysis, allows assessing whether the putative PTD is able to deliver the fluorescent dye into the inside of a cell or not. PTD in combination with fluorescein as cargo are describe in Van den Berg and Dowdy, Curr Opin Biotech, 22, 2011 and in more detail in Vives at el., J Biol Chem, 272, 1997.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The term "cell wall" as used herein refers to all components that form the outer cell enclosure in particular of a Mycobacterium and thus guarantee their integrity. In particular, the term "cell wall" as used herein refers to in particular to the arabinogalactan layer and the mycolic acid layer of Mycobacteria, but also to membranes or additional layers deposited or attached to the mycolic acid layer, such as capsule-like material, outer protein layer or slimes.

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module. The term "EAD" is used herein synonymously with the term "catalytic domain".

As used herein, the term "cationic peptide" refers to a synthetic peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides.

The term "polycationic peptide" as used herein refers to a synthetically produced peptide composed of mostly positively charged amino acid residues, in particular lysine and/or arginine residues. A peptide is composed of mostly positively charged amino acid residues of at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term "antimicrobial peptide" (AMP) as used herein refers to any naturally occurring peptide that has microbicidal and/or microbistatic activity in particular against a *Mycobacterium species*. Thus, the term "antimicrobial peptide" as used herein relates in particular to any peptide having antibacterial, anti-infectious, anti-infective and/or germicidal, microbicidal, or bactericidal properties.

The antimicrobial peptide may be a member of the RNAse A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human.

The term "amphiphatic peptide" as used herein refers to synthetic peptides having both hydrophilic and hydrophobic functional groups. Preferably, the term "amphiphatic peptide" as used herein refers to a peptide having a defined arrangement of hydrophilic and hydrophobic groups e.g. amphipathic peptides may be e.g. alpha helical, having predominantly non polar side chains along one side of the helix and polar residues along the remainder of its surface.

The term "hydrophobic group" as used herein refers to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a nonaqueous environment. Examples of amino acid residues with hydrophobic side chains are valine, isoleucine, leucine, methionine, phenylalanine, tryptophan, cysteine, alanine, tyrosine, histidine, threonin, serine, proline and glycine residues.

The term "autolysins" refers to enzymes related to endolysins but encoded by bacteria and involved in e.g. cell division. An overview of autolysins is can be found in "Bacterial peptidoglycan (murein) hydrolases. Vollmer W, Joris B, Charlier P, Foster S. FEMS Microbiol Rev. 2008 March; 32(2):259-86".

The term "bacteriocin" as used herein refers to protein-like, polypeptide-like or peptide-like substances which are able to inhibit the growth of other bacteria. Some bacteriocins are capable of degrading bacterial cell walls like Lysostaphin (degrading *Staphylococcus* cell walls), Mutanolysin (degrading *Streptococcus* cell walls) and Enterolysin (degrading *Enterococcus* cell walls). Preferably said growth inhibition is specifically by means of absorption of said other bacteria to specific receptors of the bacteriocin. A further group of bacteriocins are Nisin-like peptides (Gene encoded antimicrobial peptides, a template for the design of novel anti-mycobacterial drugs. Carroll J, Field D, O'Connor P M, Cotter P D, Coffey A, Hill C, Ross R P, O'Mahony J. Bioeng Bugs. 2010 November-December; 1(6):408-12). In general, bacteriocins are produced by microorganisms. However, the term "bacteriocin" as used herein refers both to an isolated form produced by a microorganism or to a synthetically produced form, and refers also to variants which substantially retain the activities of their parent bacteriocins, but whose sequences have been altered by insertion or deletion of one or more amino acid residues.

The present invention relates to a composition having the activity of degrading the cell wall of a *Mycobacterium species* comprising: (a) a first fusion protein including (i) a first endolysin or a first domain, both having a first enzymatic activity, the enzymatic activity being at least one or more of the following: N-acetyl-b-D-muramidase (lysozyme, lytic transglycosylase), N-acetyl-b-D-glucosaminidase, N-acetylmuramoyl-L-alanine amidase, L-alanoyl-D-glutamate (LD) endopeptidase, c-D-glutamyl-meso-diaminopimelic acid (DL) peptidase, L-alanyl-D-iso-glutaminyl-meso-diaminopimelic acid (D-Ala-m-DAP) (DD) endopeptidase, or m-DAP-m-DAP (LD) endopeptidase, (ii) at least one peptide stretch fused to the N- or C-terminus of the endolysin having the first enzymatic activity or the domain having the first enzymatic activity, wherein the peptide stretch is selected from the group consisting of synthetic amphipathic peptide, synthetic cationic peptide, synthetic polycationic peptide, synthetic hydrophobic peptide, synthetic antimicrobial peptide (AMP) or naturally occurring AMP; and (iii) a protein transduction domain (PTD) being at the N- or C-terminus of the first fusion protein, wherein the PTD is having the characteristic to deliver a cargo from the extracellular to the intracellular space of a cell; and (b) a second fusion protein including (i) a second endolysin or a second domain, both having a second enzymatic activity, the enzymatic activity being at least one or more of the following: lipolytic activity, cutinase, mycolarabinogalactanesterase, or alpha/beta hydrolase; (ii) at least one peptide stretch fused to the N- or C-terminus of the endolysin having a second enzymatic activity or the domain having the second enzymatic activity, wherein the peptide stretch is selected from the group consisting of synthetic amphipathic peptide, synthetic cationic peptide, synthetic polycationic peptide, synthetic hydrophobic peptide, synthetic antimicrobial peptide (AMP) or naturally occurring AMP; and (iii) a protein transduction domain (PTD) being at the N- or C-terminus of the second fusion protein, wherein the PTD is having the characteristic to deliver a cargo from the extracellular to the intracellular space of a cell, for use as diagnostic agent.

In the context of mycobacteria infection, it is known that mycobacteria may be present inside of cells, such as macrophages. Therefore, there are some difficulties to reach mycobacteria which reside intracellularly and which are thus not directly accessible. Therefore, according to the present invention the PTD functions to deliver the first and second fusion protein of the present invention inside of a cell, such as preferably eukaryotic cells, e.g. macrophages.

In the context of mycobacteria infection, the function of a PTD according to the present invention is preferably determined according to the following: cells infected with mycobacteria are contacted with the compositions of first and second fusion proteins of the present invention. The PTD delivers the first and second fusion protein of the composition of the invention inside of the infected cell. The function of the PTD can then be shown by assessing the intracellular survival of the mycobacteria. Preferably this intracellular survival of the mycobacteria is assessed by lysing of the infected cells, such as infected eukaryotic cells, e.g. macrophages, which have been contacted with a composition of first and second fusion protein of the present invention, and e.g. plating of serial dilutions of the lysed cells on agar plates. Colonies of mycobacteria which have been detected with the compositions of the present invention, and are grown on the agar plate can be enumerated after a distinct incubation period. Accordingly, a person skilled in the art is able to determine the function of the PTD of the first and second fusion protein of the present invention by determining the intracellular detection of mycobacteria. Distinct methods for the determination of the intracellular detection of mycobacteria are known to the person skilled in the art.

In particular, a person skilled in the art is able to identify amino acid sequences which are PTDs e.g. in form of an experimental setting wherein it is foreseen to use an amino acid sequence which is supposed to be a PTD together with a dye, such as a fluorescent dye, as a cargo. Using e.g. fluorescent microscopy or Fluorescent-activated cell sorting (FACS) analysis, allows assessing whether the putative PTD is able to deliver the fluorescent dye into the inside of a cell or not. PTD in combination with fluorescein as cargo are describe in Van den Berg and Dowdy, Curr Opin Biotech, 22, 2011 and in more detail in Vives at el., J Biol Chem, 272, 1997.

According to the invention, a functionally effective PTD in the first and second fusion protein of the composition of the present invention is given if a distinct amount of the first and second fusion protein is intracellularly present. A skilled person is aware how to measure the intracellular amount the first and second fusion protein, in a preferred embodiment in form of measuring of the first and second fusion protein together with a target, such as a dye, e.g. fluorescent dye, or enzyme product, such as in a luciferase assay.

Accordingly, the present invention relates to a composition comprising two distinct fusion proteins which include distinct enzymatic activities combined with a peptide stretch and a protein transduction domain. This distinct combination of a first and a second fusion protein, wherein the first and the second fusion protein include each a first and a second enzymatic activity, a peptide stretch and the PTD, in a composition according to the present invention is advantageous. The composition according to the present invention provides the distinct advantage that the combination of two fusion proteins exert a strong activity in respect of the degradation of the cell wall of *Mycobacteria species*. Moreover, due to the presence of the PTD in each of the both fusion proteins, the structure of the outer cell membrane can be more easily overcome with the present invention. This is in particular of importance in the case that the mycobacteria are surviving inside of a host cell, such as in a human macrophage. Therefore, the composition of the present invention is beneficial advantages to target mycobacteria also inside of a cell. This allows the detection and diagnosis also of latent stages of infection with mycobacteria.

In a preferred embodiment of the composition of the present invention the first endolysin is Lysin A (LysA) or the first enzymatic activity of the first domain is exerted by Lysin A (LysA) or Lysin A like enzymes and the second endolysin is Lysin B (LysB) or the second enzymatic activity of the second domain is exerted by Lysin B (LysB) or Lysin B like enzymes.

Examples for the first and second endolysins or the first and second enzymatic activity of the first and second domain are listed in the following table 1.

TABLE 1

| Mycobacteriophage | endolysin/domain | type of endolysin or domain | amino acid sequence | nucleic acid sequence |
|---|---|---|---|---|
| TM4 | TM4gp29 | Lysin A | SEQ ID NO: 1 | SEQ ID NO: 2 |
| Bxz2 | Bxz2gp11 | Lysin A | SEQ ID NO: 3 | SEQ ID NO: 4 |
| D29 | D29gp10 | Lysin A | SEQ ID NO: 5 | SEQ ID NO: 6 |
| L5 | L5gp10 | Lysin A | SEQ ID NO: 7 | SEQ ID NO: 8 |
| TM4 | TM4gp30 | Lysin B | SEQ ID NO: 9 | SEQ ID NO: 10 |
| Bxz2 | Bxz2gp12 | Lysin B | SEQ ID NO: 11 | SEQ ID NO: 12 |
| D29 | D29gp12 | Lysin B | SEQ ID NO: 13 | SEQ ID NO: 14 |
| L5 | L5gp12 | Lysin B | SEQ ID NO: 15 | SEQ ID NO: 16 |

In a preferred embodiment the first and the second enzymatic activity of the first and second fusion protein of the composition is exerted by enzymes derived from mycobacteriophages selected from the group consisting of TM4, D29, L5, and Bxz2.

In a further preferred embodiment the peptide stretch of the first and second fusion protein of the composition of the present invention comprises an antimicrobial peptide (AMP), the AMP being selected from the group consisting of Cathelicidins (hCAP-18/LL37), alpha defensins, beta defensins, hepcidin, NK-2, and Ci-MAM-A24.

Examples for antimicrobial peptides according to the present invention are listed in the following table 2.

TABLE 2

| Peptid | amino acid sequence | nucleic acid sequence |
|---|---|---|
| LL-37 | LLGDFFRKSKEKIGKEFKRIVQRIKDFLRNLVP RTES SEQ ID NO: 17 | SEQ ID NO: 18 |
| alpha-defensin | DCYCRIPACIAGERRYGTCIYQGRLWAFCC SEQ ID NO: 19 | SEQ ID NO: 20 |
| beta-defensin | NPVSCVRNKGICVPIRCPGSMKQIGTCVGRAV KCCRKK SEQ ID NO: 21 | SEQ ID NO: 22 |
| Hepcidin | DTHFPICIFCCGCCHRSKCGMCCKT SEQ ID NO: 23 | SEQ ID NO: 24 |

TABLE 2-continued

| Peptid | amino acid sequence | nucleic acid sequence |
|---|---|---|
| NK-2 | KILRGVCKKIMRTFLRRISKDILTGKK; SEQ ID NO: 25 | SEQ ID NO: 26 |
| Ci-MAM-A24 | WRSLGRTLLRLSHALKPLARRSGW SEQ ID NO: 27 | SEQ ID NO: 28 |

In a preferred embodiment the PTD of the first and second fusion protein of the composition of the present invention is selected from the group consisting of TAT48-60, TAT47-57, TAT47-55, PTD3, PolyArginine, CADY, PepFect6, RXR, Antennapedia, Kala Syn, M918, MAP, Penetratin, PTD5-Syn, Pvec, Poly Arg 8, TAT 48-60, Transportan, Transportan10, and TAT-9.

Examples for PTDs according to the present invention are listed in the following table 3.

TABLE 3

| PTD | amino acid sequence | SEQ ID NO |
|---|---|---|
| TAT48-60 Ref. 1 | GRKKRRQRRRPPQC | SEQ ID NO: 29 |
| TAT47-57 Ref. 1 | YGRKKRRQRRR | SEQ ID NO: 30 |
| TAT47-55 Ref. 1 | YGRKKRRQR | SEQ ID NO: 31 |
| PTD3 Ref. 1 | YARKARRQARR | SEQ ID NO: 32 |
| PolyArginine Ref. 1 | RRRRRRRRR | SEQ ID NO: 33 |
| CADY Ref. 1 | GLWRALWRLLRSLWRLLWRA | SEQ ID NO: 34 |
| PepFect6 Ref. 1 | AGYLLGKINLKALAALAKKIL | SEQ ID NO: 35 |
| RXR Ref. 1 | RXRRXRRXRRXRXB | SEQ ID NO: 36 |
| Antennapedia Ref. 2 | RQIKIWFQNRRMKWKK | SEQ ID NO: 37 |
| Kala Syn Ref. 3 | WEAKLAKALAKALAKHLAKALAKALKACEA | SEQ ID NO: 38 |
| M918 Ref. 4 | MVTVLFRRLRIRRASGPPRVRV | SEQ ID NO: 39 |
| MAP Ref. 5 | KLALKLALKALKAALKLA | SEQ ID NO: 40 |
| Penetratin Ref. 6 | RQIKIWFQNRRMKWKK | SEQ ID NO: 41 |
| PTD5-Syn Ref. 7 | RRQRRTSKLMKR | SEQ ID NO: 42 |
| Pvec Ref. 8 | LLIILRRRIRKQAHAHSK | SEQ ID NO: 43 |
| Poly Arg 8 Ref. 2 | RRRRRRRR | SEQ ID NO: 44 |
| TAT48-60 Ref. 9 | GRKKRRQRRRPPQ | SEQ ID NO: 45 |
| Transportan Ref. 10 | GWTLNSAGYLLGKINLKALAALAKKIL | SEQ ID NO: 46 |
| Transportan10 Ref. 11 | AGYLLGKINLKALAALAKKIL | SEQ ID NO: 47 |
| TAT-9 Ref. 9 | RKKRRQRRR | SEQ ID NO: 48 |

The PTDs are disclosed in the following references:
1. Van den Berg and Dowdy, Curr Opin Biotech, 22, 2011. 2. Kabouridis, P. S. Biological applications of protein transduction technology. *Trends Biotechnol.* 21, 498-503 (2003). 3. MM, S. H. et al. Gene delivery using a derivative of the protein transduction domain peptide, K-Antp. Biomaterials. 31, 1858-1864 (2010). 4. El-Andaloussi, S., Johansson, H. J., Holm, T., & Langel, U. A novel cell-penetrating peptide, M918, for efficient delivery of proteins and peptide nucleic acids. Mol. Ther. 15, 1820-1826 (2007). 5. Saar, K. et al. Cell-penetrating peptides: a comparative membrane toxicity study. Anal. Biochem. 345, 55-65 (2005). 6. Splith, K. & Neundorf, I. Antimicrobial peptides with cell-penetrating peptide properties and vice versa. Eur. Biophys. J. (2011). 7. Mi, Z. et al. Identification of a synovial fibroblast-specific protein transduction domain for delivery of apoptotic agents to hyperplastic synovium. Mol. Ther. 8, 295-305 (2003). 8. Herbig, M. E. et al. Bilayer interaction and localization of cell penetrating peptides with model membranes: a comparative study of a human calcitonin (hCT)-derived peptide with pVEC and pAntp(43-58). Biochim Biophys. Acta. 1712, 197-211 (2005). 9. Eguchi, A. et al. Protein transduction domain of HIV-1 Tat protein promotes efficient delivery of DNA into mammalian cells. J. Biol. Chem. 276, 26204-26210 (2001). 10. Jones, S. W. et al. Characterisation of cell-penetrating peptide-mediated peptide delivery. Br. J. Pharmacol. 145, 1093-1102 (2005). 11. Fisher, L. et al. Cellular delivery of a double-stranded oligonucleotide NFkappaB decoy by hybridization to complementary PNA linked to a cell-penetrating peptide. Gene Ther. 11, 1264-1272 (2004).

In a particular preferred embodiment of the composition of the present invention, the first fusion protein is exhibiting an amino acid sequence selected from the group consisting SEQ ID NO:49, 51, 53, 55, 57, 59, 61, 77, 79, 81, 89, 81, 93, 95, 97, 99, 113, and 115, and the second fusion protein is exhibiting an amino acid sequence selected from the group consisting SEQ ID NO:63, 65, 67, 69, 71, 73, 75, 83, 85, 87, 101, 103, 105, 107, 109, 111, and 117.

Specific examples of fusion proteins according to the present invention are listed in the following table.

TABLE 4

| | amino acid sequence | nucleic acid sequence |
|---|---|---|
| First fusion protein | | |
| TM4gp29/LL-37/TAT47-57 | SEQ ID NO: 49 | SEQ ID NO: 50 |
| TM4gp29/LL-37/TAT47-57 | SEQ ID NO: 51 | SEQ ID NO: 52 |
| Bzx2gp11/alpha-defensin/PTD3 | SEQ ID NO: 53 | SEQ ID NO: 54 |
| PTD3/alpha-defensin/Bzx2gp11 | SEQ ID NO: 55 | SEQ ID NO: 56 |
| PTD3/alpha-defensin/Bzx2gp11/alpha-defensin | SEQ ID NO: 57 | SEQ ID NO: 58 |
| beta-defensin/L5gp10/TAT47-57 | SEQ ID NO: 59 | SEQ ID NO: 60 |
| alpha-defensin/Hepcidin/L5gp10/TAT47-57 | SEQ ID NO: 61 | SEQ ID NO: 62 |
| TM4gp29/LL-37/TAT47-57 | SEQ ID NO: 77 | SEQ ID NO: 78 |
| TM4gp29/LL-37/TAT47-57 | SEQ ID NO: 79 | SEQ ID NO: 80 |
| Bzx2gp11/alpha-defensin/PTD3 | SEQ ID NO: 81 | SEQ ID NO: 82 |
| TM4gp29/LL-37/TAT47-57 | SEQ ID NO: 89 | SEQ ID NO: 90 |
| Bzx2gp11/alpha-defensin/PTD3 | SEQ ID NO: 91 | SEQ ID NO: 92 |
| PTD3/alpha-defensin/Bzx2gp11 | SEQ ID NO: 93 | SEQ ID NO: 94 |
| PTD3/alpha-defensin/Bzx2gp11/alpha-defensin | SEQ ID NO: 95 | SEQ ID NO: 96 |
| beta-defensin/L5gp10/TAT47-57 | SEQ ID NO: 97 | SEQ ID NO: 98 |
| alpha-defensin/Hepcidin/L5gp10/TAT47-57 | SEQ ID NO: 99 | SEQ ID NO: 100 |
| TM4gp29/LL-37/TAT47-57 | SEQ ID NO: 113 | SEQ ID NO: 114 |
| PTD3/alpha-defensin/Bzx2gp11 | SEQ ID NO: 115 | SEQ ID NO: 116 |
| Second fusion protein | | |
| TM4gp30/LL-37/TAT47-57 | SEQ ID NO: 63 | SEQ ID NO: 64 |
| TM4gp30/LL-37/TAT47-57 | SEQ ID NO: 65 | SEQ ID NO: 66 |
| D29gp12/alpha-defensin/PTD3 | SEQ ID NO: 67 | SEQ ID NO: 68 |
| PTD3/alpha-defensin/D29gp12 | SEQ ID NO: 69 | SEQ ID NO: 70 |
| PTD3/alpha-defensin/D29gp12/alpha-defensin | SEQ ID NO: 71 | SEQ ID NO: 72 |
| beta-defensin/D29gp12/TAT47-57 | SEQ ID NO: 73 | SEQ ID NO: 74 |
| beta-defensin/Hepcidin/L5gp12/TAT47-57 | SEQ ID NO: 75 | SEQ ID NO: 76 |
| TM4gp30/LL-37/TAT47-57 | SEQ ID NO: 83 | SEQ ID NO: 84 |
| TM4gp30/LL-37/TAT47-57 | SEQ ID NO: 85 | SEQ ID NO: 86 |
| D29gp12/alpha-defensin/PTD3 | SEQ ID NO: 87 | SEQ ID NO: 88 |
| TM4gp30/LL-37/TAT47-57 | SEQ ID NO: 101 | SEQ ID NO: 102 |
| D29gp12/alpha-defensin/PTD3 | SEQ ID NO: 103 | SEQ ID NO: 104 |
| PTD3/alpha-defensin/D29gp12 | SEQ ID NO: 105 | SEQ ID NO: 106 |
| PTD3/alpha-defensin/D29gp12/alpha-defensin | SEQ ID NO: 107 | SEQ ID NO: 108 |
| beta-defensin/D29gp12/TAT47-57 | SEQ ID NO: 109 | SEQ ID NO: 110 |
| beta-defensin/Hepcidin/L5gp12/TAT47-57 | SEQ ID NO: 111 | SEQ ID NO: 112 |
| beta-defensin/D29gp12/TAT47-57 | SEQ ID NO: 117 | SEQ ID NO: 118 |

In a preferred embodiment of the present invention the first and/or second fusion protein of the composition further exhibits an affinity tag or a spacer molecule, optionally having an affinity tag or a biotin.

In a further preferred embodiment of the present invention the affinity tag of the fusion protein is a His-Tag, Strep-Tag, Avi-Tag, or a biotinylation domain.

In a further preferred embodiment of the present invention the spacer molecule is GFP, MBP or a biotinylation domain.

In a further preferred embodiment the composition of the present invention is having activity of degrading the cell wall of a *Mycobacterium species* which is selected from the group consisting of *Mycobacterium tuberculosis*, *Mycobacterium microti*, *Mycobacterium africanum*, *Mycobacterium bovis*, *Mycobacterium canettii*, *Mycobacterium pinnipedii*, *Mycobacterium caprae*, *Mycobacterium mungi*, *Mycobacterium leprae*, *Mycobacterium ulcerans*, *Mycobacterium xenopi*, *Mycobacterium shottsii*, *Mycobacterium avium*, *Mycobacterium avium* subsp. *paratuberculosis*, *Mycobacterium paratuberculosis*, *Mycobacterium intracellulare*, *Mycobacterium smegmatis*, *Mycobacterium abscessus*, *Mycobacterium kansasii*, *Mycobacterium terrae*, *Mycobacterium nonchromogenicum*, *Mycobacterium gordonae*, and *Mycobacterium triviale*.

In a preferred embodiment of the composition of the present invention, the domain with the first enzymatic activity of the first fusion protein exhibits an amino acid sequence selected from the group consisting of SEQ ID NO:1, 3, 5, and 7, wherein the domain with the second enzymatic activity of the second fusion protein exhibits an amino acid sequence selected from the group consisting SEQ ID NO:9, 11, 13, and 15, wherein the peptide stretch of the first and second fusion protein exhibits an amino acid sequence selected from the group consisting SEQ ID NO:17, 19, 21, 23, 25, and 27, and wherein the PTD exhibits an amino acid sequence selected from the group consisting SEQ ID NO:29, 30, 31, 32, 33, 34, 35, 36, 37, 38, 39, 40, 41, 42, 43, 44, 45, 46, 47, and 48.

In a particular preferred embodiment of the composition of the present invention, the first fusion protein is exhibiting an amino acid sequence selected from the group consisting SEQ ID NO:49, 51, 53, 55, 57, 59, 61, 77, 79, 81, 89, 81, 93, 95, 97, 99, 113, and 115, and the second fusion protein is exhibiting an amino acid sequence selected from the group consisting SEQ ID NO:63, 65, 67, 69, 71, 73, 75, 83, 85, 87, 101, 103, 105, 107, 109, 111, and 117.

In another preferred embodiment of the present invention the enzymes, such as endolysins, autolysins and bacteriocins of the first and second fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, SH- or carboxyl-groups. Said endolysins, autolysins and bacteriocins of the fusion protein according to the present invention exhibit the lytic activity of the respective wild-type endolysin, autolysin and bacteriocin. However, said activity can be the same, higher or lower as the activity of the respective wild-type endolysin, autolysin and bacteriocin. Said activity can be about 10, 20, 30, 40, 50, 60, 70, 80, 90, 100, 110, 120, 130, 140, 150, 160, 170, 180, 190 or about 200% of the activity of the respective wild-type endolysin, autolysin and bacteriocin or even more. The activity can be measured by assays well known in the art by a person skilled in the art as e.g. the plate lysis assay or the liquid lysis assay which are e.g. described in Briers et al., *J. Biochem. Biophys Methods* 70: 531-533, (2007), Donovan D M, Lardeo M, Foster-Frey J. *FEMS Microbiol Lett.* 2006 December; 265(1), Payne K M, Hatfull G F *PLoS One*, 2012.

The peptide stretch and the PTD of the fusion proteins according to the present invention may be linked to the endolysin or the domain having an enzymatic activity by additional amino acid residues e.g. due to cloning reasons. Preferably, said additional amino acid residues may be not recognized and/or cleaved by proteases. Preferably the peptide stretch and the PTD may be linked to the endolysin or the domain having an enzymatic activity by at least 1, 2, 3, 4, 5, 6, 7, 8, 9 or 10 additional amino acid residues. In a preferred embodiment the peptide stretch is fused to the N- or C-terminus of the endolysin or the domain having an enzymatic activity by the additional amino acid residues glycine, serine, and alanine (Gly-Ser-Ala). Moreover, the PTD is located on the N-terminus or on the C-Terminus of the first fusion protein or of the second fusion protein according to the invention.

The PTD may further comprise additional amino acids on its N- or C-terminus. Preferably the peptide stretch or the PTD comprise the amino acid methionine (Met), or methionine, glycine and serine (Met-Gly-Ser). In another preferred embodiment the first peptide stretch is linked to the N-terminus of the enzyme by the additional amino acid residues, in particular glycine and serine (Gly-Ser) and the second peptide stretch is linked to the N-terminus of the first peptide stretch by the additional amino acid residues, in particular glycine and serine (Gly-Ser). In another preferred embodiment the first peptide stretch is linked to the C-terminus of the enzyme by the additional amino acid residues, in particular glycine and serine (Gly-Ser) and the second peptide stretch is linked to the C-terminus of the first peptide stretch by the additional amino acid residues, in particular glycine and serine (Gly-Ser).

Within the first and second fusion protein according to the present invention the peptide stretch and the PTD are preferably covalently bound to the endolysin or to the domain, both having enzymatic activity. Preferably, the peptide stretch and the PTD consist of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred are peptide stretches and PTDs comprising about 5 to about 100 amino acid residues, about 5 to about 50 or about 5 to about 30 amino acid residues. More preferred are peptide stretches and PTDs comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

Preferably, the peptide stretches and the PTDs are no tag such as a His-tag, Strep-tag, Avi-tag, Myc-tag, Gst-tag, JS-tag, cystein-tag, FLAG-tag or other tags known in the art and no thioredoxin or maltose binding proteins (MBP). However, the first and second fusion protein according to the present invention may comprise in addition such tag or tags.

More preferably the peptide stretches and in particular the PTDs have the function to lead the first and second fusion protein of the composition of the present invention through the outer membrane but may have activity or may have no or only low activity when administered without being fused to the endolysin or the domain, both having enzymatic activity. The function to lead the first and second fusion protein through the outer membrane of mycobacteria is caused by the potential of the outer membrane or mycolic acid/arabinogalactan disrupting or permeabilising or destabilizing activity of said peptide stretches in combination with the PTDs and the endolysins or the domains. Such outer membrane or LPS disrupting or permeabilising or destabilizing activity of the peptide stretches may be determined in a method as follows: The bacteria cells to be treated are cultured in liquid medium or on agar plates. Then the bacteria cell concentration in the liquid medium is determined photometrically at OD600 nm or the colonies on the agar plates are counted, respectively. Now, the bacteria cells in liquid medium or on the plates are treated with a first and second fusion protein according to the invention. After incubation the bacteria cell concentration in the liquid medium is determined photometrically at OD600 nm or the colonies on the agar plates are counted again. If the first and second fusion protein exhibits such outer membrane or LPS disrupting or permeabilising or destabilizing activity, the bacteria cells are lysed due to the treatment with the fusion protein and thus, the bacteria cell concentration in the liquid medium or the number of the bacteria colonies on the agar plate is reduced. Thus, the reduction in bacteria cell concentration or in the number of bacteria colonies after treatment with the first and second fusion protein is indicative for an outer membrane or LPS disrupting or permeabilising or destabilizing activity of the first and second fusion protein.

Fusion proteins are constructed by linking at least three nucleic acid sequences using standard cloning techniques as described e.g. by Sambrook et al. 2001, Molecular Cloning: A Laboratory Manual. Such a protein may be produced, e.g., in recombinant DNA expression systems. Such fusion proteins according to the present invention can be obtained by fusing the nucleic acids for endolysin and the respective peptide stretches.

A further subject-matter of the present invention relates to an isolated nucleic acid molecule encoding the first fusion protein of the composition of to the present invention or to an isolated nucleic acid molecule encoding the second fusion protein of the composition of the present invention.

Preferably the isolated nucleic acid molecule encoding the first fusion protein of the composition of to the present invention is selected from the group consisting of SEQ ID NO:50, 52, 54, 56, 58, 60 and 62. Preferably the isolated nucleic acid molecule encoding the second fusion protein of the composition of to the present invention is selected from the group consisting of SEQ ID NO:64, 66, 68, 70, 72, 74, and 76.

The present invention further relates to a vector comprising a nucleic acid molecule according to the present invention. Said vector may provide for the constitutive or inducible expression of said fusion protein according to the present invention.

The invention also relates to a method for obtaining said first and second fusion protein of the composition of the present invention from a micro-organism, such as a genetically modified suitable host cell which expresses said fusion proteins. Said host cell may be a microorganism such as bacteria or yeast or an animal cell as e.g. a mammalian cell, in particular a human cell. In one embodiment of the present invention the host cell is a *Pichia pastoris* cell. The host may be selected due to mere biotechnological reasons, e.g. yield, solubility, costs, etc. but may be also selected from a medical point of view, e.g. a non-pathological bacteria or yeast, human cells.

Another subject-matter of the present invention relates to a method for genetically transforming a suitable host cell in order to obtain the expression of the first and second fusion protein of the composition according to the invention, wherein the host cell is genetically modified by the introduction of a genetic material encoding said fusion proteins into the host cell and obtain their translation and expression by genetic engineering methods well known by a person skilled in the art.

A further subject-matter of the present invention is a method for the detection of a *Mycobacterium species* in a sample, the method comprising the steps of: step a) incubating or contacting a sample with a composition comprising a first and a second fusion protein according to the present invention, the first and the second fusion protein being in solution, step b) detecting of the *Mycobacterium species*.

A further subject-matter of the present invention is a method for the detection of a *Mycobacterium species* in a sample, the method comprising the steps of: step a) incubating or contacting a sample with a composition comprising a first and a second fusion protein according to the present invention, the first and the second fusion protein being unspecifically or directedly immobilized to a solid carrier, step b) separating the carrier-fusion proteins-*Mycobacterium species*-complex from the sample, and step c) detecting of the *Mycobacterium* species.

In a preferred embodiment of the present invention the sample is treated with a cell cracking buffer before the conduction of step a) to facilitate step a).

The method according to the present invention is foreseen to be applied to detect a *Mycobacterium species*, in particular *Mycobacterium tuberculosis, Mycobacterium microti, Mycobacterium africanum, Mycobacterium bovis, Mycobacterium canettii, Mycobacterium pinnipedii, Mycobacterium caprae, Mycobacterium mungi, Mycobacterium leprae, Mycobacterium ulcerans, Mycobacterium xenopi, Mycobacterium shottsii, Mycobacterium avium, Mycobacterium avium* subsp. *paratuberculosis, Mycobacterium paratuberculosis, Mycobacterium intracellulare, Mycobacterium smegmatis, Mycobacterium abcessus, Mycobacterium kansasii, Mycobacterium terrae, Mycobacterium nonchromogenicum, Mycobacterium gordonae*, and *Mycobacterium triviale*.

It is foreseen that with the method for the detection according to the present invention it is possible to detect a *Mycobacterium species* not only in the case the mycobacteria is present outside of the infected cell but also in the case that the mycobacteria are present within the infected cell. Due to the presence of the protein transduction domain (PTD) it is possible to target and thereby detect the mycobacteria residing in infected host cells. In view of this it is possible to provide a method for detection of a *Mycobacteria species* which is able to differentiate between distinct infection stages, such as latent forms of the infection or active forms of the infection. In particular in the case of tuberculosis caused by *Mycobacterium tuberculosis* such a distinction is important to provide a reliable diagnosis which allows an efficient treatment of the infection.

In a preferred embodiment of the present invention the method is further comprising after step b) and before step c) the step b') washing away of sample components unspecifically adhering to the carrier-fusion proteins-*Mycobacterium species*-complex.

In a further preferred embodiment of the present invention the method for the detection is conducted such that the steps a) and b) are performed in a chromatography column flow through method.

In a preferred embodiment of the present invention the solid carrier is cellulose, filtration media, glass particles, magnet particles, centrifugation-, sedimentation-materials or filling materials for chromatography columns.

A further subject-matter of the present invention relates to a method for the detection of a *Mycobacterium species* in a sample, the method comprising the steps of: step a) incubating or contacting a sample with a composition comprising a first and a second fusion protein according to the present invention, step b) contacting and incubating of *Mycobacterium species*-fusion proteins-complex with a carrier, which is coated with the respective binding partner of the polypeptide or a chemical group, step c) separating the carrier-fusion proteins-*Mycobacterium species*-complex from the sample, and step d) detecting of the *Mycobacterium species*.

In a preferred embodiment of the present invention the sample is treated with a cell cracking buffer before conduction step a).

In a further preferred embodiment of the present invention, the method for the detection further comprises after step c) and before step d) the step c') washing away of sample components unspecifically adhering to the carrier-fusion proteins-*Mycobacterium species*-complex.

A further subject-matter of the present invention relates to a kit comprising a carrier immobilized with a composition comprising a first and a second fusion protein according to the present invention and washing buffer, detaching buffer and/or cell cracking buffer.

A further subject-matter of the present invention relates to a kit comprising a composition comprising a first and a second fusion protein, wherein the first and/or second fusion protein further exhibits an affinity tag or a spacer molecule, the kit further comprising a carrier coated with the respective binding partner of the affinity tag, the spacer molecule or the biotinylation domains, and washing buffer, detaching buffer and/or cell cracking buffer.

Further scope of applicability of the present invention will become apparent from the detailed description given hereinafter, however, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

EXAMPLE 1

Cloning, Expression and Purification of the Respective Proteins Modified with Various Peptide Stretches and Protein Transduction Domains at the N-Terminus or the C-Terminus Proteins TM4gp29 according to SEQ ID NO:1 is a Lys A-type endolysin originating from *Mycobacteria* phage TM4. The endolysin TM4gp29 is encoded by the nucleic acid molecule according to SEQ ID NO:2. The nucleic acid molecule according to SEQ ID NO:2 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

Bxz2gp11 according to SEQ ID NO:3 is a Lys A-type endolysin originating from *Mycobacteria* phage Bxz2. The endolysin Bxz2gp11 is encoded by the nucleic acid molecule according to SEQ ID NO:4. The nucleic acid molecule according to SEQ ID NO:4 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

D29gp10 according to SEQ ID NO:5 is a Lys A-type endolysin originating from *Mycobacteria* phage D29. The endolysin D29gp10 is encoded by the nucleic acid molecule according to SEQ ID NO:6. The nucleic acid molecule according to SEQ ID NO:6 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

L5gp10 according to SEQ ID NO:7 is a Lys A-type endolysin originating from Mycobacteria phage L5. The endolysin L5gp10 is encoded by the nucleic acid molecule according to SEQ ID NO:8. The nucleic acid molecule according to SEQ ID NO: 8 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

TM4gp30 according to SEQ ID NO: 9 is a Lys B-type endolysin originating from *Mycobacteria* phage TM4. The endolysin TM4gp30 is encoded by the nucleic acid molecule according to SEQ ID NO: 10. The nucleic acid molecule according to SEQ ID NO: 10 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

Bxz2gp12 according to SEQ ID NO: 11 is a Lys B-type endolysin originating from *Mycobacteria* phage Bxz2. The endolysin Bxz2gp12 is encoded by the nucleic acid molecule according to SEQ ID NO: 12. The nucleic acid molecule according to SEQ ID NO: 12 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

D29gp12 according to SEQ ID NO: 13 is a Lys B-type endolysin originating from *Mycobacteria* phage D29. The endolysin D29gp12 is encoded by the nucleic acid molecule according to SEQ ID NO:14. The nucleic acid molecule according to SEQ ID NO: 14 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

L5gp12 according to SEQ ID NO: 15 is a Lys B-type endolysin originating from *Mycobacteria* phage L5. The endolysin L5gp12 is encoded by the nucleic acid molecule according to SEQ ID NO: 16. The nucleic acid molecule according to SEQ ID NO: 16 was synthetically produced with a BamH I (5'-GGA TCC-3') restriction site at the 5'-end of the nucleic acid molecule and an Xho I (5'-CTC GAG-3') restriction site at the 3'-end of the nucleic acid molecule.

The following peptide stretches in table 5 were used for production of fusion proteins with the endolysins above:

TABLE 5

| Peptide stretch | amino acid sequence | nucleic acid sequence |
| --- | --- | --- |
| LL-37 | SEQ ID NO: 17 | SEQ ID NO: 18 |
| alpha-defensin | SEQ ID NO: 19 | SEQ ID NO: 20 |
| beta-defensin | SEQ ID NO: 21 | SEQ ID NO: 22 |
| Hepcidin | SEQ ID NO: 23 | SEQ ID NO: 24 |

The following protein transduction domains in table 6 were used for production of fusion proteins with the endolysins above:

TABLE 6

| PTD | amino acid sequence | SEQ ID NO |
| --- | --- | --- |
| TAT47-57 | YGRKKRRQRRR | SEQ ID NO: 30 |
| PTD3 | YARKARRQARR | SEQ ID NO: 32 |

The nucleic acid molecules encoding the respective peptide stretches and protein transduction domains were synthetically produced with a Nde I (5'-CAT ATG-3') restriction site at the 5'-end of the nucleic acid molecule and a BamH I (5'-GGA TCC-3') restriction site at the 3'-end of the nucleic acid molecule.

Fusion proteins are constructed by linking at least two nucleic acid sequences using standard cloning techniques as described e.g. by Sambrook et al. 2001, Molecular Cloning: A Laboratory Manual or by sequence extension by PCR with designed primers. Accordingly the nucleic acid molecules encoding the peptide stretches were cleaved in a restriction digestion with the respective restriction enzymes, whereas NdeI, necessary for the pert21b vector system, or NcoI, necessary for the pet32b vector system, was at the 5' end and XhoI was at the 3'-end of the nucleic acid molecules. If necessary the restriction sites of the 5'-end where changed by PCR reactions using primers designed for the restriction site exchange. Furthermore the lysin sequence was extended by a 6xHis-tag which was introduced, by PCR with designed primers, between the 3'end of the lysin sequence and the lysin 3'-end restriction site. Subsequently the cleaved nucleic acids encoding the proteins of interest were ligated into a modified pet21b expression vector, whereas two STOP-codons where introduced 5' of the vector-encoded 6xHis-tag (unmodified vector obtainable from Novagen, Darmstadt, Germany), or into a modified pet32b expression vector, whereas the sequence encoding the S-tag and the central 6xHis-tag was deleted (unmodified vector obtainable from Novagen, Darmstadt, Germany). The used expression vector was also cleaved in a digestion with the respective restriction enzymes, so NdeI and XhoI or NcoI and XhoI respectively, before.

Alternatively, the nucleic acid molecules encoding the peptides stretches were cleaved in a restriction digestion with the respective restriction enzymes Nde I and BamH I and in case of the nucleic acid molecule encoding the peptide stretch and PTD for ligation with the proteins the digestion was performed with the restriction enzymes Nco I and BamH I. Subsequently the cleaved nucleic acids encoding the peptide stretches were ligated into the pET21 b expression vector (Novagen, Darmstadt, Germany), which was also cleaved in a digestion with the respective restriction enzymes Nde I and BamH I before. The cleaved nucleic acid molecule encoding the peptide stretch and PTD for ligation with toxic proteins was ligated into a modified pET32 b expression vector (unmodified vector obtainable from Novagen, Darmstadt, Germany), which was also cleaved in a digestion with the respective restriction enzymes Nco I and BamH I before. The modification of the pET32b expression vector refers to the deletion of the sequence encoding an S-tag and the central His-tag.

Afterwards, the nucleic acid molecules encoding the proteins were cleaved in a digestion with the restriction enzyme BamH I and Xho I, so that the proteins could be ligated into the pET21b expression vector (Novagen, Darmstadt, Germany) and the modified pET32 b expression vector, respectively, which were also cleaved in a digest with the respective restriction enzymes BamH I and Xho I before.

In the case of the peptide stretch, which was introduced by PCR to the C-terminus of the proteins, the resulting fusion protein has a His-tag on the N-terminus, wherein the His-tag is linked to the N-terminus by a linker. For the cloning of the respective nucleic acid molecules the pET32 b expression vector (Novagen, Darmstadt, Germany) was used.

Thus, the nucleic acid molecule encoding the peptide stretch is ligated into the respective vector at the 5'-end of the nucleic acid molecule encoding the respective enzyme. Moreover, the nucleic acid molecule encoding the respective enzyme is ligated into the respective plasmid, so that a nucleic acid molecule encoding a His-tag consisting of six histidine residues is associated at the 3'-end of the nucleic acid molecule encoding the endolysin.

As some fusion proteins may either be toxic upon expression in bacteria, or not homogenous due to protein degradation, the strategy might be to express these fusion proteins fused or linked to other additional proteins. Example for these other additional protein is thioredoxin, which was shown to mediate expression of toxic antimicrobial peptides in *E. coli* (TrxA mediating fusion expression of antimicrobial peptide CM4 from multiple joined genes in *Escherichia coli*. Zhou L, Zhao Z, Li B, Cai Y, Zhang S. Protein Expr Purif. 2009 April; 64(2):225-230). In the case of the fusion proteins of the present invention, the peptide was ligated into the modified pET32 b expression vector, so that an additional thioredoxin is associated at the 5'-end of the peptide. The thioredoxin could be removed from the expressed fusion protein by the use of enterokinase, therefore between the nucleic acid molecule encoding the peptide and the nucleic acid molecule encoding the thioredoxin an enterokinase restriction site has been introduced.

The sequence of the fusion proteins of the present invention was controlled via DNA-sequencing and correct clones were transformed into *E. coli* BL21(DE3) or *E. coli* BL21 (DE3) pLysS (Novagen, Darmstadt, Germany) for protein expression.

Recombinant expression of the fusion proteins according to SEQ ID NO: 49, 51, 53, 55, 57, 59, 61, 63, 65, 67, 69, 71, 73, and 75 as well as the further fusion proteins of the present invention is performed in *E. coli* BL21 (DE3) cells or *E. coli* BL21 pLysS (DE3) cells (Novagen, Darmstadt, Germany). The cells were growing until an optical density of OD 600 nm of 0.4 to 0.6 was reached. Then the expression of the fusion protein was induced with 1 mM IPTG (isopropylthiogalactoside) and the expression was performed at 37° C. for a period of 4 hours, alternatively an overnight expression at 16° C. was performed.

*E. coli* BL21 cells were harvested by centrifugation for 20 min at 6000 g and disrupted via sonication on ice. Soluble and insoluble fraction of the *E. coli* crude extract were separated by centrifugation (Sorvall, SS34, 30 min, 15 000 rpm). All proteins were purified by $Ni^{2+}$ affinity chromatography (Aekta FPLC, GE Healthcare) using the 6xHis-tag, encoded by the protein sequence.

Toxic proteins were expressed using a modified pET32b vector (S-tag and central His-tag deleted), which fuses thioredoxin on the N-terminus of the proteins of interest. The vector also contains an enterokinase cleavage site right before the protein of interest. This site allows the proteolytic cleavage between thioredoxin and the protein of interest, which can purified via the remaining C-terminal His-tag. Expressed fusion proteins were not toxic to the host resulting in high yields of produced protein. For antimicrobial function of the fusion protein it was necessary to remove the thioredoxin by proteolytic cleavage. Therefore the fusion protein was cleaved with 8-10 units/mg recombinant enterokinase (Novagen, Darmstadt, Germany) to remove the thioredoxin following the protocol provided by the manufacturer, whereas a NaCl concentration of 400 mM was chosen to prevent the aggregation of the protein of interest. After enterokinase cleavage the fusion protein was purified via His-tag purification as described below.

The $Ni^{2+}$ affinity chromatography is performed in 4 subsequent steps, all at room temperature:
1. Equilibration of the Histrap FF 5 ml column (GE Healthcare) with up to 10 column volumes of Washing Buffer (500 mM to 1 M NaCl, 5% Glycerole and 40 mM Hepes on pH 7.4 or 50 mM Tris-HCl on pH 8.2) at a flow rate of 5 ml/min
2. Loading of the total lysate (with wanted fusion protein) on the Histrap FF 5 ml column at a flow rate of 5 ml/min. Washing of the column with Washing Buffer until the UV 280 nm signal drops below 10 mAU or 20 column volumes followed by a washing step with 4% Elution buffer (500 mM imidazole, 0.5 M NaCl, 5% glycerol and 40 mM Hepes on pH 7.4 or 50 mM Tris-HCl on pH 8.2) at a flow rate of 5 ml/min until the UV 280 nm signal drops below 5 mAU or 20 column volumes.
3. Elution of bounded fusion proteins from the column with a linear gradient of 15 column volumes of Elution Buffer (500 mM imidazole, 0.5 M NaCl, 5% glycerol and 40 mM Hepes on pH 7.4 and 50 mM Tris-HCl on pH 8.2) to 100% at a flow rate of 5 ml/min.

Purified stock solutions of fusion proteins in Elution Buffer (40 mM Hepes pH 7.4 or 50 mM Tris-HCl pH 8.2; 0.5 M NaCl; 500 mM imidazole; 5% glycerol) were at least 60-90% pure as determined visually on SDS-PAGE gels (data not shown).

Alternatively, the $Ni^{2+}$ affinity chromatography is performed in 4 subsequent steps, all at room temperature:
1. Equilibration of the Histrap FF 5 ml column (GE Healthcare) with up to 10 column volumes of Washing Buffer (20 mM imidazole, 1 M NaCl and 20 mM Hepes on pH 7.4) at a flow rate of 3-5 ml/min
2. Loading of the total lysate (with wanted fusion protein) on the Histrap FF 5 ml column at a flow rate of 3-5 ml/min.
3. Washing of the column with up to 10 column volumes of Washing Buffer to remove unbound sample followed by a second washing step with 10% Elution buffer (500 mM imidazole, 0.5 M NaCl and 20 mM Hepes on pH 7.4) at a flow rate of 3-5 ml/min
4. Elution of bounded fusion proteins from the column with a linear gradient of 4 column volumes of Elution Buffer (500 mM imidazole, 0.5 M NaCl and 20 mM Hepes on pH 7.4) to 100% at a flow rate of 3-5 ml/min.

Purified stock solutions of fusion proteins in Elution Buffer (20 mM Hepes pH 7.4; 0.5 M NaCl; 500 mM imidazole) were at least 90% pure as determined visually on SDS-PAGE gels (data not shown).

Lysin A like activity was controlled in a Chloroform assay. *Escherichia coli* BL21 transformed with the respective Lysin A variant were grown at 37° C. in LB broth supplemented with 100 mg/mL ampicillin to an OD600 nm of 0.5 and then induced with a final concentration of 1 mM IPTG. One hour after induction, 2% chloroform was added to the cell suspension and OD600 nm was monitored. Chloroform permeabilizes the inner membrane, thus replacing the holin function, and allows the putative lysin to reach its target in the peptidoglycan layer. The reduction in OD600 nm after addition of chloroform to 10 mL of induced clones was recorded.

Alternatively, the *Micrococcus lysodeikticus* Turbidity Reduction Assay has been used as Lysin A activity test. This assay has been adapted from Molecular Microbiology (2009) 71(6), 1509-1522: Structural basis for autoinhibition and activation of Auto, a virulence-associated peptidoglycan hydrolase of *Listeria monocytogenes*—Maike Bublitz, Lilia Polle, Christin Holland, Dirk W. Heinz, Manfred Nimtz and Wolf-Dieter Schubert. Accordingly, lyophilised cells of *Micrococcus Lysodeikticus* (*Micrococcus lysodeikticus* ATCC No. 4698/Sigma-Aldrich/USA/St. Louis) were resuspended in Reaction Buffer (50 mM Hepes, 10 mM $MgCl_2$, pH 7.4) and diluted to an OD450 nm of 0.5-0.7. Subsequently 400 µl of the cell solution were mixed with 100 µl protein solution, containing ~50 µg of the fusion protein of the invention, or 100 µl Protein Storage Buffer (50 mM Tris, 500 mM NaCl 500 mM Imidazole 5% glycerol, pH 8.2). The samples were incubated at 20° C. for 1 h and the decrease of the OD450 nm was measured during the incubation time, whereas the OD450 nm of the samples was determined every 14 seconds. The turbidity reduction graphs were used to determine the ΔOD450 nm with the formula: ΔOD450 nm=OD450 $nm_{0sec}$–OD450 $nm_{3600sec}$. Activity has been observed by a steeper turbidity reduction graph, and a resulting increase in the ΔOD450 nm. For the LysinA proteins TM4gp29, Bxz2gp11 and D29gp10 and the fusion proteins based thereon, the turbidity reduction assay revealed good activity.

Lysin B like activity was controlled by enzymatic assays for lipolytic activity like from those described by Payne et al. 2009. Briefly one milliliter of p-nitrophenyl substrates (50 µM) (Sigma) was incubated with 100 µl of the lysine B variants, containing roughly 1 µg dissolved in storage buffer (50 mM Tris-HCl pH 8.2, 500 mM NaCl, 500 mM imidazole, 5% glycerol), or 10 µg of purified native lysine B, dissolved in 100 µl storage buffer, (derived from pET21 or pET32 containing cells) in buffer (20 mM Tris-HCl pH 8.0, 100 mM NaCl, 0.1% Triton X-100) at room temperature for 30 min. Release of p-nitrophenol was determined by measuring absorbance at 420 nm (A420). For the LysinB proteins TM4gp30, Bxz2gp12, L5gp12 and D29gp12 and the fusion proteins based thereon, the lipolytic activity assay revealed good activity.

An overview of distinct parameters of first and second fusion proteins of the compositions of the present invention is given in FIG. 1.

EXAMPLE 2

Antimicrobial Activity of Compositions of Fusion Proteins According to the Invention Modified with Various Peptide Stretches and PTDs on the N-Terminus or the C-Terminus Determined with Spot Test on Agar Plates Liquid overnight cultures of mycobacteria, namely *Mycobacterium smegmatis* (DSM 43277 termed LiCC S462, DSM 43468 termed LiCC S463 and DSM 43756 termed LiCC S464), were grown at 37° C. in Middlebrook 7H9 pH 6.6 medium (0.5 g ammonium sulfate, 0.5 g L-glutamic acid, 0.1 g sodium citrate, 1 mg pyridoxine, 0.5 mg biotin, 2.5 g disodium phosphate, 1 g monopotassium phosphate, 0.04 g ferric ammonium citrate, 0.05 g magnesium sulfate, 0.5 mg calcium chloride, 1 mg zinc sulfate, 1 mg copper sulfate, 4 ml 50% (v/v) glycerol, pH 6.6. After autoclavation at 121° C. for 20 minutes 2.5 ml 20% (v/v) Tween80 were added) at 200 rpm in baffled flasks. The clumps were dispersed, as good as possible, by vortexing. A volume of 100 µl was added to 3 ml Middlebrook 7H9 pH 6.6 top agar and poured onto Middlebrook 7H9 agar plates five-microlitre volumes of the fusion proteins of the present invention were pipetted onto the top agar, whereas for the mixtures a total volume of ten microliters was used (5 µl each protein), and the spots were allowed to dry completely. The plates were incubated for 2 days at 37° C.

Additionally 200 µl liquid overnight culture of mycobacteria were plated on Middlebrook 7H9 agar plates and five-microlitre volumes of the fusion proteins of the present invention were pipetted onto the top agar, whereas for the mixtures a total volume of ten microliters was used (5 µl each protein), and the spots were allowed to dry completely. The plates were incubated for 2 days at 37° C.

The results are shown in tale 7 and 8:

TABLE 7

| First fusion protein | Second fusion protein | Composition comprising the first and second fusion protein | control |
|---|---|---|---|
| SEQ ID NO 49: − | SEQ ID NO 63: − | SEQ ID NO 49 +<br>SEQ ID NO 63: ++ | − |
| SEQ ID NO 51: − | SEQ ID NO 67: − | SEQ ID NO 51 +<br>SEQ ID NO 67: ++ | − |
| SEQ ID NO 53: − | SEQ ID NO 67: − | SEQ ID NO 53 +<br>SEQ ID NO 67: + | − |
| SEQ ID NO 55: − | SEQ ID NO: 71: − | SEQ ID NO 55 +<br>SEQ ID NO 73: + | − |
| SEQ ID NO 59: − | SEQ ID NO 75: − | SEQ ID NO 59 +<br>SEQ ID NO 75: ++ | − |
| SEQ ID NO 61: − | SEQ ID NO 73: − | SEQ ID NO 61 +<br>SEQ ID NO 73: + | − |
| SEQ ID NO 61:− | SEQ ID NO 69: − | SEQ ID NO 61 +<br>SEQ ID NO 69: ++ | − |

Abbreviations: − no activity; +: 1 log; ++: 2-3 log; +++: 4 log.

The results as shown in table 7 above provide evidence that the first fusion protein and the second fusion protein alone do not exert an anti-mycobacterial activity. In contrast to this, the combination of the first and the second fusion protein in the composition according to the present invention provides a good, in some examples very good activity against mycobacteria. This shows that mycobacteria are specifically detected with the composition of the first and second fusion proteins according to the present invention.

TABLE 8

| | Amount [μg] | Concentration [5 μl or 5 + 5 μl addition respect.] [mg/ml] | M. smegmatis S462 plated | M. smegmatis S462 Top Agar | M. smegmatis S463 plated | M. smegmatis S463 Top Agar | M. smegmatis S464 plated | M. smegmatis S464 Top Agar |
|---|---|---|---|---|---|---|---|---|
| Elution buffer B pH 8.2 | 0 | 0 | — | — | — | — | — | — |
| Lysozyme (1 mg/ml) | 5 | 1 | — | — | v | + | — | — |
| Lipase (1 mg/ml) | 5 | 1 | — | — | — | — | — | — |
| Lysozyme + Lipase (1 mg/ml) | 5/5 | 1/1 | 0.9+ | 0.8+ | 1+ | 1+ | 1+ | 0.7+ |
| TM4gp29 | 1.06 | 0.212 | v | — | — | — | — | — |
| Bxz2gp11 | 1.41 | 0.282 | — | — | — | — | — | — |
| D29gp10 | 3.695 | 0.739 | — | — | — | — | — | — |
| L5gp12 | 0.765 | 0.153 | v | v | v | v | — | — |
| Pat2 E2 | 0.78 | 0.156 | — | — | — | — | — | — |
| Pat8 | 0.75 | 0.15 | — | + | — | v | — | — |
| Pat3 | 1.165 | 0.233 | — | — | — | — | — | — |
| Pat3 + Pat8 | 1.165/ 0.75 | 0.233/ 0.15 | ++ | ++ | +++ | + | + | + |
| Pat2 + Pat8 | 0.78/ 0.75 | 0.156/ 0.15 | ++ | + | ++ | + | nd | nd |
| Pat2 + Pat11 | 0.875/ 0.46 | 0.175/ 0.092 | ++ | +++ | ++ | + | ++ | ++ |
| Pat11 + Pat8 | 0.46/ 0.75 | 0.092/ 0.15 | ++ | +++ | ++ | + | ++ | ++ |
| Pat11 + Pat3 | 0.46/ 1.165 | 0.092/ 0.233 | ++ | +++ | ++ | + | nd | ++ |

| Estimation | appearance |
|---|---|
| Spot not clearly detectable | v |
| Spot with equal size as in control (lysozyme + lipase) | + |
| Spot with greater size than in control (lysozyme + lipase) | ++ |
| Spot with even greater size than in control (lysozyme + lipase) | +++ |
| No spot | — |
| Not determined | nd |

Diameter in control lysozyme + lipase is given in cm

The results as shown in table 8 above provide evidence that the first and second endolysin of the endolysin type Lysin A and Lysin B alone do not exert an anti-mycobacterial activity, since no spots can be detected in the samples TM4gp29, Bxz2gp11, and D29gp10 as well as L5gp12.

No anti-mycobacterial activity can be seen with one fusion protein alone, as seen in the samples with Bxz2gp11-alpha defensin-PTD3 (Pat2 in table 8), D29gp12-alpha defensin-PTD3 (Pat8 in table 8), and PTD3-alpha defensin-Bxz2gp11 (Pat3 in table 8). This provides evidence that only one fusion protein with Lysin A or Lysin B type of endolysin is not sufficient to achieve lysis of the mycobacteria.

In contrast to this, the combination of the first and the second fusion proteins in the compositions according to the present invention provides a good, in some examples very good activity against mycobacteria. This is in particular shown for the following compositions of first and second fusion proteins: PTD3-alpha defensin-Bxz2gp11 (Pat3 in table 8) and D29gp12-alpha defensin-PTD3 (Pat8 in table 8); Bxz2gp11-alpha defensin-PTD3 (Pat2 in table 8) and D29gp12-alpha defensin-PTD3 (Pat8 in table 8); Bxz2gp11-alpha defensin-PTD3 (Pat2 in table 8) and beta defensin-D29gp12-TAT47-57 (Pat11 in table 8); beta defensin-D29gp12-TAT47-57 (Pat11 in table 8) and D29gp12-alpha defensin-PTD3 (Pat8 in table 8); and beta defensin-D29gp12-TAT47-57 (Pat11 in table 8) and PTD3-alpha defensin-Bxz2gp11 (Pat3 in table 8).

The results of the spot test are also illustrated in FIG. 2. FIG. 2A shows the results of the spot test on bacterial lawn, and FIG. 2b shows the results of the spot test on top agar. The results are also summarized in the following table:

TABLE 9

| Number of the well | Construct | Lysis |
|---|---|---|
| 19 | Pat2 + Pat3 | − |
| 20 | Pat2 + Pat8 | ++ |
| 21 | Pat2 | − |
| 22 | Pat11 | − |
| 23 | Pat2 + Pat11 | ++ |
| 24 | Pat11 + Pat8 | ++ |
| 25 | Pat11 + Pat3 | ++ |
| 26 | Pat2 | − |
| 27 | Pat11 | − |

According to the results as described above, no lysis has been detected on mycobacterial lawns in agar plates only treated with lysin B like fusion proteins (well 19), or in agar plates treated with only one fusion protein (wells 21, 22, 26, and 27).

The above-described results provide evidence that the compositions of the present invention comprising a first and second fusion protein are able to specifically recognize and degrade mycobacteria.

EXAMPLE 3

Antimicrobial Activity of Compositions of Fusion Proteins According to the Invention Modified with Various Peptide Stretches and PTDs on the N-Terminus or the C-Terminus Determined with Light Microscopy and Electron Microscopy Light Microscopy Mycobacterial cells from the strains LiCC S463 and LiCC S464 were pelleted, washed with reaction puffer (50 mM Hepes, 100 mM NaCl, 10 mM $MgCl_2$, pH 7.4) and resuspended in reaction buffer to a cell number of roughly $1 \times 10^7$ cells/ml. The cell suspension was mixed in a 9 (cell solution):1 (protein solution) ratio (90 µl cell solution mixed with 10 µl protein solution) with the Lysin-Solution containing a mixture of Construct 2 and Construct 11, namely Bxz2gp11/Alpha-Defensin/PTD3 and Beta-Defensin/D29gp12/TAT47-57 (both with a concentration of 0.32 mg/ml). The samples were incubated at 24° C. for one day and 15 µl samples were taken after 1 h, 2 h, 3 h, 4 h, 5 h and 15 h incubation (overnight) for microscopic analysis. After 2 h increased cell aggregation was observed and after 4 h the morphology of the cells started to change from a normal rod structure to constricted rod structures (data not shown). After 15 h of incubation mostly clusters of cells were observed and less single cells, whereas the single cells seemed hyaline-like.

After 5 h a 20 µl sample was platted on Middlebrook 7H9 agar plates and incubated at 37° C. The control-plate, containing LiCC S462, showed a lawn after 2 days, whereas the plates with the treated cells showed a lawn after 3 days of incubation, thereby showing a decreased number of living cells or decreased fitness of the living cells in the treated samples (data not shown).

Electron Microscopy (EM)

Mycobacterial cells from the strain LiCC S463 were pelleted, washed with reaction puffer (50 mM Hepes, 100 mM NaCl, 10 mM MgCl2, pH 7.4) and resuspended in reaction buffer to a cell number of $5 \times 10^8$ cells/ml. The cell suspension was mixed in a 9 (cell solution):1 (protein solution) ratio (900 µl cell solution mixed with 100 µl sample solution) with a composition of the present invention. As one example a composition of the present invention is used with the fusion proteins of construct 2, namely Bxz2gp11/Alpha-Defensin/PTD3, with a concentration of 0.25 mg/ml, and construct 11, namely Beta-Defensin/D29gp12/TAT47-57, with a concentration of 0.22 mg/ml, a Lysin-mixture-solution of construct 2 and construct 11 or the control solution (50 mM Tris 500 mM NaCl 500 mM Imidazol 5% glycerol pH 8.2). The four samples, construct 1 together with construct 11 (nomenclature see FIG. 1), control with buffer only, construct 2, construct 11, were incubated at 24° C. for 5 h and 15 h and 15 µl samples were taken after 1 h, 2 h, 3 h, 4 h, 5 h and 15 h incubation (overnight) for microscopic analysis. After 15 h the cells treated with the composition of the present invention showed distinct morphological changes. The result is shown in FIG. 3. The transmission EM pictures show cells with a normal rod like structure in the control samples (FIG. 3A) and in samples only treated with the construct 11 alone (FIG. 3A, B), whereas the sample treated with the composition according to the present invention of construct 2 and construct 11 showed cells with drastically changed morphology which was club-shaped (FIG. 3 B). The altered appearance in form of a wider extension and less defined outer structure of the single mycobacteria. This altered, club-shaped morphology provides evidence that integrity of the mycobacteria is lost due to the treatment with the compositions of the present invention. Thus, the compositions of the present invention are able to detect and degrade mycobacteria.

EXAMPLE 4

PCR-Test

40 µl of mycobacterial cells, with a cell number of about $1 \times 10^8$, were incubated with 10 µl of the composition of first and second fusion protein solution of the present invention, 5 µl per fusion protein of the present invention was used, overnight at 24° C. The solution was centrifuged at 13000 rpm for 5 min to pellet the cell fragments and the intact cells, whereas the supernatant contains the released DNA and 10 µl of this supernatant were used as template for 50 µl PCR reactions, whereas the DNA was multiplied by the PCR. For the samples Taq-DNA Polymerase (Peqlab/Germany/Erlangen) and the primer pair 27f and 1492r, which was used at a 10 pM concentration, were used in a suitable reaction buffer. The given PCR Reaction protocol was performed in the Peqstar 2x gradient thermo cycler (Peqlab/Germany/Erlangen). The PCR reaction product was detected by Agarose-Gel-Electrophoresis and purified with the Qiagen Gel Extraction Kit (Qiagen/Germany/Hilden). Subsequently the purified DNA was sequenced with the primer 27f.

Used Primer Pair:

```
Primer 27f (190):
                                    (SEQ ID NO: 119)
aga gtt tga tcc tgg ctc ag Primer 1492r (191):
                                    (SEQ ID NO: 120)
tac ggt tac ctt gtt acg act t
```

PCR Reaction Protocol:

| | | |
|---|---|---|
| 95° C. | 2 min | |
| 98° C. | 20 sec | |
| 65° C. | 30 sec | ⎤ 15 x (reducing 1° C./cycle) |
| 72° C. | 1 min | ⎦ |
| 98° C. | 20 sec | ⎤ |
| 50° C. | 30 sec | ⎥ 20 x |
| 72° C. | 1 min | ⎦ |
| 72° C. | 5 min | |
| 10° C. | ∞ | |

The results of the PCR are shown in FIG. 4. FIG. 4 shows a picture of an agarose gel electrophoresis. With the above described PCR setting amplification of 16 S RNA PCL of the mycobacteria has been achieved. Thus, a strong signal of this 16 S RNA PCL in the agarose gel is a hint to a good degradation of the mycobacteria. As shown in FIG. 4, the exemplary used composition of the present invention of the first fusion protein PTD3-alpha defensin-Bxz2gp11-alpha defensin (Pat4 in FIG. 4) and the second fusion protein D29gp12-alpha defensin-PTD3 (Pat8 in FIG. 4) shows a good signal for 16 S RNA PCL (indicated with an arrow). This signal is stronger compared to the D29gp10 Lysin A-type endolysin alone. Therefore, the results of FIG. 4 show that the composition according the invention allows a good lysis of mycobacteria. Further, the compositions of the invention thus show to be useful for further diagnosis of mycobacteria due their ability to degrade mycobacteria in such an effective way.

EXAMPLE 5

Ability of the Compositions of First and Second Fusion Protein According to the Invention to Degrade Intracellular Mycobacteria

*M. smegmatis* strains were grown in Middlebrook's 7H9 broth medium supplemented with 10% OADC (Oleic acid-albumin-dextrose-catalase) and 0.05% Tween 80 at 37° C. on a shaker at 120 rpm. The mouse macrophage cell line RAW264.7 (described in: Membrane-active antimicrobial peptides and human placental lysosomal extracts are highly active against mycobacteria. Jena P, Mishra B, Leippe M, Hasilik A, Griffiths G, Sonawane A. Peptides. 2011 May; 32(5):881-7. doi: 10.1016/j.peptides.2011.03.002. Epub 2011 Mar. 17) was cultured in DMEM supplemented with 10% fetal calf serum (FCS), 1% penicillin-streptomycin solution, 1% l-glutamine and HEPES. To investigate whether the compositions with the first and second fusion proteins according to the invention were able to kill intracellular *M. smegmatis*, $5 \times 10^5$ RAW264.7 cells were infected with bacteria for 1 h at multiplicity of infection 10. Then extracellular bacteria were killed by addition of 10 µg/ml gentamicin. Infected macrophages were incubated with the compositions of first and second fusion proteins in DMEM medium for at least 4-8 h. After the incubation period, cells were washed, lysed with sterile $H_2O$ and the intracellular survival was estimated by plating serial dilution of the cultures on 7H10 plates. Subsequently the colonies were enumerated after 72 h. The result whether lysis can be observed is shown in the following table 10:

TABLE 10

| Construct | lysis |
| --- | --- |
| Pat 2 | − |
| Pat 3 | − |
| Pat 8 | − |
| Pat 11 | − |
| Pat 2 + Pat 8 | ++ |
| Pat 2 + Pat 11 | + |
| Pat 3 + Pat 8 | ++ |

The results as shown above provide evidence that the compositions of the present invention comprising the first and second fusion protein are able to degrade also mycobacteria which are intracellular within the macrophages.

This provides evidence that the Protein Transduction Domain which is comprised within the first and second fusion protein of the composition of the present invention is able to deliver the first and second fusion protein through the eukaryotic cell membrane into the intracellular space. Further, the above results demonstrate that the first and second fusion proteins of the compositions of the present invention are still able to degrade mycobacteria after the passage through the eukaryotic membrane.

The invention claimed is:

1. A composition comprising having the activity of degrading the cell wall of a *Mycobacterium species* comprising:
   (a) a first fusion protein including
      (i) a first endolysin or a first domain, both having a first enzymatic activity, the enzymatic activity being at least one or more of the following: N-acetyl-b-D-muramidase (lysozyme, lytic transglycosylase), N-acetyl-b-D-glucosaminidase, N-acetylmuramoyl-L-alanine amidase, L-alanoyl-D-glutamate (LD) endopeptidase, c-D-glutamyl-meso-diaminopimelic acid (DL) peptidase, L-alanyl-D-iso-glutaminyl-meso-diaminopimelic acid (D-Ala-m-DAP) (DD) endopeptidase, or m-DAP-m-DAP (LD) endopeptidase;
      (ii) at least one peptide stretch fused to the N- or C-terminus of the endolysin having the first enzymatic activity or the domain having the first enzymatic activity, wherein the peptide stretch is selected from the group consisting of synthetic amphipathic peptide, synthetic cationic peptide, synthetic polycationic peptide, synthetic hydrophobic peptide, synthetic antimicrobial peptide (AMP) or naturally occurring AMP; and
      (iii) a protein transduction domain (PTD) being at the N- or C-terminus of the first fusion protein, wherein the PTD is having the characteristic to deliver a cargo from the extracellular to the intracellular space of a cell; and
   (b) a second fusion protein including
      (i) a second endolysin or a second domain, both having a second enzymatic activity, the enzymatic activity being at least one or more of the following: lipolytic activity, cutinase, mycolarabinogalactanesterase, or alpha/beta hydrolase;
      (ii) at least one peptide stretch fused to the N- or C-terminus of the endolysin having a second enzymatic activity or the domain having the second enzymatic activity, wherein the peptide stretch is selected from the group consisting of synthetic amphipathic peptide, synthetic cationic peptide, synthetic polycationic peptide, synthetic hydrophobic peptide, synthetic antimicrobial peptide (AMP) or naturally occurring AMP; and
      (iii) a protein transduction domain (PTD) being at the N- or C-terminus of the second fusion protein, wherein the PTD is having the characteristic to deliver a cargo from the extracellular to the intracellular space of a cell.

2. The composition according to claim 1, wherein the first fusion protein exhibits an amino acid sequence selected from the group consisting SEQ ID NO:49, 51, 53, 55, 57, 59, 61, 77, 79, 81, 89, 91, 93, 95, 97, 99, 113, and 115, and wherein the second fusion protein exhibits an amino acid sequence selected from the group consisting SEQ ID NO:63, 65, 67, 69, 71, 73, 75, 83, 85, 87, 101, 103, 105, 107, 109, 111, and 117.

3. The composition according to claim 1, wherein the first and/or the second fusion protein further exhibits an affinity tag or a spacer molecule, optionally having an affinity tag or a biotin.

4. The composition according to claim 1, wherein the affinity tag is a His-Tag, Strep-Tag, Avi-Tag, or a biotinylation domain.

5. The composition according to claim 1, wherein the spacer molecule is GFP, MBP or a biotinylation domain.

6. The composition according to claim 1, wherein the *Mycobacterium species* is selected from the group consisting of *Mycobacterium tuberculosis, Mycobacterium microti, Mycobacterium africanum, Mycobacterium bovis, Mycobacterium canettii, Mycobacterium pinnipedii, Mycobacterium caprae, Mycobacterium mungi, Mycobacterium leprae, Mycobacterium ulcerans, Mycobacterium xenopi, Mycobacterium shottsii, Mycobacterium avium, Mycobacterium avium* subsp. *paratuberculosis, Mycobacterium paratuberculosis, Mycobacterium intracellulare, Mycobacterium smegmatis, Mycobacterium abcessus, Mycobacterium kansasii, Mycobacterium terse, Mycobacterium nonchromogenicum, Mycobacterium gordonae,* and *Mycobacterium triviale*.

7. Isolated nucleic acid molecule encoding the first fusion protein of the composition according to claim 1.

8. A method for the detection of a *Mycobacterium species* in a sample, the method comprising the steps of:
  a) incubating or contacting a sample with a composition according to claim 1, the first and the second fusion proteins being in solution, and
  b) detecting of the *Mycobacterium species*.

9. A method for the detection of a *Mycobacterium species* in a sample, the method comprising the steps of:
  a) incubating or contacting a sample with a composition according to claim 1, the first and the second fusion proteins being unspecifically or directedly immobilized to a solid carrier,
  b) separating the carrier-fusion proteins-*Mycobacterium species*-complex from the sample, and
  c) detecting of the *Mycobacterium species*.

10. The method according to claim 9, further comprising after step b) and before step c) the step of:
  b') washing away of sample components unspecifically adhering to the carrier-fusion proteins-*Mycobacterium species*-complex.

11. The method according to claim 9, wherein the solid carrier is cellulose, filtration media, glass particles, magnet particles, centrifugation-, sedimentation-materials or filling materials for chromatography columns.

12. A method for the detection of a *Mycobacterium species* in a sample, the method comprising the steps of:
  a) incubating or contacting a sample with a composition according to claim 1,
  b) contacting and incubating of *Mycobacterium species*-fusion proteins-complex with a carrier, which is coated with the respective binding partner of the polypeptide or a chemical group,
  c) separating the carrier-fusion proteins-*Mycobacterium species* -complex from the sample, and
  d) detecting of the *Mycobacterium species*.

13. The method according to claim 12, further comprising after step c) and before step d) the step of:
  c') washing away of sample components unspecifically adhering to the carrier-fusion proteins-*Mycobacterium species*-complex.

14. A kit comprising a carrier immobilized with a composition comprising a first and a second fusion protein according to claim 1 and washing buffer, detaching buffer and/or cell cracking buffer.

15. A kit comprising a composition comprising a first and a second fusion protein according to claim 3, wherein the first and/or second fusion protein further exhibits an affinity tag or a spacer molecule, a carrier coated with the respective binding partner of the affinity tag, the spacer molecule or the biotinylation domains, and washing buffer, detaching buffer and/or cell cracking buffer.

16. An isolated nucleic acid molecule encoding the second fusion protein of the composition according to claim 1.

* * * * *

SEQUENCE LISTING

```
<160> NUMBER OF SEQ ID NOS: 120

<210> SEQ ID NO 1
<211> LENGTH: 547
<212> TYPE: PRT
<213> ORGANISM: Artificial sequence
<220> FEATURE:
<223> OTHER INFORMATION: TM4gp29 Lysin A

<400> SEQUENCE: 1

Met Ser Phe Thr Arg Phe Leu Gln Asp Asp Pro Leu Leu Thr Arg Glu
1               5                   10                  15

Gln Val Met Ala Glu Leu Ile Arg Val Ala Asp Glu Leu Asn Met Pro
                20                  25                  30

Asp Lys Arg Gly Ala Cys Val Ile Ala Gly Met Thr Ile Ser Gln Glu
            35                  40                  45

Val Gly Val Lys Asp Asn Asp Pro Pro Phe Glu Arg Arg Phe Trp Cys
        50                  55                  60

Pro Ala Asn Arg Ala Asp Pro Glu Ser Phe Asn Tyr Pro His Asp Ser
65                  70                  75                  80

Glu Ser Asn Asp Gly Arg Ser Val Gly Tyr Phe Gln Gln Lys Gly
                85                  90                  95

Pro Asn Gly Glu Leu Trp Trp Gly Thr Thr Ala Ser Glu Met Asn Leu
                100                 105                 110

His Ser Ala Ala Thr Gln Phe Met Thr Arg Leu Lys Ala Ala Gly Tyr
            115                 120                 125

Asn Ala Ser Asn Ala Gln Ala Ala Asn Asp Ser Ala Gln Ala Ile Gln
        130                 135                 140

Arg Ser Gly Val Pro Gln Ala Tyr Lys Gln Trp Trp Asp Asp Ile Asn
145                 150                 155                 160
```

```
Arg Leu Tyr Asp Lys Val Lys Gly Ser Gly Gly Pro Ala Pro Ala
            165                 170                 175

Pro Lys Pro Pro Gln Ser Gly Pro Trp Thr Gly Asp Pro Val Trp Leu
            180                 185                 190

Ala Asp Val Leu Arg Ala Glu Gly Leu Asn Val Glu Leu Pro Gly
            195                 200                 205

Trp Leu Asp Arg Gly His Gly Asp Met Gly Arg Leu Trp Gly Val Val
210                 215                 220

Cys His His Thr Gly Ser Asp Asn Thr Pro Ser Ser Glu Ile Ala Phe
225                 230                 235                 240

His Pro Ser Leu Gly Leu Cys Ser Gln Ile His Leu Ala Arg Asn Gly
            245                 250                 255

Thr Val Thr Leu Cys Gly Val Gly Ile Ala Trp His Ala Gly Val Gly
            260                 265                 270

Ser Tyr Pro Gly Leu Pro Glu Asp Asn Ala Asn Ala Val Thr Ile Gly
            275                 280                 285

Ile Glu Ala Gln Asn Ser Gly Thr Tyr Asp Gly Ala Pro His Arg Thr
290                 295                 300

Asn Trp Pro Asp Ala Gln Tyr Asp Ala Tyr Val Lys Cys Cys Ala Ala
305                 310                 315                 320

Ile Cys Arg Arg Leu Gly Val Arg Ala Asp His Val Ile Ser His Lys
            325                 330                 335

Glu Trp Ala Gly Arg Lys Gln Gly Lys Trp Asp Pro Gly Ala Ile Asp
            340                 345                 350

Met Asn Ile Phe Arg Ala Asp Val Gln Arg Arg Ile Asp Ala His Gln
            355                 360                 365

Pro Asn Gly Glu Asp Asp Phe Met Ala Ala Leu Ser Ala Asp Glu Gln
            370                 375                 380

Arg Glu Val Leu Asn Leu Leu Arg Val Leu Ala Asp Arg Arg Phe Val
385                 390                 395                 400

Ser Arg Ser Pro Phe Arg His Leu Gly Glu Gly Pro Ser Glu Thr Val
            405                 410                 415

Ala Gly Phe Gly Leu Asn Thr Asp Gly Leu Asn His Ala Gln Tyr Thr
            420                 425                 430

Ile Glu Leu Ala Arg Leu Gly Asp Pro Thr His Leu Ala Leu Leu Arg
            435                 440                 445

Glu Val Ala Ser Ala Glu Gly Asp Ser Arg Tyr Pro Asp Arg Gln Tyr
450                 455                 460

Asp Ala Lys Leu Ala Lys Arg Val Leu Ala Glu Ile Glu Gly Ala Ala
465                 470                 475                 480

Thr Ala Pro Ala Lys Pro Ser Thr Pro Ser Ala Pro Thr Glu Pro Ala
            485                 490                 495

Pro Glu Ala Pro Thr Pro Pro Val Lys Ala Cys Ala Leu Ser Ala
            500                 505                 510

Ala Gly Cys Val Val Ala Gly Ser Thr Ser Gly Gly Cys Ala Leu
            515                 520                 525

Ser Thr Asp Gly Thr Gly Lys Cys Val Val Thr Ala Thr Asp Gly
            530                 535                 540

Gly Ala Ala
545

<210> SEQ ID NO 2
<211> LENGTH: 1644
```

```
<212> TYPE: DNA
<213> ORGANISM: Artificial sequence
<220> FEATURE:
<223> OTHER INFORMATION: TM4gp29 Lysin A

<400> SEQUENCE: 2
atgagtttca cccggttcct gcaggatgac ccgctgctca cccgcgagca agtgatggcc     60
gagctgattc gggtcgccga cgagctgaac atgcccgaca agcgcggcgc ctgcgtcatt    120
gcgggcatga cgatttcgca agaggtcggc gtaaaggaca cgacccgcc gttcgagcgg     180 cggttctggt gcccggccaa ccgcgccgac ccgaatcgt tcaactaccc gcacgactcg     240
gaatcgaacg acgccgctc ggtcggctac ttccagcagc agaaggggcc taacggcgag     300
ctgtggtggg gcacaacggc atccgagatg aacctgcaca gcgccgcgac gcagtttatg    360
acgcggctca aggcggccgg atacaacgcg agcaacgccc aggcggcgaa cgactcggcg    420
caggcgatcc agcggtcggg cgtcccgcag gcgtacaagc aatggtggga cgacattaac    480
cgcctgtacg acaaggtgaa gggctcgggc ggtggcccgg cgcccgcgcc taagccgccg    540
cagtcggggc cgtggaccgg cgacccggtg tggctggccg acgtgctgcg cgccgagggg    600
ctgaacgtcg tcgagctgcc cggctggctc gaccgcgggc acggcgacat gggccgcttg    660
tggggcgtgg tgtgccatca caccggcagc gataacaccc cgtcgagcga gattgcgttt    720
cacccgtcgc tcggcctgtg ctcgcagatt cacctggcgc gcaacggaac tgtgacgctg    780
tgcggtgtcg gcatcgcctg gcatgcgggc gtcggcagct atcccggcct gcccgaggac    840
aacgccaacg cggtcactat cggcatcgag gcccaaaaca gcggcaccta tgacggcgca    900
ccgcaccgga cgaattggcc tgacgcgcaa tacgacgcct atgtgaagtg ctgcgccgcg    960
atctgccgcc gctcggcgt gcgcgccgat cacgtgatca gtcacaagga atgggccggg   1020
cgcaagcaag gcaaatggga tccaggcgcc atcgacatga acatctttcg cgccgacgta   1080
cagcggcgca tcgacgccca tcaaccaaac ggagaggacg atttcatggc cgcactatca   1140
gccgacgagc agcgcgaggt gctgaacctg ctgcgcgtcc tggccgaccg gcggttcgtc   1200
agccgcagcc cgttccgcca ccttggcgag gggccgagcg aaactgtcgc cgggttcggg   1260
ctcaacaccg acggcctcaa tcacgcgcag tacacgattg agcttgcgcg cctgggcgac   1320
ccgacgcacc tcgccctgct gcgcgaggtc gccagcgccg agggtgactc gcgctatccc   1380
gaccggcagt acgacgccaa gctcgccaag cgcgtgctcg ccgaaatcga gggcgccgca   1440
acggcaccgg ccaagccgag cacgccgagc gccccgaccg agcccgcccc cgaggcgccc   1500
acgccgccgc tcaaggccgc cgtgtgcgct gtctgcggccg ggtgcgtggt ggctggctcg   1560
acctcgggcg gtggctgcgc cctgtccacc gacggcaccg gcaagtgcgt tgtgaccgcc   1620
gcgaccgacg cgggggccgc ctga                                          1644

<210> SEQ ID NO 3
<211> LENGTH: 514
<212> TYPE: PRT
<213> ORGANISM: Artificial sequence
<220> FEATURE:
<223> OTHER INFORMATION: BXZ2gp11 Lysin A

<400> SEQUENCE: 3

Met Thr Glu Lys Val Leu Pro Tyr Asp Arg Ser Ile Val Thr Gln Glu
1               5                   10                  15

Thr Gly Trp Trp Cys Gly Pro Ala Ala Thr Gln Val Val Leu Asn Ser
                20                  25                  30
```

-continued

```
Arg Gly Ile Ile Val Pro Glu Ala Thr Leu Ala Ala Glu Ile Glu Ala
            35                  40                  45
Ile Glu Asn Pro Gly Arg Gly Asp Asp Arg Asp Gly Thr Asp Tyr Val
 50                  55                  60
Gly Leu Ile Glu Gln Val Leu Asp Arg Arg Val Pro Gln Ala Arg Tyr
 65                  70                  75                  80
Thr Ser Val Tyr Leu Thr Asn Asp Pro Pro Thr Gln Ala Gln Lys Asp
                 85                  90                  95
Arg Leu Trp Glu His Ile Val Arg Ser Ile Asn Ala Gly Tyr Gly Val
                100                 105                 110
Val Met Asn Trp Val Ala Pro Pro Ser Asn Lys Pro Arg Gly Val Lys
            115                 120                 125
Gly Ser Val Ser Pro Arg Tyr Ser Gly Gly Thr Thr Tyr His Tyr Val
130                 135                 140
Ala Cys Met Gly Tyr Asp Asp Thr Pro Gly Ala Arg Ala Val Trp Ile
145                 150                 155                 160
Ala Asp Ser Gly Phe Gln Pro Gln Gly Tyr Trp Ile Ser Phe Asp Gln
                165                 170                 175
Cys Ala Thr Leu Ile Pro Pro Lys Gly Tyr Ala Tyr Ala Asp Ala Ala
                180                 185                 190
Pro Ala Ala Pro Ala Pro Ala Pro Thr Pro Val Val Asp Ala Ala Pro
            195                 200                 205
Ile Leu Ala Arg Ala Ala Gly Ile Ser Glu Ala Lys Ala Arg Glu Ile
210                 215                 220
Leu Pro Thr Met Arg Asp Gly Leu Lys Gln Ala Asp Cys Thr Thr Val
225                 230                 235                 240
Asn Arg Ile Ala Met Phe Ile Ala Gln Thr Gly His Glu Ser Asp Asp
                245                 250                 255
Phe Arg Ala Thr Glu Glu Tyr Ala Asn Gly Pro Leu Asp Gln Glu Arg
                260                 265                 270
Trp Ile Tyr Lys Gly Arg Thr Trp Ile Gln Ile Thr Trp Arg Glu His
            275                 280                 285
Tyr Ala Arg Phe Gly Lys Trp Cys Phe Asp Arg Gly Leu Val Thr Asp
290                 295                 300
Pro Asp Val Phe Val Lys Asn Pro Arg Ala Leu Ala Asp Leu Lys Trp
305                 310                 315                 320
Ala Gly Ile Gly Ala Ala Trp Tyr Trp Thr Val Glu Arg Pro Asp Ile
                325                 330                 335
Asn Ala Leu Cys Asp Arg Arg Asp Ile Glu Thr Val Ser Arg Arg Ile
                340                 345                 350
Asn Gly Thr Asn Pro Asn Thr Gly Arg Ala Asn His Ile Glu Glu Arg
            355                 360                 365
Ile Ala Arg Trp Asn Arg Ala Leu Ala Val Gly Asp Asp Leu Leu Gln
370                 375                 380
Leu Ile Arg Glu Glu Asp Gly Phe Leu Ser Ala Leu Thr Pro Ala
385                 390                 395                 400
Glu Gln Arg Ala Leu Tyr Asn Glu Ile Met Lys Lys Gly Pro Thr Arg
                405                 410                 415
Ser Phe Met Ala Glu Asp Gln Asn Gln Ile Glu Thr Leu Leu Gly Phe
                420                 425                 430
Val Tyr Asn Ile Asp Gly Asn Ile Trp Asn Asp Ala Val Thr Arg Ala
            435                 440                 445
Tyr Leu Phe Asp Val Pro Leu Ala Val Glu Tyr Val Glu Arg Val Ala
```

```
               450                 455                 460
Arg Asp Gly Val His Pro Lys Ser Trp Ala Phe Gln Gln Leu Asp Gly
465                 470                 475                 480

Lys Gly Glu Arg Trp Leu Ala Lys Phe Gly Gln Glu Tyr Cys Lys Gly
                485                 490                 495

Leu Ile Arg Phe Lys Lys Lys Leu Asn Asp Leu Leu Glu Pro Tyr Gly
            500                 505                 510

Glu Asn

<210> SEQ ID NO 4
<211> LENGTH: 1545
<212> TYPE: DNA
<213> ORGANISM: Artificial sequence
<220> FEATURE:
<223> OTHER INFORMATION: Bxz2gp11 Lysin A

<400> SEQUENCE: 4
atgacggaga aggtacttcc ctacgaccgc agcatcgtca cgcaggagac cggctggtgg      60
tgtggccctg cggccaccca ggtcgtgctc aactcgcgag gcatcatcgt cccggaggcc     120
acgctcgctg ccgagatcga ggccatcgag aaccccggac ggggtgacga ccgcgacggc     180
accgactacg tcggcctgat cgagcaggtg ctggatcgcc gtgtgccgca ggcgcgctac     240
acgtcggtct acctgacgaa cgatccgccc acgcaggctc agaaggaccg gctgtgggag     300
cacatcgtcc ggtcgatcaa cgcgggctac ggcgtggtca tgaactgggt cgcgcctccg     360
tcgaacaagc cacgcggagt gaagggctcg gtgagcccgc gctactcggg cggcaccacg     420
taccactacg tcgcgtgcat gggctacgac gacaccccg tgctcgggc ggtctggatc     480 gccgacagcg gcttccagcc gcagggctac tggatctcgt tcgaccagtg cgccacgctg     540
atcccgccga agggctacgc gtacgccgac gccgcaccgg ctgctcccgc acccgcaccg     600 accccgtgg tcgacgccgc gccgatcctg gcgcgtgctg cgggcatctc cgaggccaag     660
gcccgcgaga tcctgccgac gatgcgtgac gggctgaagc aggccgactg caccaccgtc     720
aaccggatcg cgatgttcat cgcccagacc ggccacgagt ccgacgactt ccgggccacc     780
gaggagtacg ccaacggtcc cctggaccag gagcgctgga tctacaaggg acgcacctgg     840
attcagatca cctggcgcga gcactacgcc cggttcggga agtggtgctt cgaccgcggc     900
ctggtgaccg accccgacgt gttcgtcaag aacccgcgtg cgctggccga tctgaagtgg     960
gccggcatcg cgcgcggcctg gtactggacg gtcgagcgcc cggacatcaa cgcgctgtgc    1020
gaccgccgcg acatcgagac ggtctcgcga cggatcaacg ggacgaaccc gaacaccgga    1080
cgcgccaacc acatcgaaga gcggatcgcc cgctggaacc gcgcactcgc ggtcggtgac    1140
gacctgctgc aacttatccg agaggaggag acggcttct tgtccgcact cacacccgct     1200
gaacagcgcg ctctctacaa cgagatcatg aagaagggtc cgacccggtc gttcatggcc    1260
gaggaccaga accagatcga gacgctgctc ggcttcgtct acaacatcga cggcaacatc    1320
tggaacgacg cggtgacccg cgcctacctg ttcgacgtgc cactggctgt tgagtacgtc    1380
gagcgcgttg ctcgcgacgg cgtccacccg aagtcgtggg cgttccagca gctcgacggc    1440
aagggcgagc gctggctggc caagttcggc caggagtact gcaagggcct gatccgcttc    1500
aagaagaagc tgaacgacct gcttgagccg tacggggaga actga                    1545

<210> SEQ ID NO 5
<211> LENGTH: 493
<212> TYPE: PRT
```

-continued

<213> ORGANISM: Artificial sequence
<220> FEATURE:
<223> OTHER INFORMATION: D29gp10 Lysin A

<400> SEQUENCE: 5

```
Met Thr Leu Ile Val Thr Arg Asp His Ala Gln Trp Val His Asp Met
1               5                   10                  15

Cys Arg Ala Arg Ala Gly Asn Arg Tyr Gly Tyr Gly Gly Ala Phe Thr
            20                  25                  30

Leu Asn Pro Arg Asp Thr Thr Asp Cys Ser Gly Leu Val Leu Gln Thr
        35                  40                  45

Ala Ala Trp Tyr Gly Gly Arg Lys Asp Trp Ile Gly Asn Arg Tyr Gly
    50                  55                  60

Ser Thr Glu Ser Phe Arg Leu Asp His Lys Ile Val Tyr Asp Leu Gly
65                  70                  75                  80

Phe Arg Arg Leu Pro Pro Gly Val Ala Ala Leu Gly Phe Thr Pro
                85                  90                  95

Val Met Leu Val Gly Leu Gln His Gly Gly Gly Arg Tyr Ser His
                100                 105                 110

Thr Ala Cys Thr Leu Met Thr Met Asp Ile Pro Gly Gly Pro Val Lys
                115                 120                 125

Val Ser Gln Arg Gly Val Asp Trp Glu Ser Arg Gly Glu Val Asn Gly
130                 135                 140

Val Gly Val Phe Leu Tyr Asp Gly Ala Arg Ala Trp Asn Asp Pro Leu
145                 150                 155                 160

Phe His Asp Phe Trp Tyr Leu Asp Ala Lys Leu Glu Asp Gly Pro Thr
                165                 170                 175

Gln Ser Val Asp Ala Ala Glu Ile Leu Ala Arg Ala Thr Gly Leu Ala
                180                 185                 190

Tyr Asn Arg Ala Val Ala Leu Leu Pro Ala Val Arg Asp Gly Leu Ile
            195                 200                 205

Gln Ala Asp Cys Thr Asn Pro Asn Arg Ile Ala Met Trp Leu Ala Gln
        210                 215                 220

Ile Gly His Glu Ser Asp Asp Phe Lys Ala Thr Ala Glu Tyr Ala Ser
225                 230                 235                 240

Gly Asp Ala Tyr Asp Thr Arg Thr Asp Leu Gly Asn Thr Pro Glu Val
                245                 250                 255

Asp Gly Asp Gly Arg Leu Tyr Lys Gly Arg Ser Trp Ile Met Ile Thr
                260                 265                 270

Gly Lys Asp Asn Tyr Arg Asp Phe Ser Arg Trp Ala His Gly Arg Gly
        275                 280                 285

Leu Val Pro Thr Pro Asp Tyr Phe Val Val His Pro Leu Glu Leu Ser
        290                 295                 300

Glu Leu Arg Trp Ala Gly Ile Gly Ala Ala Trp Tyr Trp Thr Val Glu
305                 310                 315                 320

Arg Pro Asp Ile Asn Ala Leu Ser Asp Arg Asp Leu Glu Thr Val
                325                 330                 335

Thr Arg Arg Ile Asn Gly Gly Leu Thr Asn Leu Asp Asp Arg Arg
            340                 345                 350

Arg Tyr Asn Leu Ala Leu Ala Val Gly Asp Gln Leu Leu Thr Leu Ile
            355                 360                 365

Gly Asp Asp Asp Glu Leu Ala Asp Pro Thr Ile Gln Arg Phe Ile Arg
370                 375                 380

Glu Ile His Gly Ala Leu Phe Asn Thr Val Val Thr Gln Ser Pro Tyr
```

```
                385                 390                 395                 400
        Gly Asp Pro Gln Asn Pro Asp Gly Ser Glu Pro Arg Ser Asn Leu Trp
                        405                 410                 415
        Gln Leu His Glu Leu Ile Lys Asn Gly Asp Gly Met Gly His Ala Arg
                        420                 425                 430
        Tyr Val Glu Glu Ser Ala Arg Ala Gly Asp Leu Arg Glu Leu Glu Arg
                        435                 440                 445
        Val Val Arg Ala Ala Lys Gly Leu Gly Arg Asp Arg Ser Pro Glu Phe
                450                 455                 460
        Ile Ala Arg Ala Arg Asn Val Leu Ala Gln Ile Glu Ala Ala Asn Pro
        465                 470                 475                 480
        Glu Tyr Leu Gln Ala Tyr Ile Ala Arg Asn Gly Ala Leu
                        485                 490

<210> SEQ ID NO 6
<211> LENGTH: 1482
<212> TYPE: DNA
<213> ORGANISM: Artificial sequence
<220> FEATURE:
<223> OTHER INFORMATION: D29gp10 Lysin A

<400> SEQUENCE: 6
atgacgctca tagtcacacg cgaccacgcg cagtgggtcc acgacatgtg ccgcgctcgc        60
gctggcaaca ggtacggcta cggcggggcg ttcacactca accccgaga caccaccgac       120
tgctcgggtc tggttctgca cggcagcc tggtacggcg tcggaagga ctggatcgga         180
aaccggtacg gctcgactga gagcttccgg ctcgaccaca gatcgtcta cgacctcggg       240
ttcaggcgac tccctccggg aggcgttgcg gccctgggat tcacccccggt catgctcgtc    300
gggctccagc acggcggcgg gggccggtac tcgcacaccg cttgcacgct gatgacgatg     360
gacatccccg gtggcccggt gaaggtctcg caacgaggcg tcgactggga gtcccgagga     420
gaagtcaacg cgtgggggt gttcctctac gacggcgcac gcgcctggaa cgacccgctc       480
ttccacgact tctggtacct ggacgcgaag cttgaagacg cccgacgca gagtgtcgac       540
gctgccgaaa tcctcgctcg cgcaacgggt ctcgcgtaca accgagcggt agcactgctg     600
ccggccgtgc gtgacggcct catccaggcc gactgcacca acccgaatcg catcgcgatg     660
tggctcgccc agatcggcca tgagtcgac gatttcaagg ccactgcgga gtacgccagc       720
ggggacgcct acgacacccg aaccgacctc ggcaacaccc cggaggtcga cggagacggt     780
cggctctaca agggccggtc ctggatcatg atcacgggca aggacaacta ccgggacttc     840
tcccggtggg ctcacggcag gggcctggtc cccacgcccg actacttcgt ggttcacccg     900
ctggagctgt cggagctgcg ctgggcaggc atcggtgccg cctggtactg gaccgtcgag     960
cgcccagaca tcaacgcact cagcgaccgc cgcgacctcg aaacggtcac gcgccggatc    1020
aacggcgggc tcaccaacct cgatgaccgc cgacgccggt acaacctggc cctcgctgtg    1080
ggcgaccaac tactgactct gatcggagat gacgacgaat ggctgatcc aacgattcag     1140
cggttcatcc gcgagatcca cggggcgctg ttcaacaccg tcgtgacgca gtccccctac    1200
ggcgaccccg agaacccgga cggctcgag ccccggagca acctctggca gctccatgag     1260
ctgatcaaga acggcgacgg catggggcac gcccgctacg tcgaggaatc ggcgcgagcc    1320
ggtgacctcc gcgagctgga gcgagttgtc cgcgccgcca agggacttgg tagggatcgc    1380
tcccccgagt tcatcgcacg cgctcggaac gtgctggccc agatcgaggc agccaacccc    1440
gagtacctac aggcgtacat cgccaggaat ggagccctat ga                        1482
```

<210> SEQ ID NO 7
<211> LENGTH: 292
<212> TYPE: PRT
<213> ORGANISM: Artificial sequence
<220> FEATURE:
<223> OTHER INFORMATION: L5gp10 Lysin A

<400> SEQUENCE: 7

```
Met Thr Phe Thr Val Thr Arg Glu Arg Ala Gln Trp Val His Asp Met
1               5                   10                  15

Ala Arg Ala Arg Asp Gly Leu Pro Tyr Ala Tyr Gly Gly Ala Phe Thr
            20                  25                  30

Asn Asn Pro Arg Val Ser Thr Asp Cys Ser Gly Leu Val Leu Gln Thr
        35                  40                  45

Gly Ala Trp Tyr Gly Gly Arg Thr Asp Trp Val Gly Asn Arg Tyr Gly
    50                  55                  60

Ser Thr Glu Ser Phe Arg Leu Asp His Lys Ile Val Tyr Asp Leu Gly
65                  70                  75                  80

Phe Lys Arg Met Pro Arg Gly Gly Pro Ala Ala Leu Pro Ile Lys Pro
                85                  90                  95

Val Met Leu Val Gly Leu Gln His Gly Gly Gly Val Tyr Ser His
            100                 105                 110

Thr Ala Cys Thr Leu Met Thr Met Asp His Pro Gly Gly Pro Val Lys
        115                 120                 125

Met Ser Asp Arg Gly Val Asp Trp Glu Ser His Gly Asn Arg Asn Gly
    130                 135                 140

Val Gly Val Glu Leu Tyr Glu Gly Ala Arg Ala Trp Asn Asp Pro Leu
145                 150                 155                 160

Phe His Asp Phe Trp Tyr Leu Asp Ala Val Leu Glu Asp Glu Gly Asp
                165                 170                 175

Asp Asp Glu Leu Ala Asp Pro Val Leu Gly Lys Met Ile Arg Glu Ile
            180                 185                 190

His Ala Cys Leu Phe Asn Gln Thr Ala Ser Thr Ser Asp Leu Ala Thr
        195                 200                 205

Pro Gly Glu Gly Ala Ile Trp Gln Leu His Gln Lys Ile His Ser Ile
    210                 215                 220

Asp Gly Met Leu His Pro Ile His Ala Glu Arg Arg Ala Arg Ala Gly
225                 230                 235                 240

Asp Leu Gly Glu Leu His Arg Ile Val Leu Ala Ala Lys Gly Leu Gly
                245                 250                 255

Val Lys Arg Asp Glu Val Thr Lys Arg Val Tyr Gln Ser Ile Leu Ala
            260                 265                 270

Asp Ile Glu Arg Asp Asn Pro Glu Val Leu Gln Arg Tyr Ile Ala Glu
        275                 280                 285

Arg Gly Gly Leu
    290
```

<210> SEQ ID NO 8
<211> LENGTH: 879
<212> TYPE: DNA
<213> ORGANISM: Artificial sequence
<220> FEATURE:
<223> OTHER INFORMATION: L5gp10 Lysin A

<400> SEQUENCE: 8
atgaccttca cagtcacccg cgagagagcg cagtgggtcc acgacatggc ccgcgctcgc    60

```
gacggtctcc cctacgcgta cggcggggcg ttcaccaaca acccgagggt gtcgactgac    120
tgctctggcc tggtgctgca gaccggggct tggtatggag gtcgcaccga ctgggtcgga    180
aaccgttacg gctcaaccga atcgttccgg ctcgaccaca agatcgtcta cgacctaggg    240
ttcaagcgga tgccccgagg cgggccagcg gccttgccga tcaagccggt gatgctcgtc    300
gggctccagc acggaggcgg cggggtctac tcgcacaccg cttgcacgtt gatgacgatg    360
gaccaccccg gtgcccggt caagatgtcc gaccgaggcg tcgactggga gtcccacggc     420
aaccgcaacg gcgtaggcgt cgaactttac gagggcgcac gggcatggaa cgaccctctg    480
ttccatgact tttggtacct ggacgcagtc ctcgaagacg aaggagacga tgacgaattg    540
gctgacccag ttctagggaa gatgatccgc gagatccacg cgtgcctgtt caatcagacc    600
gcgtcgacca gcgatctggc gaccctggt gaaggcgcta tctggcagct acaccagaag     660
atccactcga ttgacggcat gctccacccg atccacgctg agcggcgcgc tcgcgcaggc    720
gatctcggtg agctgcaccg aatcgtgttg gccgcgaagg gcttgggcgt gaagcgcgac    780
gaggtgacca gcgggtcta ccagagcatc ctcgccgaca tcgagcggga caaccccgaa     840
gtacttcagc gatacatcgc agaaagaggt ggcctatga                          879
```

```
<210> SEQ ID NO 9
<211> LENGTH: 400
<212> TYPE: PRT
<213> ORGANISM: Artificial sequence
<220> FEATURE:
<223> OTHER INFORMATION: TM4gp30 Lysin B

<400> SEQUENCE: 9
```

Met Ala Trp Val Gly Trp Gln Leu Gly Met Gln Gly Glu Gln Val Lys
1               5                   10                  15

Val Ile Gln Gln Lys Leu Ile Ala Lys Tyr Gln Trp Val Arg Asp Arg
            20                  25                  30

Tyr Pro Arg Leu Thr Ala Ser Gly Val Tyr Asp Val Asn Thr Gln Ala
        35                  40                  45

Ala Ile Val Glu Phe Gln Phe Arg Ala Gly Leu Pro Val Thr Gly Ile
    50                  55                  60

Ala Asp Tyr Ala Thr Gln Val Arg Leu Gly Ala Val Ala Pro Ala Pro
65                  70                  75                  80

Pro Pro Arg Gln Arg Ile Met Val Leu Thr Phe Ser Gly Thr Ser Ala
                85                  90                  95

Asp Met Trp Thr Gly Tyr Pro Ala Asp Val Ala Arg Ala Leu Asp Pro
            100                 105                 110

Ser Ile Phe Tyr Trp Gln Pro Val Cys Tyr Gly Pro Asn Gly Ile Pro
        115                 120                 125

Ala Ile Phe Pro Met Gly Ser Ser Ala Lys Ser Gly Glu Val Glu Gly
    130                 135                 140

Leu Arg Leu Leu Asp Glu Lys Ala Arg Asp Phe Asp Tyr Ile Val Leu
145                 150                 155                 160

Ile Gly Tyr Ser Gln Gly Ala Leu Pro Ala Ser Arg Leu Met Arg Arg
                165                 170                 175

Ile Leu Ser Gly Asp Leu Gln Arg Phe Lys Ser Lys Leu Ile Ala Gly
            180                 185                 190

Val Thr Phe Gly Asn Pro Met Arg Glu Lys Gly His Thr Phe Pro Gly
        195                 200                 205

Gly Ala Asp Pro Gly Gly His Gly Leu Asp Pro Gln Cys Leu Val Asn

```
                    210                 215                 220
Thr Pro Asp Trp Trp His Asp Tyr Ala Ala Lys Gly Asp Ile Tyr Thr
225                 230                 235                 240

Val Gly Ser Gly Ser Asn Asp Glu Lys Ala Asn Ala Asp Met Thr Phe
                245                 250                 255

Ile Tyr Gln Leu Val Gln Gly Asp Ile Leu Gly Met Met Phe Gly Thr
            260                 265                 270

Gly Asn Pro Leu Asp Ile Leu Gly Leu Leu Gly Leu Gly Gly Gly
        275                 280                 285

Leu Leu Gly Gly Leu Gly Gly Leu Leu Gly Gly Lys Gly Gly
290                 295                 300

Leu Gln Leu Pro Ser Gly Leu Val Leu Pro Gly Val Gln Gly Gly Ala
305                 310                 315                 320

Leu Thr Asp His Gln Arg Gly Leu Val Glu Ala Val Leu Ala Leu Leu
                325                 330                 335

Ala Asn Pro Phe Ala Glu Val Pro Ala Ala Val Lys Ala Ile Val Ser
                340                 345                 350

Gly Val Gly Phe Ile Ala Thr Asn Pro Pro Thr Ala Pro His Ile Glu
            355                 360                 365

Tyr His Ile Arg Glu Ala Ala Pro Gly Val Thr Tyr Phe Gln His Ala
        370                 375                 380

Ile Asp Tyr Leu Arg Gln Val Gly Ala Ser Val Ala Ala Arg Ala Ala
385                 390                 395                 400
```

<210> SEQ ID NO 10
<211> LENGTH: 1203
<212> TYPE: DNA
<213> ORGANISM: Artificial sequence
<220> FEATURE:
<223> OTHER INFORMATION: TM4gp30 Lysin B

<400> SEQUENCE: 10

```
atggcctggg tcggttggca gctcggcatg caggggagc aggtcaaggt gatacagcaa      60
aagctgatcg ccaagtacca gtgggtgcgt gaccgttacc cgcggctgac ggccagcggc    120
gtctatgacg tgaacacgca ggccgcgatc gtcgagtttc agttccgcgc agggcttccc    180
gtcaccggca tagctgacta tgcgacgcag gttcggctcg gcgcggtggc cccggcgccg    240
ccgccgcggc agcgcatcat ggtgctgacg tttagcggca cctcggccga catgtggacc    300
ggctatccgg ccgacgtcgc gcgtgcgctc gacccgtcga tcttctactg cagccagtg    360
tgctacggcc ccaacggcat cccggcgata ttcccgatgg gttccagcgc caagagcggc    420
gaggtcgagg ggctgcggct gctcgacgag aaggcgcgcg atttcgacta catcgtgctt    480
atcggatact cgcagggcgc gctgcccgcg tcgcggctca tgcggcgcat cctgtcgggc    540
gacctgcagc ggttcaagtc caagctgatc gccggtgtca cgttcggcaa cccgatgcgc    600
gagaagggga cacgttcc cggcggcgcc gaccccggcg gcacggcct cgacccgcag       660
tgcctcgtga atacgcccga ctggtggcac gactacgccg ccaagggcga catttacacc    720
gtcggctcgg gcagtaacga cgagaaggcc aacgccgaca tgacgttcat ttaccagctc    780
gtgcagggcg acattctcgg catgatgttc ggcaccggca cccgctcga cattctcggc    840
ctgctcggcg gctcggtgg cggcctgctc ggcggcctgg cggtggcct gctcggtggc    900
ggcaagggtg gcctgcagtt gccgagcggc ctggtgctcc ccggcgtcca gggcggcgcg    960
ctcaccgacc accagcgcgg cctcgtcgag gcggtgctgg cgctgctcgc taacccgttc   1020
```

-continued

```
gccgaggttc cggcggcggt caaggcgatt gtgtccggtg tcgggttcat cgccaccaac    1080
ccgccgacgg cgccgcacat cgagtaccac attcgcgagg ctgcgcccgg cgtgacgtat    1140
ttccagcacg cgatcgacta cctgcgccag gtcggcgcgt ccgtcgccgc tcgcgcggcc    1200
tga                                                                 1203
```

<210> SEQ ID NO 11
<211> LENGTH: 321
<212> TYPE: PRT
<213> ORGANISM: Artificial sequence
<220> FEATURE:
<223> OTHER INFORMATION: Bxz2gp12 Lysin B

<400> SEQUENCE: 11

```
Met Pro Leu Arg Val Gly Ser Asn Asp Ala Asn Thr Gly Gly Leu Val
1               5                   10                  15

Ser Arg Trp Gln Lys Thr Met Leu Ala Arg Tyr Ala Ala Tyr Ala Lys
            20                  25                  30

Ala Tyr Asp Gly Gly Pro Leu Arg Val Asp Gly Tyr Phe Gly Tyr Asp
        35                  40                  45

Asp Ala Asp Val Gln Arg Glu Tyr Glu Arg Arg Thr His Gln Val Val
50                  55                  60

Asp Gly Glu Val Ser Asp Ala Asp Leu Arg Ala Leu Gly Leu Glu Ala
65                  70                  75                  80

Ala Lys Arg Trp Leu Phe Thr Val His Gly Thr Gly Gln Ala Asp Pro
                85                  90                  95

Leu Gly Pro Gly Leu Pro Ala Asp Thr Ala Arg Ala Val Leu Asp Lys
            100                 105                 110

Tyr Thr Trp Gln Pro Ile Gly Asn Tyr Pro Ala Arg Ala Phe Pro Met
        115                 120                 125

Trp Ser Ser Ile Met Asp Gly Ala Arg Glu Leu Arg Ser Gln Ile Ala
130                 135                 140

Ser Lys Ser Gly Glu Val Asn Leu Ala Gly Tyr Ser Gln Gly Ala Val
145                 150                 155                 160

Val Val Gly Gln Val Leu Lys His Asp Ile Met Asp Pro Lys Gly Ser
                165                 170                 175

Leu His His Arg Leu Gly Asp Val Arg Lys Val Val Leu Trp Gly Asn
            180                 185                 190

Pro Met Arg Gln Arg Gly Ile Ala His Phe Asp Glu Trp Ile His Pro
        195                 200                 205

Val Ala Gly Pro Asp Ser Tyr Gly Ile Leu Asp Arg Leu Glu Gly
210                 215                 220

Leu Glu Lys Ala Pro Phe Glu Ile Arg Asp Tyr Ala His Ala Gly Asp
225                 230                 235                 240

Met Tyr Ala Ser Ile Thr Asp Gly Asp Lys Asp Glu Tyr Lys Ile Ala
                245                 250                 255

Ile Cys Lys Ile Val Met Thr Ala Thr Asp Phe Tyr Arg Gly Pro Asn
            260                 265                 270

Ser Val Val Ser Gln Leu Ile Glu Leu Gly Gln Arg Pro Leu Thr Glu
        275                 280                 285

Gly Ile Ala Met Ala Leu Ala Ile Ile Asp Thr Leu Arg Phe Phe Thr
290                 295                 300

Asn Thr Ala His Gly Tyr Asn Ile Gly Pro Ala Ile Asp Phe Leu Arg
305                 310                 315                 320

Ser
```

<210> SEQ ID NO 12
<211> LENGTH: 966
<212> TYPE: DNA
<213> ORGANISM: Artificial sequence
<220> FEATURE:
<223> OTHER INFORMATION: Bxz2gp12 Lysin B

<400> SEQUENCE: 12

```
atgcccctgc gggtcgggtc gaacgacgcc ataccggcg ggctggtgag ccgttggcag      60
aagacgatgc tggcccgcta cgcggcctac gccaaggcgt acgacggcgg ccgctgcga    120
gtcgacggct atttcggcta cgacgacgct gacgttcagc gcgagtacga acgccgcacc   180
caccaggtgg tcgacggtga ggtcagtgac gccgacctcc gggctctggg cctggaggcg   240
gcgaagcgct ggctgttcac ggtccacggc accggacagg ccgacccgct gggtccggga   300
ctccccgccg acacggcgcg ggcggtgctc gacaagtaca cctggcagcc catcggcaac   360
taccccgctc gggcgttccc gatgtggtcc tcgatcatgg acggtgccag ggagcttcgc   420
tcccagatcg cgtcaaagtc cggtgaggtc aacctggcgg gctactcgca aggcgcggtg   480
gtcgtcggcc aggtgctcaa gcacgacatc atggacccga agggcagcct gcaccacagg   540
ctcggcgatg tccgcaaggt agtgctctgg ggaaatccca tgcgccagag gggaatcgct   600
cacttcgatg agtggattca cccggtggca ggcccagact cgtacggcat cctcgatgac   660
cggctcgaag gctggagaa ggcaccgttc gagatccggg actacgcgca cgctggtgac   720
atgtacgcct ccatcacgga cggcgacaag gacgagtaca agatcgcgat ctgcaagatc   780
gtcatgacgg cgacggactt ctaccgaggc ccgaactccg ttgtgtccca actgatcgag   840
cttggacagc gtccgctcac cgagggcatc gcaatggccc tggcgatcat cgacacgctg   900
cggttcttca cgaacaccgc gcacggctac aacatcggac cagctatcga cttcctgcgt   960
agctga                                                              966
```

<210> SEQ ID NO 13
<211> LENGTH: 254
<212> TYPE: PRT
<213> ORGANISM: Artificial sequence
<220> FEATURE:
<223> OTHER INFORMATION: D29gp12 Lysin B

<400> SEQUENCE: 13

Met Ser Lys Pro Trp Leu Phe Thr Val His Gly Thr Gly Gln Pro Asp
1               5                   10                  15

Pro Leu Gly Pro Gly Leu Pro Ala Asp Thr Ala Arg Asp Val Leu Asp
            20                  25                  30

Ile Tyr Arg Trp Gln Pro Ile Gly Asn Tyr Pro Ala Ala Ala Phe Pro
        35                  40                  45

Met Trp Pro Ser Val Glu Lys Gly Val Ala Glu Leu Ile Leu Gln Ile
    50                  55                  60

Glu Leu Lys Leu Asp Ala Asp Pro Tyr Ala Asp Phe Ala Met Ala Gly
65                  70                  75                  80

Tyr Ser Gln Gly Ala Ile Val Val Gly Gln Val Leu Lys His Ile
                85                  90                  95

Leu Pro Pro Thr Gly Arg Leu His Arg Phe Leu His Arg Leu Lys Lys
            100                 105                 110

Val Ile Phe Trp Gly Asn Pro Met Arg Gln Lys Gly Phe Ala His Ser
        115                 120                 125

Asp Glu Trp Ile His Pro Val Ala Ala Pro Asp Thr Leu Gly Ile Leu
    130                 135                 140

Glu Asp Arg Leu Glu Asn Leu Glu Gln Tyr Gly Phe Glu Val Arg Asp
145                 150                 155                 160

Tyr Ala His Asp Gly Asp Met Tyr Ala Ser Ile Lys Glu Asp Asp Leu
                165                 170                 175

His Glu Tyr Glu Val Ala Ile Gly Arg Ile Val Met Lys Ala Ser Gly
            180                 185                 190

Phe Ile Gly Gly Arg Asp Ser Val Val Ala Gln Leu Ile Glu Leu Gly
        195                 200                 205

Gln Arg Pro Ile Thr Glu Gly Ile Ala Leu Ala Gly Ala Ile Ile Asp
210                 215                 220

Ala Leu Thr Phe Phe Ala Arg Ser Arg Met Gly Asp Lys Trp Pro His
225                 230                 235                 240

Leu Tyr Asn Arg Tyr Pro Ala Val Glu Phe Leu Arg Gln Ile
                245                 250

<210> SEQ ID NO 14
<211> LENGTH: 765
<212> TYPE: DNA
<213> ORGANISM: Artificial sequence
<220> FEATURE:
<223> OTHER INFORMATION: D29gp12 Lysin B

<400> SEQUENCE: 14

```
atgagcaagc cctggctgtt caccgttcac ggcacgggcc agcccgatcc cctcgggcct      60
ggcctgcctg ccgatacggc acgcgacgta cttgacatct accggtggca gcccatcggc     120
aactaccccg ctgcggcctt cccgatgtgg ccgtcggtcg agaagggtgt cgccgagctg     180
atcctgcaga tcgagctgaa gctggacgcg gaccccacg cggacttcgc gatggcgggt     240
tactcgcagg gagccatcgt ggttggccag gtgctcaagc accacatcct gcctccgacg     300
ggcaggctcc acaggttcct gcaccggctc aagaaggtca tcttctgggg taatcccatg     360
cggcagaagg gctttgccca ctctgacgag tggatccacc cggtcgctgc ccctgacacc     420
ctcggaatcc tcgaggaccg gctcgaaaac ctggagcagt acggcttcga ggtccgcgac     480
tacgcccacg acggtgacat gtacgcctcc atcaaagagg acgacctgca cgaatacgag     540
gtcgccatcg gccggatcgt gatgaaggcc agcggcttca tcggtggccg ggactccgtg     600
gtagcccagc tcatcgagct tggccagcgt ccgatcaccg agggaattgc gttggcggga     660
gccatcatcg acgccctcac gttcttcgcc cgctctcgta tgggcgacaa gtggccgcac     720
ctctacaacc gctacccggc ggtcgagttc tacgacaga tctga                     765
```

<210> SEQ ID NO 15
<211> LENGTH: 254
<212> TYPE: PRT
<213> ORGANISM: Artificial sequence
<220> FEATURE:
<223> OTHER INFORMATION: L5gp12 Lysin B

<400> SEQUENCE: 15

Met Ser Lys Pro Trp Leu Phe Thr Val His Gly Thr Gly Gln Pro Asp
1               5                   10                  15

Pro Leu Gly Pro Gly Leu Pro Ala Asp Thr Ala Arg Asp Val Leu Asp
            20                  25                  30

Ile Tyr Arg Trp Gln Pro Ile Gly Asn Tyr Pro Ala Ala Ala Phe Pro
        35                  40                  45

Met Trp Pro Ser Val Glu Lys Gly Val Ala Glu Leu Ile Leu Gln Ile
50                  55                  60

Glu Leu Lys Leu Asp Ala Asp Pro Tyr Ala Asp Phe Ala Leu Ala Gly
65                  70                  75                  80

Tyr Ser Gln Gly Ala Ile Val Val Gly Gln Val Leu Lys His His Ile
                85                  90                  95

Ile Asn Pro Arg Gly Arg Leu His Arg Phe Leu His Arg Leu Arg Lys
            100                 105                 110

Val Ile Phe Trp Gly Asn Pro Met Arg Gln Lys Gly Phe Ala His Thr
        115                 120                 125

Asp Glu Trp Ile His Gln Val Ala Ala Ser Asp Thr Met Gly Ile Leu
130                 135                 140

Glu Asp Arg Leu Glu Asn Leu Glu Gln Tyr Gly Phe Glu Val Arg Asp
145                 150                 155                 160

Tyr Ala His Asp Gly Asp Met Tyr Ala Ser Ile Lys Glu Asp Asp Met
                165                 170                 175

His Glu Tyr Glu Val Ala Ile Gly Arg Ile Val Met Ser Ala Arg Arg
            180                 185                 190

Phe Ile Gly Gly Lys Asp Ser Val Ile Ala Gln Leu Ile Glu Leu Gly
        195                 200                 205

Gln Arg Pro Ile Trp Glu Gly Ile Ala Met Ala Arg Ala Ile Ile Asp
210                 215                 220

Ala Leu Thr Phe Phe Ala Lys Ser Thr Gln Gly Pro Ser Trp Pro His
225                 230                 235                 240

Leu Tyr Asn Arg Phe Pro Ala Val Glu Phe Leu Arg Arg Ile
                245                 250

<210> SEQ ID NO 16
<211> LENGTH: 765
<212> TYPE: DNA
<213> ORGANISM: Artificial sequence
<220> FEATURE:
<223> OTHER INFORMATION: L5gp12 Lysin B

<400> SEQUENCE: 16
atgagcaagc cctggctgtt caccgtccac ggcacaggcc agcccgaccc gctcgggcct      60
ggtctgcctg ccgataccgc acgggacgta cttgacatct accggtggca gcccatcggc     120
aactacccgg cagcggcgtt cccgatgtgg ccgtcggtcg aaaagggtgt cgctgagctg     180
atcctgcaga tcgagctgaa gctggacgca gatccgtacg cggacttcgc gctggccggc     240
tactcgcagg gagccatcgt ggtgggccag gtgctcaagc accacatcat caacccgaga     300
ggtcgactgc accggttcct gcaccggctc aggaaggtca tcttctgggg taatccgatg     360
cggcagaagg gctttgccca caccgacgag tggattcacc aggtcgctgc ctcggacacg     420
atgggcatcc tcgaggaccg actggagaac ctcgagcagt acggctttga ggtccgcgac     480
tacgcgcacg acggcgacat gtacgcctcc atcaaggagg acgacatgca cgagtacgag     540
gtggccattg ccgaatcgt gatgagcgct aggcgattca tcggaggtaa ggactccgtc     600
atcgcccagc tcatcgagct tggacagcgt ccgatctggg agggaatcgc gatggccaga     660
gccatcatcg acgccctcac gttcttcgcc aagtcgaccc aaggcccgag ctggccgcat     720
ttgtacaacc gcttcccggc ggtcgagttc ctacgacgaa tctga                     765

<210> SEQ ID NO 17
<211> LENGTH: 37
<212> TYPE: PRT

```
<213> ORGANISM: Artificial sequence
<220> FEATURE:
<223> OTHER INFORMATION: LL-37

<400> SEQUENCE: 17

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 18
<211> LENGTH: 111
<212> TYPE: DNA
<213> ORGANISM: Artificial sequence
<220> FEATURE:
<223> OTHER INFORMATION: LL-37

<400> SEQUENCE: 18
ttattgggtg atttctttcg gaagagcaaa gaaaagatag gaaaggagtt taaacgaatt     60
gttcaacgta tcaaagactt cctaaggaat cttgtaccaa gaacagaaag t             111

<210> SEQ ID NO 19
<211> LENGTH: 30
<212> TYPE: PRT
<213> ORGANISM: Artificial sequence
<220> FEATURE:
<223> OTHER INFORMATION: alpha-defensin

<400> SEQUENCE: 19

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 20
<211> LENGTH: 90
<212> TYPE: DNA
<213> ORGANISM: Artificial sequence
<220> FEATURE:
<223> OTHER INFORMATION: alpha-defensin

<400> SEQUENCE: 20
gattgttatt gtagaatacc agcatgcatt gcgggagaac gtaggtacgg aacatgcatc     60
tatcaaggtc gattatgggc tttttgttgc                                     90

<210> SEQ ID NO 21
<211> LENGTH: 38
<212> TYPE: PRT
<213> ORGANISM: Artificial sequence
<220> FEATURE:
<223> OTHER INFORMATION: beta-defensin

<400> SEQUENCE: 21

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
                20                  25                  30

Lys Cys Cys Arg Lys Lys
            35
```

```
<210> SEQ ID NO 22
<211> LENGTH: 114
<212> TYPE: DNA
<213> ORGANISM: Artificial sequence
<220> FEATURE:
<223> OTHER INFORMATION: beta-defensin

<400> SEQUENCE: 22
aatccagtaa gctgtgttcg taataagggt atttgcgttc caatacgatg cccaggaagt    60
atgaaacaaa tcggtacatg cgtaggaaga gcagtaaagt gttgtaggaa aaaa          114

<210> SEQ ID NO 23
<211> LENGTH: 25
<212> TYPE: PRT
<213> ORGANISM: Artificial sequence
<220> FEATURE:
<223> OTHER INFORMATION: Hepcidin

<400> SEQUENCE: 23

Asp Thr His Phe Pro Ile Cys Ile Phe Cys Cys Gly Cys Cys His Arg
 1               5                  10                  15

Ser Lys Cys Gly Met Cys Cys Lys Thr
             20                  25

<210> SEQ ID NO 24
<211> LENGTH: 75
<212> TYPE: DNA
<213> ORGANISM: Artificial sequence
<220> FEATURE:
<223> OTHER INFORMATION: Hepcidin

<400> SEQUENCE: 24
gatacacact ttccaatatg cattttctgt tgcggttgct gtcatagaag taaatgtgga    60
atgtgctgta agaca                                                     75

<210> SEQ ID NO 25
<211> LENGTH: 27
<212> TYPE: PRT
<213> ORGANISM: Artificial sequence
<220> FEATURE:
<223> OTHER INFORMATION: NK-2

<400> SEQUENCE: 25

Lys Ile Leu Arg Gly Val Cys Lys Lys Ile Met Arg Thr Phe Leu Arg
 1               5                  10                  15

Arg Ile Ser Lys Asp Ile Leu Thr Gly Lys Lys
             20                  25

<210> SEQ ID NO 26
<211> LENGTH: 81
<212> TYPE: DNA
<213> ORGANISM: Artificial sequence
<220> FEATURE:
<223> OTHER INFORMATION: NK-2

<400> SEQUENCE: 26
aaaatcttac gaggtgtatg taaaaagatt atgagaacat ttttgcgtag gataagtaaa    60
gatatactaa caggaaagaa g                                              81

<210> SEQ ID NO 27
<211> LENGTH: 24
<212> TYPE: PRT
<213> ORGANISM: Artificial sequence
<220> FEATURE:
```

<223> OTHER INFORMATION: Ci-MAM-A24

<400> SEQUENCE: 27

Trp Arg Ser Leu Gly Arg Thr Leu Leu Arg Leu Ser His Ala Leu Lys
1               5                   10                  15

Pro Leu Ala Arg Arg Ser Gly Trp
            20

<210> SEQ ID NO 28
<211> LENGTH: 72
<212> TYPE: DNA
<213> ORGANISM: Artificial sequence
<220> FEATURE:
<223> OTHER INFORMATION: Ci-MAM-A24

<400> SEQUENCE: 28
tggcgaagtt taggaagaac actacttcgg ttgagccatg cattgaaacc attagctagg      60
cgtagtggtt gg                                                          72

<210> SEQ ID NO 29
<211> LENGTH: 14
<212> TYPE: PRT
<213> ORGANISM: Artificial sequence
<220> FEATURE:
<223> OTHER INFORMATION: TAT48-60

<400> SEQUENCE: 29

Gly Arg Lys Lys Arg Arg Gln Arg Arg Pro Pro Gln Cys
1               5                   10

<210> SEQ ID NO 30
<211> LENGTH: 11
<212> TYPE: PRT
<213> ORGANISM: Artificial sequence
<220> FEATURE:
<223> OTHER INFORMATION: TAT47-57

<400> SEQUENCE: 30

Tyr Gly Arg Lys Lys Arg Arg Gln Arg Arg
1               5                   10

<210> SEQ ID NO 31
<211> LENGTH: 9
<212> TYPE: PRT
<213> ORGANISM: Artificial sequence
<220> FEATURE:
<223> OTHER INFORMATION: TAT47-55

<400> SEQUENCE: 31

Tyr Gly Arg Lys Lys Arg Arg Gln Arg
1               5

<210> SEQ ID NO 32
<211> LENGTH: 11
<212> TYPE: PRT
<213> ORGANISM: Artificial sequence
<220> FEATURE:
<223> OTHER INFORMATION: PTD3

<400> SEQUENCE: 32

Tyr Ala Arg Lys Ala Arg Arg Gln Ala Arg Arg
1               5                   10

<210> SEQ ID NO 33
<211> LENGTH: 9

```
<212> TYPE: PRT
<213> ORGANISM: Artificial sequence
<220> FEATURE:
<223> OTHER INFORMATION: PolyArginine

<400> SEQUENCE: 33

Arg Arg Arg Arg Arg Arg Arg Arg Arg
1               5

<210> SEQ ID NO 34
<211> LENGTH: 20
<212> TYPE: PRT
<213> ORGANISM: Artificial sequence
<220> FEATURE:
<223> OTHER INFORMATION: CADY

<400> SEQUENCE: 34

Gly Leu Trp Arg Ala Leu Trp Arg Leu Leu Arg Ser Leu Trp Arg Leu
1               5                   10                  15

Leu Trp Arg Ala
            20

<210> SEQ ID NO 35
<211> LENGTH: 21
<212> TYPE: PRT
<213> ORGANISM: Artificial sequence
<220> FEATURE:
<223> OTHER INFORMATION: PepFect6

<400> SEQUENCE: 35

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 36
<211> LENGTH: 14
<212> TYPE: PRT
<213> ORGANISM: Artificial sequence
<220> FEATURE:
<223> OTHER INFORMATION: RXR
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 36

Arg Xaa Arg Arg Xaa Arg Arg Xaa Arg Arg Xaa Arg Xaa Asx
1               5                   10

<210> SEQ ID NO 37
<211> LENGTH: 16
<212> TYPE: PRT
```

```
<213> ORGANISM: Artificial sequence
<220> FEATURE:
<223> OTHER INFORMATION: Antennapedia

<400> SEQUENCE: 37

Arg Gln Ile Lys Ile Trp Phe Gln Asn Arg Arg Met Lys Trp Lys Lys
1               5                   10                  15

<210> SEQ ID NO 38
<211> LENGTH: 30
<212> TYPE: PRT
<213> ORGANISM: Artificial sequence
<220> FEATURE:
<223> OTHER INFORMATION: Kala Syn

<400> SEQUENCE: 38

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 39
<211> LENGTH: 22
<212> TYPE: PRT
<213> ORGANISM: Artificial sequence
<220> FEATURE:
<223> OTHER INFORMATION: M918

<400> SEQUENCE: 39

Met Val Thr Val Leu Phe Arg Arg Leu Arg Ile Arg Arg Ala Ser Gly
1               5                   10                  15

Pro Pro Arg Val Arg Val
            20

<210> SEQ ID NO 40
<211> LENGTH: 18
<212> TYPE: PRT
<213> ORGANISM: Artificial sequence
<220> FEATURE:
<223> OTHER INFORMATION: MAP

<400> SEQUENCE: 40

Lys Leu Ala Leu Lys Leu Ala Leu Lys Ala Leu Lys Ala Ala Leu Lys
1               5                   10                  15

Leu Ala

<210> SEQ ID NO 41
<211> LENGTH: 16
<212> TYPE: PRT
<213> ORGANISM: Artificial sequence
<220> FEATURE:
<223> OTHER INFORMATION: Penetratin

<400> SEQUENCE: 41

Arg Gln Ile Lys Ile Trp Phe Gln Asn Arg Arg Met Lys Trp Lys Lys
1               5                   10                  15

<210> SEQ ID NO 42
<211> LENGTH: 12
<212> TYPE: PRT
<213> ORGANISM: Artificial sequence
<220> FEATURE:
<223> OTHER INFORMATION: PTD5-Syn

<400> SEQUENCE: 42
```

Arg Arg Gln Arg Arg Thr Ser Lys Leu Met Lys Arg
1               5                   10

<210> SEQ ID NO 43
<211> LENGTH: 18
<212> TYPE: PRT
<213> ORGANISM: Artificial sequence
<220> FEATURE:
<223> OTHER INFORMATION: Pvec

<400> SEQUENCE: 43

Leu Leu Ile Ile Leu Arg Arg Arg Ile Arg Lys Gln Ala His Ala His
1               5                   10                  15

Ser Lys

<210> SEQ ID NO 44
<211> LENGTH: 8
<212> TYPE: PRT
<213> ORGANISM: Artificial sequence
<220> FEATURE:
<223> OTHER INFORMATION: Poly Arg 8

<400> SEQUENCE: 44

Arg Arg Arg Arg Arg Arg Arg Arg
1               5

<210> SEQ ID NO 45
<211> LENGTH: 13
<212> TYPE: PRT
<213> ORGANISM: Artificial sequence
<220> FEATURE:
<223> OTHER INFORMATION: TAT48-60

<400> SEQUENCE: 45

Gly Arg Lys Lys Arg Arg Gln Arg Arg Arg Pro Pro Gln
1               5                   10

<210> SEQ ID NO 46
<211> LENGTH: 27
<212> TYPE: PRT
<213> ORGANISM: Artificial sequence
<220> FEATURE:
<223> OTHER INFORMATION: Transportan

<400> SEQUENCE: 46

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 47
<211> LENGTH: 21
<212> TYPE: PRT
<213> ORGANISM: Artificial sequence
<220> FEATURE:
<223> OTHER INFORMATION: Transportan10

<400> SEQUENCE: 47

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 48
<211> LENGTH: 9

```
<212> TYPE: PRT
<213> ORGANISM: Artificial sequence
<220> FEATURE:
<223> OTHER INFORMATION: TAT-9

<400> SEQUENCE: 48

Arg Lys Lys Arg Gln Arg Arg Arg
1               5

<210> SEQ ID NO 49
<211> LENGTH: 603
<212> TYPE: PRT
<213> ORGANISM: Artificial sequence
<220> FEATURE:
<223> OTHER INFORMATION: TM4gp29/LL-37/TAT47-57

<400> SEQUENCE: 49

Met Ser Phe Thr Arg Phe Leu Gln Asp Asp Pro Leu Leu Thr Arg Glu
1               5                   10                  15

Gln Val Met Ala Glu Leu Ile Arg Val Ala Asp Glu Leu Asn Met Pro
            20                  25                  30

Asp Lys Arg Gly Ala Cys Val Ile Ala Gly Met Thr Ile Ser Gln Glu
        35                  40                  45

Val Gly Val Lys Asp Asn Asp Pro Pro Phe Glu Arg Arg Phe Trp Cys
    50                  55                  60

Pro Ala Asn Arg Ala Asp Pro Glu Ser Phe Asn Tyr Pro His Asp Ser
65                  70                  75                  80

Glu Ser Asn Asp Gly Arg Ser Val Gly Tyr Phe Gln Gln Gln Lys Gly
                85                  90                  95

Pro Asn Gly Glu Leu Trp Trp Gly Thr Thr Ala Ser Glu Met Asn Leu
            100                 105                 110

His Ser Ala Ala Thr Gln Phe Met Thr Arg Leu Lys Ala Ala Gly Tyr
        115                 120                 125

Asn Ala Ser Asn Ala Gln Ala Ala Asn Asp Ser Ala Gln Ala Ile Gln
    130                 135                 140

Arg Ser Gly Val Pro Gln Ala Tyr Lys Gln Trp Trp Asp Asp Ile Asn
145                 150                 155                 160

Arg Leu Tyr Asp Lys Val Lys Gly Ser Gly Gly Pro Ala Pro Ala
                165                 170                 175

Pro Lys Pro Pro Gln Ser Gly Pro Trp Thr Gly Asp Pro Val Trp Leu
            180                 185                 190

Ala Asp Val Leu Arg Ala Glu Gly Leu Asn Val Val Glu Leu Pro Gly
        195                 200                 205

Trp Leu Asp Arg Gly His Gly Asp Met Gly Arg Leu Trp Gly Val Val
    210                 215                 220

Cys His Thr Gly Ser Asp Asn Thr Pro Ser Ser Glu Ile Ala Phe
225                 230                 235                 240

His Pro Ser Leu Gly Leu Cys Ser Gln Ile His Leu Ala Arg Asn Gly
                245                 250                 255

Thr Val Thr Leu Cys Gly Val Gly Ile Ala Trp His Ala Gly Val Gly
            260                 265                 270

Ser Tyr Pro Gly Leu Pro Glu Asp Asn Ala Asn Ala Val Thr Ile Gly
        275                 280                 285

Ile Glu Ala Gln Asn Ser Gly Thr Tyr Asp Gly Ala Pro His Arg Thr
    290                 295                 300

Asn Trp Pro Asp Ala Gln Tyr Asp Ala Tyr Val Lys Cys Cys Ala Ala
305                 310                 315                 320
```

Ile Cys Arg Arg Leu Gly Val Arg Ala Asp His Val Ile Ser His Lys
            325                 330                 335

Glu Trp Ala Gly Arg Lys Gln Gly Lys Trp Asp Pro Gly Ala Ile Asp
        340                 345                 350

Met Asn Ile Phe Arg Ala Asp Val Gln Arg Ile Asp Ala His Gln
    355                 360                 365

Pro Asn Gly Glu Asp Asp Phe Met Ala Ala Leu Ser Ala Asp Glu Gln
370                 375                 380

Arg Glu Val Leu Asn Leu Leu Arg Val Leu Ala Asp Arg Arg Phe Val
385                 390                 395                 400

Ser Arg Ser Pro Phe Arg His Leu Gly Glu Gly Pro Ser Glu Thr Val
                405                 410                 415

Ala Gly Phe Gly Leu Asn Thr Asp Gly Leu Asn His Ala Gln Tyr Thr
            420                 425                 430

Ile Glu Leu Ala Arg Leu Gly Asp Pro Thr His Leu Ala Leu Leu Arg
        435                 440                 445

Glu Val Ala Ser Ala Glu Gly Asp Ser Arg Tyr Pro Asp Arg Gln Tyr
    450                 455                 460

Asp Ala Lys Leu Ala Lys Arg Val Leu Ala Glu Ile Glu Gly Ala Ala
465                 470                 475                 480

Thr Ala Pro Ala Lys Pro Ser Thr Pro Ser Ala Pro Thr Glu Pro Ala
                485                 490                 495

Pro Glu Ala Pro Thr Pro Val Lys Ala Ala Cys Ala Leu Ser Ala
            500                 505                 510

Ala Gly Cys Val Val Ala Gly Ser Thr Ser Gly Gly Cys Ala Leu
        515                 520                 525

Ser Thr Asp Gly Thr Gly Lys Cys Val Val Thr Ala Ala Thr Asp Gly
530                 535                 540

Gly Ala Ala Gly Ser Gly Ser Leu Leu Gly Asp Phe Phe Arg Lys Ser
545                 550                 555                 560

Lys Glu Lys Ile Gly Lys Glu Phe Lys Arg Ile Val Gln Arg Ile Lys
                565                 570                 575

Asp Phe Leu Arg Asn Leu Val Pro Arg Thr Glu Ser Gly Ala Gly Ala
            580                 585                 590

Tyr Gly Arg Lys Lys Arg Arg Gln Arg Arg
        595                 600

<210> SEQ ID NO 50
<211> LENGTH: 1809
<212> TYPE: DNA
<213> ORGANISM: Artificial sequence
<220> FEATURE:
<223> OTHER INFORMATION: TM4gp29/LL-37/TAT47-57

<400> SEQUENCE: 50
atgagtttca cacgtttttt acaagatgac ccactattaa cacgtgagca agttatggcg    60
gagttaatac gggttgctga cgaacttaat atgccagaca agcgtggagc gtgcgtaata   120
gctggaatga caattagcca agaggttggt gttaaagaca atgatccacc atttgagagg   180
cgtttctggt gcccagctaa tcgtgccgat ccagaaagtt tcaattatcc acacgatagc   240
gaaagcaatg atggtaggag cgttggatat tttcaacaac aaaagggtcc aaatggagaa   300
ttgtggtggg gtacaacagc tagcgaaatg aatttacaca gtgcagcgac acaattcatg   360
acaaggctaa aggcggctgg atacaatgcc agtaatgcgc aagccgctaa tgatagcgca   420

```
caagccatac aacgaagcgg tgttccacaa gcatataagc aatggtggga tgacataaat    480
cggctttatg acaaagtaaa gggaagcggt ggaggtccag cgccagcccc aaaaccacca    540
caaagcggtc catggacagg agatccagta tggttagccg atgtactaag ggcagaagga    600
ttgaatgttg tagaattacc aggttggcta gaccgaggac atggtgatat gggacggttg    660
tggggtgttg tatgtcatca cacaggaagc gataatacac caagcagtga aatcgccttt    720
catccaagcc ttggattatg cagccaaata catttggcca gaaatggaac agttacattg    780
tgtggagttg gtattgcatg gcacgcaggt gttggtagtt atccaggtct accagaggac    840
aatgcaaatg ctgttacaat tggtattgaa gctcaaaata gcggaacata tgacggtgcg    900
ccacatcgga caaattggcc agacgcgcaa tacgatgctt acgttaaatg ctgtgcagct    960
atctgtcggc gattgggagt aagggcggac catgtaatca gtcacaaaga atgggcaggt   1020
aggaaacaag gtaaatggga cccaggtgca atagatatga atatatttag agccgatgta   1080
caacgtcgga tcgatgccca tcaaccaaat ggagaagacg atttttatggc ggctttgagc   1140
gcagacgaac aacgagaggt attgaatctt ttgcgtgtac tagccgatcg agattcgta   1200
agtaggagtc cattcaggca ccttggagaa ggtccaagcg aaacagtagc aggatttggt   1260
cttaatacag acggattgaa tcatgcccaa tatacaattg aacttgcccg attaggtgac   1320
ccaacacact tggcactttt aagagaggta gcgagtgcgg aaggtgacag cagatacca   1380
gatcggcaat acgacgccaa gcttgcgaaa agggttctag cagaaattga aggagcagcc   1440
acagcgccag ctaagccaag tacaccaagt gcgccaacag agccagcccc agaagctcca   1500
acaccaccag ttaaggctgc gtgcgcctta agtgcggctg gatgtgttgt agcgggtagt   1560
acaagtggtg gaggttgcgc actaagtaca gatggtacag gaaagtgtgt agttacagcc   1620
gctacagacg gtggagcagc tggaagtgga agtctttag gagacttctt tcgtaagagc   1680
aaagagaaaa tcggaaaaga atttaaacgt atcgtacaac gaattaagga tttcctaaga   1740
aatctagtac cacgaacaga gagtggtgca ggagcttacg gtagaaagaa acggcgacaa   1800
agacgaaga                                                           1809
```

<210> SEQ ID NO 51
<211> LENGTH: 595
<212> TYPE: PRT
<213> ORGANISM: Artificial sequence
<220> FEATURE:
<223> OTHER INFORMATION: TM4gp29/LL-37/TAT47-57

<400> SEQUENCE: 51

```
Met Ser Phe Thr Arg Phe Leu Gln Asp Asp Pro Leu Leu Thr Arg Glu
 1               5                  10                  15

Gln Val Met Ala Glu Leu Ile Arg Val Ala Asp Glu Leu Asn Met Pro
            20                  25                  30

Asp Lys Arg Gly Ala Cys Val Ile Ala Gly Met Thr Ile Ser Gln Glu
        35                  40                  45

Val Gly Val Lys Asp Asn Asp Pro Pro Phe Glu Arg Arg Phe Trp Cys
    50                  55                  60

Pro Ala Asn Arg Ala Asp Pro Glu Ser Phe Asn Tyr Pro His Asp Ser
65                  70                  75                  80

Glu Ser Asn Asp Gly Arg Ser Val Gly Tyr Phe Gln Gln Lys Gly
                85                  90                  95

Pro Asn Gly Glu Leu Trp Trp Gly Thr Thr Ala Ser Glu Met Asn Leu
            100                 105                 110
```

```
His Ser Ala Ala Thr Gln Phe Met Thr Arg Leu Lys Ala Ala Gly Tyr
            115                 120                 125
Asn Ala Ser Asn Ala Gln Ala Asn Asp Ser Ala Gln Ala Ile Gln
        130                 135                 140
Arg Ser Gly Val Pro Gln Ala Tyr Lys Gln Trp Trp Asp Asp Ile Asn
145                 150                 155                 160
Arg Leu Tyr Asp Lys Val Lys Gly Ser Gly Gly Pro Ala Pro Ala
                165                 170                 175
Pro Lys Pro Gln Ser Gly Pro Trp Thr Gly Asp Pro Val Trp Leu
            180                 185                 190
Ala Asp Val Leu Arg Ala Glu Gly Leu Asn Val Val Glu Leu Pro Gly
                195                 200                 205
Trp Leu Asp Arg Gly His Gly Asp Met Gly Arg Leu Trp Gly Val Val
            210                 215                 220
Cys His His Thr Gly Ser Asp Asn Thr Pro Ser Ser Glu Ile Ala Phe
225                 230                 235                 240
His Pro Ser Leu Gly Leu Cys Ser Gln Ile His Leu Ala Arg Asn Gly
                245                 250                 255
Thr Val Thr Leu Cys Gly Val Gly Ile Ala Trp His Ala Gly Val Gly
            260                 265                 270
Ser Tyr Pro Gly Leu Pro Glu Asp Asn Ala Asn Ala Val Thr Ile Gly
    275                 280                 285
Ile Glu Ala Gln Asn Ser Gly Thr Tyr Asp Gly Ala Pro His Arg Thr
    290                 295                 300
Asn Trp Pro Asp Ala Gln Tyr Asp Ala Tyr Val Lys Cys Cys Ala Ala
305                 310                 315                 320
Ile Cys Arg Arg Leu Gly Val Arg Ala Asp His Val Ile Ser His Lys
                325                 330                 335
Glu Trp Ala Gly Arg Lys Gln Gly Lys Trp Asp Pro Gly Ala Ile Asp
            340                 345                 350
Met Asn Ile Phe Arg Ala Asp Val Gln Arg Arg Ile Asp Ala His Gln
            355                 360                 365
Pro Asn Gly Glu Asp Asp Phe Met Ala Ala Leu Ser Ala Asp Glu Gln
    370                 375                 380
Arg Glu Val Leu Asn Leu Leu Arg Val Leu Ala Asp Arg Arg Phe Val
385                 390                 395                 400
Ser Arg Ser Pro Phe Arg His Leu Gly Glu Gly Pro Ser Glu Thr Val
                405                 410                 415
Ala Gly Phe Gly Leu Asn Thr Asp Gly Leu Asn His Ala Gln Tyr Thr
            420                 425                 430
Ile Glu Leu Ala Arg Leu Gly Asp Pro Thr His Leu Ala Leu Leu Arg
            435                 440                 445
Glu Val Ala Ser Ala Glu Gly Asp Ser Arg Tyr Pro Asp Arg Gln Tyr
    450                 455                 460
Asp Ala Lys Leu Ala Lys Arg Val Leu Ala Glu Ile Glu Gly Ala Ala
465                 470                 475                 480
Thr Ala Pro Ala Lys Pro Ser Thr Pro Ser Ala Pro Thr Glu Pro Ala
                485                 490                 495
Pro Glu Ala Pro Thr Pro Val Lys Ala Ala Cys Ala Leu Ser Ala
            500                 505                 510
Ala Gly Cys Val Val Ala Gly Ser Thr Ser Gly Gly Cys Ala Leu
            515                 520                 525
Ser Thr Asp Gly Thr Gly Lys Cys Val Val Thr Ala Ala Thr Asp Gly
```

Gly Ala Ala Leu Leu Gly Asp Phe Phe Arg Lys Ser Lys Glu Lys Ile
545                 550                 555                 560

Gly Lys Glu Phe Lys Arg Ile Val Gln Arg Ile Lys Asp Phe Leu Arg
                565                 570                 575

Asn Leu Val Pro Arg Thr Glu Ser Tyr Gly Arg Lys Lys Arg Arg Gln
            580                 585                 590

Arg Arg Arg
    595

<210> SEQ ID NO 52
<211> LENGTH: 1785
<212> TYPE: DNA
<213> ORGANISM: Artificial sequence
<220> FEATURE:
<223> OTHER INFORMATION: TM4gp29/LL-37/TAT47-57

<400> SEQUENCE: 52

| | | | | | |
|---|---|---|---|---|---|
| atgagtttta | caaggttcct | acaagatgac | ccactattga | cacgagaaca | agtaatggct | 60 |
| gagctaatac | gagtagcaga | tgaattaaat | atgccagata | gaggggagc | ttgtgttatc | 120 |
| gccggtatga | caatcagtca | agaagttgga | gttaaggaca | atgatccacc | attcgagcgt | 180 |
| aggttctggt | gtccagcgaa | tcgtgctgat | ccagaaagtt | ttaattaccc | acacgacagc | 240 |
| gaaagcaatg | acggacgtag | tgtaggttat | ttccaacaac | aaaagggacc | aaatggagag | 300 |
| ctttggtggg | gtacaacagc | tagtgagatg | aatctacata | gtgcagcgac | acaatttatg | 360 |
| acaagactta | aagctgccgg | ttataatgcc | agtaatgcgc | aagcggctaa | tgacagtgca | 420 |
| caagctatac | aacgtagtgg | tgtaccacaa | gcctataagc | aatggtggga | tgacataaat | 480 |
| aggttatacg | ataaggtaaa | gggtagtggt | ggaggtccag | caccagcacc | aaaaccacca | 540 |
| caaagcggtc | catggacagg | agatccagtt | tggttggcgg | acgtattacg | agcagaaggt | 600 |
| ttgaatgtag | ttgaacttcc | aggatggctt | gacagaggac | acggtgacat | gggacgtctt | 660 |
| tggggtgtag | tttgtcacca | tacaggtagt | gacaatacac | caagtagcga | aattgccttt | 720 |
| cacccaagtt | tgggactttg | cagccaaatt | catcttgcca | ggaatggtac | agttacacta | 780 |
| tgcggagtag | aatagcttg | cacgccggt | gttggtagct | atccaggttt | accagaagat | 840 |
| aatgctaatg | cagtaacaat | tggaattgaa | gcacaaaata | gcggaacata | cgacggtgca | 900 |
| ccacatagaa | caaattggcc | agacgctcaa | tacgatgcgt | atgttaaatg | ctgtgctgcc | 960 |
| atatgccggc | gattaggtgt | acgggctgac | catgttatta | gccacaagga | atgggccgga | 1020 |
| agaaaacaag | gaaaatggga | cccaggagct | atcgatatga | atatctttcg | ggcggatgta | 1080 |
| caacggcgaa | ttgatgctca | tcaaccaaat | ggagaagatg | actttatggc | ggccttaagt | 1140 |
| gccgacgaac | aacgtgaggt | tttaaatctt | ttacgggtat | tggcggaccg | gcgattcgtt | 1200 |
| agtaggagcc | cattccgaca | tttggtgag | ggaccaagcg | agacagtagc | gggattcggt | 1260 |
| ttgaatacag | atggtttgaa | tcatgcacaa | tatacaatag | aattggcaag | attgggtgac | 1320 |
| ccaacacacc | tagcgctttt | aagggaagta | gcaagtgcag | aaggtgatag | ccgttatcca | 1380 |
| gatcgtcaat | acgatgccaa | gctagcgaaa | cgagttttag | cagaaattga | aggagccgcg | 1440 |
| acagcgccag | ccaaaccaag | cacaccaagt | gctccaacag | aaccagcacc | agaggcgcca | 1500 |
| acaccaccag | ttaaagctgc | ctgtgcccta | agtgcagcgg | gatgcgtagt | tgccggaagc | 1560 |
| acaagcggag | gtggatgcgc | tttgagcaca | gacggaacg | gtaaatgtgt | agttacagct | 1620 |
| gcgacagatg | gtggagcagc | attactaggt | gacttttca | ggaaaagcaa | agaaaagatc | 1680 |

```
ggtaaagagt ttaaaagaat agtacaacgg atcaaggatt ttcttagaaa tctagttcca   1740
cggacagaga gctacggaag aaagaagcgg agacaaaggc gacgt                    1785
```

<210> SEQ ID NO 53
<211> LENGTH: 555
<212> TYPE: PRT
<213> ORGANISM: Artificial sequence
<220> FEATURE:
<223> OTHER INFORMATION: Bzx2gp11/alpha-defensin/PTD3

<400> SEQUENCE: 53

| | | | | | | | | | | | | | | |
|---|---|---|---|---|---|---|---|---|---|---|---|---|---|---|
| Met | Thr | Glu | Lys | Val | Leu | Pro | Tyr | Asp | Arg | Ser | Ile | Val | Thr | Gln | Glu |
| 1 | | | | 5 | | | | | 10 | | | | | 15 | |
| Thr | Gly | Trp | Trp | Cys | Gly | Pro | Ala | Ala | Thr | Gln | Val | Val | Leu | Asn | Ser |
| | | | 20 | | | | | 25 | | | | | 30 | | |
| Arg | Gly | Ile | Ile | Val | Pro | Glu | Ala | Thr | Leu | Ala | Ala | Glu | Ile | Glu | Ala |
| | | | 35 | | | | | 40 | | | | | 45 | | |
| Ile | Glu | Asn | Pro | Gly | Arg | Gly | Asp | Asp | Arg | Asp | Gly | Thr | Asp | Tyr | Val |
| | | 50 | | | | | 55 | | | | | 60 | | | |
| Gly | Leu | Ile | Glu | Gln | Val | Leu | Asp | Arg | Arg | Val | Pro | Gln | Ala | Arg | Tyr |
| 65 | | | | | 70 | | | | | 75 | | | | | 80 |
| Thr | Ser | Val | Tyr | Leu | Thr | Asn | Asp | Pro | Pro | Thr | Gln | Ala | Gln | Lys | Asp |
| | | | | 85 | | | | | 90 | | | | | 95 | |
| Arg | Leu | Trp | Glu | His | Ile | Val | Arg | Ser | Ile | Asn | Ala | Gly | Tyr | Gly | Val |
| | | | | 100 | | | | | 105 | | | | | 110 | |
| Val | Met | Asn | Trp | Val | Ala | Pro | Pro | Ser | Asn | Lys | Pro | Arg | Gly | Val | Lys |
| | | | 115 | | | | | 120 | | | | | 125 | | |
| Gly | Ser | Val | Ser | Pro | Arg | Tyr | Ser | Gly | Gly | Thr | Thr | Tyr | His | Tyr | Val |
| | 130 | | | | | 135 | | | | | 140 | | | | |
| Ala | Cys | Met | Gly | Tyr | Asp | Asp | Thr | Pro | Gly | Ala | Arg | Ala | Val | Trp | Ile |
| 145 | | | | | 150 | | | | | 155 | | | | | 160 |
| Ala | Asp | Ser | Gly | Phe | Gln | Pro | Gln | Gly | Tyr | Trp | Ile | Ser | Phe | Asp | Gln |
| | | | | 165 | | | | | 170 | | | | | 175 | |
| Cys | Ala | Thr | Leu | Ile | Pro | Pro | Lys | Gly | Tyr | Ala | Tyr | Ala | Asp | Ala | Ala |
| | | | 180 | | | | | 185 | | | | | 190 | | |
| Pro | Ala | Ala | Pro | Ala | Pro | Ala | Pro | Thr | Pro | Val | Val | Asp | Ala | Ala | Pro |
| | | 195 | | | | | 200 | | | | | 205 | | | |
| Ile | Leu | Ala | Arg | Ala | Ala | Gly | Ile | Ser | Glu | Ala | Lys | Ala | Arg | Glu | Ile |
| | | 210 | | | | | 215 | | | | | 220 | | | |
| Leu | Pro | Thr | Met | Arg | Asp | Gly | Leu | Lys | Gln | Ala | Asp | Cys | Thr | Thr | Val |
| 225 | | | | | 230 | | | | | 235 | | | | | 240 |
| Asn | Arg | Ile | Ala | Met | Phe | Ile | Ala | Gln | Thr | Gly | His | Glu | Ser | Asp | Asp |
| | | | | 245 | | | | | 250 | | | | | 255 | |
| Phe | Arg | Ala | Thr | Glu | Glu | Tyr | Ala | Asn | Gly | Pro | Leu | Asp | Gln | Glu | Arg |
| | | | 260 | | | | | 265 | | | | | 270 | | |
| Trp | Ile | Tyr | Lys | Gly | Arg | Thr | Trp | Ile | Gln | Ile | Thr | Trp | Arg | Glu | His |
| | | 275 | | | | | 280 | | | | | 285 | | | |
| Tyr | Ala | Arg | Phe | Gly | Lys | Trp | Cys | Phe | Asp | Arg | Gly | Leu | Val | Thr | Asp |
| | 290 | | | | | 295 | | | | | 300 | | | | |
| Pro | Asp | Val | Phe | Val | Lys | Asn | Pro | Arg | Ala | Leu | Ala | Asp | Leu | Lys | Trp |
| 305 | | | | | 310 | | | | | 315 | | | | | 320 |
| Ala | Gly | Ile | Gly | Ala | Ala | Trp | Tyr | Trp | Thr | Val | Glu | Arg | Pro | Asp | Ile |
| | | | | 325 | | | | | 330 | | | | | 335 | |
| Asn | Ala | Leu | Cys | Asp | Arg | Arg | Asp | Ile | Glu | Thr | Val | Ser | Arg | Arg | Ile |

```
              340              345              350
Asn Gly Thr Asn Pro Asn Thr Gly Arg Ala Asn His Ile Glu Glu Arg
            355                  360                  365

Ile Ala Arg Trp Asn Arg Ala Leu Ala Val Gly Asp Asp Leu Leu Gln
        370                  375                  380

Leu Ile Arg Glu Glu Glu Asp Gly Phe Leu Ser Ala Leu Thr Pro Ala
385                  390                  395                  400

Glu Gln Arg Ala Leu Tyr Asn Glu Ile Met Lys Lys Gly Pro Thr Arg
                405                  410                  415

Ser Phe Met Ala Glu Asp Gln Asn Gln Ile Glu Thr Leu Leu Gly Phe
            420                  425                  430

Val Tyr Asn Ile Asp Gly Asn Ile Trp Asn Asp Ala Val Thr Arg Ala
                435                  440                  445

Tyr Leu Phe Asp Val Pro Leu Ala Val Glu Tyr Val Glu Arg Val Ala
            450                  455                  460

Arg Asp Gly Val His Pro Lys Ser Trp Ala Phe Gln Gln Leu Asp Gly
465                  470                  475                  480

Lys Gly Glu Arg Trp Leu Ala Lys Phe Gly Gln Glu Tyr Cys Lys Gly
                485                  490                  495

Leu Ile Arg Phe Lys Lys Lys Leu Asn Asp Leu Leu Glu Pro Tyr Gly
            500                  505                  510

Glu Asn Asp Cys Tyr Cys Arg Ile Pro Ala Cys Ile Ala Gly Glu Arg
                515                  520                  525

Arg Tyr Gly Thr Cys Ile Tyr Gln Gly Arg Leu Trp Ala Phe Cys Cys
            530                  535                  540

Tyr Ala Arg Lys Ala Arg Arg Gln Ala Arg Arg
545                  550                  555

<210> SEQ ID NO 54
<211> LENGTH: 1665
<212> TYPE: DNA
<213> ORGANISM: Artificial sequence
<220> FEATURE:
<223> OTHER INFORMATION: Bzx2gp11/alpha-defensin/PTD3

<400> SEQUENCE: 54
atgacagaga aagttttacc atacgatcgg agtatagtta cacaagagac aggttggtgg    60
tgtggtccag ccgcaacaca gtagttttta aatagtcgtg aataatcgt accagaagct   120
acattggccg ctgaaatcga agccatagaa atccaggtc gtggtgatga ccgagacgga   180
acagattatg taggtcttat tgagcaagtt cttgatcgga gggttccaca agctcgttac   240
acaagcgtat atttaacaaa tgatccacca acacaagcac aaaaggaccg attgtgggaa   300
catattgtaa aagcataaa tgcaggttac ggagtagtta tgaattgggt agctccacca   360
agtaataagc cacgtggagt taaaggtagc gttagcccac gatatagtgg aggtacaaca   420
tatcactatg tagcgtgcat gggatatgac gatacaccag gtgccagagc agtatgata    480
gcggacagcg gattccaacc acaaggatac tggatcagct ttgaccaatg cgccacactt   540
atcccaccaa aaggttatgc atacgcagac gcggcaccag ctgcaccagc tccagctcca   600
acaccagttg tagacgccgc gccaatattg gcccgggcgg caggtattag cgaagcaaag   660
gcaagggaaa ttcttccaac aatgcgggat ggactaaaac aagcggattg tacaacagtt   720
aatcgaattg caatgtttat agcccaaaca ggacacgaaa gtgatgactt tcgggctaca   780
gaagagtatg caaatggacc attggatcaa gaacgttgga tttacaaagg tcgaacatgg   840
```

```
atacaaatta catggaggga acactacgct cgtttcggta aatggtgttt cgaccgtgga    900
cttgttacag atccagatgt atttgttaaa aatccacgag ctttggccga cctaaaatgg    960
gcgggtatag gagcggcttg gtactggaca gtagaacggc cagatatcaa tgccttatgc   1020
gatcgaagag acatcgaaac agttagtaga aggataaatg gaacaaatcc aaatacaggt   1080
agagcgaatc atatcgagga acgaattgcg aggtggaatc gtgcactagc agtaggtgac   1140
gatttacttc aactaattag agaagaggaa gacggttttt taagtgcttt gacaccagcc   1200
gagcaacgag cgttgtataa tgaaatcatg aagaaaggac caacacgtag tttcatggct   1260
gaggatcaaa atcaaatcga gacattattg ggattcgtat acaatataga cggaaatatc   1320
tggaatgacg ctgtaacacg ggcttattta tttgatgttc cattagccgt agaatacgtt   1380
gagagggttg cgagggatgg agtacatcca aagagctggg catttcaaca actgacgga   1440 aagggagaaa ggtggctagc caagttcgga caagaatact gtaaaggtct aatccggttc   1500
aagaaaaagt tgaatgatct acttgaacca tatggagaga atgactgcta ctgtcggatt   1560
ccagcgtgca ttgctggtga aaggagatat ggtacatgta tatatcaagg tagactttgg   1620
gccttttgtt gctacgcgag aaaggccaga aggcaagcgc gtcga                   1665

<210> SEQ ID NO 55
<211> LENGTH: 555
<212> TYPE: PRT
<213> ORGANISM: Artificial sequence
<220> FEATURE:
<223> OTHER INFORMATION: PTD3/alpha-defensin/Bzx2gp11

<400> SEQUENCE: 55

Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30

Gln Gly Arg Leu Trp Ala Phe Cys Cys Met Thr Glu Lys Val Leu Pro
        35                  40                  45

Tyr Asp Arg Ser Ile Val Thr Gln Glu Thr Gly Trp Trp Cys Gly Pro
    50                  55                  60

Ala Ala Thr Gln Val Val Leu Asn Ser Arg Gly Ile Ile Val Pro Glu
65                  70                  75                  80

Ala Thr Leu Ala Ala Glu Ile Glu Ala Ile Glu Asn Pro Gly Arg Gly
                85                  90                  95

Asp Asp Arg Asp Gly Thr Asp Tyr Val Gly Leu Ile Glu Gln Val Leu
            100                 105                 110

Asp Arg Arg Val Pro Gln Ala Arg Tyr Thr Ser Val Tyr Leu Thr Asn
        115                 120                 125

Asp Pro Pro Thr Gln Ala Gln Lys Asp Arg Leu Trp Glu His Ile Val
    130                 135                 140

Arg Ser Ile Asn Ala Gly Tyr Gly Val Val Met Asn Trp Val Ala Pro
145                 150                 155                 160

Pro Ser Asn Lys Pro Arg Gly Val Lys Gly Ser Val Ser Pro Arg Tyr
                165                 170                 175

Ser Gly Gly Thr Thr Tyr His Tyr Val Ala Cys Met Gly Tyr Asp Asp
            180                 185                 190

Thr Pro Gly Ala Arg Ala Val Trp Ile Ala Asp Ser Gly Phe Gln Pro
        195                 200                 205

Gln Gly Tyr Trp Ile Ser Phe Asp Gln Cys Ala Thr Leu Ile Pro Pro
    210                 215                 220
```

Lys Gly Tyr Ala Tyr Ala Asp Ala Ala Pro Ala Ala Pro Ala
225                 230                 235                 240

Pro Thr Pro Val Val Asp Ala Ala Pro Ile Leu Ala Arg Ala Ala Gly
                245                 250                 255

Ile Ser Glu Ala Lys Ala Arg Glu Ile Leu Pro Thr Met Arg Asp Gly
            260                 265                 270

Leu Lys Gln Ala Asp Cys Thr Thr Val Asn Arg Ile Ala Met Phe Ile
        275                 280                 285

Ala Gln Thr Gly His Glu Ser Asp Asp Phe Arg Ala Thr Glu Glu Tyr
    290                 295                 300

Ala Asn Gly Pro Leu Asp Gln Glu Arg Trp Ile Tyr Lys Gly Arg Thr
305                 310                 315                 320

Trp Ile Gln Ile Thr Trp Arg Glu His Tyr Ala Arg Phe Gly Lys Trp
                325                 330                 335

Cys Phe Asp Arg Gly Leu Val Thr Asp Pro Asp Val Phe Val Lys Asn
            340                 345                 350

Pro Arg Ala Leu Ala Asp Leu Lys Trp Ala Gly Ile Gly Ala Ala Trp
        355                 360                 365

Tyr Trp Thr Val Glu Arg Pro Asp Ile Asn Ala Leu Cys Asp Arg Arg
    370                 375                 380

Asp Ile Glu Thr Val Ser Arg Arg Ile Asn Gly Thr Asn Pro Asn Thr
385                 390                 395                 400

Gly Arg Ala Asn His Ile Glu Glu Arg Ile Ala Arg Trp Asn Arg Ala
                405                 410                 415

Leu Ala Val Gly Asp Asp Leu Leu Gln Leu Ile Arg Glu Glu Asp
            420                 425                 430

Gly Phe Leu Ser Ala Leu Thr Pro Ala Glu Gln Arg Ala Leu Tyr Asn
        435                 440                 445

Glu Ile Met Lys Lys Gly Pro Thr Arg Ser Phe Met Ala Glu Asp Gln
    450                 455                 460

Asn Gln Ile Glu Thr Leu Leu Gly Phe Val Tyr Asn Ile Asp Gly Asn
465                 470                 475                 480

Ile Trp Asn Asp Ala Val Thr Arg Ala Tyr Leu Phe Asp Val Pro Leu
                485                 490                 495

Ala Val Glu Tyr Val Glu Arg Val Ala Arg Asp Gly Val His Pro Lys
            500                 505                 510

Ser Trp Ala Phe Gln Gln Leu Asp Gly Lys Gly Glu Arg Trp Leu Ala
        515                 520                 525

Lys Phe Gly Gln Glu Tyr Cys Lys Gly Leu Ile Arg Phe Lys Lys Lys
    530                 535                 540

Leu Asn Asp Leu Leu Glu Pro Tyr Gly Glu Asn
545                 550                 555

<210> SEQ ID NO 56
<211> LENGTH: 1665
<212> TYPE: DNA
<213> ORGANISM: Artificial sequence
<220> FEATURE:
<223> OTHER INFORMATION: PTD3/alpha-defensin/Bzx2gp11

<400> SEQUENCE: 56
tatgcacgca aagcgagacg acaagcccgt cgcgactgct attgtcgcat ccctgcatgt      60
atagcaggtg agcgtcggta cgggacatgc atttatcaag gtaggttatg gcttttttgt    120
tgcatgacgg agaaggtttt gccttacgat cgtagtatag ttacccagga aaccggctgg    180

```
tggtgtggac cagcagccac gcaggtggtc ttgaatagca ggggcatcat tgtgccagag    240
gcgactcttg ccgctgaaat tgaggctatc gagaatccag ggaggggaga tgacagagat    300
ggtactgatt acgtaggctt aatagaacag gtccttgatc gacgtgtgcc tcaagctagg    360
tatacgtctg tttatttaac aaacgatccc ccaactcaag cgcagaaaga ccgcttatgg    420
gaacacatag tacggagcat caatgcgggt tacggcgttg tcatgaactg ggtggcccca    480
ccttctaaca aacccgtggg ggtcaagggt tccgtatctc cccggtattc aggcggaact    540
acatatcatt atgtcgcttg catgggttac gacgatacac cgggagccag agctgtatgg    600
atagcagatt ccgcgattcca acctcagggc tattggatta gtttcgacca gtgcgctacg    660
ttaataccgc ctaagggata tgcctacgca gacgccgctc cggcggctcc cgcaccagca    720
ccgacgccgg tagttgacgc cgcaccgatt tggcgagggg ctgcggggat aagtgaagcg    780
aaagcacgag agatcttacc cactatgcga gacggcctta agcaggcgga ctgcacaacg    840
gtaaacagga tcgcgatgtt tatagctcaa accgggcatg aaagcgatga cttcagggca    900
accgaggaat acgctaatgg tccacttgat caagagcggt ggatttacaa aggcagaacc    960
tggatacaaa ttacgtggcg cgagcactac gcccgatttg ggaagtggtg ttttgatcgg   1020
ggtctcgtca cagatccaga tgtgtttgtg aaaaacccca gagctttggc agacctcaaa   1080
tgggcgggga tcggcgcagc ctggtactgg actgtcgagc gtccggatat taatgcgctg   1140
tgtgacagac gagatattga gaccgtctcg cgacggatca atggaacaaa tcccaataca   1200
gggcgcgcta accatattga agagcgcata gcccggtgga acagagctct ggcagttgga   1260
gacgatctcc tgcaactgat ccgcgaggaa gaggacgggt ttctgtcagc tctaacccca   1320
gcggaacaaa gagcgcttta caacgagatc atgaagaaag ggcctactcg ttcattcatg   1380
gccgaagacc agaatcagat agaaacgcta ttgggctttg tatataacat tgacggtaat   1440
atctggaacg atgccgtaac tcgggcgtat ctattcgacg tgccgctagc cgttgaatac   1500
gtggaaagag ttgcacgaga cggagtacac cctaagtcgt gggcattcca acagctcgat   1560
ggtaaaggag agaggtggct agccaaattc ggtcaggaat actgtaaggg acttatacgt   1620
tttaagaaaa agctcaacga tttgctagaa ccctatgggg aaaat                   1665
```

<210> SEQ ID NO 57
<211> LENGTH: 585
<212> TYPE: PRT
<213> ORGANISM: Artificial sequence
<220> FEATURE:
<223> OTHER INFORMATION: PTD3/alpha-defensin/bzx2gp11/alpha-defensin

<400> SEQUENCE: 57

```
Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30

Gln Gly Arg Leu Trp Ala Phe Cys Cys Met Thr Glu Lys Val Leu Pro
        35                  40                  45

Tyr Asp Arg Ser Ile Val Thr Gln Glu Thr Gly Trp Trp Cys Gly Pro
    50                  55                  60

Ala Ala Thr Gln Val Val Leu Asn Ser Arg Gly Ile Ile Val Pro Glu
65                  70                  75                  80

Ala Thr Leu Ala Ala Glu Ile Glu Ala Ile Glu Asn Pro Gly Arg Gly
                85                  90                  95
```

```
Asp Asp Arg Asp Gly Thr Asp Tyr Val Gly Leu Ile Glu Gln Val Leu
            100                 105                 110

Asp Arg Arg Val Pro Gln Ala Arg Tyr Thr Ser Val Tyr Leu Thr Asn
        115                 120                 125

Asp Pro Pro Thr Gln Ala Gln Lys Asp Arg Leu Trp Glu His Ile Val
    130                 135                 140

Arg Ser Ile Asn Ala Gly Tyr Gly Val Val Met Asn Trp Val Ala Pro
145                 150                 155                 160

Pro Ser Asn Lys Pro Arg Gly Val Lys Gly Ser Val Ser Pro Arg Tyr
                165                 170                 175

Ser Gly Gly Thr Thr Tyr His Tyr Val Ala Cys Met Gly Tyr Asp Asp
            180                 185                 190

Thr Pro Gly Ala Arg Ala Val Trp Ile Ala Asp Ser Gly Phe Gln Pro
        195                 200                 205

Gln Gly Tyr Trp Ile Ser Phe Asp Gln Cys Ala Thr Leu Ile Pro Pro
    210                 215                 220

Lys Gly Tyr Ala Tyr Ala Asp Ala Ala Pro Ala Ala Pro Ala Pro Ala
225                 230                 235                 240

Pro Thr Pro Val Val Asp Ala Ala Pro Ile Leu Ala Arg Ala Ala Gly
                245                 250                 255

Ile Ser Glu Ala Lys Ala Arg Glu Ile Leu Pro Thr Met Arg Asp Gly
            260                 265                 270

Leu Lys Gln Ala Asp Cys Thr Thr Val Asn Arg Ile Ala Met Phe Ile
        275                 280                 285

Ala Gln Thr Gly His Glu Ser Asp Asp Phe Arg Ala Thr Glu Glu Tyr
    290                 295                 300

Ala Asn Gly Pro Leu Asp Gln Glu Arg Trp Ile Tyr Lys Gly Arg Thr
305                 310                 315                 320

Trp Ile Gln Ile Thr Trp Arg Glu His Tyr Ala Arg Phe Gly Lys Trp
                325                 330                 335

Cys Phe Asp Arg Gly Leu Val Thr Asp Pro Asp Val Phe Val Lys Asn
            340                 345                 350

Pro Arg Ala Leu Ala Asp Leu Lys Trp Ala Gly Ile Gly Ala Ala Trp
        355                 360                 365

Tyr Trp Thr Val Glu Arg Pro Asp Ile Asn Ala Leu Cys Asp Arg Arg
    370                 375                 380

Asp Ile Glu Thr Val Ser Arg Arg Ile Asn Gly Thr Asn Pro Asn Thr
385                 390                 395                 400

Gly Arg Ala Asn His Ile Glu Glu Arg Ile Ala Arg Trp Asn Arg Ala
                405                 410                 415

Leu Ala Val Gly Asp Asp Leu Leu Gln Leu Ile Arg Glu Glu Asp
            420                 425                 430

Gly Phe Leu Ser Ala Leu Thr Pro Ala Glu Gln Arg Ala Leu Tyr Asn
        435                 440                 445

Glu Ile Met Lys Lys Gly Pro Thr Arg Ser Phe Met Ala Glu Asp Gln
    450                 455                 460

Asn Gln Ile Glu Thr Leu Leu Gly Phe Val Tyr Asn Ile Asp Gly Asn
465                 470                 475                 480

Ile Trp Asn Asp Ala Val Thr Arg Ala Tyr Leu Phe Asp Val Pro Leu
                485                 490                 495

Ala Val Glu Tyr Val Glu Arg Val Ala Arg Asp Gly Val His Pro Lys
            500                 505                 510

Ser Trp Ala Phe Gln Gln Leu Asp Gly Lys Gly Glu Arg Trp Leu Ala
```

|  | 515 |  |  | 520 |  |  |  | 525 |  |  |
|---|---|---|---|---|---|---|---|---|---|---|

Lys Phe Gly Gln Glu Tyr Cys Lys Gly Leu Ile Arg Phe Lys Lys
530                     535                     540

Leu Asn Asp Leu Leu Glu Pro Tyr Gly Glu Asn Asp Cys Tyr Cys Arg
545                     550                     555                     560

Ile Pro Ala Cys Ile Ala Gly Glu Arg Arg Tyr Gly Thr Cys Ile Tyr
                565                     570                     575

Gln Gly Arg Leu Trp Ala Phe Cys Cys
                580                     585

<210> SEQ ID NO 58
<211> LENGTH: 1755
<212> TYPE: DNA
<213> ORGANISM: Artificial sequence
<220> FEATURE:
<223> OTHER INFORMATION: PTD3/alpha-defensin/Bzx2gp11/alpha-defensin

<400> SEQUENCE: 58

| tatgctcgta | aggcgcgccg | acaggctcgg | cgcgactgtt | attgtcggat | cccggcgtgc | 60 |
|---|---|---|---|---|---|---|
| attgccggcg | agcgcaggta | cggtacgtgt | atctaccagg | gacggttatg | ggcattttgc | 120 |
| tgtatgaccg | aaaaggtcct | accatacgac | agaagcatcg | tgacacagga | gaccggttgg | 180 |
| tggtgtggtc | ctgcggctac | acaggtggtc | cttaattctc | gaggcattat | agtgccggag | 240 |
| gccactcttg | ccgctgaaat | agaagccatt | gaaaatcccg | ccggggagat | gaccgggac | 300 |
| gggacggact | acgttgggtt | gattgaacaa | gtattggatc | gccgtgtacc | gcaagcgaga | 360 |
| tatacgagtg | tatacctgac | taacgatccc | ccgacgcaag | cacaaaaaga | tcgcctctgg | 420 |
| gaacatatag | ttaggtccat | aaatgcgggt | tatggagtcg | ttatgaactg | ggtagcgccg | 480 |
| ccaagtaata | aaccacgagg | agtcaaaggt | agtgtgtcac | ctcgatactc | aggcgggact | 540 |
| acgtatcact | atgtagcttg | tatgggctac | gacgatacac | caggcgcaag | ggcggtttgg | 600 |
| atagcagatt | cgggcttcca | acctcaagga | tattggatct | cgtttgatca | atgcgcaacc | 660 |
| cttattccgc | caaagggata | tgcgtacgca | gacgctgcgc | ccgcggcacc | agctccggcc | 720 |
| cctactcctg | ttgtagacgc | agcccctata | ttagcacgtg | cagccgggat | ctccgaggca | 780 |
| aaggctcgtg | agatcttgcc | cactatgcga | gacgggctaa | acaggcaga | ctgcacaacc | 840 |
| gttaatagaa | tagccatgtt | catagcccaa | accggtcatg | agagcgacga | ttttcgggcc | 900 |
| acggaggaat | acgctaacgg | tccctggac | caggaaaggt | ggatctataa | ggggagaact | 960 |
| tggatacaga | ttacctggag | ggagcattat | gcgcgtttcg | gcaagtggtg | cttcgaccga | 1020 |
| ggtttggtca | ccgaccctga | cgtctttgtt | aaaaacccac | gcgcactcgc | ggacttgaaa | 1080 |
| tgggctggaa | ttggggcagc | ttggtattgg | accgtagaaa | gacctgatat | caacgccctg | 1140 |
| tgcgaccgga | gagatattga | gacagtatca | aggcgcatca | atggaacgaa | cccaaacact | 1200 |
| gggagggcca | accacattga | agagcgtatc | gctagatgga | atcgtgccct | ggccgtgggc | 1260 |
| gatgacctat | tacaactcat | tcgcgaagag | gaagatggtt | tcttagcgc | gctcacgcct | 1320 |
| gctgaacaaa | gagctctttta | caacgagata | atgaagaaag | acccacacg | atcttttatg | 1380 |
| gcagaggacc | aaaaccagat | cgaaacacta | ttaggtttcg | tctataatat | agatgggaat | 1440 |
| atatggaatg | atgcagtgac | tcgtgcttat | ttattcgatg | tacccttggc | cgtggagtac | 1500 |
| gtcgagaggg | tggcgcggga | tggagttcac | cccaagtctt | gggcctttca | acagctggat | 1560 |
| gggaagggca | agcgttggct | agcaaaattc | ggtcaggaat | actgcaaagg | tttaatccgg | 1620 |
| tttaaaaaga | aactgaacga | tctacttgag | ccatacggcg | aaaatgattg | ttattgtaga | 1680 |

```
ataccggcgt gcattgcggg ggaacgaagg tacggaacat gtatttatca gggacgactc    1740
tgggctttct gctgt                                                    1755
```

<210> SEQ ID NO 59
<211> LENGTH: 341
<212> TYPE: PRT
<213> ORGANISM: Artificial sequence
<220> FEATURE:
<223> OTHER INFORMATION: beta-defensin/L5gp10/TAT47-57

<400> SEQUENCE: 59

```
Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys Met Thr Phe Thr Val Thr Arg Glu Arg Ala
        35                  40                  45

Gln Trp Val His Asp Met Ala Arg Ala Arg Asp Gly Leu Pro Tyr Ala
    50                  55                  60

Tyr Gly Gly Ala Phe Thr Asn Asn Pro Arg Val Ser Thr Asp Cys Ser
65                  70                  75                  80

Gly Leu Val Leu Gln Thr Gly Ala Trp Tyr Gly Arg Thr Asp Trp
                85                  90                  95

Val Gly Asn Arg Tyr Gly Ser Thr Glu Ser Phe Arg Leu Asp His Lys
            100                 105                 110

Ile Val Tyr Asp Leu Gly Phe Lys Arg Met Pro Arg Gly Gly Pro Ala
        115                 120                 125

Ala Leu Pro Ile Lys Pro Val Met Leu Val Gly Leu Gln His Gly Gly
    130                 135                 140

Gly Gly Val Tyr Ser His Thr Ala Cys Thr Leu Met Thr Met Asp His
145                 150                 155                 160

Pro Gly Gly Pro Val Lys Met Ser Asp Arg Gly Val Asp Trp Glu Ser
                165                 170                 175

His Gly Asn Arg Asn Gly Val Gly Val Glu Leu Tyr Glu Gly Ala Arg
            180                 185                 190

Ala Trp Asn Asp Pro Leu Phe His Asp Phe Trp Tyr Leu Asp Ala Val
        195                 200                 205

Leu Glu Asp Glu Gly Asp Asp Glu Leu Ala Asp Pro Val Leu Gly
    210                 215                 220

Lys Met Ile Arg Glu Ile His Ala Cys Leu Phe Asn Gln Thr Ala Ser
225                 230                 235                 240

Thr Ser Asp Leu Ala Thr Pro Gly Glu Gly Ala Ile Trp Gln Leu His
                245                 250                 255

Gln Lys Ile His Ser Ile Asp Gly Met Leu His Pro Ile His Ala Glu
            260                 265                 270

Arg Arg Ala Arg Ala Gly Asp Leu Gly Glu Leu His Arg Ile Val Leu
        275                 280                 285

Ala Ala Lys Gly Leu Gly Val Lys Arg Asp Glu Val Thr Lys Arg Val
    290                 295                 300

Tyr Gln Ser Ile Leu Ala Asp Ile Glu Arg Asp Asn Pro Glu Val Leu
305                 310                 315                 320

Gln Arg Tyr Ile Ala Glu Arg Gly Gly Leu Tyr Gly Arg Lys Lys Arg
                325                 330                 335

Arg Gln Arg Arg Arg
```

<210> SEQ ID NO 60
<211> LENGTH: 1023
<212> TYPE: DNA
<213> ORGANISM: Artificial sequence
<220> FEATURE:
<223> OTHER INFORMATION: beta-defensin/L5gp10/TAT47-57

<400> SEQUENCE: 60

```
aacccggtca gctgtgtcag gaacaaggga atatgtgttc ccattcgctg cccggggagc      60
atgaaacaaa ttggtacatg cgtagggcgt gcggtgaagt gctgtcgaaa gaaaatgacc     120
tttactgtga cacgggaaag ggctcagtgg gtccatgata tggcgcgcgc tagggacggt     180
ctaccttatg catatggagg ggcgtttacg aataacccac gctttcgac agactgttcg      240
ggcctggtcc tgcagactgg agcatggtat ggtggccgaa cagattgggt tgggaatcga     300
tatgggtcta cggagtcatt tagactcgac cataaaattg tatatgattt aggttttaaa     360
cgtatgcctc ggggggggacc ggcagctctg cccatcaagc cagtaatgtt agtaggtcta    420
caacacggcg gtggagggggt gtactcccat actgcgtgca cgttaatgac catggaccat    480
ccaggcgggc cagtgaaaat gtctgatcgt ggagtagact gggaaagtca tgggaaccgc    540
aacggagttg gcgttgaact gtacgagggc gcccgggctt ggaatgatcc cttgttccac    600
gatttctggt acttggatgc cgtattggag atgaggggtg acgatgacga gctagccgat    660
ccggtccttg gcaaaatgat acgagagatc cacgcctgtt tattcaatca aaccgcttcc    720
actagtgatt tggcgacccc tggcgaaggt gccatatggc agctccatca gaagatccac    780
tcaatcgacg gtatgcttca ccctatccac gccgagagaa gggcacgcgc aggagactta    840
ggagaactac atagaatagt gctcgctgcg aaagggcttg gcgttaagcg ggacgaggtc    900
acgaagcgtg tataccaaag tattttggca gatattgaaa gagacaatcc gaagtgctt    960
cagagataca tagcagaaag gggaggcctc tatggtagaa agaaacgaag gcaacgtcga   1020
cgg                                                                 1023
```

<210> SEQ ID NO 61
<211> LENGTH: 370
<212> TYPE: PRT
<213> ORGANISM: Artificial sequence
<220> FEATURE:
<223> OTHER INFORMATION: alpha-defensin/Hepcidin/L5gp10/TAT47-57

<400> SEQUENCE: 61

```
Asn Pro Val Ser Cys Val Arg Asn Lys Gly Ile Cys Val Pro Ile Arg
  1               5                  10                  15

Cys Pro Gly Ser Met Lys Gln Ile Gly Thr Cys Val Gly Arg Ala Val
             20                  25                  30

Lys Cys Cys Arg Lys Lys Gly Ala Gly Ala Asp Thr His Phe Pro Ile
         35                  40                  45

Cys Ile Phe Cys Cys Gly Cys Cys His Arg Ser Lys Cys Gly Met Cys
     50                  55                  60

Cys Lys Thr Met Thr Phe Thr Val Thr Arg Glu Arg Ala Gln Trp Val
 65                  70                  75                  80

His Asp Met Ala Arg Ala Arg Asp Gly Leu Pro Tyr Ala Tyr Gly Gly
                 85                  90                  95

Ala Phe Thr Asn Asn Pro Arg Val Ser Thr Asp Cys Ser Gly Leu Val
            100                 105                 110
```

```
Leu Gln Thr Gly Ala Trp Tyr Gly Gly Arg Thr Asp Trp Val Gly Asn
            115                 120                 125

Arg Tyr Gly Ser Thr Glu Ser Phe Arg Leu Asp His Lys Ile Val Tyr
        130                 135                 140

Asp Leu Gly Phe Lys Arg Met Pro Arg Gly Pro Ala Ala Leu Pro
145                 150                 155                 160

Ile Lys Pro Val Met Leu Val Gly Leu Gln His Gly Gly Gly Val
                165                 170                 175

Tyr Ser His Thr Ala Cys Thr Leu Thr Met Asp His Pro Gly Gly
            180                 185                 190

Pro Val Lys Met Ser Asp Arg Gly Val Asp Trp Glu Ser His Gly Asn
        195                 200                 205

Arg Asn Gly Val Gly Val Glu Leu Tyr Glu Gly Ala Arg Ala Trp Asn
    210                 215                 220

Asp Pro Leu Phe His Asp Phe Trp Tyr Leu Asp Ala Val Leu Glu Asp
225                 230                 235                 240

Glu Gly Asp Asp Asp Glu Leu Ala Asp Pro Val Leu Gly Lys Met Ile
                245                 250                 255

Arg Glu Ile His Ala Cys Leu Phe Asn Gln Thr Ala Ser Thr Ser Asp
            260                 265                 270

Leu Ala Thr Pro Gly Glu Gly Ala Ile Trp Gln Leu His Gln Lys Ile
        275                 280                 285

His Ser Ile Asp Gly Met Leu His Pro Ile His Ala Glu Arg Arg Ala
    290                 295                 300

Arg Ala Gly Asp Leu Gly Glu Leu His Arg Ile Val Leu Ala Ala Lys
305                 310                 315                 320

Gly Leu Gly Val Lys Arg Asp Glu Val Thr Lys Arg Val Tyr Gln Ser
                325                 330                 335

Ile Leu Ala Asp Ile Glu Arg Asp Asn Pro Glu Val Leu Gln Arg Tyr
            340                 345                 350

Ile Ala Glu Arg Gly Gly Leu Tyr Gly Arg Lys Lys Arg Gln Arg
        355                 360                 365

Arg Arg
    370

<210> SEQ ID NO 62
<211> LENGTH: 1110
<212> TYPE: DNA
<213> ORGANISM: Artificial sequence
<220> FEATURE:
<223> OTHER INFORMATION: alpha-defensin/Hepcidin/L5gp10/TAT47-57

<400> SEQUENCE: 62
aatcctgtta gctgcgttcg caataaaggc atctgtgtgc aatacgatg tccaggtagt      60 atgaaacaaa tcggaacatg cgtgggaaga gccgttaagt gttgccggaa gaaaggagct    120
ggtgcggata cacacttccc aatatgcatt ttctgttgcg ggtgttgcca tcgttctaaa    180
tgtggtatgt gctgtaagac catgacattt acggtaacac gggagcgagc ccaatgggta    240
catgacatgg cgcgcgccag agatggatta ccgtacgcat acggcggtgc atttacaaac    300
aatccgaggg tatccaccga ctgttctggg ctcgtattac aaacgggcgc gtggtacggt    360
ggcaggacgg attgggtagg gaaccggtat ggaagcactg agtcgtttag attggaccac    420
aagatagtgt atgacctcgg ctttaaaaga atgccccggg gaggccctgc tgcgttaccc    480
atcaagccag tcatgttagt tgggctacag cacggtggag gcggggtcta ttcacacacg    540
```

-continued

```
gcttgcactt taatgactat ggaccatccc gggggccccg ttaagatgag cgaccgtggg    600
gtcgattggg agtcccatgg aaatcgcaac ggggtaggtg tggaattgta tgaaggcgca    660
agagcctgga acgacccgct cttccatgat ttctggtatc ttgatgcggt tttggaagac    720
gagggcgatg acgatgaact agctgatcca gtgctgggta agatgatacg tgaaatccat    780
gcatgtctat ttaaccagac tgcatcgacc tcagacctcg cgactcctgg agagggagca    840
atatggcaac tgcaccagaa atccacagt attgatggga tgctgcaccc tattcatgcg    900
gaacgtaggg ctagggccgg tgatttgggt gagctacatc gaattgtctt ggctgccaaa    960
gggcttggag tcaagcggga cgaggtgacc aaacgcgtat accagagtat tctggcagat   1020
attgaaaggg acaatccgga agtccttcaa cgatatatag ctgagcgtgg cggtctttac   1080
gggcgaaaga aacgtaggca gcgccgaaga                                    1110
```

<210> SEQ ID NO 63
<211> LENGTH: 456
<212> TYPE: PRT
<213> ORGANISM: Artificial sequence
<220> FEATURE:
<223> OTHER INFORMATION: TM4gp30/LL-37/TAT47-57

<400> SEQUENCE: 63

```
Met Ala Trp Val Gly Trp Gln Leu Gly Met Gln Gly Glu Gln Val Lys
1               5                   10                  15

Val Ile Gln Gln Lys Leu Ile Ala Lys Tyr Gln Trp Val Arg Asp Arg
            20                  25                  30

Tyr Pro Arg Leu Thr Ala Ser Gly Val Tyr Asp Val Asn Thr Gln Ala
        35                  40                  45

Ala Ile Val Glu Phe Gln Phe Arg Ala Gly Leu Pro Val Thr Gly Ile
    50                  55                  60

Ala Asp Tyr Ala Thr Gln Val Arg Leu Gly Ala Val Ala Pro Ala Pro
65                  70                  75                  80

Pro Pro Arg Gln Arg Ile Met Val Leu Thr Phe Ser Gly Thr Ser Ala
                85                  90                  95

Asp Met Trp Thr Gly Tyr Pro Ala Asp Val Ala Arg Ala Leu Asp Pro
            100                 105                 110

Ser Ile Phe Tyr Trp Gln Pro Val Cys Tyr Gly Pro Asn Gly Ile Pro
        115                 120                 125

Ala Ile Phe Pro Met Gly Ser Ser Ala Lys Ser Gly Glu Val Glu Gly
    130                 135                 140

Leu Arg Leu Leu Asp Glu Lys Ala Arg Asp Phe Asp Tyr Ile Val Leu
145                 150                 155                 160

Ile Gly Tyr Ser Gln Gly Ala Leu Pro Ala Ser Arg Leu Met Arg Arg
                165                 170                 175

Ile Leu Ser Gly Asp Leu Gln Arg Phe Lys Ser Lys Leu Ile Ala Gly
            180                 185                 190

Val Thr Phe Gly Asn Pro Met Arg Glu Lys Gly His Thr Phe Pro Gly
        195                 200                 205

Gly Ala Asp Pro Gly Gly His Gly Leu Asp Pro Gln Cys Leu Val Asn
    210                 215                 220

Thr Pro Asp Trp Trp His Asp Tyr Ala Ala Lys Gly Asp Ile Tyr Thr
225                 230                 235                 240

Val Gly Ser Gly Ser Asn Asp Glu Lys Ala Asn Ala Asp Met Thr Phe
                245                 250                 255

Ile Tyr Gln Leu Val Gln Gly Asp Ile Leu Gly Met Met Phe Gly Thr
```

```
                260                 265                 270
Gly Asn Pro Leu Asp Ile Leu Gly Leu Leu Gly Leu Gly Gly Gly
            275                 280                 285
Leu Leu Gly Gly Leu Gly Gly Gly Leu Leu Gly Gly Lys Gly Gly
            290                 295                 300
Leu Gln Leu Pro Ser Gly Leu Val Leu Pro Gly Val Gln Gly Gly Ala
305                 310                 315                 320
Leu Thr Asp His Gln Arg Gly Leu Val Glu Ala Val Leu Ala Leu Leu
                325                 330                 335
Ala Asn Pro Phe Ala Glu Val Pro Ala Ala Val Lys Ala Ile Val Ser
                340                 345                 350
Gly Val Gly Phe Ile Ala Thr Asn Pro Pro Thr Ala Pro His Ile Glu
                355                 360                 365
Tyr His Ile Arg Glu Ala Ala Pro Gly Val Thr Tyr Phe Gln His Ala
                370                 375                 380
Ile Asp Tyr Leu Arg Gln Val Gly Ala Ser Val Ala Ala Arg Ala Ala
385                 390                 395                 400
Gly Ser Gly Ser Leu Leu Gly Asp Phe Phe Arg Lys Ser Lys Glu Lys
                405                 410                 415
Ile Gly Lys Glu Phe Lys Arg Ile Val Gln Arg Ile Lys Asp Phe Leu
                420                 425                 430
Arg Asn Leu Val Pro Arg Thr Glu Ser Gly Ala Gly Ala Tyr Gly Arg
                435                 440                 445
Lys Lys Arg Arg Gln Arg Arg
    450                 455

<210> SEQ ID NO 64
<211> LENGTH: 1368
<212> TYPE: DNA
<213> ORGANISM: Artificial sequence
<220> FEATURE:
<223> OTHER INFORMATION: TM4gp30/LL-37/TAT47-57

<400> SEQUENCE: 64
atggcttggg tcggctggca gcttggtatg cagggtgaac aggttaaggt aatccagcaa      60
aagttgatag ccaagtacca gtgggtgcgt gatagatatc cccggttgac cgcaagtggg     120
gtttacgacg tcaacaccca agcagcgatt gttgagtttc aatttagagc cggacttcca     180
gtcacgggca tagccgacta tgcgacacag gtgcggcttg agctgtcgc accagctcca     240
cccctaggc aacggattat ggtactcaca tttagcggga cgtcggctga tatgtggaca     300
ggctacccgg ctgacgttgc aagagcccta gatccttcaa tttttttattg caacccgtt     360
tgttatggcc caaacggtat tcccgcgata ttcccgatgg ggtcgagtgc caagtccggg     420
gaagttgaag gcttgcgact attagacgag aaagctcgcg atttcgacta cattgtcctg     480
atcgggtata gtcagggtgc gttgcctgcg agcaggttga tgcgtcgcat cctatcaggt     540
gatctgcaaa ggttcaaatc aaaactgata gcaggagtga cgtttgggaa cccgatgcga     600
gaaaaaggtc acacctttcc tggcggggct gacccgggtg ccacggcttt agacccacag     660
tgcctcgtga atactccgga ttggtggcac gactacgcgg ccaaaggcga tatctacaca     720
gtaggttctg gatctaatga tgagaaggcc aatgcggaca tgactttcat atatcaatta     780
gtccaaggag acatactcgg tatgatgttc ggtacgggta acccttttgga tatattaggg     840
ttgctggag gctagcggg aggtctactt ggaggcctag gtgggggctt gcttggaggt     900
ggaaagggg gattacaact gcctagcgga cttgtttac ctggggttca gggggtgca     960
```

```
ttaaccgacc atcaacgtgg acttgtagaa gcggtgctgg ctttactcgc aaatcccttc    1020
gcggaagtac ccgccgcggt gaaggcaatc gtaagtggcg tcggtttcat cgccactaat    1080
ccgccaactg ccccacatat tgagtaccat attagggagg cagctcccgg cgtgacatat    1140
ttccaacatg caatcgatta tctcaggcaa gtcggagcct ccgtggctgc acgggctgcg    1200
ggatctggat cactactggg agatttttt cgaaagtcta aagagaaaat agggaaagaa     1260
tttaagcgaa ttgtacagcg catcaaggat tttctacgaa acctcgtacc gcgtactgag    1320
agcggggcag gggcttacgg tcgcaaaaaa cgccggcaga gacgtaga                 1368
```

<210> SEQ ID NO 65
<211> LENGTH: 448
<212> TYPE: PRT
<213> ORGANISM: Artificial sequence
<220> FEATURE:
<223> OTHER INFORMATION: TM4gp30/LL-37/TAT47-57

<400> SEQUENCE: 65

```
Met Ala Trp Val Gly Trp Gln Leu Gly Met Gln Gly Glu Gln Val Lys
1               5                   10                  15

Val Ile Gln Gln Lys Leu Ile Ala Lys Tyr Gln Trp Val Arg Asp Arg
            20                  25                  30

Tyr Pro Arg Leu Thr Ala Ser Gly Val Tyr Asp Val Asn Thr Gln Ala
        35                  40                  45

Ala Ile Val Glu Phe Gln Phe Arg Ala Gly Leu Pro Val Thr Gly Ile
    50                  55                  60

Ala Asp Tyr Ala Thr Gln Val Arg Leu Gly Ala Val Ala Pro Ala Pro
65                  70                  75                  80

Pro Pro Arg Gln Arg Ile Met Val Leu Thr Phe Ser Gly Thr Ser Ala
                85                  90                  95

Asp Met Trp Thr Gly Tyr Pro Ala Asp Val Ala Arg Ala Leu Asp Pro
            100                 105                 110

Ser Ile Phe Tyr Trp Gln Pro Val Cys Tyr Gly Pro Asn Gly Ile Pro
        115                 120                 125

Ala Ile Phe Pro Met Gly Ser Ser Ala Lys Ser Gly Glu Val Glu Gly
    130                 135                 140

Leu Arg Leu Leu Asp Glu Lys Ala Arg Asp Phe Asp Tyr Ile Val Leu
145                 150                 155                 160

Ile Gly Tyr Ser Gln Gly Ala Leu Pro Ala Ser Arg Leu Met Arg Arg
                165                 170                 175

Ile Leu Ser Gly Asp Leu Gln Arg Phe Lys Ser Lys Leu Ile Ala Gly
            180                 185                 190

Val Thr Phe Gly Asn Pro Met Arg Glu Lys Gly His Thr Phe Pro Gly
        195                 200                 205

Gly Ala Asp Pro Gly Gly His Gly Leu Asp Pro Gln Cys Leu Val Asn
    210                 215                 220

Thr Pro Asp Trp Trp His Asp Tyr Ala Ala Lys Gly Asp Ile Tyr Thr
225                 230                 235                 240

Val Gly Ser Gly Ser Asn Asp Glu Lys Ala Asn Ala Asp Met Thr Phe
                245                 250                 255

Ile Tyr Gln Leu Val Gln Gly Asp Ile Leu Gly Met Met Phe Gly Thr
            260                 265                 270

Gly Asn Pro Leu Asp Ile Leu Gly Leu Leu Gly Leu Gly Gly Gly
        275                 280                 285
```

```
Leu Leu Gly Gly Leu Gly Gly Gly Leu Leu Gly Gly Gly Lys Gly Gly
    290                 295                 300

Leu Gln Leu Pro Ser Gly Leu Val Leu Pro Gly Val Gln Gly Gly Ala
305                 310                 315                 320

Leu Thr Asp His Gln Arg Gly Leu Val Glu Ala Val Leu Ala Leu Leu
                325                 330                 335

Ala Asn Pro Phe Ala Glu Val Pro Ala Ala Val Lys Ala Ile Val Ser
                340                 345                 350

Gly Val Gly Phe Ile Ala Thr Asn Pro Pro Thr Ala Pro His Ile Glu
                355                 360                 365

Tyr His Ile Arg Glu Ala Ala Pro Gly Val Thr Tyr Phe Gln His Ala
    370                 375                 380

Ile Asp Tyr Leu Arg Gln Val Gly Ala Ser Val Ala Ala Arg Ala Ala
385                 390                 395                 400

Leu Leu Gly Asp Phe Phe Arg Lys Ser Lys Glu Lys Ile Gly Lys Glu
                405                 410                 415

Phe Lys Arg Ile Val Gln Arg Ile Lys Asp Phe Leu Arg Asn Leu Val
                420                 425                 430

Pro Arg Thr Glu Ser Tyr Gly Arg Lys Lys Arg Arg Gln Arg Arg
                435                 440                 445

<210> SEQ ID NO 66
<211> LENGTH: 1344
<212> TYPE: DNA
<213> ORGANISM: Artificial sequence
<220> FEATURE:
<223> OTHER INFORMATION: TM4gp30/LL-37/TAT47-57

<400> SEQUENCE: 66
atggcctggg ttggctggca gttaggaatg cagggtgaac aggtgaaggt aatacagcaa        60
aaacttatag ccaagtacca gtgggtcagg gatagatatc cccgcctaac cgcgagtggg       120
gtttacgacg tgaatactca ggcagctatc gttgagttcc aatttagagc tggcctacca       180
gtaactggta tagcagacta tgctactcaa gtgcggttag gggcggtcgc gcctgctccg       240
ccaccccgtc aacgaatcat ggtactgaca ttttcaggca catcagcgga tatgtggact       300
ggatatcccg cagacgtcgc gagggctctt gacccctcaa tattctattg cagcccgtg        360 tgctacgggc ccaacggaat tccggccata ttccctatgg ggtcctctgc aaaatctggc       420
gaggttgagg gtttgcgtct actggacgaa aaagcccgag actttgatta catagtgctg       480
ataggttata gtcaaggagc gctcccggcg agtaggttaa tgcggcgaat tctgagcggc       540
gatctccaac ggtttaaaag caagcttatc gcaggtgtaa cctttgggaa tcctatgcgg       600
gagaagggac atacatttcc tggaggtgcc gacccaggtg gacacggctt agatcctcaa       660
tgtctcgtca atacccccgga ttggtggcac gattacgccg cgaagggaga tatctacaca       720
gttggaagcg gtagcaatga cgaaaaagct aacgcggaca tgacatttat ttatcagctg       780 gtgcagggg acatcctagg catgatgttc ggaacgggta accctctgga tatattgggt       840
cttctcgggg gcttaggcgg gggcttattg gcggtctag gggcggtct tctgggcgga         900 gggaagggag gtctacagtt accctctgga ctagtgttgc cggggtaca aggaggtgct        960 ttgactgatc atcagagagg gcttgtagaa gcagtcctcg ctttgctcgc caatccgttt      1020
gctgaagttc cagcggccgt taaggccatt gtgtccggcg tcggattcat cgcaacgaac      1080
ccacctaccg caccgcatat cgaatatcat attcgcgagg cagccccagg ggtcacgtat      1140
ttccaacacg cgattgatta cttgagacaa gtaggggcct cggttgcagc tcgtgctgca      1200
```

```
ttacttggtg attttttccg caaatcgaag gagaagattg gtaaagaatt caaacgtatc    1260
gtccaacgca ttaaagactt cctacgaaac ttggtaccaa ggacggagag ttacggacgc    1320
aaaaagcggc gacaaaggag acgt                                          1344
```

<210> SEQ ID NO 67
<211> LENGTH: 295
<212> TYPE: PRT
<213> ORGANISM: Artificial sequence
<220> FEATURE:
<223> OTHER INFORMATION: D29gp12/alpha-defensin/PTD3

<400> SEQUENCE: 67

```
Met Ser Lys Pro Trp Leu Phe Thr Val His Gly Thr Gly Gln Pro Asp
1               5                   10                  15

Pro Leu Gly Pro Gly Leu Pro Ala Asp Thr Ala Arg Asp Val Leu Asp
            20                  25                  30

Ile Tyr Arg Trp Gln Pro Ile Gly Asn Tyr Pro Ala Ala Ala Phe Pro
        35                  40                  45

Met Trp Pro Ser Val Glu Lys Gly Val Ala Glu Leu Ile Leu Gln Ile
50                  55                  60

Glu Leu Lys Leu Asp Ala Asp Pro Tyr Ala Asp Phe Ala Met Ala Gly
65                  70                  75                  80

Tyr Ser Gln Gly Ala Ile Val Val Gly Gln Val Leu Lys His His Ile
                85                  90                  95

Leu Pro Pro Thr Gly Arg Leu His Arg Phe Leu His Arg Leu Lys Lys
            100                 105                 110

Val Ile Phe Trp Gly Asn Pro Met Arg Gln Lys Gly Phe Ala His Ser
        115                 120                 125

Asp Glu Trp Ile His Pro Val Ala Ala Pro Asp Thr Leu Gly Ile Leu
130                 135                 140

Glu Asp Arg Leu Glu Asn Leu Glu Gln Tyr Gly Phe Glu Val Arg Asp
145                 150                 155                 160

Tyr Ala His Asp Gly Asp Met Tyr Ala Ser Ile Lys Glu Asp Asp Leu
                165                 170                 175

His Glu Tyr Glu Val Ala Ile Gly Arg Ile Val Met Lys Ala Ser Gly
            180                 185                 190

Phe Ile Gly Gly Arg Asp Ser Val Val Ala Gln Leu Ile Glu Leu Gly
        195                 200                 205

Gln Arg Pro Ile Thr Glu Gly Ile Ala Leu Ala Gly Ala Ile Ile Asp
210                 215                 220

Ala Leu Thr Phe Phe Ala Arg Ser Arg Met Gly Asp Lys Trp Pro His
225                 230                 235                 240

Leu Tyr Asn Arg Tyr Pro Ala Val Glu Phe Leu Arg Gln Ile Asp Cys
                245                 250                 255

Tyr Cys Arg Ile Pro Ala Cys Ile Ala Gly Glu Arg Tyr Gly Thr
            260                 265                 270

Cys Ile Tyr Gln Gly Arg Leu Trp Ala Phe Cys Cys Tyr Ala Arg Lys
        275                 280                 285

Ala Arg Arg Gln Ala Arg Arg
    290                 295
```

<210> SEQ ID NO 68
<211> LENGTH: 885
<212> TYPE: DNA
<213> ORGANISM: Artificial sequence
<220> FEATURE:
<223> OTHER INFORMATION: D29gp12/alpha-defensin/PTD3

<400> SEQUENCE: 68

| | | | | | |
|---|---|---|---|---|---|
| atgagtaaac | cttggctatt | cacagtgcac | ggtacgggtc | agcctgaccc | actaggtcct | 60 |
| gggcttccag | cagatactgc | gcgcgatgtg | ctcgacattt | atcgctggca | acccatcgga | 120 |
| aattatcctg | cagcggcttt | tccgatgtgg | ccgtccgttg | aaaaagggt | agcagagctc | 180 |
| atattacaga | tcgaactgaa | attggatgct | gacccgtatg | cagattttgc | gatggcgggg | 240 |
| tatagccagg | gagccatcgt | tgtgggccaa | gttcttaagc | accatattct | accaccgacc | 300 |
| ggacgtctcc | ataggttcct | gcatcgttta | aaaaaggtca | ttttttgggg | caaccccatg | 360 |
| cggcaaaagg | gtttcgctca | ctcggatgag | tggatccacc | cagtagctgc | acccgacacg | 420 |
| ttaggtatcc | tggaggatcg | tctggagaac | ttagagcagt | acggatttga | agtcagagac | 480 |
| tacgctcatg | atggtgatat | gtatgcgagc | attaaggaag | acgatcttca | tgagtacgaa | 540 |
| gtggcgatag | cagaatagt | tatgaaagcc | tctggattta | tcggcgggag | ggatagtgtc | 600 |
| gtagcccaat | tgattgaatt | gggccaacgg | cccataactg | agggtattgc | cctagctgga | 660 |
| gctataatcg | acgcattaac | cttctttgcc | cgatcacgga | tgggcgacaa | atggccacac | 720 |
| ctctataata | gatacccctgc | ggtagaattc | cttcgtcaga | ttgactgtta | ctgccgcata | 780 |
| ccggcgtgca | tagcagggga | aaggcgctac | gggacatgca | tatatcaggg | acgattgtgg | 840 |
| gccttctgtt | gttacgccag | gaaggcacga | agacaagctc | gacgg | | 885 |

<210> SEQ ID NO 69
<211> LENGTH: 295
<212> TYPE: PRT
<213> ORGANISM: Artificial sequence
<220> FEATURE:
<223> OTHER INFORMATION: PTD3/alpha-defensin/D29gp12

<400> SEQUENCE: 69

Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30

Gln Gly Arg Leu Trp Ala Phe Cys Cys Met Ser Lys Pro Trp Leu Phe
        35                  40                  45

Thr Val His Gly Thr Gly Gln Pro Asp Pro Leu Gly Pro Gly Leu Pro
    50                  55                  60

Ala Asp Thr Ala Arg Asp Val Leu Asp Ile Tyr Arg Trp Gln Pro Ile
65                  70                  75                  80

Gly Asn Tyr Pro Ala Ala Ala Phe Pro Met Trp Pro Ser Val Glu Lys
                85                  90                  95

Gly Val Ala Glu Leu Ile Leu Gln Ile Glu Leu Lys Leu Asp Ala Asp
            100                 105                 110

Pro Tyr Ala Asp Phe Ala Met Ala Gly Tyr Ser Gln Gly Ala Ile Val
        115                 120                 125

Val Gly Gln Val Leu Lys His His Ile Leu Pro Pro Thr Gly Arg Leu
    130                 135                 140

His Arg Phe Leu His Arg Leu Lys Lys Val Ile Phe Trp Gly Asn Pro
145                 150                 155                 160

Met Arg Gln Lys Gly Phe Ala His Ser Asp Glu Trp Ile His Pro Val
                165                 170                 175

Ala Ala Pro Asp Thr Leu Gly Ile Leu Glu Asp Arg Leu Glu Asn Leu

```
                180              185              190
Glu Gln Tyr Gly Phe Glu Val Arg Asp Tyr Ala His Asp Gly Asp Met
            195              200              205

Tyr Ala Ser Ile Lys Glu Asp Asp Leu His Glu Tyr Glu Val Ala Ile
        210              215              220

Gly Arg Ile Val Met Lys Ala Ser Gly Phe Ile Gly Arg Asp Ser
225              230              235              240

Val Val Ala Gln Leu Ile Glu Leu Gly Gln Arg Pro Ile Thr Glu Gly
            245              250              255

Ile Ala Leu Ala Gly Ala Ile Ile Asp Ala Leu Thr Phe Phe Ala Arg
                260              265              270

Ser Arg Met Gly Asp Lys Trp Pro His Leu Tyr Asn Arg Tyr Pro Ala
        275              280              285

Val Glu Phe Leu Arg Gln Ile
        290              295
```

<210> SEQ ID NO 70
<211> LENGTH: 885
<212> TYPE: DNA
<213> ORGANISM: Artificial sequence
<220> FEATURE:
<223> OTHER INFORMATION: PTD3/alpha-defensin/D29gp12

<400> SEQUENCE: 70

```
tacgcacgga aggctcgcag acaggcccgc agagactgtt attgtcgtat accagcgtgt      60
atcgctgggg agaggcgtta tggcacgtgc atctaccaag ggaggctgtg ggcgttttgc     120
tgcatgagca aaccatggct ctttacggta cacggtactg acaaccaga cccgctaggc      180
ccaggactac ccgcggatac agccagagat gtattagata tttatcggtg caaccgata      240
ggaaactacc ccgctgcagc tttcccaatg tggcctagtg ttgaaaaagg tgtcgccgaa     300
ctgattcttc aaattgaact caaattagac gcggacccct tatgctgatt tgcgatggca     360
ggatattcac agggcgcaat agtcgtgggt caagtgttga agcatcacat cctgccccg      420
accggtcggt tacacagatt tttgcacagg ctaaagaaag ttatttctg gggtaatcct      480
atgcgccaaa aagggtttgc gcattccgac gagtggatac atccggttgc tgcccctgac    540
actcttggca tccttgagga tcgattggag aacttggaac agtacgggtt cgaagtacga     600
gattacgccc atgatggcga tatgtacgca agcattaagg aggatgacct ccacgagtat     660
gaggtcgcaa ttggaaggat cgtgatgaaa gcaagtggat tcataggtgg acgcgactcg     720
gtggttgccc agttaattga actcggtcag cgaccgataa cagaaggcat cgctctggcc     780
ggggctataa tcgacgcatt aacctttttc gcgcggtctc gtatggggga taagtggccc     840
catctttata atcgataccc tgcggtagaa ttcctacgtc agata                     885
```

<210> SEQ ID NO 71
<211> LENGTH: 325
<212> TYPE: PRT
<213> ORGANISM: Artificial sequence
<220> FEATURE:
<223> OTHER INFORMATION: PTD3/alpha-defensin/D29gp12/alpha-defensin

<400> SEQUENCE: 71

```
Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30
```

```
Gln Gly Arg Leu Trp Ala Phe Cys Cys Met Ser Lys Pro Trp Leu Phe
         35                  40                  45

Thr Val His Gly Thr Gly Gln Pro Asp Pro Leu Gly Pro Gly Leu Pro
 50                  55                  60

Ala Asp Thr Ala Arg Asp Val Leu Asp Ile Tyr Arg Trp Gln Pro Ile
 65                  70                  75                  80

Gly Asn Tyr Pro Ala Ala Ala Phe Pro Met Trp Pro Ser Val Glu Lys
                 85                  90                  95

Gly Val Ala Glu Leu Ile Leu Gln Ile Glu Leu Lys Leu Asp Ala Asp
                100                 105                 110

Pro Tyr Ala Asp Phe Ala Leu Ala Gly Tyr Ser Gln Gly Ala Ile Val
            115                 120                 125

Val Gly Gln Val Leu Lys His His Ile Ile Asn Pro Arg Gly Arg Leu
130                 135                 140

His Arg Phe Leu His Arg Leu Arg Lys Val Ile Phe Trp Gly Asn Pro
145                 150                 155                 160

Met Arg Gln Lys Gly Phe Ala His Thr Asp Glu Trp Ile His Gln Val
                165                 170                 175

Ala Ala Ser Asp Thr Met Gly Ile Leu Glu Asp Arg Leu Glu Asn Leu
            180                 185                 190

Glu Gln Tyr Gly Phe Glu Val Arg Asp Tyr Ala His Asp Gly Asp Met
        195                 200                 205

Tyr Ala Ser Ile Lys Glu Asp Asp Met His Glu Tyr Glu Val Ala Ile
    210                 215                 220

Gly Arg Ile Val Met Ser Ala Arg Arg Phe Ile Gly Gly Lys Asp Ser
225                 230                 235                 240

Val Ile Ala Gln Leu Ile Glu Leu Gly Gln Arg Pro Ile Trp Glu Gly
                245                 250                 255

Ile Ala Met Ala Arg Ala Ile Ile Asp Ala Leu Thr Phe Phe Ala Lys
            260                 265                 270

Ser Thr Gln Gly Pro Ser Trp Pro His Leu Tyr Asn Arg Phe Pro Ala
        275                 280                 285

Val Glu Phe Leu Arg Arg Ile Asp Cys Tyr Cys Arg Ile Pro Ala Cys
    290                 295                 300

Ile Ala Gly Glu Arg Arg Tyr Gly Thr Cys Ile Tyr Gln Gly Arg Leu
305                 310                 315                 320

Trp Ala Phe Cys Cys
                325

<210> SEQ ID NO 72
<211> LENGTH: 975
<212> TYPE: DNA
<213> ORGANISM: Artificial sequence
<220> FEATURE:
<223> OTHER INFORMATION: PTD3/alpha-defensin/D29gp12/alpha-defensin

<400> SEQUENCE: 72
tacgcccgta aggcccggag acaggccagg cgtgactgtt attgcagaat ccccgcatgc      60
attgctggcg agcgtcgata tggtacgtgt atataccaag gccgcctttg ggccttttgc     120
tgtatgtcaa aaccctggtt attcaccgta cacggaacag gtcagcctga tccactgggt     180
ccggggcttc ctgccgacac agcgcgtgac gtactcgata tctacagatg cagccaata     240 gggaattacc ccgcggctgc ctttccaatg tggccgtcag tcgagaaggg tgttgcagag     300 cttatttgc agattgagtt aaagctggac gctgatccat atgctgactt tgcactcgct     360
```

```
ggatatagtc aaggagcaat cgtcgtagga caggttctga acatcacat tatcaaccca      420 cgaggacggt tgcatcgctt tttgcatagg ctccggaaag taatattttg gggtaatcct      480
atgaggcaga agggggtttgc acacacggat gaatggattc accaagttgc ggcaagtgac    540
accatgggca tactagagga cagattggaa aacttagaac aatacgggtt cgaggtgagg     600
gattatgcgc acgatggcga tatgtacgcg agcattaaag aagacgatat gcatgaatat     660
gaggtcgcga ttgggcgcat tgtgatgtct gcgagacgat ttataggtgg caaggattcg     720
gttatagccc aactgataga actaggtcaa cgacctatct gggaaggaat cgctatggcg     780
cgtgctatca ttgacgcact aactttcttc gctaaaagca ctcagggacc ctcctggccg     840
catctttata atcggttccc ggccgtggaa ttcctacggc gcatagattg ctattgcagg     900
atccctgcat gtatcgcagg ggagcgacgc tacgggacat gtatatacca aggcagatta    960
tgggctttct gctgt                                                     975
```

<210> SEQ ID NO 73
<211> LENGTH: 303
<212> TYPE: PRT
<213> ORGANISM: Artificial sequence
<220> FEATURE:
<223> OTHER INFORMATION: beta-defensin/D29gp12/TAT47-57

<400> SEQUENCE: 73

```
Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys Met Ser Lys Pro Trp Leu Phe Thr Val His
        35                  40                  45

Gly Thr Gly Gln Pro Asp Pro Leu Gly Pro Gly Leu Pro Ala Asp Thr
    50                  55                  60

Ala Arg Asp Val Leu Asp Ile Tyr Arg Trp Gln Pro Ile Gly Asn Tyr
65                  70                  75                  80

Pro Ala Ala Ala Phe Pro Met Trp Pro Ser Val Glu Lys Gly Val Ala
                85                  90                  95

Glu Leu Ile Leu Gln Ile Glu Leu Lys Leu Asp Ala Asp Pro Tyr Ala
            100                 105                 110

Asp Phe Ala Met Ala Gly Tyr Ser Gln Gly Ala Ile Val Val Gly Gln
        115                 120                 125

Val Leu Lys His His Ile Leu Pro Pro Thr Gly Arg Leu His Arg Phe
    130                 135                 140

Leu His Arg Leu Lys Lys Val Ile Phe Trp Gly Asn Pro Met Arg Gln
145                 150                 155                 160

Lys Gly Phe Ala His Ser Asp Glu Trp Ile His Pro Val Ala Ala Pro
                165                 170                 175

Asp Thr Leu Gly Ile Leu Glu Asp Arg Leu Glu Asn Leu Glu Gln Tyr
            180                 185                 190

Gly Phe Glu Val Arg Asp Tyr Ala His Asp Gly Asp Met Tyr Ala Ser
        195                 200                 205

Ile Lys Glu Asp Asp Leu His Glu Tyr Glu Val Ala Ile Gly Arg Ile
    210                 215                 220

Val Met Lys Ala Ser Gly Phe Ile Gly Gly Arg Asp Ser Val Val Ala
225                 230                 235                 240

Gln Leu Ile Glu Leu Gly Gln Arg Pro Ile Thr Glu Gly Ile Ala Leu
                245                 250                 255
```

```
Ala Gly Ala Ile Ile Asp Ala Leu Thr Phe Phe Ala Arg Ser Arg Met
            260                 265                 270

Gly Asp Lys Trp Pro His Leu Tyr Asn Arg Tyr Pro Ala Val Glu Phe
        275                 280                 285

Leu Arg Gln Ile Tyr Gly Arg Lys Lys Arg Gln Arg Arg Arg
    290                 295                 300
```

<210> SEQ ID NO 74
<211> LENGTH: 909
<212> TYPE: DNA
<213> ORGANISM: Artificial sequence
<220> FEATURE:
<223> OTHER INFORMATION: beta defensin/D29gp12/TAT47-57

<400> SEQUENCE: 74

| | | | | | |
|---|---|---|---|---|---|
| aatcctgtaa | gttgcgtacg | gaacaaaggt | atatgtgttc | caattagatg | cccaggtagc | 60 |
| atgaaacaga | tagggacctg | cgttggacgg | gccgtaaaat | gttgtcgcaa | gaaaatgtct | 120 |
| aagccgtggc | tattcacggt | tcacggtaca | ggccaacctg | acccactcgg | cccaggactt | 180 |
| cctgccgata | ctgctcgcga | cgtgttagat | atatatcgtt | ggcagccaat | tggtaattac | 240 |
| ccggctgcag | ctttccccat | gtggccctcg | gtcgagaagg | gtgtggccga | gctcatattg | 300 |
| cagattgaat | tgaaattgga | tgccgatccg | tatgccgact | ttgctatggc | ggggtacagt | 360 |
| caaggcgcga | tagtcgtagg | ccaagtgcta | aagcatcaca | tcctccctcc | cactggacga | 420 |
| ctccaccgtt | ttctacatcg | acttaaaaag | gtcatctttt | ggggaaaccc | catgaggcaa | 480 |
| aagggctttg | cacactccga | cgagtggatc | catccggttg | ctgcaccaga | cacgttgggt | 540 |
| attcttgaag | acaggctgga | gaacctggaa | cagtatgggt | tcgaagttcg | ggattatgcg | 600 |
| catgatgggg | acatgtacgc | atcaataaaa | gaagatgact | acacgaata | tgaagtggca | 660 |
| attggaagaa | tcgtcatgaa | ggcgtcagga | tttattggag | gtagggatag | cgtggtagca | 720 |
| caactaatcg | agctgggcca | gcgtcccatc | accgagggga | tagcgcttgc | tggggctatt | 780 |
| atcgacgccc | tgacattctt | tgcgcgctct | cgaatggggg | ataaatggcc | tcatttatac | 840 |
| aatcgctatc | cggcagtcga | gttcttaaga | cagatatacg | gcagaaagaa | aaggagacaa | 900 |
| cgacggcgt | | | | | | 909 |

<210> SEQ ID NO 75
<211> LENGTH: 332
<212> TYPE: PRT
<213> ORGANISM: Artificial sequence
<220> FEATURE:
<223> OTHER INFORMATION: beta-defensin/Hepcidin/L5gp12/TAT47-57

<400> SEQUENCE: 75

```
Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys Gly Ala Gly Ala Asp Thr His Phe Pro Ile
        35                  40                  45

Cys Ile Phe Cys Cys Gly Cys Cys His Arg Ser Lys Cys Gly Met Cys
    50                  55                  60

Cys Lys Thr Met Ser Lys Pro Trp Leu Phe Thr Val His Gly Thr Gly
65                  70                  75                  80

Gln Pro Asp Pro Leu Gly Pro Gly Leu Pro Ala Asp Thr Ala Arg Asp
                85                  90                  95
```

```
Val Leu Asp Ile Tyr Arg Trp Gln Pro Ile Gly Asn Tyr Pro Ala Ala
            100                 105                 110

Ala Phe Pro Met Trp Pro Ser Val Glu Lys Gly Val Ala Glu Leu Ile
            115                 120                 125

Leu Gln Ile Glu Leu Lys Leu Asp Ala Asp Pro Tyr Ala Asp Phe Ala
            130                 135                 140

Leu Ala Gly Tyr Ser Gln Gly Ala Ile Val Gly Gln Val Leu Lys
145                 150                 155                 160

His His Ile Ile Asn Pro Arg Gly Arg Leu His Arg Phe Leu His Arg
                165                 170                 175

Leu Arg Lys Val Ile Phe Trp Gly Asn Pro Met Arg Gln Lys Gly Phe
            180                 185                 190

Ala His Thr Asp Glu Trp Ile His Gln Val Ala Ala Ser Asp Thr Met
            195                 200                 205

Gly Ile Leu Glu Asp Arg Leu Glu Asn Leu Glu Gln Tyr Gly Phe Glu
            210                 215                 220

Val Arg Asp Tyr Ala His Asp Gly Asp Met Tyr Ala Ser Ile Lys Glu
225                 230                 235                 240

Asp Asp Met His Glu Tyr Glu Val Ala Ile Gly Arg Ile Val Met Ser
                245                 250                 255

Ala Arg Arg Phe Ile Gly Gly Lys Asp Ser Val Ile Ala Gln Leu Ile
            260                 265                 270

Glu Leu Gly Gln Arg Pro Ile Trp Glu Gly Ile Ala Met Ala Arg Ala
            275                 280                 285

Ile Ile Asp Ala Leu Thr Phe Phe Ala Lys Ser Thr Gln Gly Pro Ser
    290                 295                 300

Trp Pro His Leu Tyr Asn Arg Phe Pro Ala Val Glu Phe Leu Arg Arg
305                 310                 315                 320

Ile Tyr Gly Arg Lys Lys Arg Gln Arg Arg
                325                 330

<210> SEQ ID NO 76
<211> LENGTH: 996
<212> TYPE: DNA
<213> ORGANISM: Artificial sequence
<220> FEATURE:
<223> OTHER INFORMATION: beta-defensin/Hepcidin/L5gp12/TAT47-57

<400> SEQUENCE: 76
aatcccgtga gctgtgtaag aaataaaggt atttgtgtgc caattcgatg cccaggaagt       60
atgaagcaga ttggaacatg tgttggccgt gcggtaaagt gctgtaggaa gaaaggcgca     120
ggagctgata ctcacttccc aatatgcatt ttctgctgtg ggtgctgtca tcgctcaaaa     180
tgcggtatgt gttgcaaaac aatgagtaaa ccttggttgt tcactgtcca tgggaccggc     240
caacctgatc ctttggggcc gggttttgcca gcggatacag ctaggatgt cttagatatc     300 taccgttggc aaccgatagg caattacccc gcggctgcgt tccctatgtg gccgagcgtt     360
gaaaagggag tagcggagct gatcctacag attgaactca agctggacgc tgaccctat     420 gctgactttg cacttgcagg gtactcgcaa ggagccattg tggtcggaca agttctaaaa     480
caccatatca taacccccg aggccgatta catagattcc tacacaggct aaggaaggta     540
atattttggg gtaatcctat gcggcagaag ggctttgctc acactgacga gtggatacac     600
caggtcgcag cttcggatac catgggcata ttagaggatc gccttgagaa cttggaacaa     660
tatggttttg aagttcggga ctatgcccac gacggtgaca tgtacgcctc catcaaggag     720
```

-continued

```
gatgacatgc atgagtatga agtggcgatc gggcgaattg taatgtcagc ccgcagattc    780
atcggaggga aggattctgt gatcgcacaa ctcatagaac tgggacaacg gccgatatgg    840
gagggtattg ccatggcacg ggcaattata gacgcgctta cgttttccgc caaatctacg    900
cagggtccat cctggccgca tctctacaac cgttttcccg ccgttgaatt tttaaggaga    960
atctatgggc gcaaaaaacg tagacagcgt cgacgg                              996
```

<210> SEQ ID NO 77
<211> LENGTH: 602
<212> TYPE: PRT
<213> ORGANISM: Artificial sequence
<220> FEATURE:
<223> OTHER INFORMATION: TM4gp29/LL-37/TATA47-57

<400> SEQUENCE: 77

```
Ser Phe Thr Arg Phe Leu Gln Asp Asp Pro Leu Leu Thr Arg Glu Gln
1               5                   10                  15

Val Met Ala Glu Leu Ile Arg Val Ala Asp Glu Leu Asn Met Pro Asp
            20                  25                  30

Lys Arg Gly Ala Cys Val Ile Ala Gly Met Thr Ile Ser Gln Glu Val
        35                  40                  45

Gly Val Lys Asp Asn Asp Pro Pro Phe Glu Arg Arg Phe Trp Cys Pro
    50                  55                  60

Ala Asn Arg Ala Asp Pro Glu Ser Phe Asn Tyr Pro His Asp Ser Glu
65                  70                  75                  80

Ser Asn Asp Gly Arg Ser Val Gly Tyr Phe Gln Gln Gln Lys Gly Pro
                85                  90                  95

Asn Gly Glu Leu Trp Trp Gly Thr Thr Ala Ser Glu Met Asn Leu His
            100                 105                 110

Ser Ala Ala Thr Gln Phe Met Thr Arg Leu Lys Ala Ala Gly Tyr Asn
        115                 120                 125

Ala Ser Asn Ala Gln Ala Ala Asn Asp Ser Ala Gln Ala Ile Gln Arg
    130                 135                 140

Ser Gly Val Pro Gln Ala Tyr Lys Gln Trp Trp Asp Asp Ile Asn Arg
145                 150                 155                 160

Leu Tyr Asp Lys Val Lys Gly Ser Gly Gly Gly Pro Ala Pro Ala Pro
                165                 170                 175

Lys Pro Pro Gln Ser Gly Pro Trp Thr Gly Asp Pro Val Trp Leu Ala
            180                 185                 190

Asp Val Leu Arg Ala Glu Gly Leu Asn Val Val Glu Leu Pro Gly Trp
        195                 200                 205

Leu Asp Arg Gly His Gly Asp Met Gly Arg Leu Trp Gly Val Val Cys
    210                 215                 220

His His Thr Gly Ser Asp Asn Thr Pro Ser Ser Glu Ile Ala Phe His
225                 230                 235                 240

Pro Ser Leu Gly Leu Cys Ser Gln Ile His Leu Ala Arg Asn Gly Thr
                245                 250                 255

Val Thr Leu Cys Gly Val Gly Ile Ala Trp His Ala Gly Val Gly Ser
            260                 265                 270

Tyr Pro Gly Leu Pro Glu Asp Asn Ala Asn Ala Val Thr Ile Gly Ile
        275                 280                 285

Glu Ala Gln Asn Ser Gly Thr Tyr Asp Gly Ala Pro His Arg Thr Asn
    290                 295                 300

Trp Pro Asp Ala Gln Tyr Asp Ala Tyr Val Lys Cys Cys Ala Ala Ile
```

```
                305                 310                 315                 320
Cys Arg Arg Leu Gly Val Arg Ala Asp His Val Ile Ser His Lys Glu
                325                 330                 335
Trp Ala Gly Arg Lys Gln Gly Lys Trp Asp Pro Gly Ala Ile Asp Met
                340                 345                 350
Asn Ile Phe Arg Ala Asp Val Gln Arg Ile Asp Ala His Gln Pro
                355                 360                 365
Asn Gly Glu Asp Asp Phe Met Ala Ala Leu Ser Ala Asp Glu Gln Arg
                370                 375                 380
Glu Val Leu Asn Leu Leu Arg Val Leu Ala Asp Arg Arg Phe Val Ser
385                 390                 395                 400
Arg Ser Pro Phe Arg His Leu Gly Glu Gly Pro Ser Glu Thr Val Ala
                405                 410                 415
Gly Phe Gly Leu Asn Thr Asp Gly Leu Asn His Ala Gln Tyr Thr Ile
                420                 425                 430
Glu Leu Ala Arg Leu Gly Asp Pro Thr His Leu Ala Leu Leu Arg Glu
                435                 440                 445
Val Ala Ser Ala Glu Gly Asp Ser Arg Tyr Pro Asp Arg Gln Tyr Asp
                450                 455                 460
Ala Lys Leu Ala Lys Arg Val Leu Ala Glu Ile Glu Gly Ala Ala Thr
465                 470                 475                 480
Ala Pro Ala Lys Pro Ser Thr Pro Ser Ala Pro Thr Glu Pro Ala Pro
                485                 490                 495
Glu Ala Pro Thr Pro Pro Val Lys Ala Ala Cys Ala Leu Ser Ala Ala
                500                 505                 510
Gly Cys Val Val Ala Gly Ser Thr Ser Gly Gly Cys Ala Leu Ser
                515                 520                 525
Thr Asp Gly Thr Gly Lys Cys Val Val Thr Ala Ala Thr Asp Gly Gly
                530                 535                 540
Ala Ala Gly Ser Gly Ser Leu Leu Gly Asp Phe Phe Arg Lys Ser Lys
545                 550                 555                 560
Glu Lys Ile Gly Lys Glu Phe Lys Arg Ile Val Gln Arg Ile Lys Asp
                565                 570                 575
Phe Leu Arg Asn Leu Val Pro Arg Thr Glu Ser Gly Ala Gly Ala Tyr
                580                 585                 590
Gly Arg Lys Lys Arg Arg Gln Arg Arg
                595                 600
```

<210> SEQ ID NO 78
<211> LENGTH: 1806
<212> TYPE: DNA
<213> ORGANISM: Artificial sequence
<220> FEATURE:
<223> OTHER INFORMATION: TM4gp29/LL-37/TAT47-57

<400> SEQUENCE: 78

```
agtttcacac gttttttaca agatgaccca ctattaacac gtgagcaagt tatggcggag    60
ttaatacggg ttgctgacga acttaatatg ccagacaagc gtggagcgtg cgtaatagct   120
ggaatgacaa ttagccaaga ggttggtgtt aaagacaatg atccaccatt tgagaggcgt   180
ttctggtgcc cagctaatcg tgccgatcca gaaagtttca attatccaca cgatagcgaa   240
agcaatgatg gtaggagcgt tggatatttt caacaacaaa agggtccaaa tggagaattg   300
tggtggggta caacagctag cgaaatgaat ttacacagtg cagcgacaca attcatgaca   360
aggctaaagg cggctggata caatgccagt aatgcgcaag ccgctaatga tagcgcacaa   420
```

```
gccatacaac gaagcggtgt tccacaagca tataagcaat ggtgggatga cataaatcgg    480
ctttatgaca aagtaaaggg aagcggtgga ggtccagcgc cagccccaaa accaccacaa    540
agcggtccat ggacaggaga tccagtatgg ttagccgatg tactaagggc agaaggattg    600
aatgttgtag aattaccagg ttggctagac cgaggacatg gtgatatggg acggttgtgg    660
ggtgttgtat gtcatcacac aggaagcgat aatacaccaa gcagtgaaat cgcctttcat    720
ccaagccttg gattatgcag ccaaatacat ttggccagaa atggaacagt acattgtgt    780 ggagttggta ttgcatggca cgcaggtgtt ggtagttatc caggtctacc agaggacaat    840
gcaaatgctg ttacaattgg tattgaagct caaaatagcg aacatatga cggtgcgcca    900 catcggacaa attggccaga cgcgcaatac gatgcttacg ttaaatgctg tgcagctatc    960
tgtcggcgat tgggagtaag gcggaccat gtaatcagtc acaagaatg ggcaggtagg   1020 aaacaaggta atgggaccc aggtgcaata gatatgaata tatttagagc cgatgtacaa   1080
cgtcggatcg atgcccatca accaaatgga aagacgatt ttatggcggc tttgagcgca   1140
gacgaacaac gagaggtatt gaatcttttg cgtgtactag ccgatcggag attcgtaagt   1200
aggagtccat tcaggcacct tggagaaggt ccaagcgaaa cagtagcagg atttggtctt   1260
aatacagacg gattgaatca tgcccaatat acaattgaac ttgcccgatt aggtgaccca   1320
acacacttgg cacttttaag agaggtagcg agtgcggaag gtgacagcag atacccagat   1380
cggcaatacg acgccaagct tgcgaaaagg gttctagcag aaattgaagg agcagccaca   1440
gcgccagcta agccaagtac accaagtgcg ccaacagagc cagccccaga agctccaaca   1500
ccaccagtta aggctgcgtg cgccttaagt gcggctggat gtgttgtagc gggtagtaca   1560
agtggtggag gttgcgcact aagtacagat ggtacaggaa agtgtgtagt tacagccgct   1620
acagacggtg gagcagctgg aagtggaagt cttttaggag acttctttcg taagagcaaa   1680
gagaaaatcg gaaaagaatt taaacgtatc gtacaacgaa ttaaggattt cctaagaaat   1740
ctagtaccac gaacagagag tggtgcagga gcttacggta gaaagaaacg gcgacaaaga   1800
cgaaga                                                              1806
```

<210> SEQ ID NO 79
<211> LENGTH: 594
<212> TYPE: PRT
<213> ORGANISM: Artificial sequence
<220> FEATURE:
<223> OTHER INFORMATION: TM4gp29/LL-37/TAT47-57

<400> SEQUENCE: 79

```
Ser Phe Thr Arg Phe Leu Gln Asp Asp Pro Leu Leu Thr Arg Glu Gln
1               5                   10                  15

Val Met Ala Glu Leu Ile Arg Val Ala Asp Glu Leu Asn Met Pro Asp
            20                  25                  30

Lys Arg Gly Ala Cys Val Ile Ala Gly Met Thr Ile Ser Gln Glu Val
        35                  40                  45

Gly Val Lys Asp Asn Asp Pro Pro Phe Glu Arg Arg Phe Trp Cys Pro
    50                  55                  60

Ala Asn Arg Ala Asp Pro Glu Ser Phe Asn Tyr Pro His Asp Ser Glu
65                  70                  75                  80

Ser Asn Asp Gly Arg Ser Val Gly Tyr Phe Gln Gln Gln Lys Gly Pro
                85                  90                  95

Asn Gly Glu Leu Trp Trp Gly Thr Thr Ala Ser Glu Met Asn Leu His
            100                 105                 110
```

-continued

```
Ser Ala Ala Thr Gln Phe Met Thr Arg Leu Lys Ala Ala Gly Tyr Asn
            115                 120                 125

Ala Ser Asn Ala Gln Ala Ala Asn Asp Ser Ala Gln Ala Ile Gln Arg
        130                 135                 140

Ser Gly Val Pro Gln Ala Tyr Lys Gln Trp Trp Asp Ile Asn Arg
145                 150                 155                 160

Leu Tyr Asp Lys Val Lys Gly Ser Gly Gly Pro Ala Pro Ala Pro
                165                 170                 175

Lys Pro Pro Gln Ser Gly Pro Trp Thr Gly Asp Pro Val Trp Leu Ala
                180                 185                 190

Asp Val Leu Arg Ala Glu Gly Leu Asn Val Val Glu Leu Pro Gly Trp
        195                 200                 205

Leu Asp Arg Gly His Gly Asp Met Gly Arg Leu Trp Gly Val Val Cys
        210                 215                 220

His His Thr Gly Ser Asp Asn Thr Pro Ser Ser Glu Ile Ala Phe His
225                 230                 235                 240

Pro Ser Leu Gly Leu Cys Ser Gln Ile His Leu Ala Arg Asn Gly Thr
                245                 250                 255

Val Thr Leu Cys Gly Val Gly Ile Ala Trp His Ala Val Gly Ser
        260                 265                 270

Tyr Pro Gly Leu Pro Glu Asp Asn Ala Asn Ala Val Thr Ile Gly Ile
        275                 280                 285

Glu Ala Gln Asn Ser Gly Thr Tyr Asp Gly Ala Pro His Arg Thr Asn
290                 295                 300

Trp Pro Asp Ala Gln Tyr Asp Ala Tyr Val Lys Cys Cys Ala Ala Ile
305                 310                 315                 320

Cys Arg Arg Leu Gly Val Arg Ala Asp His Val Ile Ser His Lys Glu
                325                 330                 335

Trp Ala Gly Arg Lys Gln Gly Lys Trp Asp Pro Gly Ala Ile Asp Met
            340                 345                 350

Asn Ile Phe Arg Ala Asp Val Gln Arg Ile Asp Ala His Gln Pro
            355                 360                 365

Asn Gly Glu Asp Asp Phe Met Ala Ala Leu Ser Ala Asp Glu Gln Arg
        370                 375                 380

Glu Val Leu Asn Leu Leu Arg Val Leu Ala Asp Arg Arg Phe Val Ser
385                 390                 395                 400

Arg Ser Pro Phe Arg His Leu Gly Glu Gly Pro Ser Glu Thr Val Ala
                405                 410                 415

Gly Phe Gly Leu Asn Thr Asp Gly Leu Asn His Ala Gln Tyr Thr Ile
                420                 425                 430

Glu Leu Ala Arg Leu Gly Asp Pro Thr His Leu Ala Leu Leu Arg Glu
            435                 440                 445

Val Ala Ser Ala Glu Gly Asp Ser Arg Tyr Pro Asp Arg Gln Tyr Asp
        450                 455                 460

Ala Lys Leu Ala Lys Arg Val Leu Ala Glu Ile Gly Ala Ala Thr
465                 470                 475                 480

Ala Pro Ala Lys Pro Ser Thr Pro Ser Ala Pro Thr Glu Pro Ala Pro
                485                 490                 495

Glu Ala Pro Thr Pro Pro Val Lys Ala Ala Cys Ala Leu Ser Ala Ala
                500                 505                 510

Gly Cys Val Val Ala Gly Ser Thr Ser Gly Gly Cys Ala Leu Ser
            515                 520                 525
```

Thr Asp Gly Thr Gly Lys Cys Val Val Thr Ala Ala Thr Asp Gly Gly
            530                 535                 540

Ala Ala Leu Leu Gly Asp Phe Phe Arg Lys Ser Lys Glu Lys Ile Gly
545                 550                 555                 560

Lys Glu Phe Lys Arg Ile Val Gln Arg Ile Lys Asp Phe Leu Arg Asn
                565                 570                 575

Leu Val Pro Arg Thr Glu Ser Tyr Gly Arg Lys Lys Arg Arg Gln Arg
            580                 585                 590

Arg Arg

<210> SEQ ID NO 80
<211> LENGTH: 1782
<212> TYPE: DNA
<213> ORGANISM: Artificial sequence
<220> FEATURE:
<223> OTHER INFORMATION: TM4gp29/LL-37/TAT47-57

<400> SEQUENCE: 80

```
agttttacaa ggttcctaca agatgaccca ctattgacac gagaacaagt aatggctgag      60
ctaatacgag tagcagatga attaaatatg ccagataaga ggggagcttg tgttatcgcc     120
ggtatgacaa tcagtcaaga agttggagtt aaggacaatg atccaccatt cgagcgtagg     180
ttctggtgtc cagcgaatcg tgctgatcca gaaagtttta attacccaca cgacagcgaa     240
agcaatgacg gacgtagtgt aggttatttc aacaacaaa agggaccaaa tggagagctt      300
tggtggggta acacagctag tgagatgaat ctacatagtg cagcgacaca atttatgaca     360
agacttaaag ctgccggtta taatgccagt aatgcgcaag cggctaatga cagtgcacaa     420
gctatacaac gtagtggtgt accacaagcc tataagcaat ggtgggatga cataaatagg     480
ttatacgata aggtaaaggg tagtggtgga ggtccagcac cagcaccaaa accaccacaa     540
agcggtccat ggacaggaga tccagtttgg ttggcggacg tattacgagc agaaggtttg     600
aatgtagttg aacttccagg atggcttgac agaggcacg tgacatggg acgtctttgg      660
ggtgtagttt gtcaccatac aggtagtgac aatacaccaa gtagcgaaat tgcctttcac     720
ccaagtttgg gactttgcag ccaaattcat cttgccagga atggtacagt tacactatgc     780
ggagtaggaa tagcttggca cgccggtgtt ggtagctatc caggtttacc agaagataat     840
gctaatgcag taacaattgg aattgaagca caaaatagcg aacatacga cggtgcacca      900
catagaacaa attggccaga cgctcaatac gatgcgtatg ttaaatgctg tgctgccata     960
tgccggcgat taggtgtacg ggctgaccat gttattagcc acaaggaatg ggccggaaga    1020
aaacaaggaa atgggacccc aggagctatc gatatgaata tctttcgggc ggatgtacaa    1080
cggcgaattg atgctcatca accaaatgga gaagatgact ttatggcggc cttaagtgcc    1140
gacgaacaac gtgaggtttt aaatctttta cgggtattgg cggaccggcg attcgttagt    1200
aggagcccat tccgacattt gggtgaggga ccaagcgaga cagtagcggg attcggtttg    1260
aatacagatg gtttgaatca tgcacaatat acaatagaat tggcaagatt gggtgaccca    1320
acacacctag cgcttttaag ggaagtagca agtgcagaag gtgatagccg ttatccagat    1380
cgtcaatacg atgccaagct agcgaaacga gttttagcag aaattgaagg agccgcgaca    1440
gcgccagcca aaccaagcac accaagtgct ccaacagaac cagcaccaga ggcgccaaca    1500
ccaccagtta aagctgcctg tgccctaagt gcagcgggat gcgtagttgc cggaagcaca    1560
agcggaggtg gatgcgcttt gagcacagac ggaacaggta atgtgtagt tacagctgcg    1620
acagatggtg gagcagcatt actaggtgac ttttttcagga aaagcaaaga aaagatcggt    1680
```

```
aaagagttta aaagaatagt acaacggatc aaggattttc ttagaaatct agttccacgg    1740
acagagagct acggaagaaa gaagcggaga caaaggcgac gt                      1782
```

<210> SEQ ID NO 81
<211> LENGTH: 554
<212> TYPE: PRT
<213> ORGANISM: Artificial sequence
<220> FEATURE:
<223> OTHER INFORMATION: Bzx2gp11/alpha-defensin/PTD3

<400> SEQUENCE: 81

```
Thr Glu Lys Val Leu Pro Tyr Asp Arg Ser Ile Val Thr Gln Glu Thr
1               5                   10                  15

Gly Trp Trp Cys Gly Pro Ala Ala Thr Gln Val Val Leu Asn Ser Arg
            20                  25                  30

Gly Ile Ile Val Pro Glu Ala Thr Leu Ala Ala Glu Ile Glu Ala Ile
        35                  40                  45

Glu Asn Pro Gly Arg Gly Asp Asp Arg Asp Gly Thr Asp Tyr Val Gly
    50                  55                  60

Leu Ile Glu Gln Val Leu Asp Arg Arg Val Pro Gln Ala Arg Tyr Thr
65                  70                  75                  80

Ser Val Tyr Leu Thr Asn Asp Pro Pro Thr Gln Ala Gln Lys Asp Arg
                85                  90                  95

Leu Trp Glu His Ile Val Arg Ser Ile Asn Ala Gly Tyr Gly Val Val
            100                 105                 110

Met Asn Trp Val Ala Pro Pro Ser Asn Lys Pro Arg Gly Val Lys Gly
        115                 120                 125

Ser Val Ser Pro Arg Tyr Ser Gly Gly Thr Thr Tyr His Tyr Val Ala
    130                 135                 140

Cys Met Gly Tyr Asp Asp Thr Pro Gly Ala Arg Ala Val Trp Ile Ala
145                 150                 155                 160

Asp Ser Gly Phe Gln Pro Gln Gly Tyr Trp Ile Ser Phe Asp Gln Cys
                165                 170                 175

Ala Thr Leu Ile Pro Pro Lys Gly Tyr Ala Tyr Ala Asp Ala Ala Pro
            180                 185                 190

Ala Ala Pro Ala Pro Ala Pro Thr Pro Val Val Asp Ala Ala Pro Ile
        195                 200                 205

Leu Ala Arg Ala Ala Gly Ile Ser Glu Ala Lys Ala Arg Glu Ile Leu
    210                 215                 220

Pro Thr Met Arg Asp Gly Leu Lys Gln Ala Asp Cys Thr Thr Val Asn
225                 230                 235                 240

Arg Ile Ala Met Phe Ile Ala Gln Thr Gly His Glu Ser Asp Asp Phe
                245                 250                 255

Arg Ala Thr Glu Glu Tyr Ala Asn Gly Pro Leu Asp Gln Glu Arg Trp
            260                 265                 270

Ile Tyr Lys Gly Arg Thr Trp Ile Gln Ile Thr Trp Arg Glu His Tyr
        275                 280                 285

Ala Arg Phe Gly Lys Trp Cys Phe Asp Arg Gly Leu Val Thr Asp Pro
    290                 295                 300

Asp Val Phe Val Lys Asn Pro Arg Ala Leu Asp Leu Lys Trp Ala
305                 310                 315                 320

Gly Ile Gly Ala Ala Trp Tyr Trp Thr Val Glu Arg Pro Asp Ile Asn
                325                 330                 335

Ala Leu Cys Asp Arg Arg Asp Ile Glu Thr Val Ser Arg Arg Ile Asn
```

```
                   340                 345                 350
Gly Thr Asn Pro Asn Thr Gly Arg Ala Asn His Ile Glu Glu Arg Ile
                355                 360                 365

Ala Arg Trp Asn Arg Ala Leu Ala Val Gly Asp Asp Leu Leu Gln Leu
            370                 375                 380

Ile Arg Glu Glu Glu Asp Gly Phe Leu Ser Ala Leu Thr Pro Ala Glu
385                 390                 395                 400

Gln Arg Ala Leu Tyr Asn Glu Ile Met Lys Lys Gly Pro Thr Arg Ser
                405                 410                 415

Phe Met Ala Glu Asp Gln Asn Gln Ile Glu Thr Leu Leu Gly Phe Val
            420                 425                 430

Tyr Asn Ile Asp Gly Asn Ile Trp Asn Asp Ala Val Thr Arg Ala Tyr
                435                 440                 445

Leu Phe Asp Val Pro Leu Ala Val Glu Tyr Val Glu Arg Val Ala Arg
            450                 455                 460

Asp Gly Val His Pro Lys Ser Trp Ala Phe Gln Gln Leu Asp Gly Lys
465                 470                 475                 480

Gly Glu Arg Trp Leu Ala Lys Phe Gly Gln Glu Tyr Cys Lys Gly Leu
                485                 490                 495

Ile Arg Phe Lys Lys Leu Asn Asp Leu Leu Glu Pro Tyr Gly Glu
            500                 505                 510

Asn Asp Cys Tyr Cys Arg Ile Pro Ala Cys Ile Ala Gly Glu Arg Arg
                515                 520                 525

Tyr Gly Thr Cys Ile Tyr Gln Gly Arg Leu Trp Ala Phe Cys Cys Tyr
            530                 535                 540

Ala Arg Lys Ala Arg Arg Gln Ala Arg Arg
545                 550
```

<210> SEQ ID NO 82
<211> LENGTH: 1662
<212> TYPE: DNA
<213> ORGANISM: Artificial sequence
<220> FEATURE:
<223> OTHER INFORMATION: Bzx2gp11/alpha-defensin/PTD3

<400> SEQUENCE: 82

```
acagagaaag ttttaccata cgatcggagt atagttacac aagagacagg ttggtggtgt    60
ggtccagccg caacacaagt agttttaaat agtcgtggaa taatcgtacc agaagctaca   120
ttggccgctg aaatcgaagc catagaaaat ccaggtcgtg gtgatgaccg agacggaaca   180
gattatgtag gtcttattga gcaagttctt gatcggaggg ttccacaagc tcgttacaca   240
agcgtatatt taacaaatga tccaccaaca caagcacaaa aggaccgatt gtgggaacat   300
attgtaagaa gcataaatgc aggttacgga gtagttatga attgggtagc tccaccaagt   360
aataagccac gtggagttaa aggtagcgtt agcccacgat atagtggagg tacaacatat   420
cactatgtag cgtgcatggg atatgacgat acaccaggtg ccagagcagt atggatagcg   480
gacagcggat ccaaccaca aggatactgg atcagctttg accaatgcgc cacacttatc   540
ccaccaaaag gttatgcata cgcagacgcg gcaccagctg caccagctcc agctccaaca   600
ccagttgtag acgccgcgcc aatattggcc cgggcggcag gtattagcga agcaaaggca   660
agggaaattc ttccaacaat gcgggatgga ctaaacaag cggattgtac aacagttaat   720
cgaattgcaa tgtttatagc ccaaacagga cacgaaagtg atgactttcg ggctacagaa   780
gagtatgcaa atggaccatt ggatcaagaa cgttggattt acaaaggtcg aacatggata   840
```

```
caaattacat ggagggaaca ctacgctcgt ttcggtaaat ggtgtttcga ccgtggactt    900
gttacagatc cagatgtatt tgttaaaaat ccacgagctt tggccgacct aaaatgggcg    960
ggtataggag cggcttggta ctggacagta gaacggccag atatcaatgc cttatgcgat   1020
cgaagagaca tcgaaacagt tagtagaagg ataaatggaa caaatccaaa tacaggtaga   1080
gcgaatcata tcgaggaacg aattgcgagg tggaatcgtg cactagcagt aggtgacgat   1140
ttacttcaac taattagaga agaggaagac ggttttttaa gtgctttgac accagccgag   1200
caacgagcgt tgtataatga aatcatgaag aaaggaccaa cacgtagttt catggctgag   1260
gatcaaaatc aaatcgagac attattggga ttcgtataca atatagacgg aaatatctgg   1320
aatgacgctg taacacgggc ttatttattt gatgttccat tagccgtaga atacgttgag   1380
agggttgcga gggatggagt acatccaaag agctgggcat tcaacaact agacggaaag    1440 ggagaaaggt ggctagccaa gttcggacaa gaatactgta aaggtctaat ccggttcaag   1500
aaaaagttga atgatctact tgaaccatat ggagagaatg actgctactg tcggattcca   1560
gcgtgcattg ctggtgaaag gagatatggt acatgtatat atcaaggtag actttgggcc   1620
ttttgttgct acgcgagaaa ggccagaagg caagcgcgtc ga                      1662
```

<210> SEQ ID NO 83
<211> LENGTH: 455
<212> TYPE: PRT
<213> ORGANISM: Artificial sequence
<220> FEATURE:
<223> OTHER INFORMATION: TM4gp30/LL-37/TAT47-57

<400> SEQUENCE: 83

```
Ala Trp Val Gly Trp Gln Leu Gly Met Gln Gly Glu Gln Val Lys Val
1               5                   10                  15

Ile Gln Gln Lys Leu Ile Ala Lys Tyr Gln Trp Val Arg Asp Arg Tyr
            20                  25                  30

Pro Arg Leu Thr Ala Ser Gly Val Tyr Asp Val Asn Thr Gln Ala Ala
        35                  40                  45

Ile Val Glu Phe Gln Phe Arg Ala Gly Leu Pro Val Thr Gly Ile Ala
    50                  55                  60

Asp Tyr Ala Thr Gln Val Arg Leu Gly Ala Val Ala Pro Ala Pro Pro
65                  70                  75                  80

Pro Arg Gln Arg Ile Met Val Leu Thr Phe Ser Gly Thr Ser Ala Asp
                85                  90                  95

Met Trp Thr Gly Tyr Pro Ala Asp Val Ala Arg Ala Leu Asp Pro Ser
            100                 105                 110

Ile Phe Tyr Trp Gln Pro Val Cys Tyr Gly Pro Asn Gly Ile Pro Ala
        115                 120                 125

Ile Phe Pro Met Gly Ser Ser Ala Lys Ser Gly Glu Val Glu Gly Leu
    130                 135                 140

Arg Leu Leu Asp Glu Lys Ala Arg Asp Phe Asp Tyr Ile Val Leu Ile
145                 150                 155                 160

Gly Tyr Ser Gln Gly Ala Leu Pro Ala Ser Arg Leu Met Arg Arg Ile
                165                 170                 175

Leu Ser Gly Asp Leu Gln Arg Phe Lys Ser Lys Leu Ile Ala Gly Val
            180                 185                 190

Thr Phe Gly Asn Pro Met Arg Glu Lys Gly His Thr Phe Pro Gly Gly
        195                 200                 205

Ala Asp Pro Gly Gly His Gly Leu Asp Pro Gln Cys Leu Val Asn Thr
    210                 215                 220
```

Pro Asp Trp Trp His Asp Tyr Ala Ala Lys Gly Asp Ile Tyr Thr Val
225                 230                 235                 240

Gly Ser Gly Ser Asn Asp Glu Lys Ala Asn Ala Asp Met Thr Phe Ile
            245                 250                 255

Tyr Gln Leu Val Gln Gly Asp Ile Leu Gly Met Met Phe Gly Thr Gly
        260                 265                 270

Asn Pro Leu Asp Ile Leu Gly Leu Gly Gly Leu Gly Gly Gly Leu
        275                 280                 285

Leu Gly Gly Leu Gly Gly Leu Leu Gly Gly Gly Lys Gly Gly Leu
290                 295                 300

Gln Leu Pro Ser Gly Leu Val Leu Pro Gly Val Gln Gly Gly Ala Leu
305                 310                 315                 320

Thr Asp His Gln Arg Gly Leu Val Glu Ala Val Leu Ala Leu Leu Ala
                325                 330                 335

Asn Pro Phe Ala Glu Val Pro Ala Ala Val Lys Ala Ile Val Ser Gly
            340                 345                 350

Val Gly Phe Ile Ala Thr Asn Pro Pro Thr Ala Pro His Ile Glu Tyr
        355                 360                 365

His Ile Arg Glu Ala Ala Pro Gly Val Thr Tyr Phe Gln His Ala Ile
370                 375                 380

Asp Tyr Leu Arg Gln Val Gly Ala Ser Val Ala Arg Ala Ala Gly
385                 390                 395                 400

Ser Gly Ser Leu Leu Gly Asp Phe Phe Arg Lys Ser Lys Glu Lys Ile
            405                 410                 415

Gly Lys Glu Phe Lys Arg Ile Val Gln Arg Ile Lys Asp Phe Leu Arg
        420                 425                 430

Asn Leu Val Pro Arg Thr Glu Ser Gly Ala Gly Ala Tyr Gly Arg Lys
        435                 440                 445

Lys Arg Arg Gln Arg Arg Arg
    450                 455

<210> SEQ ID NO 84
<211> LENGTH: 1365
<212> TYPE: DNA
<213> ORGANISM: Artificial sequence
<220> FEATURE:
<223> OTHER INFORMATION: TM4gp30/LL-37/TAT47-57

<400> SEQUENCE: 84
gcttgggtcg ctggcagct tggtatgcag ggtgaacagg ttaaggtaat ccagcaaaag    60
ttgatagcca agtaccagtg ggtgcgtgat agatatcccc ggttgaccgc aagtggggtt   120
tacgacgtca acacccaagc agcgattgtt gagtttcaat ttagagccgg acttccagtc   180
acgggcatag ccgactatgc gacacaggtg cggcttggag ctgtcgcacc agctccaccc   240
cctaggcaac ggattatggt actcacattt agcgggacgt cggctgatat gtggacaggc   300
tacccggctg acgttgcaag agccctagat ccttcaattt tttattggca acccgtttgt   360
tatggcccaa acggtattcc cgcgatattc ccgatggggt cgagtgccaa gtccggggaa   420
gttgaaggct tgcgactatt agacgagaaa gctcgcgatt cgactacat tgtcctgatc   480 gggtatagtc agggtgcgtt gcctgcgagc aggttgatgc gtcgcatcct atcaggtgat   540
ctgcaaaggt tcaaatcaaa actgatagca ggagtgacgt ttgggaaccc gatgcgagaa   600
aaaggtcaca cctttcctgg cggggctgac ccgggtggcc acggcttaga cccacagtgc   660
ctcgtgaata ctccggattg gtggcacgac tacgcggcca aaggcgatat ctacacagta   720

-continued

```
ggttctggat ctaatgatga gaaggccaat gcggacatga ctttcatata tcaattagtc    780
caaggagaca tactcggtat gatgttcggt acgggtaacc ctttggatat attaggggttg   840 ctgggaggcc taggcggagg tctacttgga ggcctaggtg ggggcttgct tggaggtgga    900 aagggggat  tacaactgcc tagcggactt gttttacctg gggttcaggg gggtgcatta   960
accgaccatc aacgtggact tgtagaagcg gtgctggctt tactcgcaaa tcccttcgcg   1020
gaagtacccg ccgcggtgaa ggcaatcgta agtggcgtcg gtttcatcgc cactaatccg   1080
ccaactgccc cacatattga gtaccatatt agggaggcag ctcccggcgt gacatatttc   1140
caacatgcaa tcgattatct caggcaagtc ggagcctccg tggctgcacg ggctgcggga   1200
tctggatcac tactgggaga ttttttccga aagtctaaag agaaaatagg gaaagaattt   1260
aagcgaattg tacagcgcat caaggatttt ctacgaaacc tcgtaccgcg tactgagagc   1320
ggggcagggg cttacggtcg caaaaaacgc cggcagagac gtaga                  1365
```

<210> SEQ ID NO 85
<211> LENGTH: 447
<212> TYPE: PRT
<213> ORGANISM: Artificial sequence
<220> FEATURE:
<223> OTHER INFORMATION: TM4gp30/LL-37/TAT47-57

<400> SEQUENCE: 85

```
Ala Trp Val Gly Trp Gln Leu Gly Met Gln Gly Glu Gln Val Lys Val
1               5                   10                  15

Ile Gln Gln Lys Leu Ile Ala Lys Tyr Gln Trp Val Arg Asp Arg Tyr
            20                  25                  30

Pro Arg Leu Thr Ala Ser Gly Val Tyr Asp Val Asn Thr Gln Ala Ala
        35                  40                  45

Ile Val Glu Phe Gln Phe Arg Ala Gly Leu Pro Val Thr Gly Ile Ala
    50                  55                  60

Asp Tyr Ala Thr Gln Val Arg Leu Gly Ala Val Ala Pro Ala Pro Pro
65                  70                  75                  80

Pro Arg Gln Arg Ile Met Val Leu Thr Phe Ser Gly Thr Ser Ala Asp
                85                  90                  95

Met Trp Thr Gly Tyr Pro Ala Asp Val Ala Arg Ala Leu Asp Pro Ser
            100                 105                 110

Ile Phe Tyr Trp Gln Pro Val Cys Tyr Gly Pro Asn Gly Ile Pro Ala
        115                 120                 125

Ile Phe Pro Met Gly Ser Ser Ala Lys Ser Gly Glu Val Glu Gly Leu
    130                 135                 140

Arg Leu Leu Asp Glu Lys Ala Arg Asp Phe Asp Tyr Ile Val Leu Ile
145                 150                 155                 160

Gly Tyr Ser Gln Gly Ala Leu Pro Ala Ser Arg Leu Met Arg Arg Ile
                165                 170                 175

Leu Ser Gly Asp Leu Gln Arg Phe Lys Ser Lys Leu Ile Ala Gly Val
            180                 185                 190

Thr Phe Gly Asn Pro Met Arg Glu Lys Gly His Thr Phe Pro Gly Gly
        195                 200                 205

Ala Asp Pro Gly Gly His Gly Leu Asp Pro Gln Cys Leu Val Asn Thr
    210                 215                 220

Pro Asp Trp Trp His Asp Tyr Ala Ala Lys Gly Asp Ile Tyr Thr Val
225                 230                 235                 240

Gly Ser Gly Ser Asn Asp Glu Lys Ala Asn Ala Asp Met Thr Phe Ile
```

```
                245                 250                 255
Tyr Gln Leu Val Gln Gly Asp Ile Leu Gly Met Met Phe Gly Thr Gly
            260                 265                 270
Asn Pro Leu Asp Ile Leu Gly Leu Gly Gly Leu Gly Gly Gly Gly Leu
        275                 280                 285
Leu Gly Gly Leu Gly Gly Gly Leu Leu Gly Gly Gly Lys Gly Gly Leu
    290                 295                 300
Gln Leu Pro Ser Gly Leu Val Leu Pro Gly Val Gln Gly Gly Ala Leu
305                 310                 315                 320
Thr Asp His Gln Arg Gly Leu Val Glu Ala Val Leu Ala Leu Leu Ala
                325                 330                 335
Asn Pro Phe Ala Glu Val Pro Ala Ala Val Lys Ala Ile Val Ser Gly
            340                 345                 350
Val Gly Phe Ile Ala Thr Asn Pro Pro Thr Ala Pro His Ile Glu Tyr
        355                 360                 365
His Ile Arg Glu Ala Ala Pro Gly Val Thr Tyr Phe Gln His Ala Ile
    370                 375                 380
Asp Tyr Leu Arg Gln Val Gly Ala Ser Val Ala Ala Arg Ala Ala Leu
385                 390                 395                 400
Leu Gly Asp Phe Phe Arg Lys Ser Lys Glu Lys Ile Gly Lys Glu Phe
                405                 410                 415
Lys Arg Ile Val Gln Arg Ile Lys Asp Phe Leu Arg Asn Leu Val Pro
            420                 425                 430
Arg Thr Glu Ser Tyr Gly Arg Lys Lys Arg Arg Gln Arg Arg
        435                 440                 445

<210> SEQ ID NO 86
<211> LENGTH: 1341
<212> TYPE: DNA
<213> ORGANISM: Artificial sequence
<220> FEATURE:
<223> OTHER INFORMATION: TM4gp30/LL-37/TAT47-57

<400> SEQUENCE: 86
gcctgggttg gctggcagtt aggaatgcag ggtgaacagg tgaaggtaat acagcaaaaa     60
cttatagcca agtaccagtg ggtcagggat agatatcccc gcctaaccgc gagtggggtt    120
tacgacgtga atactcaggc agctatcgtt gagttccaat ttagagctgg cctaccagta    180
actggtatag cagactatgc tactcaagtg cggttagggg cggtcgcgcc tgctccgcca    240
ccccgtcaac gaatcatggt actgacattt tcaggcacat cagcggatat gtggactgga    300
tatcccgcag acgtcgcgag ggctcttgac ccctcaatat tctattggca gcccgtgtgc    360
tacgggccca acggaattcc ggccatattc cctatgggt cctctgcaaa atctggcgag    420
gttgagggtt tgcgtctact ggacgaaaaa gcccgagact ttgattacat agtgctgata    480
ggttatagtc aaggagcgct cccggcgagt aggttaatgc ggcgaattct gagcggcgat    540
ctccaacggt ttaaaagcaa gcttatcgca ggtgtaacct ttgggaatcc tatgcgggag    600
aagggacata catttcctgg aggtgccgac ccaggtggac acggcttaga tcctcaatgt    660
ctcgtcaata ccccggattg gtggcacgat tacgccgcga aggagatat ctacacagtt    720
ggaagcggta gcaatgacga aaaagctaac gcggacatga catttattta tcagctggtg    780
caggggggaca tcctaggcat gatgttcgga acgggtaacc ctctggatat attgggtctt    840
ctcggggct taggcggggg cttattgggc ggtctagggg cggtcttct gggcggaggg    900
aagggaggtc tacagttacc ctctggacta gtgttgccgg gggtacaagg aggtgctttg    960
```

-continued

```
actgatcatc agagagggct tgtagaagca gtcctcgctt tgctcgccaa tccgtttgct    1020
gaagttccag cggccgttaa ggccattgtg tccggcgtcg gattcatcgc aacgaaccca    1080
cctaccgcac cgcatatcga atatcatatt cgcgaggcag ccccagggt cacgtatttc     1140 caacacgcga ttgattactt gagacaagta ggggcctcgg ttgcagctcg tgctgcatta    1200
cttggtgatt ttttccgcaa atcgaaggag aagattggta agaattcaa acgtatcgtc     1260 caacgcatta aagacttcct acgaaacttg gtaccaagga cggagagtta cggacgcaaa    1320
aagcggcgac aaaggagacg t                                              1341
```

<210> SEQ ID NO 87
<211> LENGTH: 294
<212> TYPE: PRT
<213> ORGANISM: Artificial sequence
<220> FEATURE:
<223> OTHER INFORMATION: D29/alpha-defensin/PTD3

<400> SEQUENCE: 87

Ser Lys Pro Trp Leu Phe Thr Val His Gly Thr Gly Gln Pro Asp Pro
1               5                   10                  15
Leu Gly Pro Gly Leu Pro Ala Asp Thr Ala Arg Asp Val Leu Asp Ile
            20                  25                  30
Tyr Arg Trp Gln Pro Ile Gly Asn Tyr Pro Ala Ala Ala Phe Pro Met
        35                  40                  45
Trp Pro Ser Val Glu Lys Gly Val Ala Glu Leu Ile Leu Gln Ile Glu
    50                  55                  60
Leu Lys Leu Asp Ala Asp Pro Tyr Ala Asp Phe Ala Met Ala Gly Tyr
65                  70                  75                  80
Ser Gln Gly Ala Ile Val Val Gly Gln Val Leu Lys His His Ile Leu
                85                  90                  95
Pro Pro Thr Gly Arg Leu His Arg Phe Leu His Arg Leu Lys Lys Val
            100                 105                 110
Ile Phe Trp Gly Asn Pro Met Arg Gln Lys Gly Phe Ala His Ser Asp
        115                 120                 125
Glu Trp Ile His Pro Val Ala Ala Pro Asp Thr Leu Gly Ile Leu Glu
    130                 135                 140
Asp Arg Leu Glu Asn Leu Glu Gln Tyr Gly Phe Glu Val Arg Asp Tyr
145                 150                 155                 160
Ala His Asp Gly Asp Met Tyr Ala Ser Ile Lys Glu Asp Asp Leu His
                165                 170                 175
Glu Tyr Glu Val Ala Ile Gly Arg Ile Val Met Lys Ala Ser Gly Phe
            180                 185                 190
Ile Gly Gly Arg Asp Ser Val Val Ala Gln Leu Ile Glu Leu Gly Gln
        195                 200                 205
Arg Pro Ile Thr Glu Gly Ile Ala Leu Ala Gly Ala Ile Ile Asp Ala
    210                 215                 220
Leu Thr Phe Phe Ala Arg Ser Arg Met Gly Asp Lys Trp Pro His Leu
225                 230                 235                 240
Tyr Asn Arg Tyr Pro Ala Val Glu Phe Leu Arg Gln Ile Asp Cys Tyr
                245                 250                 255
Cys Arg Ile Pro Ala Cys Ile Ala Gly Glu Arg Arg Tyr Gly Thr Cys
            260                 265                 270
Ile Tyr Gln Gly Arg Leu Trp Ala Phe Cys Cys Tyr Ala Arg Lys Ala
        275                 280                 285

Arg Arg Gln Ala Arg Arg
    290

<210> SEQ ID NO 88
<211> LENGTH: 882
<212> TYPE: DNA
<213> ORGANISM: Artificial sequence
<220> FEATURE:
<223> OTHER INFORMATION: D29gp12/alpha-defensin/PTD3

<400> SEQUENCE: 88

```
agtaaacctt ggctattcac agtgcacggt acgggtcagc ctgacccact aggtcctggg    60
cttccagcag atactgcgcg cgatgtgctc gacatttatc gctggcaacc catcggaaat   120
tatcctgcag cggcttttcc gatgtggccg tccgttgaaa aaggggtagc agagctcata   180
ttacagatcg aactgaaatt ggatgctgac ccgtatgcag attttgcgat ggcggggtat   240
agccagggag ccatcgttgt gggccaagtt cttaagcacc atattctacc accgaccgga   300
cgtctccata ggttcctgca tcgtttaaaa aaggtcattt tttggggcaa ccccatgcgg   360
caaaagggtt tcgctcactc ggatgagtgg atccacccag tagctgcacc cgacacgtta   420
ggtatcctgg aggatcgtct ggagaactta gagcagtacg gatttgaagt cagagactac   480
gctcatgatg gtgatatgta tgcgagcatt aaggaagacg atcttcatga gtacgaagtg   540
gcgataggca aatagttat gaaagcctct ggatttatcg gcgggaggga tagtgtcgta   600
gcccaattga ttgaattggg ccaacggccc ataactgagg gtattgccct agctggagct   660
ataatcgacg cattaacctt ctttgcccga tcacggatgg gcgacaaatg gcccacaccc   720
tataatagat accctgcggt agaattcctt cgtcagattg actgttactg ccgcataccg   780
gcgtgcatag caggggaaag cgctacgggg acatgcatat atcagggacg attgtgggcc   840
ttctgttgtt acgccaggaa ggcacgaaga caagctcgac gg                     882
```

<210> SEQ ID NO 89
<211> LENGTH: 602
<212> TYPE: PRT
<213> ORGANISM: Artificial sequence
<220> FEATURE:
<223> OTHER INFORMATION: TM4gp29/LL37/TAT47-57 construct 1

<400> SEQUENCE: 89

Ser Phe Thr Arg Phe Leu Gln Asp Asp Pro Leu Leu Thr Arg Glu Gln
1               5                   10                  15

Val Met Ala Glu Leu Ile Arg Val Ala Asp Glu Leu Asn Met Pro Asp
            20                  25                  30

Lys Arg Gly Ala Cys Val Ile Ala Gly Met Thr Ile Ser Gln Glu Val
        35                  40                  45

Gly Val Lys Asp Asn Asp Pro Pro Phe Glu Arg Arg Phe Trp Cys Pro
    50                  55                  60

Ala Asn Arg Ala Asp Pro Glu Ser Phe Asn Tyr Pro His Asp Ser Glu
65                  70                  75                  80

Ser Asn Asp Gly Arg Ser Val Gly Tyr Phe Gln Gln Lys Gly Pro
            85                  90                  95

Asn Gly Glu Leu Trp Trp Gly Thr Thr Ala Ser Glu Met Asn Leu His
        100                 105                 110

Ser Ala Ala Thr Gln Phe Met Thr Arg Leu Lys Ala Ala Gly Tyr Asn
    115                 120                 125

Ala Ser Asn Ala Gln Ala Ala Asn Asp Ser Ala Gln Ala Ile Gln Arg
130                 135                 140

```
Ser Gly Val Pro Gln Ala Tyr Lys Gln Trp Trp Asp Asp Ile Asn Arg
145                 150                 155                 160

Leu Tyr Asp Lys Val Lys Gly Ser Gly Gly Gly Pro Ala Pro Ala Pro
                165                 170                 175

Lys Pro Pro Gln Ser Gly Pro Trp Thr Gly Asp Pro Val Trp Leu Ala
            180                 185                 190

Asp Val Leu Arg Ala Glu Gly Leu Asn Val Val Glu Leu Pro Gly Trp
        195                 200                 205

Leu Asp Arg Gly His Gly Asp Met Gly Arg Leu Trp Gly Val Val Cys
    210                 215                 220

His His Thr Gly Ser Asp Asn Thr Pro Ser Ser Glu Ile Ala Phe His
225                 230                 235                 240

Pro Ser Leu Gly Leu Cys Ser Gln Ile His Leu Ala Arg Asn Gly Thr
                245                 250                 255

Val Thr Leu Cys Gly Val Gly Ile Ala Trp His Ala Gly Val Gly Ser
            260                 265                 270

Tyr Pro Gly Leu Pro Glu Asp Asn Ala Asn Ala Val Thr Ile Gly Ile
        275                 280                 285

Glu Ala Gln Asn Ser Gly Thr Tyr Asp Gly Ala Pro His Arg Thr Asn
    290                 295                 300

Trp Pro Asp Ala Gln Tyr Asp Ala Tyr Val Lys Cys Cys Ala Ala Ile
305                 310                 315                 320

Cys Arg Arg Leu Gly Val Arg Ala Asp His Val Ile Ser His Lys Glu
                325                 330                 335

Trp Ala Gly Arg Lys Gln Gly Lys Trp Asp Pro Gly Ala Ile Asp Met
            340                 345                 350

Asn Ile Phe Arg Ala Asp Val Gln Arg Arg Ile Asp Ala His Gln Pro
        355                 360                 365

Asn Gly Glu Asp Asp Phe Met Ala Ala Leu Ser Ala Asp Glu Gln Arg
    370                 375                 380

Glu Val Leu Asn Leu Leu Arg Val Leu Ala Asp Arg Arg Phe Val Ser
385                 390                 395                 400

Arg Ser Pro Phe Arg His Leu Gly Glu Gly Pro Ser Glu Thr Val Ala
                405                 410                 415

Gly Phe Gly Leu Asn Thr Asp Gly Leu Asn His Ala Gln Tyr Thr Ile
            420                 425                 430

Glu Leu Ala Arg Leu Gly Asp Pro Thr His Leu Ala Leu Leu Arg Glu
        435                 440                 445

Val Ala Ser Ala Glu Gly Asp Ser Arg Tyr Pro Asp Arg Gln Tyr Asp
    450                 455                 460

Ala Lys Leu Ala Lys Arg Val Leu Ala Glu Ile Glu Gly Ala Ala Thr
465                 470                 475                 480

Ala Pro Ala Lys Pro Ser Thr Pro Ser Ala Pro Thr Glu Pro Ala Pro
                485                 490                 495

Glu Ala Pro Thr Pro Pro Val Lys Ala Ala Cys Ala Leu Ser Ala Ala
            500                 505                 510

Gly Cys Val Val Ala Gly Ser Thr Ser Gly Gly Cys Ala Leu Ser
        515                 520                 525

Thr Asp Gly Thr Gly Lys Cys Val Val Thr Ala Ala Thr Asp Gly Gly
    530                 535                 540

Ala Ala His His His His His His Gly Ser Leu Leu Gly Asp Phe Phe
545                 550                 555                 560
```

Arg Lys Ser Lys Glu Lys Ile Gly Lys Glu Phe Lys Arg Ile Val Gln
565 570 575

Arg Ile Lys Asp Phe Leu Arg Asn Leu Val Pro Arg Thr Glu Ser Tyr
580 585 590

Gly Arg Lys Lys Arg Arg Gln Arg Arg Arg
595 600

<210> SEQ ID NO 90
<211> LENGTH: 1806
<212> TYPE: DNA
<213> ORGANISM: Artificial sequence
<220> FEATURE:
<223> OTHER INFORMATION: TM4gp29/LL37/TAT47-57 construct 1

<400> SEQUENCE: 90

| | | | | | | |
|---|---|---|---|---|---|---|
| agcttcactc | gctttctgca | ggatgatccg | ctgctgaccc | gtgaacaggt | gatggctgaa | 60 |
| ctgatccgtg | tggcggacga | actgaacatg | ccggataaac | gtggcgcttg | cgttatcgcc | 120 |
| ggcatgacta | tctcccagga | agtgggtgtc | aaagacaacg | acccaccatt | cgagcgccgt | 180 |
| ttttggtgcc | cggcaaaccg | tgctgatccg | gaaagcttca | actaccgca | cgactctgaa | 240 |
| tccaacgacg | tcgctccgt | aggctacttc | agcagcaga | aaggcccgaa | cggtgaactg | 300 |
| tggtggggta | cgaccgcttc | cgagatgaac | ctgcattctg | ccgcaactca | gttcatgacg | 360 |
| cgtctgaaag | ccgcaggcta | caacgcaagc | aacgcacagg | ctgcgaacga | ctccgcacag | 420 |
| gcgatccagc | gtagcggcgt | gccgcaggcc | tacaaacagt | ggtgggacga | cattaaccgc | 480 |
| ctgtatgaca | aagtgaaagg | ctctggtggc | ggtccggcac | cggcaccaaa | accaccacag | 540 |
| agcggtccgt | ggactggtga | tccggtttgg | ctggctgacg | ttctccgcgc | tgagggtctg | 600 |
| aacgtagtgg | aactgccagg | ttggctggat | cgtggccacg | tgacatggg | tcgtctgtgg | 660 |
| ggtgtcgtgt | gccatcatac | tggctccgat | aacacgccaa | gctccgaaat | cgctttccac | 720 |
| ccgagcctgg | gtctgtgttc | tcagatccac | ctggctcgta | acggtaccgt | taccctgtgc | 780 |
| ggtgtaggta | tcgcttggca | cgcaggtgtt | ggttcctacc | cgggtctccc | ggaagacaac | 840 |
| gcgaacgcgg | tcactattgg | catcgaagct | cagaactctg | gtacgtacga | cggcgctcca | 900 |
| caccgtacga | actggccaga | tgcgcagtat | gacgcgtatg | taaaatgctg | tgccgccatc | 960 |
| tgtcgtcgcc | tgggcgtacg | cgctgatcac | gttatttccc | acaaagaatg | ggctggtcgt | 1020 |
| aaacagggca | aatgggaccc | gggcgctatc | gatatgaaca | tcttccgtgc | tgacgtccag | 1080 |
| cgtcgtattg | acgcacacca | gccgaacggt | gaggacgact | ttatggcagc | gctgtctgcg | 1140 |
| gatgagcagc | gtgaagtgct | gaacctgctg | cgtgtcctgg | cagatcgccg | ttttgtatct | 1200 |
| cgctctccgt | tccgtcacct | gggtgaaggt | ccaagcgaga | cggttgcagg | tttcggcctg | 1260 |
| aacaccgacg | gcctgaacca | tgcgcagtat | actatcgaac | tggcacgtct | gggcgatcca | 1320 |
| acccacctgg | ctctgctgcg | cgaagttgcc | tctgcagaag | gcgattctcg | ctacccagat | 1380 |
| cgccagtacg | atgcgaaact | ggccaaacgt | gtcctggcgg | aaattgaagg | tgcagcgacc | 1440 |
| gctccagcta | aaccgtctac | cccaagcgct | ccaactgaac | cggctccaga | agccccgact | 1500 |
| ccgccagtaa | aagctgcctg | tgcgctgtcc | gctgccggtt | gtgttgtcgc | tggctctacc | 1560 |
| tctggtggcg | gttgcgcact | gtctactgat | ggcaccggca | aatgcgtggt | tactgcggca | 1620 |
| actgacggcg | gtgctgcaca | ccatcaccat | caccatggat | ccttattggg | tgatttcttt | 1680 |
| cggaagagca | agaaaagat | aggaaaggag | tttaaacgaa | ttgttcaacg | tatcaaagac | 1740 |
| ttcctaagga | atcttgtacc | aagaacagaa | agttatggcc | gcaaaaaacg | gcgtcagcgt | 1800 |

<210> SEQ ID NO 91
<211> LENGTH: 562
<212> TYPE: PRT
<213> ORGANISM: Artificial sequence
<220> FEATURE:
<223> OTHER INFORMATION: Bxz2gp11/alpha-defensin/PTD3 construct 2

<400> SEQUENCE: 91

```
Thr Glu Lys Val Leu Pro Tyr Asp Arg Ser Ile Val Thr Gln Glu Thr
1               5                   10                  15

Gly Trp Trp Cys Gly Pro Ala Ala Thr Gln Val Val Leu Asn Ser Arg
            20                  25                  30

Gly Ile Ile Val Pro Glu Ala Thr Leu Ala Ala Glu Ile Glu Ala Ile
        35                  40                  45

Glu Asn Pro Gly Arg Gly Asp Arg Asp Gly Thr Asp Tyr Val Gly
    50                  55                  60

Leu Ile Glu Gln Val Leu Asp Arg Arg Val Pro Gln Ala Arg Tyr Thr
65                  70                  75                  80

Ser Val Tyr Leu Thr Asn Asp Pro Pro Thr Gln Ala Gln Lys Asp Arg
                85                  90                  95

Leu Trp Glu His Ile Val Arg Ser Ile Asn Ala Gly Tyr Gly Val Val
            100                 105                 110

Met Asn Trp Val Ala Pro Pro Ser Asn Lys Pro Arg Gly Val Lys Gly
        115                 120                 125

Ser Val Ser Pro Arg Tyr Ser Gly Gly Thr Thr Tyr His Tyr Val Ala
130                 135                 140

Cys Met Gly Tyr Asp Asp Thr Pro Gly Ala Arg Ala Val Trp Ile Ala
145                 150                 155                 160

Asp Ser Gly Phe Gln Pro Gln Gly Tyr Trp Ile Ser Phe Asp Gln Cys
                165                 170                 175

Ala Thr Leu Ile Pro Pro Lys Gly Tyr Ala Tyr Ala Asp Ala Ala Pro
            180                 185                 190

Ala Ala Pro Ala Pro Ala Pro Thr Pro Val Val Asp Ala Ala Pro Ile
        195                 200                 205

Leu Ala Arg Ala Ala Gly Ile Ser Glu Ala Lys Ala Arg Glu Ile Leu
    210                 215                 220

Pro Thr Met Arg Asp Gly Leu Lys Gln Ala Asp Cys Thr Thr Val Asn
225                 230                 235                 240

Arg Ile Ala Met Phe Ile Ala Gln Thr Gly His Glu Ser Asp Asp Phe
                245                 250                 255

Arg Ala Thr Glu Glu Tyr Ala Asn Gly Pro Leu Asp Gln Glu Arg Trp
            260                 265                 270

Ile Tyr Lys Gly Arg Thr Trp Ile Gln Ile Thr Trp Arg Glu His Tyr
        275                 280                 285

Ala Arg Phe Gly Lys Trp Cys Phe Asp Arg Gly Leu Val Thr Asp Pro
    290                 295                 300

Asp Val Phe Val Lys Asn Pro Arg Ala Leu Ala Asp Leu Lys Trp Ala
305                 310                 315                 320

Gly Ile Gly Ala Ala Trp Tyr Trp Thr Val Glu Arg Pro Asp Ile Asn
                325                 330                 335

Ala Leu Cys Asp Arg Arg Asp Ile Glu Thr Val Ser Arg Arg Ile Asn
            340                 345                 350

Gly Thr Asn Pro Asn Thr Gly Arg Ala Asn His Ile Glu Glu Arg Ile
```

```
                355                 360                 365
Ala Arg Trp Asn Arg Ala Leu Ala Val Gly Asp Asp Leu Leu Gln Leu
    370                 375                 380

Ile Arg Glu Glu Asp Gly Phe Leu Ser Ala Leu Thr Pro Ala Glu
385                 390                 395                 400

Gln Arg Ala Leu Tyr Asn Glu Ile Met Lys Lys Gly Pro Thr Arg Ser
                405                 410                 415

Phe Met Ala Glu Asp Gln Asn Gln Ile Glu Thr Leu Leu Gly Phe Val
            420                 425                 430

Tyr Asn Ile Asp Gly Asn Ile Trp Asn Asp Ala Val Thr Arg Ala Tyr
        435                 440                 445

Leu Phe Asp Val Pro Leu Ala Val Glu Tyr Val Glu Arg Val Ala Arg
    450                 455                 460

Asp Gly Val His Pro Lys Ser Trp Ala Phe Gln Leu Asp Gly Lys
465                 470                 475                 480

Gly Glu Arg Trp Leu Ala Lys Phe Gly Gln Glu Tyr Cys Lys Gly Leu
                485                 490                 495

Ile Arg Phe Lys Lys Lys Leu Asn Asp Leu Leu Glu Pro Tyr Gly Glu
            500                 505                 510

Asn His His His His His Gly Ser Asp Cys Tyr Cys Arg Ile Pro
        515                 520                 525

Ala Cys Ile Ala Gly Glu Arg Arg Tyr Gly Thr Cys Ile Tyr Gln Gly
    530                 535                 540

Arg Leu Trp Ala Phe Cys Cys Tyr Ala Arg Lys Ala Arg Gln Ala
545                 550                 555                 560

Arg Arg

<210> SEQ ID NO 92
<211> LENGTH: 1686
<212> TYPE: DNA
<213> ORGANISM: Artificial sequence
<220> FEATURE:
<223> OTHER INFORMATION: Bxz2gp11/alpha-defensin/PTD3 construct 2

<400> SEQUENCE: 92
accgagaaag tgctgccgta cgaccgttct atcgttaccc aggaaaccgg ttggtggtgt      60
ggtccagcgg ctactcaggt tgttctgaac tcccgtggca tcatcgttcc agaagctacg     120
ctggcagcgg aaatcgaagc tattgaaaac ccgggtcgtg gtgacgatcg tgatggtacc     180
gactacgtag gtctgatcga gcaggttctg gatcgtcgtg ttccgcaggc tcgttacacc     240
tccgtgtatc tgaccaacga tccaccgact caggcacaga agaccgtcct ctgggagcat     300
atcgtccgtt ctatcaacgc cggttatggc gtggttatga actgggtagc ccaccgagc     360 aacaaaccac gtggcgtgaa aggctctgtg tctccgcgct attccggcgg taccacttac     420
cactacgtag cctgtatggg ttacgacgat acgccaggcg ctcgtgcggt ttggatcgcg     480
gattctggtt tccagccaca gggctactgg attagcttcg atcagtgcgc gaccctgatt     540
ccgccaaaag gctacgctta tgcagacgca gctccggctg caccagcacc agctccaact     600
ccggttgtag acgctgcacc aattctggct cgtgcggcag gtatctccga agccaaagcg     660
cgtgaaattc tgccgactat gcgcgacggt ctgaaacagg ctgattgtac gaccgtcaac     720
cgtatcgcaa tgtttattgc gcagaccggt cacgaatctg atgacttccg cgccaccgaa     780
gagtatgcga acggtccact ggaccaggaa cgttggatct acaaaggccg tacctggatt     840 cagatcaccct ggcgtgaaca ctacgctcgt ttcggcaaat ggtgcttcga tcgcggcctg     900
```

```
gtaactgatc cggatgtttt cgtgaaaaac ccacgcgctc tggcagatct gaaatgggct    960
ggtattggcg cagcgtggta ttggaccgtt gaacgtccgg acatcaacgc actgtgcgac   1020
cgccgtgata tcgaaactgt gtctcgtcgc atcaacggca ctaacccgaa cactggccgc   1080
gcgaaccaca tcgaggaacg tattgctcgc tggaaccgtg cactggctgt gggtgatgac   1140
ctgctccagc tgatccgtga agaggaagat ggtttcctga cgctctctga cccagcagaa   1200
cagcgtgccc tgtacaacga gattatgaaa aaggcccaa cccgctcttt tatgccgaa     1260
gaccagaacc agatcgagac cctgctgggt tttgtctata acatcgacgg caacatctgg   1320
aacgacgcag ttactcgcgc gtatctgttc gacgtaccac tggccgtcga atacgtggaa   1380
cgcgttgctc gtgatggtgt acacccgaaa agctgggcgt tcagcagct ggacggtaaa    1440
ggcgaacgtt ggctcgcgaa attcggtcag gaatactgca aagtctgat ccgcttcaaa    1500
aaaaaactga acgacctgct ggaaccgtac ggtgaaaacc accatcacca tcaccacgga   1560
tccgactgtt actgccgtat cccagcatgt attgctggtg aacgccgtta cggcacttgt   1620
atttaccagg gtcgcctgtg gcttttttgc tgctatgccc gtaaagcacg tcggcaggcg   1680
cgccgc                                                              1686
```

<210> SEQ ID NO 93
<211> LENGTH: 557
<212> TYPE: PRT
<213> ORGANISM: Artificial sequence
<220> FEATURE:
<223> OTHER INFORMATION: PTD3/alpha-defensin/Bxz2gp11 construct 3

<400> SEQUENCE: 93

```
Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30

Gln Gly Arg Leu Trp Ala Phe Cys Cys Leu Lys Met Thr Glu Lys Val
        35                  40                  45

Leu Pro Tyr Asp Arg Ser Ile Val Thr Gln Glu Thr Gly Trp Trp Cys
    50                  55                  60

Gly Pro Ala Ala Thr Gln Val Val Leu Asn Ser Arg Gly Ile Ile Val
65                  70                  75                  80

Pro Glu Ala Thr Leu Ala Ala Glu Ile Glu Ala Ile Glu Asn Pro Gly
                85                  90                  95

Arg Gly Asp Asp Arg Asp Gly Thr Asp Tyr Val Gly Leu Ile Glu Gln
            100                 105                 110

Val Leu Asp Arg Arg Val Pro Gln Ala Arg Tyr Thr Ser Val Tyr Leu
        115                 120                 125

Thr Asn Asp Pro Pro Thr Gln Ala Gln Lys Asp Arg Leu Trp Glu His
    130                 135                 140

Ile Val Arg Ser Ile Asn Ala Gly Tyr Gly Val Val Met Asn Trp Val
145                 150                 155                 160

Ala Pro Pro Ser Asn Lys Pro Arg Gly Val Lys Gly Ser Val Ser Pro
                165                 170                 175

Arg Tyr Ser Gly Gly Thr Thr Tyr His Tyr Val Ala Cys Met Gly Tyr
            180                 185                 190

Asp Asp Thr Pro Gly Ala Arg Ala Val Trp Ile Ala Asp Ser Gly Phe
        195                 200                 205

Gln Pro Gln Gly Tyr Trp Ile Ser Phe Asp Gln Cys Ala Thr Leu Ile
```

Pro Pro Lys Gly Tyr Ala Tyr Ala Asp Ala Ala Pro Ala Ala Pro Ala
225                 230                 235                 240

Pro Ala Pro Thr Pro Val Val Asp Ala Ala Pro Ile Leu Ala Arg Ala
            245                 250                 255

Ala Gly Ile Ser Glu Ala Lys Ala Arg Glu Ile Leu Pro Thr Met Arg
            260                 265                 270

Asp Gly Leu Lys Gln Ala Asp Cys Thr Thr Val Asn Arg Ile Ala Met
            275                 280                 285

Phe Ile Ala Gln Thr Gly His Glu Ser Asp Asp Phe Arg Ala Thr Glu
    290                 295                 300

Glu Tyr Ala Asn Gly Pro Leu Asp Gln Glu Arg Trp Ile Tyr Lys Gly
305                 310                 315                 320

Arg Thr Trp Ile Gln Ile Thr Trp Arg Gly His Tyr Ala Arg Phe Gly
                325                 330                 335

Lys Trp Cys Phe Asp Arg Gly Leu Val Thr Asp Pro Asp Val Phe Val
            340                 345                 350

Lys Asn Pro Arg Ala Leu Ala Asp Leu Lys Trp Ala Gly Ile Gly Ala
            355                 360                 365

Ala Trp Tyr Trp Thr Val Glu Arg Pro Asp Ile Asn Ala Leu Cys Asp
    370                 375                 380

Arg Arg Asp Ile Glu Thr Val Ser Arg Arg Ile Asn Gly Thr Asn Pro
385                 390                 395                 400

Asn Thr Gly Arg Ala Asn His Ile Glu Glu Arg Ile Ala Arg Trp Asn
                405                 410                 415

Arg Ala Leu Ala Val Gly Asp Asp Leu Leu Gln Leu Ile Arg Glu Glu
            420                 425                 430

Glu Asp Gly Phe Leu Ser Ala Leu Thr Pro Ala Glu Gln Arg Ala Leu
            435                 440                 445

Tyr Asn Glu Ile Met Lys Lys Gly Pro Thr Arg Ser Phe Met Ala Glu
    450                 455                 460

Asp Gln Asn Gln Ile Glu Thr Leu Leu Gly Phe Val Tyr Asn Ile Asp
465                 470                 475                 480

Gly Asn Ile Trp Asn Asp Ala Val Thr Arg Ala Tyr Leu Phe Asp Val
                485                 490                 495

Pro Leu Ala Val Glu Tyr Val Glu Arg Val Ala Arg Asp Gly Val His
            500                 505                 510

Pro Lys Ser Trp Ala Phe Gln Gln Leu Asp Gly Lys Gly Glu Arg Trp
            515                 520                 525

Leu Ala Lys Phe Gly Gln Glu Tyr Cys Lys Gly Leu Ile Arg Phe Lys
    530                 535                 540

Lys Lys Leu Asn Asp Leu Leu Glu Pro Tyr Gly Glu Asn
545                 550                 555

<210> SEQ ID NO 94
<211> LENGTH: 1671
<212> TYPE: DNA
<213> ORGANISM: Artificial sequence
<220> FEATURE:
<223> OTHER INFORMATION: PTD3/alpha-defensin/Bxz2gp11 construct 3

<400> SEQUENCE: 94
tatgcccgta aagcacgtcg gcaggcgcgc cgcgactgtt actgccgtat cccagcatgt      60
attgctggtg aacgccgtta c

```
tgccttaaga tgaccgagaa agtgctgccg tacgaccgtt ctatcgttac ccaggaaacc    180
ggttggtggt gtggtccagc ggctactcag gttgttctga actcccgtgg catcatcgtt    240
ccagaagcta cgctggcagc ggaaatcgaa gctattgaaa acccgggtcg tggtgacgat    300
cgtgatggta ccgactacgt aggtctgatc gagcaggttc tggatcgtcg tgttccgcag    360
gctcgttaca cctccgtgta tctgaccaac gatccaccga ctcaggcaca gaaagaccgt    420
ctctgggagc atatcgtccg ttctatcaac gccggttatg cgtggttat gaactgggta    480
gccccaccga gcaacaaacc acgtggcgtg aaaggctctg tgtctccgcg ctattccggc    540
ggtaccactt accactacgt agcctgtatg ggttacgacg atacgccagg cgctcgtgcg    600
gtttggatcg cggattctgg tttccagcca cagggctact ggattagctt cgatcagtgc    660
gcgaccctga ttccgccaaa aggctacgct tatgcagacg cagctccggc tgcaccagca    720
ccagctccaa ctccggttgt agacgctgca ccaattctgg ctcgtgcggc aggtatctcc    780
gaagccaaag cgcgtgaaat tctgccgact atgcgcgacg tctgaaaca ggctgattgt    840
acgaccgtca accgtatcgc aatgtttatt gcgcagaccg gtcacgaatc tgatgacttc    900
cgcgccaccg aagagtatgc gaacggtcca ctggaccagg aacgttggat ctacaaaggc    960
cgtacctgga ttcagatcac ctggcgtgaa cactacgctc gtttcggcaa atggtgcttc   1020
gatcgcggcc tggtaactga tccggatgtt ttcgtgaaaa acccacgcgc tctggcagat   1080
ctgaaatggg ctggtattgg cgcagcgtgg tattggaccg ttgaacgtcc ggacatcaac   1140
gcactgtgcg accgccgtga tatcgaaact gtgtctcgtc gcatcaacgg cactaacccg   1200
aacactggcc gcgcgaacca catcgaggaa cgtattgctc gctggaaccg tgcactggct   1260
gtgggtgatg acctgctcca gctgatccgt gaagaggaag atggtttcct gagcgctctg   1320
acccagcag aacagcgtgc cctgtacaac gagattatga aaaaggccc aacccgctct   1380
tttatggccg aagaccagaa ccagatcgag accctgctgg gttttgtcta acatcgac     1440
ggcaacatct ggaacgacgc agttactcgc gcgtatctgt tcgacgtacc actggccgtc   1500
gaatacgtgg aacgcgttgc tcgtgatggt gtacacccga aaagctgggc gtttcagcag   1560
ctggacggta aaggcgaacg ttggctcgcg aaattcggtc aggaatactg caaaggtctg   1620
atccgcttca aaaaaaaact gaacgacctg ctggaaccgt acggtgaaaa c            1671
```

<210> SEQ ID NO 95
<211> LENGTH: 595
<212> TYPE: PRT
<213> ORGANISM: Artificial sequence
<220> FEATURE:
<223> OTHER INFORMATION: PTD3/alpha-defensin/Bxz2gp11/alpha-defensin
      construct 4

<400> SEQUENCE: 95

Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30

Gln Gly Arg Leu Trp Ala Phe Cys Cys Leu Lys Met Thr Glu Lys Val
        35                  40                  45

Leu Pro Tyr Asp Arg Ser Ile Val Thr Gln Glu Thr Gly Trp Trp Cys
    50                  55                  60

Gly Pro Ala Ala Thr Gln Val Val Leu Asn Ser Arg Gly Ile Ile Val
65                  70                  75                  80

Pro Glu Ala Thr Leu Ala Ala Glu Ile Glu Ala Ile Glu Asn Pro Gly

```
                    85                  90                  95
Arg Gly Asp Asp Arg Asp Gly Thr Asp Tyr Val Gly Leu Ile Glu Gln
                100                 105                 110

Val Leu Asp Arg Arg Val Pro Gln Ala Arg Tyr Thr Ser Val Tyr Leu
            115                 120                 125

Thr Asn Asp Pro Pro Thr Gln Ala Gln Lys Asp Arg Leu Trp Glu His
        130                 135                 140

Ile Val Arg Ser Ile Asn Ala Gly Tyr Gly Val Val Met Asn Trp Val
145                 150                 155                 160

Ala Pro Pro Ser Asn Lys Pro Arg Gly Val Lys Gly Ser Val Ser Pro
                165                 170                 175

Arg Tyr Ser Gly Gly Thr Thr Tyr His Tyr Val Ala Cys Met Gly Tyr
            180                 185                 190

Asp Asp Thr Pro Gly Ala Arg Ala Val Trp Ile Ala Asp Ser Gly Phe
        195                 200                 205

Gln Pro Gln Gly Tyr Trp Ile Ser Phe Asp Gln Cys Ala Thr Leu Ile
    210                 215                 220

Pro Pro Lys Gly Tyr Ala Tyr Ala Asp Ala Ala Pro Ala Ala Pro Ala
225                 230                 235                 240

Pro Ala Pro Thr Pro Val Val Asp Ala Ala Pro Ile Leu Ala Arg Ala
                245                 250                 255

Ala Gly Ile Ser Glu Ala Lys Ala Arg Glu Ile Leu Pro Thr Met Arg
            260                 265                 270

Asp Gly Leu Lys Gln Ala Asp Cys Thr Thr Val Asn Arg Ile Ala Met
        275                 280                 285

Phe Ile Ala Gln Thr Gly His Glu Ser Asp Asp Phe Arg Ala Thr Glu
    290                 295                 300

Glu Tyr Ala Asn Gly Pro Leu Asp Gln Glu Arg Trp Ile Tyr Lys Gly
305                 310                 315                 320

Arg Thr Trp Ile Gln Ile Thr Trp Arg Glu His Tyr Ala Arg Phe Gly
                325                 330                 335

Lys Trp Cys Phe Asp Arg Gly Leu Val Thr Asp Pro Asp Val Phe Val
            340                 345                 350

Lys Asn Pro Arg Ala Leu Ala Asp Leu Lys Trp Ala Gly Ile Gly Ala
        355                 360                 365

Ala Trp Tyr Trp Thr Val Glu Arg Pro Asp Ile Asn Ala Leu Cys Asp
    370                 375                 380

Arg Arg Asp Ile Glu Thr Val Ser Arg Arg Ile Asn Gly Thr Asn Pro
385                 390                 395                 400

Asn Thr Gly Arg Ala Asn His Ile Glu Glu Arg Ile Ala Arg Trp Asn
                405                 410                 415

Arg Ala Leu Ala Val Gly Asp Asp Leu Leu Gln Leu Ile Arg Glu Glu
            420                 425                 430

Glu Asp Gly Phe Leu Ser Ala Leu Thr Pro Ala Glu Gln Arg Ala Leu
        435                 440                 445

Tyr Asn Glu Ile Met Lys Lys Gly Pro Thr Arg Ser Phe Met Ala Glu
    450                 455                 460

Asp Gln Asn Gln Ile Glu Thr Leu Leu Gly Phe Val Tyr Asn Ile Asp
465                 470                 475                 480

Gly Asn Ile Trp Asn Asp Ala Val Thr Arg Ala Tyr Leu Phe Asp Val
                485                 490                 495

Pro Leu Ala Val Glu Tyr Val Glu Arg Val Ala Arg Asp Gly Val His
            500                 505                 510
```

```
Pro Lys Ser Trp Ala Phe Gln Gln Leu Asp Gly Lys Gly Glu Arg Trp
    515                 520                 525
Leu Ala Lys Phe Gly Gln Glu Tyr Cys Lys Gly Leu Ile Arg Phe Lys
    530                 535                 540
Lys Lys Leu Asn Asp Leu Leu Glu Pro Tyr Gly Glu Asn His His His
545                 550                 555                 560
His His His Gly Ser Asp Cys Tyr Cys Arg Ile Pro Ala Cys Ile Ala
            565                 570                 575
Gly Glu Arg Arg Tyr Gly Thr Cys Ile Tyr Gln Gly Arg Leu Trp Ala
            580                 585                 590
Phe Cys Cys
    595

<210> SEQ ID NO 96
<211> LENGTH: 1785
<212> TYPE: DNA
<213> ORGANISM: Artificial sequence
<220> FEATURE:
<223> OTHER INFORMATION: PTD3/alpha-defensin/Bxz2gp11/alpha-defensin
      construct 4

<400> SEQUENCE: 96
```

| | | | | | |
|---|---|---|---|---|---|
| tatgcccgta | aagcacgtcg | gcaggcgcgc | cgcgactgtt | actgccgtat | cccagcatgt | 60 |
| attgctggtg | aacgccgtta | cggcacttgt | atttaccagg | tcgcctgtg | ggcttttttgc | 120 |
| tgccttaaga | tgaccgagaa | agtgctgccg | tacgaccgtt | ctatcgttac | ccaggaaacc | 180 |
| ggttggtggt | gtggtccagc | ggctactcag | gttgttctga | actcccgtgg | catcatcgtt | 240 |
| ccagaagcta | cgctggcagc | ggaaatcgaa | gctattgaaa | acccgggtcg | tggtgacgat | 300 |
| cgtgatggta | ccgactacgt | aggtctgatc | gagcaggttc | tggatcgtcg | tgttccgcag | 360 |
| gctcgttaca | cctccgtgta | tctgaccaac | gatccaccga | ctcaggcaca | gaaagaccgt | 420 |
| ctctgggagc | atatcgtccg | ttctatcaac | gccggttatg | cgtggttat | gaactgggta | 480 |
| gccccaccga | gcaacaaacc | acgtggcgtg | aaaggctctg | tgtctccgcg | ctattccggc | 540 |
| ggtaccactt | accactacgt | agcctgtatg | ggttacgacg | atacgccagg | cgctcgtgcg | 600 |
| gtttggatcg | cggattctgg | tttccagcca | cagggctact | ggattagctt | cgatcagtgc | 660 |
| gcgaccctga | ttccgccaaa | aggctacgct | tatgcagacg | cagctccggc | tgcaccagca | 720 |
| ccagctccaa | ctccggttgt | agacgctgca | ccaattctgg | ctcgtgcggc | aggtatctcc | 780 |
| gaagccaaag | cgcgtgaaat | tctgccgact | atgcgcgacg | tctgaaaca | ggctgattgt | 840 |
| acgaccgtca | accgtatcgc | aatgtttatt | gcgcagaccg | gtcacgaatc | tgatgacttc | 900 |
| cgcgccaccg | aagagtatgc | gaacggtcca | ctggaccagg | aacgttggat | ctacaaaggc | 960 |
| cgtacctgga | ttcagatcac | ctggcgtgaa | cactacgctc | gtttcggcaa | atggtgcttc | 1020 |
| gatcgcggcc | tggtaactga | tccggatgtt | ttcgtgaaaa | acccacgcgc | tctggcagat | 1080 |
| ctgaaatggg | ctggtattgg | cgcagcgtgg | tattggaccg | ttgaacgtcc | ggacatcaac | 1140 |
| gcactgtgcg | accgccgtga | tatcgaaact | gtgtctcgtc | gcatcaacgg | cactaacccg | 1200 |
| aacactggcc | gcgcgaacca | catcgaggaa | cgtattgctc | gctggaaccg | tgcactggct | 1260 |
| gtgggtgatg | acctgctcca | gctgatccgt | gaagaggaag | atggtttcct | gagcgctctg | 1320 |
| accccagcag | aacagcgtgc | cctgtacaac | gagattatga | aaaaggccc | aacccgctct | 1380 |
| tttatgcccg | aagaccagaa | ccagatcgag | accctgctgg | ttttgtcta | taacatcgac | 1440 |
| ggcaacatct | ggaacgacgc | agttactcgc | gcgtatctgt | tcgacgtacc | actggccgtc | 1500 |

```
gaatacgtgg aacgcgttgc tcgtgatggt gtacacccga aaagctgggc gtttcagcag    1560
ctggacggta aaggcgaacg ttggctcgcg aaattcggtc aggaatactg caaaggtctg    1620
atccgcttca aaaaaaaact gaacgacctg ctggaaccgt acggtgaaaa ccaccatcac    1680
catcaccacg gatccgactg ttactgccgt atcccagcat gtattgctgg tgaacgccgt    1740
tacggcactt gtatttacca gggtcgcctg tgggcttttt gctgc                   1785
```

<210> SEQ ID NO 97
<211> LENGTH: 351
<212> TYPE: PRT
<213> ORGANISM: Artificial sequence
<220> FEATURE:
<223> OTHER INFORMATION: beta-defensin/L5gp10/TAT47-57 construct 5

<400> SEQUENCE: 97

```
Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
                20                  25                  30

Lys Cys Cys Arg Lys Lys Leu Lys Met Thr Phe Thr Val Thr Arg Glu
            35                  40                  45

Arg Ala Gln Trp Val His Asp Met Ala Arg Ala Arg Asp Gly Leu Pro
        50                  55                  60

Tyr Ala Tyr Gly Gly Ala Phe Thr Asn Asn Pro Arg Val Ser Thr Asp
65                  70                  75                  80

Cys Ser Gly Leu Val Leu Gln Thr Gly Ala Trp Tyr Gly Gly Arg Thr
                85                  90                  95

Asp Trp Val Gly Asn Arg Tyr Gly Ser Thr Glu Ser Phe Arg Leu Asp
                100                 105                 110

His Lys Ile Val Tyr Asp Leu Gly Phe Lys Arg Met Pro Arg Gly Gly
            115                 120                 125

Pro Ala Ala Leu Pro Ile Lys Pro Val Met Leu Val Gly Leu Gln His
        130                 135                 140

Gly Gly Gly Gly Val Tyr Ser His Thr Ala Cys Thr Leu Met Thr Met
145                 150                 155                 160

Asp His Pro Gly Gly Pro Val Lys Met Ser Asp Arg Gly Val Asp Trp
                165                 170                 175

Glu Ser His Gly Asn Arg Asn Gly Val Gly Val Glu Leu Tyr Glu Gly
                180                 185                 190

Ala Arg Ala Trp Asn Asp Pro Leu Phe His Asp Phe Trp Tyr Leu Asp
            195                 200                 205

Ala Val Leu Glu Asp Glu Gly Asp Asp Asp Glu Leu Ala Asp Pro Val
        210                 215                 220

Leu Gly Lys Met Ile Arg Glu Ile His Ala Cys Leu Phe Asn Gln Thr
225                 230                 235                 240

Ala Ser Thr Ser Asp Leu Ala Thr Pro Gly Glu Gly Ala Ile Trp Gln
                245                 250                 255

Leu His Gln Lys Ile His Ser Ile Asp Gly Met Leu His Pro Ile His
                260                 265                 270

Ala Glu Arg Arg Ala Arg Ala Gly Asp Leu Gly Glu Leu His Arg Ile
            275                 280                 285

Val Leu Ala Ala Lys Gly Leu Gly Val Lys Arg Asp Glu Val Thr Lys
        290                 295                 300

Arg Val Tyr Gln Ser Ile Leu Ala Asp Ile Glu Arg Asp Asn Pro Glu
```

```
                305                 310                 315                 320
Val Leu Gln Arg Tyr Ile Ala Glu Arg Gly Gly Leu His His His
                    325                 330                 335

His His Gly Ser Tyr Gly Arg Lys Lys Arg Arg Gln Arg Arg Arg
                340                 345                 350
```

<210> SEQ ID NO 98
<211> LENGTH: 1053
<212> TYPE: DNA
<213> ORGANISM: Artificial sequence
<220> FEATURE:
<223> OTHER INFORMATION: beta-defensin/L5gp10/TAT47-57 construct 5

<400> SEQUENCE: 98

```
aacccggtat cttgcgtgcg caacaaaggt atctgcgttc cgattcgttg tccgggttct       60
atgaaacaga ttggcacttg cgttggtcgt gccgtgaaat gctgccgtaa aaaacttaag     120
atgaccttca ctgttacccg tgaacgtgcg cagtgggttc atgatatggc acgtgctcgc    180
gatggcctgc cgtatgcgta tggcggtgcg ttcaccaaca cccgcgtgt aagcaccgat     240
tgctctggtc tggtactgca gactggcgct tggtatggtg tcgtaccga ttgggtaggc     300
aaccgttacg gctccaccga atcttttcgc ctggaccaca aaatcgtcta cgacctgggc    360
ttcaaacgta tgccacgtgg tggtccagcc gcactgccga tcaaaccggt gatgctggtt    420
ggtctgcaga tggcggtgg tggcgtttac agccacacgg cttgcaccct gatgactatg      480
gatcacccag gtggcccagt aaaatgtcc gaccgtggcg ttgactggga atctcatggc     540
aaccgcaacg gtgtaggtgt tgaactgtac gaaggtgcgc gcgcttggaa cgatccgctc    600
ttccacgact tttggtacct ggatgccgtt ctggaagacg aaggcgacga tgacgaactg    660
gcagatccgc tgctgggcaa aatgattcgc gagatccacg cgtgtctgtt caaccagacg    720
gcgagcactt ctgatctggc aaccccaggt gaaggtgcga tctggcagct gcaccagaaa    780
atccactcta tcgacggtat gctgcacccg attcatgctg aacgccgtgc acgtgcaggt    840
gacctgggcg aactccaccg tatcgtactg gctgccaaag gcctgggtgt gaaacgcgac    900
gaggtgacca aacgtgtcta ccagtctatc ctggccgaca ttgagcgtga caaccccgaa    960
gtgctgcagc gttacattgc tgagcgtggt ggtctgcacc accatcacca ccacggatcc   1020
tatggccgca aaaaacggcg tcagcgtcgc cgc                                 1053
```

<210> SEQ ID NO 99
<211> LENGTH: 368
<212> TYPE: PRT
<213> ORGANISM: Artificial sequence
<220> FEATURE:
<223> OTHER INFORMATION: alpha-defensin/hepcidin/L5gp10/TAT47-57
      construct 6

<400> SEQUENCE: 99

```
Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys Asp Thr
            20                  25                  30

His Phe Pro Ile Cys Ile Phe Cys Cys Gly Cys His Arg Ser Lys
        35                  40                  45

Cys Gly Met Cys Cys Lys Thr Leu Lys Met Thr Phe Thr Val Thr Arg
    50                  55                  60

Glu Arg Ala Gln Trp Val His Asp Met Ala Arg Ala Arg Asp Gly Leu
65                  70                  75                  80
```

Pro Tyr Ala Tyr Gly Gly Ala Phe Thr Asn Asn Pro Arg Val Ser Thr
             85                  90                  95

Asp Cys Ser Gly Leu Val Leu Gln Thr Gly Ala Trp Tyr Gly Gly Arg
            100                 105                 110

Thr Asp Trp Val Gly Asn Arg Tyr Gly Ser Thr Glu Ser Phe Arg Leu
        115                 120                 125

Asp His Lys Ile Val Tyr Asp Leu Gly Phe Lys Arg Met Pro Arg Gly
    130                 135                 140

Gly Pro Ala Ala Leu Pro Ile Lys Pro Val Met Leu Val Gly Leu Gln
145                 150                 155                 160

His Gly Gly Gly Val Tyr Ser His Thr Ala Cys Thr Leu Met Thr
            165                 170                 175

Met Asp His Pro Gly Gly Pro Val Lys Met Ser Asp Arg Gly Val Asp
        180                 185                 190

Trp Glu Ser His Gly Asn Arg Asn Gly Val Gly Val Glu Leu Tyr Glu
            195                 200                 205

Gly Ala Arg Ala Trp Asn Asp Pro Leu Phe His Asp Phe Trp Tyr Leu
        210                 215                 220

Asp Ala Val Leu Glu Asp Glu Gly Asp Asp Glu Leu Ala Asp Pro
225                 230                 235                 240

Val Leu Gly Lys Met Ile Arg Glu Ile His Ala Cys Leu Phe Asn Gln
            245                 250                 255

Thr Ala Ser Thr Ser Asp Leu Ala Thr Pro Gly Glu Gly Ala Ile Trp
            260                 265                 270

Gln Leu His Gln Lys Ile His Ser Ile Asp Gly Met Leu His Pro Ile
        275                 280                 285

His Ala Glu Arg Arg Ala Arg Ala Gly Asp Leu Gly Glu Leu His Arg
    290                 295                 300

Ile Val Leu Ala Ala Lys Gly Leu Gly Val Lys Arg Asp Glu Val Thr
305                 310                 315                 320

Lys Arg Val Tyr Gln Ser Ile Leu Ala Asp Ile Glu Arg Asp Asn Pro
            325                 330                 335

Glu Val Leu Gln Arg Tyr Ile Ala Glu Arg Gly Leu His His His
        340                 345                 350

His His His Gly Ser Tyr Gly Arg Lys Lys Arg Arg Gln Arg Arg
        355                 360                 365

<210> SEQ ID NO 100
<211> LENGTH: 1104
<212> TYPE: DNA
<213> ORGANISM: Artificial sequence
<220> FEATURE:
<223> OTHER INFORMATION: alpha-defensin/hepcidin/L5gp10/TAT47-57
      construct 6

<400> SEQUENCE: 100
gactgttact gccgtatccc agcatgtatt gctggtgaac gccgttacgg cacttgtatt     60
taccagggtc gcctgtgggc ttttgctgc gacacccact tcccgatttg tatcttctgc    120
tgtggctgct gtcaccgctc caaatgtggt atgtgctgta aaacccttaa gatgaccttc    180
actgttaccc gtgaacgtgc gcagtgggtt catgatatgg cacgtgctcg cgatggcctg    240
ccgtatgcgt atggcggtgc gttcaccaac aacccgcgtg taagcaccga ttgctctggt    300
ctggtactgc agactggcgc ttggtatggt ggtcgtaccg attgggtagg caaccgttac    360
ggctccaccg aatcttttcg cctggaccac aaaatcgtct acgacctggg cttcaaacgt    420

```
atgccacgtg gtggtccagc cgcactgccg atcaaaccgg tgatgctggt tggtctgcag    480
catggcggtg gtggcgttta cagccacacg gcttgcaccc tgatgactat ggatcaccca    540
ggtggcccag ttaaaatgtc cgaccgtggc gttgactggg aatctcatgg caaccgcaac    600
ggtgtaggtg ttgaactgta cgaaggtgcg cgcgcttgga cgatccgct cttccacgac    660 ttttggtacc tggatgccgt tctggaagac gaaggcgacg atgacgaact ggcagatccg    720
gtgctgggca aaatgattcg cgagatccac gcgtgtctgt tcaaccagac ggcgagcact    780
tctgatctgg caaccccagg tgaaggtgcg atctggcagc tgcaccagaa aatccactct    840
atcgacggta tgctgcaccc gattcatgct gaacgccgtg cacgtgcagg tgacctgggc    900
gaactccacc gtatcgtact ggctgccaaa ggcctgggtg tgaaacgcga cgaggtgacc    960
aaacgtgtct accagtctat cctggccgac attgagcgtg acaacccgga agtgctgcag   1020
cgttacattg ctgagcgtgg tggtctgcac caccatcacc accacggatc ctatggccgc   1080
aaaaaacggc gtcagcgtcg ccgc                                          1104
```

<210> SEQ ID NO 101
<211> LENGTH: 455
<212> TYPE: PRT
<213> ORGANISM: Artificial sequence
<220> FEATURE:
<223> OTHER INFORMATION: TM4gp30/LL37/TAT47-57 construct 7

<400> SEQUENCE: 101

```
Ala Trp Val Gly Trp Gln Leu Gly Met Gln Gly Glu Gln Val Lys Val
1               5                   10                  15

Ile Gln Gln Lys Leu Ile Ala Lys Tyr Gln Trp Val Arg Asp Arg Tyr
            20                  25                  30

Pro Arg Leu Thr Ala Ser Gly Val Tyr Asp Val Asn Thr Gln Ala Ala
        35                  40                  45

Ile Val Glu Phe Gln Phe Arg Ala Gly Leu Pro Val Thr Gly Ile Ala
    50                  55                  60

Asp Tyr Ala Thr Gln Val Arg Leu Gly Ala Val Ala Pro Ala Pro Pro
65                  70                  75                  80

Pro Arg Gln Arg Ile Met Val Leu Thr Phe Ser Gly Thr Ser Ala Asp
                85                  90                  95

Met Trp Thr Gly Tyr Pro Ala Asp Val Ala Arg Ala Leu Asp Pro Ser
            100                 105                 110

Ile Phe Tyr Trp Gln Pro Val Cys Tyr Gly Pro Asn Gly Ile Pro Ala
        115                 120                 125

Ile Phe Pro Met Gly Ser Ser Ala Lys Ser Gly Glu Val Glu Gly Leu
    130                 135                 140

Arg Leu Leu Asp Glu Lys Ala Arg Asp Phe Asp Tyr Ile Val Leu Ile
145                 150                 155                 160

Gly Tyr Ser Gln Gly Ala Leu Pro Ala Ser Arg Leu Met Arg Arg Ile
                165                 170                 175

Leu Ser Gly Asp Leu Gln Arg Phe Lys Ser Lys Leu Ile Ala Gly Val
            180                 185                 190

Thr Phe Gly Asn Pro Met Arg Glu Lys Gly His Thr Phe Pro Gly Gly
        195                 200                 205

Ala Asp Pro Gly Gly His Gly Leu Asp Pro Gln Cys Leu Val Asn Thr
    210                 215                 220

Pro Asp Trp Trp His Asp Tyr Ala Ala Lys Gly Asp Ile Tyr Thr Val
225                 230                 235                 240
```

Gly Ser Gly Ser Asn Asp Glu Lys Ala Asn Ala Asp Met Thr Phe Ile
              245                 250                 255

Tyr Gln Leu Val Gln Gly Asp Ile Leu Gly Met Met Phe Gly Thr Gly
          260                 265                 270

Asn Pro Leu Asp Ile Leu Gly Leu Gly Gly Leu Gly Gly Leu
      275                 280                 285

Leu Gly Gly Leu Gly Gly Leu Leu Gly Gly Lys Gly Gly Leu
  290                 295                 300

Gln Leu Pro Ser Gly Leu Val Leu Pro Gly Val Gln Gly Gly Ala Leu
305                 310                 315                 320

Thr Asp His Gln Arg Gly Leu Val Glu Ala Val Leu Ala Leu Ala
              325                 330                 335

Asn Pro Phe Ala Glu Val Pro Ala Ala Val Lys Ala Ile Val Ser Gly
              340                 345                 350

Val Gly Phe Ile Ala Thr Asn Pro Pro Thr Ala Pro His Ile Glu Tyr
          355                 360                 365

His Ile Arg Glu Ala Ala Pro Gly Val Thr Tyr Phe Gln His Ala Ile
      370                 375                 380

Asp Tyr Leu Arg Gln Val Gly Ala Ser Val Ala Ala Arg Ala Ala His
385                 390                 395                 400

His His His His Gly Ser Leu Leu Gly Asp Phe Phe Arg Lys Ser
              405                 410                 415

Lys Glu Lys Ile Gly Lys Glu Phe Lys Arg Ile Val Gln Arg Ile Lys
              420                 425                 430

Asp Phe Leu Arg Asn Leu Val Pro Arg Thr Glu Ser Tyr Gly Arg Lys
              435                 440                 445

Lys Arg Arg Gln Arg Arg Arg
  450                 455

<210> SEQ ID NO 102
<211> LENGTH: 1365
<212> TYPE: DNA
<213> ORGANISM: Artificial sequence
<220> FEATURE:
<223> OTHER INFORMATION: TM4gp30/LL37/TAT47-57 construct 7

<400> SEQUENCE: 102
gcttgggtgg gttggcagct gggcatgcag ggcgaacagg tcaaagtgat ccagcagaaa      60
ctgatcgcga ataccagtg ggtccgtgac cgttatccgc gtctgaccgc ttccggtgtt     120
tatgatgtta acacgcaggc tgcgatcgtg gaatttcagt tccgtgcagg tctgccggtc     180
actggcattg cggattacgc tacccaggtt cgtctgggtg ccgtagcacc ggctccacca     240
ccacgtcagc gtatcatggt cctgacgttt tctggtactt ctgcggatat gtggaccggt     300
tacccagcag acgttgctcg cgcgctggac ccgtccattt tctactggca gccagtatgc     360
tacggtccga acggtatccc agcgattttc ccgatgggta gctccgcgaa atccggtgaa     420
gtggaaggcc tgcgcctgct ggacgagaaa gcacgtgact cgattacat cgtactgatt     480 ggctacagcc agggtgcact gccggcatct cgcctgatgc gccgtattct gtctggcgac     540
ctgcagcgct tcaaaagcaa actgatcgct ggcgtgacct cggcaaccc gatgcgtgaa     600 aaaggccaca ccttcccagg tggcgcagac ccaggcggtc atggcctgga cccacagtgt     660
ctggtgaaca cccagattg tggcacgat tacgcggcca aaggcgatat ctatactgtg     720
ggctccggtt ctaacgacga aaaagccaac gccgacatga cctttatcta tcagctcgtg     780

-continued

```
cagggtgaca ttctgggcat gatgtttggc accggtaacc cgctggacat cctgggcctg      840
ctcggcggtc tgggtggtgg tctgctgggt ggtctgggtg gtggcctgct gggcggtggc      900
aaaggtggtc tgcagctgcc gtctggtctg gtactgccag gtgttcaggg cggtgccctg      960
actgatcacc agcgtggtct ggtagaagct gttctggcgc tgctcgctaa cccgttcgca     1020
gaagtaccag ctgcggtcaa agcgatcgtt agcggtgttg gcttcatcgc taccaacccg     1080
ccgactgcac cgcacatcga gtatcacatt cgcgaagcag ctccaggtgt gacctacttc     1140
cagcacgcaa tcgattacct gcgtcaggtt ggtgcctctg ttgctgcacg tgccgcacac     1200
catcaccatc accatggatc cttattgggt gatttctttc ggaagagcaa agaaaagata     1260
ggaaaggagt ttaaacgaat tgttcaacgt atcaaagact tcctaaggaa tcttgtacca     1320
agaacagaaa gttatggccg caaaaaacgg cgtcagcgtc gccgc                      1365
```

<210> SEQ ID NO 103
<211> LENGTH: 302
<212> TYPE: PRT
<213> ORGANISM: Artificial sequence
<220> FEATURE:
<223> OTHER INFORMATION: D29gp12/alpha-defensin/PTD3 construct 8

<400> SEQUENCE: 103

```
Ser Lys Pro Trp Leu Phe Thr Val His Gly Thr Gly Gln Pro Asp Pro
1               5                  10                  15

Leu Gly Pro Gly Leu Pro Ala Asp Thr Ala Arg Asp Val Leu Asp Ile
            20                  25                  30

Tyr Arg Trp Gln Pro Ile Gly Asn Tyr Pro Ala Ala Ala Phe Pro Met
        35                  40                  45

Trp Pro Ser Val Glu Lys Gly Val Ala Glu Leu Ile Leu Gln Ile Glu
    50                  55                  60

Leu Lys Leu Asp Ala Asp Pro Tyr Ala Asp Phe Ala Met Ala Gly Tyr
65                  70                  75                  80

Ser Gln Gly Ala Ile Val Val Gly Gln Val Leu Lys His His Ile Leu
                85                  90                  95

Pro Pro Thr Gly Arg Leu His Arg Phe Leu His Arg Leu Lys Lys Val
            100                 105                 110

Ile Phe Trp Gly Asn Pro Met Arg Gln Lys Gly Phe Ala His Ser Asp
        115                 120                 125

Glu Trp Ile His Pro Val Ala Ala Pro Asp Thr Leu Gly Ile Leu Glu
    130                 135                 140

Asp Arg Leu Glu Asn Leu Glu Gln Tyr Gly Phe Glu Val Arg Asp Tyr
145                 150                 155                 160

Ala His Asp Gly Asp Met Tyr Ala Ser Ile Lys Glu Asp Asp Leu His
                165                 170                 175

Glu Tyr Glu Val Ala Ile Gly Arg Ile Val Met Lys Ala Ser Gly Phe
            180                 185                 190

Ile Gly Gly Arg Asp Ser Val Val Ala Gln Leu Ile Glu Leu Gly Gln
        195                 200                 205

Arg Pro Ile Thr Glu Gly Ile Ala Leu Ala Gly Ala Ile Asp Ala
        210                 215                 220

Leu Thr Phe Phe Ala Arg Ser Arg Met Gly Asp Lys Trp Pro His Leu
225                 230                 235                 240

Tyr Asn Arg Tyr Pro Ala Val Glu Phe Leu Arg Gln Ile His His
                245                 250                 255

His His His Gly Ser Asp Cys Tyr Cys Arg Ile Pro Ala Cys Ile Ala
```

```
                260                 265                 270
Gly Glu Arg Arg Tyr Gly Thr Cys Ile Tyr Gln Gly Arg Leu Trp Ala
                275                 280                 285

Phe Cys Cys Tyr Ala Arg Lys Ala Arg Arg Gln Ala Arg Arg
                290                 295                 300
```

<210> SEQ ID NO 104
<211> LENGTH: 906
<212> TYPE: DNA
<213> ORGANISM: Artificial sequence
<220> FEATURE:
<223> OTHER INFORMATION: D20gp12/alpha-defensin/PTD3 construct 8

<400> SEQUENCE: 104

```
agcaaaccgt ggctgttcac cgtgcatggt actggccagc cagatccgct gggtccaggt    60
ctgccagctg atactgctcg tgacgtcctg gatatctacc gttggcagcc gattggtaac   120
tacccggctg cagcgttccc aatgtggccg tccgttgaaa aaggcgtagc ggaactcatc   180
ctgcagatcg aactgaaact ggatgcggac ccgtatgctg atttcgcgat ggctggctac   240
tctcagggtg ctatcgtagt aggccaggtc ctgaaacatc acatcctgcc accgactggt   300
cgtctgcacc gtttcctgca ccgcctgaaa aaagtgatct tctggggtaa cccgatgcgt   360
cagaaaggct ttgcacactc cgacgagtgg attcacccag ttgctgcacc ggatactctg   420
ggcatcctgg aagatcgcct ggagaacctg aacagtacg gtttcgaagt gcgtgactat    480
gcccacgacg gtgatatgta cgcctccatc aaagaggacg atctgcacga gtacgaggta   540
gcgatcggtc gtatcgttat gaaagcgagc ggtttcattg cggccgtga ttctgtagtg    600
gcgcagctga tcgaactggg tcagcgcccg attacggaag gtattgcact ggcaggcgcg   660
attattgacg ccctgacctt ctttgcccgc tctcgtatgg cgacaaatg cccacacctg    720
tataaccgct acccagcagt tgagtttctg cgtcagatcc accatcacca tcaccatgga   780
tccgactgtt actgccgtat cccagcatgt attgctggtg aacgccgtta cggcacttgt   840
atttaccagg gtcgcctgtg ggcttttttgc tgctatgccc gtaaagcacg tcggcaggcg   900
cgccgc                                                              906
```

<210> SEQ ID NO 105
<211> LENGTH: 297
<212> TYPE: PRT
<213> ORGANISM: Artificial sequence
<220> FEATURE:
<223> OTHER INFORMATION: PTD3/alpha-defensin/D29gp12 construct 9

<400> SEQUENCE: 105

```
Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
                20                  25                  30

Gln Gly Arg Leu Trp Ala Phe Cys Cys Leu Lys Met Ser Lys Pro Trp
            35                  40                  45

Leu Phe Thr Val His Gly Thr Gly Gln Pro Asp Pro Leu Gly Pro Gly
        50                  55                  60

Leu Pro Ala Asp Thr Ala Arg Asp Val Leu Asp Ile Tyr Arg Trp Gln
65                  70                  75                  80

Pro Ile Gly Asn Tyr Pro Ala Ala Ala Phe Pro Met Trp Pro Ser Val
                85                  90                  95

Glu Lys Gly Val Ala Glu Leu Ile Leu Gln Ile Glu Leu Lys Leu Asp
```

```
              100                 105                 110
Ala Asp Pro Tyr Ala Asp Phe Ala Met Ala Gly Tyr Ser Gln Gly Ala
        115                 120                 125

Ile Val Val Gly Gln Val Leu Lys His His Ile Leu Pro Pro Thr Gly
    130                 135                 140

Arg Leu His Arg Phe Leu His Arg Leu Lys Lys Val Ile Phe Trp Gly
145                 150                 155                 160

Asn Pro Met Arg Gln Lys Gly Phe Ala His Ser Asp Glu Trp Ile His
                165                 170                 175

Pro Val Ala Ala Pro Asp Thr Leu Gly Ile Leu Glu Asp Arg Leu Glu
            180                 185                 190

Asn Leu Glu Gln Tyr Gly Phe Glu Val Arg Asp Tyr Ala His Asp Gly
        195                 200                 205

Asp Met Tyr Ala Ser Ile Lys Glu Asp Asp Leu His Glu Tyr Glu Val
    210                 215                 220

Ala Ile Gly Arg Ile Val Met Lys Ala Ser Gly Phe Ile Gly Gly Arg
225                 230                 235                 240

Asp Ser Val Val Ala Gln Leu Ile Glu Leu Gly Gln Arg Pro Ile Thr
                245                 250                 255

Glu Gly Ile Ala Leu Ala Gly Ala Ile Ile Asp Ala Leu Thr Phe Phe
            260                 265                 270

Ala Arg Ser Arg Met Gly Asp Lys Trp Pro His Leu Tyr Asn Arg Tyr
        275                 280                 285

Pro Ala Val Glu Phe Leu Arg Gln Ile
    290                 295

<210> SEQ ID NO 106
<211> LENGTH: 891
<212> TYPE: DNA
<213> ORGANISM: Artificial sequence
<220> FEATURE:
<223> OTHER INFORMATION: PTD3/alpha-defensin/D29gp12 construct 9

<400> SEQUENCE: 106
tatgcccgta aagcacgtcg gcaggcgcgc cgcgactgtt actgccgtat cccagcatgt      60
attgctggtg aacgccgtta cggcacttgt atttaccagg gtcgcctgtg ggcttttgc     120 tgccttaaga tgagcaaacc gtggctgttc accgtgcatg gtactggcca gccagatccg     180
ctgggtccag gtctgccagc tgatactgct cgtgacgtcc tggatatcta ccgttggcag     240
ccgattggta actacccggc tgcagcgttc ccaatgtggc cgtccgttga aaaaggcgta     300
gcggaactca tcctgcagat cgaactgaaa ctggatgcgg acccgtatgc tgatttcgcg     360
atggctggct actctcaggg tgctatcgta gtaggccagg tcctgaaaca tcacatcctg     420
ccaccgactg gtcgtctgca ccgtttcctg caccgcctga aaaagtgat cttctggggt     480 aacccgatgc gtcagaaagg ctttgcacac tccgacgagt ggattcaccc agttgctgca     540
ccggatactc tgggcatcct ggaagatcgc ctggagaacc tggaacagta cggtttcgaa     600
gtgcgtgact atgcccacga cggtgatatg tacgcctcca tcaaagagga cgatctgcac     660
gagtacgagg tagcgatcgg tcgtatcgtt atgaaagcga gcggtttcat tggcggccgt     720
gattctgtag tggcgcagct gatcgaactg ggtcagcgcc cgattacgga aggtattgca     780
ctggcaggcg cgattattga cgccctgacc ttctttgccc gctctcgtat gggcgacaaa     840
tggccacacc tgtataaccg ctacccagca gttgagtttc tgcgtcagat c              891
```

<210> SEQ ID NO 107
<211> LENGTH: 335
<212> TYPE: PRT
<213> ORGANISM: Artificial sequence
<220> FEATURE:
<223> OTHER INFORMATION: PTD3/alpha-defensin/D29gp12/alpha-defensin construct 10

<400> SEQUENCE: 107

```
Tyr Ala Arg Lys Ala Arg Arg Gln Ala Arg Arg Asp Cys Tyr Cys Arg
1               5                   10                  15

Ile Pro Ala Cys Ile Ala Gly Glu Arg Arg Tyr Gly Thr Cys Ile Tyr
            20                  25                  30

Gln Gly Arg Leu Trp Ala Phe Cys Cys Leu Lys Met Ser Lys Pro Trp
        35                  40                  45

Leu Phe Thr Val His Gly Thr Gly Gln Pro Asp Pro Leu Gly Pro Gly
    50                  55                  60

Leu Pro Ala Asp Thr Ala Arg Asp Val Leu Asp Ile Tyr Arg Trp Gln
65                  70                  75                  80

Pro Ile Gly Asn Tyr Pro Ala Ala Phe Pro Met Trp Pro Ser Val
                85                  90                  95

Glu Lys Gly Val Ala Glu Leu Ile Leu Gln Ile Glu Leu Lys Leu Asp
            100                 105                 110

Ala Asp Pro Tyr Ala Asp Phe Ala Met Ala Gly Tyr Ser Gln Gly Ala
        115                 120                 125

Ile Val Val Gly Gln Val Leu Lys His His Ile Leu Pro Pro Thr Gly
    130                 135                 140

Arg Leu His Arg Phe Leu His Arg Leu Lys Lys Val Ile Phe Trp Gly
145                 150                 155                 160

Asn Pro Met Arg Gln Lys Gly Phe Ala His Ser Asp Glu Trp Ile His
                165                 170                 175

Pro Val Ala Ala Pro Asp Thr Leu Gly Ile Leu Glu Asp Arg Leu Glu
            180                 185                 190

Asn Leu Glu Gln Tyr Gly Phe Glu Val Arg Asp Tyr Ala His Asp Gly
        195                 200                 205

Asp Met Tyr Ala Ser Ile Lys Glu Asp Leu His Glu Tyr Glu Val
    210                 215                 220

Ala Ile Gly Arg Ile Val Met Lys Ala Ser Gly Phe Ile Gly Arg
225                 230                 235                 240

Asp Ser Val Val Ala Gln Leu Ile Glu Leu Gly Gln Arg Pro Ile Thr
                245                 250                 255

Glu Gly Ile Ala Leu Ala Gly Ala Ile Ile Asp Ala Leu Thr Phe Phe
            260                 265                 270

Ala Arg Ser Arg Met Gly Asp Lys Trp Pro His Leu Tyr Asn Arg Tyr
        275                 280                 285

Pro Ala Val Glu Phe Leu Arg Gln Ile His His His His His Gly
    290                 295                 300

Ser Asp Cys Tyr Cys Arg Ile Pro Ala Cys Ile Ala Gly Glu Arg Arg
305                 310                 315                 320

Tyr Gly Thr Cys Ile Tyr Gln Gly Arg Leu Trp Ala Phe Cys Cys
                325                 330                 335
```

<210> SEQ ID NO 108
<211> LENGTH: 1005
<212> TYPE: DNA
<213> ORGANISM: Artificial sequence
<220> FEATURE:

<223> OTHER INFORMATION: PTD3/alpha-defensin/D29gp12/alpha-defensin construct 10

<400> SEQUENCE: 108

```
tatgcccgta aagcacgtcg gcaggcgcgc cgcgactgtt actgccgtat cccagcatgt      60
attgctggtg aacgccgtta cggcacttgt atttaccagg tcgcctgtg gcttttgc       120
tgccttaaga tgagcaaacc gtggctgttc accgtgcatg gtactggcca gccagatccg    180
ctgggtccag gtctgccagc tgatactgct cgtgacgtcc tggatatcta ccgttggcag    240
ccgattggta actacccggc tgcagcgttc ccaatgtggc cgtccgttga aaaaggcgta    300
gcggaactca tcctgcagat cgaactgaaa ctggatgcgg acccgtatgc tgatttcgcg    360
atggctggct actctcaggg tgctatcgta gtaggccagg tcctgaaaca tcacatcctg    420
ccaccgactg tcgtctgca ccgtttcctg caccgcctga aaaagtgat cttctggggt     480
aacccgatgc gtcagaaagg ctttgcacac tccgacgagt ggattcaccc agttgctgca    540
ccggatactc tgggcatcct ggaagatcgc ctggagaacc tggaacagta cggtttcgaa    600
gtgcgtgact atgcccacga cggtgatatg tacgcctcca tcaaagagga cgatctgcac    660
gagtacgagg tagcgatcgg tcgtatcgtt atgaaagcga gcggtttcat ggcggccgt     720
gattctgtag tggcgcagct gatcgaactg ggtcagcgcc cgattacgga aggtattgca    780
ctggcaggcg cgattattga cgccctgacc ttctttgccc gctctcgtat gggcgacaaa    840
tggccacacc tgtataaccg ctacccagca gttgagtttc tgcgtcagat ccaccatcac    900
catcaccatg gatccgactg ttactgccgt atcccagcat gtattgctgg tgaacgccgt    960
tacggcactt gtatttacca gggtcgcctg tgggcttttt gctgc                  1005
```

<210> SEQ ID NO 109
<211> LENGTH: 313
<212> TYPE: PRT
<213> ORGANISM: Artificial sequence
<220> FEATURE:
<223> OTHER INFORMATION: beta-defensin/D29gp12/TAT47-57 construct 11

<400> SEQUENCE: 109

```
Asn Pro Val Ser Cys Val Arg Asn Lys Gly Ile Cys Val Pro Ile Arg
1               5                   10                  15
Cys Pro Gly Ser Met Lys Gln Ile Gly Thr Cys Val Gly Arg Ala Val
            20                  25                  30
Lys Cys Cys Arg Lys Lys Leu Lys Met Ser Lys Pro Trp Leu Phe Thr
        35                  40                  45
Val His Gly Thr Gly Gln Pro Asp Pro Leu Gly Pro Gly Leu Pro Ala
    50                  55                  60
Asp Thr Ala Arg Asp Val Leu Asp Ile Tyr Arg Trp Gln Pro Ile Gly
65                  70                  75                  80
Asn Tyr Pro Ala Ala Ala Phe Pro Met Trp Pro Ser Val Glu Lys Gly
                85                  90                  95
Val Ala Glu Leu Ile Leu Gln Ile Glu Leu Lys Leu Asp Ala Asp Pro
            100                 105                 110
Tyr Ala Asp Phe Ala Met Ala Gly Tyr Ser Gln Gly Ala Ile Val Val
        115                 120                 125
Gly Gln Val Leu Lys His His Ile Leu Pro Pro Thr Gly Arg Leu His
    130                 135                 140
Arg Phe Leu His Arg Leu Lys Lys Val Ile Phe Trp Gly Asn Pro Met
145                 150                 155                 160
```

Arg Gln Lys Gly Phe Ala His Ser Asp Glu Trp Ile His Pro Val Ala
            165                 170                 175

Ala Pro Asp Thr Leu Gly Ile Leu Glu Asp Arg Leu Glu Asn Leu Glu
        180                 185                 190

Gln Tyr Gly Phe Glu Val Arg Asp Tyr Ala His Asp Gly Asp Met Tyr
    195                 200                 205

Ala Ser Ile Lys Glu Asp Asp Leu His Glu Tyr Glu Val Ala Ile Gly
    210                 215                 220

Arg Ile Val Met Lys Ala Ser Gly Phe Ile Gly Arg Asp Ser Val
225                 230                 235                 240

Val Ala Gln Leu Ile Glu Leu Gly Gln Arg Pro Ile Thr Glu Gly Ile
                245                 250                 255

Ala Leu Ala Gly Ala Ile Ile Asp Ala Leu Thr Phe Phe Ala Arg Ser
            260                 265                 270

Arg Met Gly Asp Lys Trp Pro His Leu Tyr Asn Arg Tyr Pro Ala Val
        275                 280                 285

Glu Phe Leu Arg Gln Ile His His His His His Gly Ser Tyr Gly
    290                 295                 300

Arg Lys Lys Arg Arg Gln Arg Arg
305                 310

<210> SEQ ID NO 110
<211> LENGTH: 939
<212> TYPE: DNA
<213> ORGANISM: Artificial sequence
<220> FEATURE:
<223> OTHER INFORMATION: beta-defensin/D29gp12/TAT47-57 construct 11

<400> SEQUENCE: 110

| | | |
|---|---|---|
| aacccggtat cttgcgtgcg caacaaaggt atctgcgttc cgattcgttg tccgggttct | 60 |
| atgaaacaga ttggcacttg cgttggtcgt gccgtgaaat gctgccgtaa aaaacttaag | 120 |
| atgagcaaac cgtggctgtt caccgtgcat ggtactggcc agccagatcc gctgggtcca | 180 |
| ggtctgccag ctgatactgc tcgtgacgtc ctggatatct accgttggca gccgattggt | 240 |
| aactacccgg ctgcagcgtt cccaatgtgg ccgtccgttg aaaaaggcgt agcggaactc | 300 |
| atcctgcaga tcgaactgaa actggatgcg gacccgtatg ctgatttcgc gatggctggc | 360 |
| tactctcagg gtgctatcgt agtaggccag gtcctgaaac atcacatcct gccaccgact | 420 |
| ggtcgtctgc accgtttcct gcaccgcctg aaaaaagtga tcttctgggg taacccgatg | 480 |
| cgtcagaaag gctttgcaca ctccgacgag tggattcacc cagttgctgc accggatact | 540 |
| ctgggcatcc tggaagatcg cctggagaac ctggaacagt acggtttcga agtgcgtgac | 600 |
| tatgcccacg acggtgatat gtacgcctcc atcaaagagg acgatctgca cgagtacgag | 660 |
| gtagcgatcg gtcgtatcgt tatgaaagcg agcggtttca ttggcggccg tgattctgta | 720 |
| gtggcgcagc tgatcgaact gggtcagcgc ccgattacgg aaggtattgc actggcaggc | 780 |
| gcgattattg acgccctgac cttctttgcc cgctctcgta tgggcgacaa atggccacac | 840 |
| ctgtataacc gctacccagc agttgagttt ctgcgtcaga tccaccatca ccatcaccat | 900 |
| ggatcctatg gccgcaaaaa acggcgtcag cgtcgccgc | 939 |

<210> SEQ ID NO 111
<211> LENGTH: 338
<212> TYPE: PRT
<213> ORGANISM: Artificial sequence
<220> FEATURE:
<223> OTHER INFORMATION: beta-defensin/hepcidin/L5gp12/TAT47-57 construct 12

<400> SEQUENCE: 111

| | | | | | | | | | | | | | | |
|---|---|---|---|---|---|---|---|---|---|---|---|---|---|---|
|Asn|Pro|Val|Ser|Cys|Val|Arg|Asn|Lys|Gly|Ile|Cys|Val|Pro|Ile|Arg|
|1| | |5| | | | |10| | | | |15| |

Asn Pro Val Ser Cys Val Arg Asn Lys Gly Ile Cys Val Pro Ile Arg
1               5                   10              15

Cys Pro Gly Ser Met Lys Gln Ile Gly Thr Cys Val Gly Arg Ala Val
            20                  25                  30

Lys Cys Cys Arg Lys Lys Asp Thr His Phe Pro Ile Cys Ile Phe Cys
        35                  40                  45

Cys Gly Cys Cys His Arg Ser Lys Cys Gly Met Cys Cys Lys Thr Leu
        50                  55                  60

Lys Met Ser Lys Pro Trp Leu Phe Thr Val His Gly Thr Gly Gln Pro
65                  70                  75                  80

Asp Pro Leu Gly Pro Gly Leu Pro Ala Asp Thr Ala Arg Asp Val Leu
                85                  90                  95

Asp Ile Tyr Arg Trp Gln Pro Ile Gly Asn Tyr Pro Ala Ala Ala Phe
            100                 105                 110

Pro Met Trp Pro Ser Val Glu Lys Gly Val Ala Glu Leu Ile Leu Gln
            115                 120                 125

Ile Glu Leu Lys Leu Asp Ala Asp Pro Tyr Ala Asp Phe Ala Leu Ala
130                 135                 140

Gly Tyr Ser Gln Gly Ala Ile Val Val Gly Gln Val Leu Lys His His
145                 150                 155                 160

Ile Ile Asn Pro Arg Gly Arg Leu His Arg Phe Leu His Arg Leu Arg
            165                 170                 175

Lys Val Ile Phe Trp Gly Asn Pro Met Arg Gln Lys Gly Phe Ala His
            180                 185                 190

Thr Asp Glu Trp Ile His Gln Val Ala Ala Ser Asp Thr Met Gly Ile
            195                 200                 205

Leu Glu Asp Arg Leu Glu Asn Leu Glu Gln Tyr Gly Phe Glu Val Arg
210                 215                 220

Asp Tyr Ala His Asp Gly Asp Met Tyr Ala Ser Ile Lys Glu Asp Asp
225                 230                 235                 240

Met His Glu Tyr Glu Val Ala Ile Gly Arg Ile Val Met Ser Ala Arg
            245                 250                 255

Arg Phe Ile Gly Gly Lys Asp Ser Val Ile Ala Gln Leu Ile Glu Leu
            260                 265                 270

Gly Gln Arg Pro Ile Trp Glu Gly Ile Ala Met Ala Arg Ala Ile Ile
            275                 280                 285

Asp Ala Leu Thr Phe Phe Ala Lys Ser Thr Gln Gly Pro Ser Trp Pro
290                 295                 300

His Leu Tyr Asn Arg Phe Pro Ala Val Glu Phe Leu Arg Arg Ile His
305                 310                 315                 320

His His His His Gly Ser Tyr Gly Arg Lys Lys Arg Arg Gln Arg
            325                 330                 335

Arg Arg

<210> SEQ ID NO 112
<211> LENGTH: 1014
<212> TYPE: DNA
<213> ORGANISM: Artificial sequence
<220> FEATURE:
<223> OTHER INFORMATION: beta-defensin/hepcidin/L5gp12/TAT47-57
      construct 12

<400> SEQUENCE: 112

```
aacccggtat cttgcgtgcg caacaaaggt atctgcgttc cgattcgttg tccgggttct    60
atgaaacaga ttggcacttg cgttggtcgt gccgtgaaat gctgccgtaa aaaagacacc   120
cacttcccga tttgtatctt ctgctgtggc tgctgtcacc gctccaaatg tggtatgtgc   180
tgtaaaaccc ttaagatgag caaaccgtgg ctgttcaccg ttcatggtac tggccagcca   240
gatccactgg gtccaggtct gccagcagat actgcacgtg acgtgctgga tatctaccgt   300
tggcagccga ttggcaacta tccagctgca gcgttcccaa tgtggccatc tgttgagaaa   360
ggcgtagccg agctgattct gcagatcgaa ctgaaactcg acgctgaccc gtatgcggat   420
ttcgcactgc tggttactc tcagggtgct atcgtagtag ccaggtcct gaaacaccat   480 atcattaacc cgcgtggtcg tctgcaccgt tttctgcatc gcctgcgcaa agtgatcttc   540
tggggtaacc caatgcgcca gaaaggcttc gcacacaccg acgagtggat tcaccaggtt   600
gcagcgtccg acactatggg cattctggaa gatcgcctgg aaaacctgga acagtacggc   660
ttcgaagtcc gtgactatgc ccacgatggc gatatgtacg cgtccatcaa agaggacgat   720
atgcacgagt acgaagtagc gatcggtcgt atcgtgatgt ctgctcgccg tttcatcggt   780
ggcaaagaca gcgtgattgc ccagctgatc gaactgggtc agcgtccgat ctgggaaggt   840
atcgctatgg ctcgcgctat tatcgacgcc ctcaccttct ttgcgaaatc tacgcagggt   900
ccgtcttggc cacacctgta caccgtttc ccagcagtcg agtttctgcg tcgtatccac   960
catcaccacc atcacggatc ctatggccgc aaaaaacggc gtcagcgtcg ccgc         1014
```

<210> SEQ ID NO 113
<211> LENGTH: 731
<212> TYPE: PRT
<213> ORGANISM: Artificial sequence
<220> FEATURE:
<223> OTHER INFORMATION: TM4gp29/LL37/TAT47-57 construct 1 Thioredoxin
      tag

<400> SEQUENCE: 113

```
Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala Gly Ser Gly Ser
            100                 105                 110

Gly Ser Gly Ser Gly Ala Gly Thr Asp Asp Asp Lys Ala Met Ala
        115                 120                 125

Met Ser Phe Thr Arg Phe Leu Gln Asp Asp Pro Leu Leu Thr Arg Glu
    130                 135                 140

Gln Val Met Ala Glu Leu Ile Arg Val Ala Asp Glu Leu Asn Met Pro
145                 150                 155                 160

Asp Lys Arg Gly Ala Cys Val Ile Ala Gly Met Thr Ile Ser Gln Glu
                165                 170                 175
```

-continued

```
Val Gly Val Lys Asp Asn Asp Pro Pro Phe Glu Arg Arg Phe Trp Cys
            180                 185                 190

Pro Ala Asn Arg Ala Asp Pro Glu Ser Phe Asn Tyr Pro His Asp Ser
            195                 200                 205

Glu Ser Asn Asp Gly Arg Ser Val Gly Tyr Phe Gln Gln Gln Lys Gly
            210                 215                 220

Pro Asn Gly Glu Leu Trp Trp Gly Thr Thr Ala Ser Glu Met Asn Leu
225                 230                 235                 240

His Ser Ala Ala Thr Gln Phe Met Thr Arg Leu Lys Ala Ala Gly Tyr
            245                 250                 255

Asn Ala Ser Asn Ala Gln Ala Ala Asn Asp Ser Ala Gln Ala Ile Gln
            260                 265                 270

Arg Ser Gly Val Pro Gln Ala Tyr Lys Gln Trp Trp Asp Asp Ile Asn
            275                 280                 285

Arg Leu Tyr Asp Lys Val Lys Gly Ser Gly Gly Pro Ala Pro Ala
            290                 295                 300

Pro Lys Pro Pro Gln Ser Gly Pro Trp Thr Gly Asp Pro Val Trp Leu
305                 310                 315                 320

Ala Asp Val Leu Arg Ala Glu Gly Leu Asn Val Val Glu Leu Pro Gly
            325                 330                 335

Trp Leu Asp Arg Gly His Gly Asp Met Gly Arg Leu Trp Gly Val Val
            340                 345                 350

Cys His His Thr Gly Ser Asp Asn Thr Pro Ser Ser Glu Ile Ala Phe
            355                 360                 365

His Pro Ser Leu Gly Leu Cys Ser Gln Ile His Leu Ala Arg Asn Gly
            370                 375                 380

Thr Val Thr Leu Cys Gly Val Gly Ile Ala Trp His Ala Gly Val Gly
385                 390                 395                 400

Ser Tyr Pro Gly Leu Pro Glu Asp Asn Ala Asn Ala Val Thr Ile Gly
            405                 410                 415

Ile Glu Ala Gln Asn Ser Gly Thr Tyr Asp Gly Ala Pro His Arg Thr
            420                 425                 430

Asn Trp Pro Asp Ala Gln Tyr Asp Ala Tyr Val Lys Cys Cys Ala Ala
            435                 440                 445

Ile Cys Arg Arg Leu Gly Val Arg Ala Asp His Val Ile Ser His Lys
450                 455                 460

Glu Trp Ala Gly Arg Lys Gln Gly Lys Trp Asp Pro Gly Ala Ile Asp
465                 470                 475                 480

Met Asn Ile Phe Arg Ala Asp Val Gln Arg Ile Asp Ala His Gln
            485                 490                 495

Pro Asn Gly Glu Asp Asp Phe Met Ala Ala Leu Ser Ala Asp Glu Gln
            500                 505                 510

Arg Glu Val Leu Asn Leu Leu Arg Val Leu Ala Asp Arg Arg Phe Val
            515                 520                 525

Ser Arg Ser Pro Phe Arg His Leu Gly Glu Gly Pro Ser Glu Thr Val
530                 535                 540

Ala Gly Phe Gly Leu Asn Thr Asp Gly Leu Asn His Ala Gln Tyr Thr
545                 550                 555                 560

Ile Glu Leu Ala Arg Leu Gly Asp Pro Thr His Leu Ala Leu Leu Arg
            565                 570                 575

Glu Val Ala Ser Ala Glu Gly Asp Ser Arg Tyr Pro Asp Arg Gln Tyr
            580                 585                 590

Asp Ala Lys Leu Ala Lys Arg Val Leu Ala Glu Ile Glu Gly Ala Ala
```

|     |     |     |     |     | 595 |     |     |     |     | 600 |     |     |     |     | 605 |     |
| --- | --- | --- | --- | --- | --- | --- | --- | --- | --- | --- | --- | --- | --- | --- | --- | --- |

Thr Ala Pro Ala Lys Pro Ser Thr Pro Ser Ala Pro Thr Glu Pro Ala
              610                 615                 620

Pro Glu Ala Pro Thr Pro Pro Val Lys Ala Ala Cys Ala Leu Ser Ala
625                 630                 635                 640

Ala Gly Cys Val Val Ala Gly Ser Thr Ser Gly Gly Cys Ala Leu
                    645                 650                 655

Ser Thr Asp Gly Thr Gly Lys Cys Val Val Thr Ala Ala Thr Asp Gly
              660                 665                 670

Gly Ala Ala His His His His His Gly Ser Leu Leu Gly Asp Phe
              675                 680                 685

Phe Arg Lys Ser Lys Glu Lys Ile Gly Lys Glu Phe Lys Arg Ile Val
              690                 695                 700

Gln Arg Ile Lys Asp Phe Leu Arg Asn Leu Val Pro Arg Thr Glu Ser
705                 710                 715                 720

Tyr Gly Arg Lys Lys Arg Arg Gln Arg Arg
                    725                 730

<210> SEQ ID NO 114
<211> LENGTH: 2193
<212> TYPE: DNA
<213> ORGANISM: Artificial sequence
<220> FEATURE:
<223> OTHER INFORMATION: TM4gp29/LL37/TAT47-57 construct 1 Thioredoxin
      tag

<400> SEQUENCE: 114

| | | |
|---|---|---|
| agcgataaaa ttattcacct gactgacgac agttttgaca cggatgtact caaagcggac | 60 |
| ggggcgatcc tcgtcgattt ctgggcagag tggtgcggtc cgtgcaaaat gatcgccccg | 120 |
| attctggatg aaatcgctga cgaatatcag ggcaaactga ccgttgcaaa actgaacatc | 180 |
| gatcaaaacc ctggcactgc gccgaaatat ggcatccgtg gtatcccgac tctgctgctg | 240 |
| ttcaaaaacg gtgaagtggc ggcaaccaaa gtgggtgcac tgtctaaagg tcagttgaaa | 300 |
| gagttcctcg acgctaacct ggccggttct ggttctgggt caggatcagg agcaggtacc | 360 |
| gacgacgacg acaaggccat ggcaatgagc ttcactcgct ttctgcagga tgatccgctg | 420 |
| ctgacccgtg aacaggtgat ggctgaactg atccgtgtgg cggacgaact gaacatgccg | 480 |
| gataaacgtg gcgcttgcgt tatcgccggc atgactatct cccaggaagt gggtgtcaaa | 540 |
| gacaacgacc caccattcga gcgccgtttt tggtgcccgg caaaccgtgc tgatccggaa | 600 |
| agcttcaact acccgcacga ctctgaatcc aacgacggtc gctccgtagg ctacttccag | 660 |
| cagcagaaag gcccgaacgg tgaactgtgg tggggtacga ccgcttccga tgaacctg | 720 |
| cattctgccg caactcagtt catgacgcgt ctgaaagccg caggctacaa cgcaagcaac | 780 |
| gcacaggctg cgaacgactc cgcacaggcg atccagcgta cggcgtgcc gcaggcctac | 840 |
| aaacagtggt gggacgacat taccgcctg tatgacaaag tgaaaggctc tggtggcggt | 900 |
| ccggcaccgg caccaaaacc accacagagc ggtccgtgga ctggtgatcc ggtttggctg | 960 |
| gctgacgttc tccgcgctga gggtctgaac gtagtggaac tgccaggttg gctggatcgt | 1020 |
| ggccacggtg acatgggtcg tctgtggggt gtcgtgtgcc atcatactgg ctccgataac | 1080 |
| acgccaagct ccgaaatcgc tttccacccg agcctgggtc tgtgttctca gatccacctg | 1140 |
| gctcgtaacg gtaccgttac cctgtgcggt gtaggtatcg cttggcacgc aggtgttggt | 1200 |
| tcctacccgg gtctcccgga agacaacgcg aacgcggtca ctattggcat cgaagctcag | 1260 |

```
aactctggta cgtacgacgg cgctccacac cgtacgaact ggccagatgc gcagtatgac    1320
gcgtatgtaa aatgctgtgc cgccatctgt cgtcgcctgg gcgtacgcgc tgatcacgtt    1380
atttcccaca aagaatgggc tggtcgtaaa cagggcaaat gggacccggg cgctatcgat    1440
atgaacatct tccgtgctga cgtccagcgt cgtattgacg cacaccagcc gaacggtgag    1500
gacgactttg tggcagcgct gtctgcggat gagcagcgtg aagtgctgaa cctgctgcgt    1560
gtcctggcag atcgccgttt tgtatctcgc tctccgttcc gtcacctggg tgaaggtcca    1620
agcgagacgg ttgcaggttt cggcctgaac accgacggcc tgaaccatgc gcagtatact    1680
atcgaactgg cacgtctggg cgatccaacc cacctggctc tgctgcgcga agttgcctct    1740
gcagaaggcg attctcgcta cccagatcgc cagtacgatg cgaaactggc caaacgtgtc    1800
ctggcggaaa ttgaaggtgc agcgaccgct ccagctaaac cgtctacccc aagcgctcca    1860
actgaaccgg ctccagaagc cccgactccg ccagtaaaag ctgcctgtgc gctgtccgct    1920
gccggttgtg ttgtcgctgg ctctacctct ggtggcggtt cgcactgtc tactgatggc    1980 accggcaaat gcgtggttac tgcggcaact gacggcggtc tgcacacca tcaccatcac    2040 catggatcct tattgggtga tttctttcgg aagagcaaag aaaagatagg aaaggagttt    2100
aaacgaattg ttcaacgtat caaagacttc ctaaggaatc ttgtaccaag aacagaaagt    2160
tatggccgca aaaacggcg tcagcgtcgc cgc                                  2193
```

<210> SEQ ID NO 115
<211> LENGTH: 686
<212> TYPE: PRT
<213> ORGANISM: Artificial sequence
<220> FEATURE:
<223> OTHER INFORMATION: PTD3/alpha-defensin/Bxz2gp11 construct 3
      Thioredoxin tag

<400> SEQUENCE: 115

```
Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala Gly Ser Gly Ser
            100                 105                 110

Gly Ser Gly Ser Gly Ala Gly Thr Asp Asp Asp Lys Ala Met Ala
        115                 120                 125

Met Tyr Ala Arg Lys Ala Arg Arg Gln Ala Arg Arg Asp Cys Tyr Cys
    130                 135                 140

Arg Ile Pro Ala Cys Ile Ala Gly Glu Arg Arg Tyr Gly Thr Cys Ile
145                 150                 155                 160

Tyr Gln Gly Arg Leu Trp Ala Phe Cys Cys Leu Lys Met Thr Glu Lys
                165                 170                 175

Val Leu Pro Tyr Asp Arg Ser Ile Val Thr Gln Glu Thr Gly Trp Trp
            180                 185                 190
```

```
Cys Gly Pro Ala Ala Thr Gln Val Leu Asn Ser Arg Gly Ile Ile
        195                 200                 205

Val Pro Glu Ala Thr Leu Ala Ala Glu Ile Glu Ala Ile Glu Asn Pro
210                 215                 220

Gly Arg Gly Asp Asp Arg Asp Gly Thr Asp Tyr Val Gly Leu Ile Glu
225                 230                 235                 240

Gln Val Leu Asp Arg Arg Val Pro Gln Ala Arg Tyr Thr Ser Val Tyr
                245                 250                 255

Leu Thr Asn Asp Pro Pro Thr Gln Ala Gln Lys Asp Arg Leu Trp Glu
            260                 265                 270

His Ile Val Arg Ser Ile Asn Ala Gly Tyr Gly Val Val Met Asn Trp
        275                 280                 285

Val Ala Pro Pro Ser Asn Lys Pro Arg Gly Val Lys Gly Ser Val Ser
290                 295                 300

Pro Arg Tyr Ser Gly Gly Thr Thr Tyr His Tyr Val Ala Cys Met Gly
305                 310                 315                 320

Tyr Asp Asp Thr Pro Gly Ala Arg Ala Val Trp Ile Ala Asp Ser Gly
                325                 330                 335

Phe Gln Pro Gln Gly Tyr Trp Ile Ser Phe Asp Gln Cys Ala Thr Leu
            340                 345                 350

Ile Pro Pro Lys Gly Tyr Ala Tyr Ala Asp Ala Ala Pro Ala Ala Pro
        355                 360                 365

Ala Pro Ala Pro Thr Pro Val Asp Ala Ala Pro Ile Leu Ala Arg
370                 375                 380

Ala Ala Gly Ile Ser Glu Ala Lys Ala Arg Glu Ile Leu Pro Thr Met
385                 390                 395                 400

Arg Asp Gly Leu Lys Gln Ala Asp Cys Thr Thr Val Asn Arg Ile Ala
                405                 410                 415

Met Phe Ile Ala Gln Thr Gly His Glu Ser Asp Asp Phe Arg Ala Thr
            420                 425                 430

Glu Glu Tyr Ala Asn Gly Pro Leu Asp Gln Glu Arg Trp Ile Tyr Lys
        435                 440                 445

Gly Arg Thr Trp Ile Gln Ile Thr Trp Arg Glu His Tyr Ala Arg Phe
450                 455                 460

Gly Lys Trp Cys Phe Asp Arg Gly Leu Val Thr Asp Pro Asp Val Phe
465                 470                 475                 480

Val Lys Asn Pro Arg Ala Leu Ala Asp Leu Lys Trp Ala Gly Ile Gly
                485                 490                 495

Ala Ala Trp Tyr Trp Thr Val Gly Arg Pro Asp Ile Asn Ala Leu Cys
            500                 505                 510

Asp Arg Arg Asp Ile Glu Thr Val Ser Arg Arg Ile Asn Gly Thr Asn
        515                 520                 525

Pro Asn Thr Gly Arg Ala Asn His Ile Glu Glu Arg Ile Ala Arg Trp
530                 535                 540

Asn Arg Ala Leu Ala Val Gly Asp Asp Leu Leu Gln Leu Ile Arg Glu
545                 550                 555                 560

Glu Glu Asp Gly Phe Leu Ser Ala Leu Thr Pro Ala Glu Gln Arg Ala
                565                 570                 575

Leu Tyr Asn Glu Ile Met Lys Lys Gly Pro Thr Arg Ser Phe Met Ala
            580                 585                 590

Glu Asp Gln Asn Gln Ile Glu Thr Leu Leu Gly Phe Val Tyr Asn Ile
        595                 600                 605

Asp Gly Asn Ile Trp Asn Asp Ala Val Thr Arg Ala Tyr Leu Phe Asp
```

```
                610              615              620
Val Pro Leu Ala Val Glu Tyr Val Glu Arg Val Ala Arg Asp Gly Val
625              630              635              640

His Pro Lys Ser Trp Ala Phe Gln Gln Leu Asp Gly Lys Gly Glu Arg
             645              650              655

Trp Leu Ala Lys Phe Gly Gln Glu Tyr Cys Lys Gly Leu Ile Arg Phe
             660              665              670

Lys Lys Lys Leu Asn Asp Leu Leu Glu Pro Tyr Gly Glu Asn
             675              680              685

<210> SEQ ID NO 116
<211> LENGTH: 2058
<212> TYPE: DNA
<213> ORGANISM: Artificial sequence
<220> FEATURE:
<223> OTHER INFORMATION: PTD3/alpha-defensin/Bxz2gp11 construct 3
      Thioredoxin tag

<400> SEQUENCE: 116
agcgataaaa ttattcacct gactgacgac agttttgaca cggatgtact caaagcggac       60
ggggcgatcc tcgtcgattt ctgggcagag tggtgcggtc cgtgcaaaat gatcgccccg      120
attctggatg aaatcgctga cgaatatcag ggcaaactga ccgttgcaaa actgaacatc      180
gatcaaaacc ctggcactgc gccgaaatat ggcatccgtg gtatcccgac tctgctgctg      240
ttcaaaaacg gtgaagtggc ggcaaccaaa gtgggtgcac tgtctaaagg tcagttgaaa      300
gagttcctcg acgctaacct ggccggttct ggttctgggt caggatcagg agcaggtacc      360
gacgacgacg acaaggccat ggcaatgtat gcccgtaaag cacgtcggca ggcgcgccgc      420
gactgttact gccgtatccc agcatgtatt gctggtgaac gccgttacgg cacttgtatt      480
taccagggtc gcctgtgggc tttttgctgc cttaagatga ccgagaaagt gctgccgtac      540
gaccgttcta tcgttaccca ggaaaccggt tggtggtgtg gtccagcggc tactcaggtt      600
gttctgaact cccgtggcat catcgttcca gaagctacgt ggcagcggga atcgaagct       660 attgaaaacc cgggtcgtgg tgacgatcgt gatggtaccg actacgtagg tctgatcgag      720
caggttctgg atcgtcgtgt tccgcaggct cgttacacct ccgtgtatct gaccaacgat      780
ccaccgactc aggcacagaa agaccgtctc tgggagcata tcgtccgttc tatcaacgcc      840
ggttatggcg tggttatgaa ctgggtagcc ccaccgagca caaaccacg tggcgtgaaa       900 ggctctgtgt ctccgcgcta ttccggcggt accacttacc actacgtagc ctgtatgggt      960
tacgacgata cgccaggcgc tcgtgcggtt tggatcgcgg attctggttt ccagccacag     1020
ggctactgga ttagcttcga tcagtgcgcg accctgattc cgccaaaagg ctacgcttat     1080
gcagacgcag ctccggctgc accagcacca gctccaactc cggttgtaga cgctgcacca     1140
attctggctc gtgcggcagg tatctccgaa gccaaagcgc gtgaaattct gccgactatg     1200
cgcgacggtc tgaaacaggc tgattgtacg accgtcaacc gtatcgcaat gtttattgcg     1260
cagaccggtc acgaatctga tgacttccgc gccaccgaag agtatgcgaa cggtccactg     1320
gaccaggaac gttggatcta caaaggccgt acctggattc agatcacctg gcgtgaacac     1380
tacgctcgtt tcggcaaatg gtgcttcgat cgcggcctgg taactgatcc ggatgttttc     1440
gtgaaaaacc cacgcgctct ggcagatctg aaatgggctg gtattggcgc agcgtggtat     1500
tggaccgttg aacgtccgga catcaacgca ctgtgcgacc gcgtgatat cgaaactgtg      1560 tctcgtcgca tcaacggcac taacccgaac actggccgcg cgaaccacat cgaggaacgt     1620
```

-continued

```
attgctcgct ggaaccgtgc actggctgtg ggtgatgacc tgctccagct gatccgtgaa    1680
gaggaagatg gtttcctgag cgctctgacc ccagcagaac agcgtgccct gtacaacgag    1740
attatgaaaa aaggcccaac ccgctctttt atggccgaag accagaacca gatcgagacc    1800
ctgctgggtt ttgtctataa catcgacggc aacatctgga cgacgcagt tactcgcgcg    1860 tatctgttcg acgtaccact ggccgtcgaa tacgtggaac gcgttgctcg tgatggtgta    1920
cacccgaaaa gctgggcgtt tcagcagctg gacggtaaag cgaacgttg gctcgcgaaa     1980 ttcggtcagg aatactgcaa aggtctgatc cgcttcaaaa aaaaactgaa cgacctgctg    2040
gaaccgtacg gtgaaaac                                                  2058
```

<210> SEQ ID NO 117
<211> LENGTH: 423
<212> TYPE: PRT
<213> ORGANISM: Artificial sequence
<220> FEATURE:
<223> OTHER INFORMATION: beta-defensin/D29gp12/TAT47-57 construct 11 Thioredoxin tag

<400> SEQUENCE: 117

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala Gly Ser Gly Ser
            100                 105                 110

Gly Ser Gly Ser Gly Ala Gly Thr Asp Asp Asp Asp Lys Ala Met Ala
        115                 120                 125

Met Asn Pro Val Ser Cys Val Arg Asn Lys Gly Ile Cys Val Pro Ile
130                 135                 140

Arg Cys Pro Gly Ser Met Lys Gln Ile Gly Thr Cys Val Gly Arg Ala
145                 150                 155                 160

Val Lys Cys Cys Arg Lys Lys Leu Lys Met Ser Lys Pro Trp Leu Phe
                165                 170                 175

Thr Val His Gly Thr Gly Gln Pro Asp Pro Leu Gly Pro Gly Leu Pro
            180                 185                 190

Ala Asp Thr Ala Arg Asp Val Leu Asp Ile Tyr Arg Trp Gln Pro Ile
        195                 200                 205

Gly Asn Tyr Pro Ala Ala Ala Phe Pro Met Trp Pro Ser Val Glu Lys
    210                 215                 220

Gly Val Ala Glu Leu Ile Leu Gln Ile Glu Leu Lys Leu Asp Ala Asp
225                 230                 235                 240

Pro Tyr Ala Asp Phe Ala Met Ala Gly Tyr Ser Gln Gly Ala Ile Val
                245                 250                 255

Val Gly Gln Val Leu Lys His His Ile Leu Pro Pro Thr Gly Arg Leu
            260                 265                 270

His Arg Phe Leu His Arg Leu Lys Lys Val Ile Phe Trp Gly Asn Pro

```
                275                 280                 285
Met Arg Gln Lys Gly Phe Ala His Ser Asp Glu Trp Ile His Pro Val
            290                 295                 300
Ala Ala Pro Asp Thr Leu Gly Ile Leu Glu Asp Arg Leu Glu Asn Leu
305                 310                 315                 320
Glu Gln Tyr Gly Phe Glu Val Arg Asp Tyr Ala His Asp Gly Asp Met
                325                 330                 335
Tyr Ala Ser Ile Lys Glu Asp Asp Leu His Gly Tyr Glu Val Ala Ile
            340                 345                 350
Gly Arg Ile Val Met Lys Ala Ser Gly Phe Ile Gly Gly Arg Asp Ser
            355                 360                 365
Val Val Ala Gln Leu Ile Glu Leu Gly Gln Arg Pro Ile Thr Glu Gly
            370                 375                 380
Ile Ala Leu Ala Gly Ala Ile Ile Asp Ala Leu Thr Phe Phe Ala Arg
385                 390                 395                 400
Ser Arg Met Gly Asp Lys Trp Pro His Leu Tyr Asn Arg Tyr Pro Ala
                405                 410                 415
Val Glu Phe Leu Arg Gln Ile
            420

<210> SEQ ID NO 118
<211> LENGTH: 1269
<212> TYPE: DNA
<213> ORGANISM: Artificial sequence
<220> FEATURE:
<223> OTHER INFORMATION: beta-defensin/D29gp12/TAT47-57 construct 11
      Thioredoxin tag

<400> SEQUENCE: 118
agcgataaaa ttattcacct gactgacgac agtttgaca cggatgtact caaagcggac    60
ggggcgatcc tcgtcgattt ctgggcagag tggtgcggtc cgtgcaaaat gatcgccccg   120
attctggatg aaatcgctga cgaatatcag ggcaaactga ccgttgcaaa actgaacatc   180
gatcaaaacc ctggcactgc gccgaaatat ggcatccgtg gtatcccgac tctgctgctg   240
ttcaaaaacg gtgaagtggc ggcaaccaaa gtgggtgcac tgtctaaagg tcagttgaaa   300
gagttcctcg acgctaacct ggccggttct ggttctgggt caggatcagg agcaggtacc   360
gacgacgacg acaaggccat ggcaatgaac ccggtatctt gcgtgcgcaa caaaggtatc   420
tgcgttccga ttcgttgtcc gggttctatg aaacagattg gcacttgcgt tggtcgtgcc   480
gtgaaatgct gccgtaaaaa acttaagatg agcaaaccgt ggctgttcac cgtgcatggt   540
actggccagc cagatccgct gggtccaggt ctgccagctg atactgctcg tgacgtcctg   600
gatatctacc gttggcagcc gattggtaac tacccggctg cagcgttccc aatgtggccg   660
tccgttgaaa aaggcgtagc ggaactcatc ctgcagatcg aactgaaact ggatgcggac   720
ccgtatgctg atttcgcgat ggctggctac tctcagggtg ctatcgtagt aggccaggtc   780
ctgaaacatc acatcctgcc accgactggt cgtctgcacc gtttcctgca ccgcctgaaa   840
aaagtgatct tctggggtaa cccgatgcgt cagaaaggct tgcacactc cgacgagtgg   900
attcacccag ttgctgcacc ggatactctg ggcatcctgg aagatcgcct ggagaacctg   960
gaacagtacg gtttcgaagt cgtgactat gcccacgacg gtgatatgta cgcctccatc  1020
aaagaggacg atctgcacga gtacgaggta gcgatcggtc gtatcgttat gaaagcgagc  1080
ggtttcattg gcgccgtga ttctgtagtg gcgcagctga tcgaactggg tcagcgcccg  1140
attacggaag gtattgcact ggcaggcgcg attattgacg ccctgacctt ctttgcccgc  1200
```

```
tctcgtatgg gcgacaaatg gccacacctg tataaccgct acccagcagt tgagtttctg    1260
cgtcagatc                                                            1269

<210> SEQ ID NO 119
<211> LENGTH: 20
<212> TYPE: DNA
<213> ORGANISM: Artificial sequence
<220> FEATURE:
<223> OTHER INFORMATION: primer 27f (190)

<400> SEQUENCE: 119
agagtttgat cctggctcag                                                  20

<210> SEQ ID NO 120
<211> LENGTH: 22
<212> TYPE: DNA
<213> ORGANISM: Artificial sequence
<220> FEATURE:
<223> OTHER INFORMATION: primer 1492r (191)

<400> SEQUENCE: 120
tacggttacc ttgttacgac tt                                               22
```